United States Patent
Pissarnitski et al.

(10) Patent No.: US 7,208,602 B2
(45) Date of Patent: Apr. 24, 2007

(54) GAMMA SECRETASE INHIBITORS

(75) Inventors: Dmitri A. Pissarnitski, Scotch Plains, NJ (US); Hubert B. Josien, Hoboken, NJ (US); Elizabeth M. Smith, Verona, NJ (US); John W. Clader, Cranford, NJ (US); Theodros Asberom, West Orange, NJ (US); Tao Guo, Dayton, NJ (US); Douglas W. Hobbs, Yardley, PA (US)

(73) Assignees: Schering Corporation, Kenilworth, NJ (US); Pharacopeia Drug Discovery, Inc., Cranbury, NJ (US)

( * ) Notice: Subject to any disclaimer, the term of this patent is extended or adjusted under 35 U.S.C. 154(b) by 494 days.

(21) Appl. No.: 10/358,898

(22) Filed: Feb. 5, 2003

(65) Prior Publication Data
US 2004/0048848 A1    Mar. 11, 2004

Related U.S. Application Data

(60) Provisional application No. 60/355,618, filed on Feb. 6, 2002.

(51) Int. Cl.
| | |
|---|---|
| C07D 211/08 | (2006.01) |
| C07D 207/46 | (2006.01) |
| C07D 205/00 | (2006.01) |
| C07D 279/00 | (2006.01) |
| A01N 43/00 | (2006.01) |

(52) U.S. Cl. .......... 546/192; 546/18; 546/148; 546/186; 546/339; 546/1; 546/236; 548/542; 548/952; 548/950; 540/604; 514/210.01; 514/418; 514/345; 514/212.01

(58) Field of Classification Search ............ 546/192, 546/18, 148, 186, 208, 542, 952, 339, 235; 540/212.01, 604; 514/210.01, 418, 345, 514/212.01; 548/542, 952
See application file for complete search history.

(56) References Cited

U.S. PATENT DOCUMENTS 5,387,591 A * 2/1995 Lavielle et al. ............ 514/307
6,166,037 A * 12/2000 Budhu et al. ............... 514/326

FOREIGN PATENT DOCUMENTS

| WO | WO 99/45006 A | 9/1999 |
| WO | WO 00/58285 | * 10/2000 |
| WO | WO 02/02554 A | 1/2002 |

OTHER PUBLICATIONS

Ohno et al., "2-Ethynylaziridines as Chiral Carbon Nucleophiles . . . ", Journal of Organic Chemistry (2001), 66(5), 1867-1875.*
International Search Report; International Application No. PCT/US 03/03471; filing date Feb. 5, 2003; Priority Date Feb. 6, 2002.
S. Chackalamannil et al., "Total Synthesis of (+)-Himbacine and (+)-Himbeline," *J. Org. Chem.* 64: 1932-1940 (1999).
Zhang et al., "Biochemical Characterization of the γ-Secretase Activity That Produces β-Amyloid Peptides," *Biochemistry* 40(16): 5049-5055 (2001).
Zhang et al., "Calpain Ihhibitor I Increases β-Amyloid Peptide Production by Inhibiting the Degradation of the Substrate of γ-Secretase," *J. Biol. Chem.* 274(13): 8966-8972 (1999).

* cited by examiner

*Primary Examiner*—Richard Raymond
*Assistant Examiner*—Paul V. Ward
(74) *Attorney, Agent, or Firm*—Thomas A. Blinka

(57) ABSTRACT

This invention discloses novel gamma secretase inhibitors of the formula:

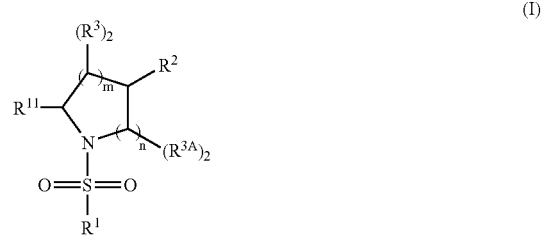

(I)

wherein:
$R^1$ is a substituted aryl or substituted heteroaryl group;
$R^2$ is an $R^1$ group, alkyl, —X(CO)Y, or alkylene-X(CO)Y wherein X and Y are as defined herein;
each $R^3$ and each $R^{3A}$ are independently H, or alkyl;
$R^{11}$ is aryl, heteroaryl, alkyl, cycloalkyl, arylalkyl, arylcycloalkyl, heteroarylalkyl, heteroarylcycloalkyl, arylheterocycloalkyl, or alkoxyalkyl. Also disclosed is a method of treating Alzheimer's Disease using one or more compounds of the invention.

19 Claims, No Drawings

GAMMA SECRETASE INHIBITORS

This application claims priority from provisional application Ser. No. 60/355,618 filed Feb. 6, 2002.

BACKGROUND

WO 00/50391, published Aug. 13, 2000, discloses compounds having a sulfonamide moiety that are useful for the treatment and prevention of Alzheimer's Disease and other diseases relating to the deposition of amyloid protein.

In view of the present interest in the treatment or prevention of neurodegenerative diseases, such as Alzheimer's Disease, a welcome contribution to the art would be compounds for use in such treatment or prevention. This invention provides such a contribution.

SUMMARY OF THE INVENTION

This invention provides compounds that are inhibitors (e.g., antagonists) of Gamma Secretase and have the formula:

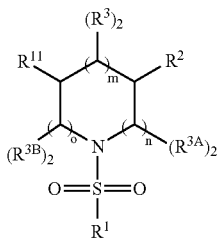

(I)

or a pharmaceutically acceptable salt or solvate thereof, wherein:

(A) $R^1$ is selected from the group consisting of:
(1) unsubstituted aryl;
(2) aryl substituted with one or more (e.g., 1–3) $R^5$ groups;
(3) unsubstituted heteroaryl; and
(4) heteroaryl substituted with one or more (e.g., 1–3) $R^5$ groups;

(B) $R^2$ is selected from the group consisting of:
(1) alkyl;
(2) —X(CO)Y;
(3) —$(C_1$–$C_6)$alkylene-X(CO)Y;
(4) —$(C_0$–$C_6)$alkylene-$(C_2$–$C_6)$cycloalkylene-$(C_0$–$C_6)$alkylene-X(CO)Y;
(5) aryl;
(6) aryl substituted with one or more (e.g., 1–3) $R^5$ groups;
(7) heteroaryl;
(8) heteroaryl substituted with one or more (e.g., 1–3) $R^5$ groups;

(C) Each $R^3$ is independently selected from the group consisting of:
(1) H, and
(2) alkyl, and (D) Each $R^{3A}$ and $R^{3B}$ are independently selected from the group consisting of:
(1) H; and
(2) alkyl;

(E) $R^5$ is independently selected from the group consisting of:
(1) halo;
(2) —$CF_3$;
(3) —OH;
(4) —Oalkyl;
(5) —$OCF_3$;
(6) —CN;
(7) —$NH_2$;
(8) —$CO_2$alkyl;
(9) —$CONR^6R^7$;
(10) -alkylene-$NR^6R^7$;
(11) —$NR^6$COalkyl;
(12) —$NR^6$COaryl;
(13) —$NR^6$COheteroaryl; and
(14) —$NR^6CONR^6R^7$;

(F) X is selected from the group consisting of:
(1) —O—;
(2) —NH—;
(3) —Nalkyl; and
(4) —Oalkylene;

(G) Y is selected from the group consisting of:
(1) —$NR^6R^7$;
(2) —$N(R^3)(CH_2)_bNR^6R^7$ wherein b is 2–6;
(3) unsubstituted aryl;
(4) unsubstituted heteroaryl;
(5) -alkyl;
(6) -cycloalkyl,
(7) unsubstituted arylalkyl;
(8) unsubstituted arylcycloalkyl;
(9) unsubstituted heteroarylalkyl;
(10) unsubstituted heteroarylcycloalkyl;
(11) unsubstituted arylheterocycloalkyl;
(12) substituted aryl;
(13) substituted heteroaryl;
(14) substituted arylalkyl;
(15) substituted arylcycloalkyl;
(16) substituted heteroarylalkyl;
(17) substituted heteroarylcycloalkyl; and
(18) substituted arylheterocycloalkyl;

wherein the aryl moiety in said substituted groups (12), (14), (15) and (18) of said Y group, and the heteroaryl moiety in said substituted groups (13), (16), and (17) of said Y group, are substituted with one or more (e.g., 1 to 3) substituents independently selected from the group consisting of:
(a) halo;
(b) —$CF_3$;
(c) —OH;
(d) —Oalkyl;
(e) —$OCF_3$;
(f) —CN;
(g) —$NH_2$;
(h) —$CO_2(C_1$–$C_6)$alkyl;
(i) —$C(O)NR^6R^7$;
(j) —$(C_1$–$C_6)$alkylene-$NR^6R^7$;
(k) —$NR^6$COalkyl;
(l) —$NR^6$COaryl;
(m) —$NR^6$COheteroaryl; and
(n) —$NR^6CONR^6R^7$;

or Y is selected from the group consisting of:

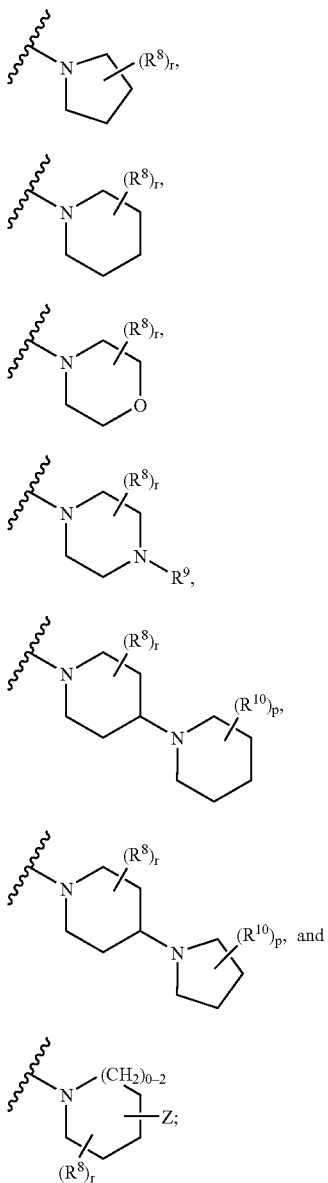

(H) $R^6$ and $R^7$ are independently selected from the group consisting of
(1) H;
(2) alkyl;
(3) cycloalkyl;
(4) arylalkyl;
(5) heteroarylalkyl;
(6)

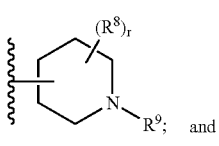

(7)

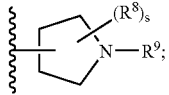

(I) Each $R^8$ is independently selected from the group consisting of:
(1) alkyl; and
(2) alkyl substituted with 1 to 4 hydroxy groups;
(J) Each $R^9$ is independently selected from the group consisting of:
(1) H;
(2) alkyl;
(3) alkyl substituted with 1 to 4 hydroxy groups;
(4) cycloalkyl;
(5) cycloalkyl substituted with 1 to 4 hydroxy groups;
(6) arylalkyl;
(7) heteroarylalkyl;
(8) —C(O)Oalkyl;
(9) alkylene-O-alkylene-OH (preferably, —($C_2$–$C_6$)alkylene-O—($C_1$–$C_6$)alkylene-OH, most preferably —$(CH_2)_2$—O—$(CH_2)_2$—OH);
(10) aryl substituted with one or more (e.g., 1–3) $R^5$ groups; and
(11) heteroaryl substituted with one or more (e.g., 1–3) $R^5$ groups;
(12) unsubstituted heteroaryl;
(13) unsubstituted aryl; and
(14) -alkylene-C(O)Oalkyl (e.g., —($C_1$–$C_6$)alkylene-C(O)O($C_1$–$C_6$)alkyl);
(K) Each $R^{10}$ is independently selected from the group consisting of:
(1) H; and
(2) alkyl;
(L) $R^{11}$ is selected from the group consisting of:
(1) unsubstituted aryl;
(2) substituted aryl;
(3) unsubstituted heteroaryl;
(4) alkyl;
(5) cycloalkyl;
(6) unsubstituted arylalkyl;
(7) unsubstituted arylcycloalkyl;
(8) unsubstituted heteroarylalkyl;
(9) unsubstituted heteroarylcycloalkyl;
(10) unsubstituted arylheterocycloalkyl;
(11) alkoxyalkyl;
(12) substituted heteroaryl;
(13) substituted arylalkyl;
(14) substituted arylcycloalkyl;
(15) substituted heteroarylalkyl;
(16) substituted arylheterocycloalkyl;

wherein the aryl moiety in said substituted groups (2), (13), (14) and (16) of said $R^{11}$ group, and the heteroaryl moiety in said substituted groups (12) and (15) of said $R^{11}$ group, are substituted with one or more (e.g., 1 to 3) substituents independently selected from the group consisting of:
(a) halo;
(b) —$CF_3$;
(c) —OH;
(d) —Oalkyl;
(e) —$OCF_3$;
(f) —CN;
(g) —$NH_2$;

(h) —CO$_2$(C$_1$–C$_6$)alkyl;
(i) —CONR$^6$R$^7$;
(j) —(C$_1$–C$_6$)alkylene-NR$^6$R$^7$;
(k) —NR$^6$COalkyl;
(l) —NR$^6$COaryl;
(m) —NR$^6$COheteroaryl; and
(n) —NR$^6$CONR$^6$R$^7$;
  (M) m is 0 to 3, and n is 0 to 3, o is 0–3, such that m+n+o is 1, 2, 3 or 4;
  (N) p is 0 to 4;
  (O) r is 0 to 4;
  (P) s is 0 to 3; and
  (Q) Z is selected from the group consisting of:
(1) unsubstituted heterocycloalkyl;
(2) substituted heterocycloalkyl;
(3) —NH$_2$;
(4) —NH(alkyl);
(5) —N(alkyl)$_2$ wherein each alkyl is the same or different;
(6) —NH(unsubstituted cycloalkyl);
(7) —NH(substituted cycloalkyl);
(8) —N(alkyl)(unsubstituted cycloalkyl);
(9) —N(alkyl)(substituted cycloalkyl);
(10) —NH(unsubstituted aralkyl);
(11) —NH(substituted aralkyl);
(12) —N(alkyl)(aralkyl);
(13) —NH(unsubstituted heterocycloalkyl);
(14) —NH(substituted heterocycloalkyl);
(15) —N(alkyl)(unsubstituted heterocycloalkyl),
(16) —N (alkyl)(substituted heterocycloalkyl);
(17) —NH(unsubstituted heteroaralkyl);
(18) —NH(substituted heteroaralkyl);
(19) —NH-alkylene-(unsubstituted cycloalkyl);
(20) —NH-alkylene-(substituted cycloalkyl);
(21) —N(alkyl)alkylene-(unsubstituted cycloalkyl);
(22) —N(alkyl)alkylene-(substituted cycloalkyl);
(23) —NHalkylene-(unsubstituted heterocycloalkyl);
(24) —NHalkylene-(substituted heterocycloalkyl);
(25) —N(alkyl)alkylene-(unsubstituted heterocycloalkyl);
(26) —N(alkyl)alkylene-(substituted heterocycloalkyl);
(27) unsubstituted benzofused heterocycloalkyl (e.g., structures o and ab); and
(28) substituted benzofused heterocycloalkyl;

wherein said substituted heterocycloalkyl moiety of substituents (2), (14), (16), (24), (26) and (27) of group Z, and said substituted cycloalkyl moiety of substituents (7), (9), (20) and (22) of group Z, and said substituted aryl moiety of substituent (11) of group Z, and said substituted heteroaryl moiety of substituent (18) of group Z, are substituted with 1 to 3 groups independently selected from the group consisting of:
(a) alkyl;
(b) —OH;
(c) —Oalkyl;
(d) —O(CO)alkyl;
(e) —O(CO)aryl;
(f) —NH$_2$;
(g) —NH(alkyl);
(h) —N(alkyl)$_2$ wherein each alkyl is the same or different;
(i) —NH(CO)alkyl;
(j) —N(alkyl)(CO)alkyl;
(k) —NH(CO)aryl;
(l) —N(alkyl)(CO)aryl;
(m) —COalkyl;
(n) —COaryl;
(o) —CONH$_2$;
(p) —CONH(alkyl);
(q) —CON(alkyl)$_2$ wherein each alkyl is the same or different;
(r) —COOalkyl;
(s) -alkylene-C(O)Oalkyl (e.g., —(C$_1$–C$_3$)alkylene-C(O)O(C$_1$–C$_6$)alkyl);
(t) piperidinyl;
(u) pyrrolidinyl;
(v) 1,1-ethylenedioxy;
(w) aryl;
(x) heteroaryl; and
(y) —O—CH$_2$CH$_2$—O— wherein both oxygen atoms are bound to the same carbon atom, and provided that the aryl and heteroaryl moieties of said Z group are not substituted with said —O—CH$_2$CH$_2$—O— group.

This invention also provides a pharmaceutical composition comprising an effective amount of one or more compounds of formula I (generally one compound) and at least one pharmaceutically acceptable carrier.

This invention also provides a method for inhibiting gamma-secretase comprising administering an effective (i.e., therapeutically effective) amount of one or more compounds (generally one compound) of formula I to a patient in need of treatment.

This invention also provides a method of treating one or more neurodegenerative diseases comprising administering an effective (i.e., therapeutically effective) amount of one or more compounds (generally one compound) of formula I to a patient in need of treatment.

This invention also provides a method of inhibiting the deposition of amyloid protein (e.g., amyloid beta protein) in, on or around neurological tissue (e.g., the brain) comprising administering an effective (i.e., therapeutically effective) amount of one or more compounds (generally one compound) of formula I to a patient in need of treatment.

This invention also provides a method of treating Alzheimer's disease comprising administering an effective (i.e., therapeutically effective) amount of one or more compounds (generally one compound) of formula I to a patient in need of treatment.

DETAILED DESCRIPTION OF THE INVENTION

As used herein the following terms have the following meanings unless otherwise defined:

AcOEt represents: ethyl acetate;

AcOH represents: acetic acid;

alkoxy: represents a —Oalkyl group wherein alkyl is as defined below;

alkoxyalkyl: represents an alkoxy group as defined above bound to an alkyl group as defined below, wherein said alkoxyalkyl group is bound by the alkyl moiety to a part of a molecule (e.g., the alkyl moiety is bound to a part of a compound of this invention);

alkyl: represents straight and branched carbon chains and contains from one to twenty carbon atoms, preferably one to six carbon atoms, said alkyl group being optionally substituted with one or more (e.g., 1, 2 or 3) substituents independently selected from the group consisting of: (1) halo; (2) —OH; (3) —O(alkyl), preferably —O((C$_1$–C$_6$)alkyl), and most preferably —OCH$_3$; (4) —NH$_2$; (5) —NH(alkyl), preferably —NH((C$_1$–C$_6$)alkyl), and most preferably —NHCH$_3$; (6) —N(alkyl)$_2$ wherein each alkyl group is independently selected, preferably —N((C$_1$–C$_6$)alkyl)$_2$ wherein each alkyl group is independently selected, and most preferably —N(CH$_3$)$_2$; and (7) —S(alkyl), preferably —S((C$_1$–C$_6$)alkyl), and most preferably —SCH$_3$;

alkylene: represents a —(CH$_2$)$_q$— group wherein q is 1 to 20, generally 1 to 6 and more usually 1 to 4, optionally one or more (e.g., 1 to 3, or 1 to 2) hydrogens in said alkylene group can be replaced with the same or different alkyl group (preferably —(C$_1$–C$_6$)alkyl, most preferably —(C$_1$ to C$_3$)alkyl, more preferably —(C$_1$–C$_2$)alkyl) such that the total number of carbons in the entire alkylene group is 2 to 20, also said alkylene group can be optionally substituted with one or more (e.g., 1 to 3) substituents independently selected from the group consisting of: (1) halo; (2) —OH; (3) —O(alkyl), preferably —O((C$_1$–C$_6$)alkyl), and most preferably —OCH$_3$; (4) —NH$_2$; (5) —NH(alkyl), preferably —NH((C$_1$–C$_6$)alkyl), and most preferably —NHCH$_3$; (6) —N(alkyl)$_2$ wherein each alkyl group is independently selected, preferably —N((C$_1$–C$_6$)alkyl)$_2$ wherein each alkyl group is independently selected, and most preferably —N(CH$_3$)$_2$; and (7) —S(alkyl), preferably —S((C$_1$–C$_6$)alkyl), and most preferably —SCH$_3$;

ar: represents aryl as defined below;

aralkyl (arylalkyl): represents an aryl group, as defined below, bound to an alkyl group, as defined above, wherein said aralkyl group is bound by the alkyl moiety to a part of a molecule (e.g., the alkyl moiety is bound to a part of a compound of this invention);

aryl: represents a carbocyclic group comprising from 6 to 15 carbon atoms and having at least one aromatic ring (e.g., phenyl, naphthyl, phenanthryl, tetrahydronaphthyl or indanyl, and preferably phenyl, naphthyl, tetrahydronaphthyl and indanyl), with all available substitutable carbon atoms of the carbocyclic group being intended as possible points of attachment of the aryl group; said carbocyclic group being optionally substituted with one or more (e.g., 1 to 3) substituents independently selected from the group consisting of: (1) halo; (2) alkyl (preferably —(C$_1$ to C$_6$)alkyl); (3) —OCF$_3$; (4) hydroxy; (5) alkoxy (preferably —(C$_1$ to C$_6$)alkoxy); (6) —CN; (7) —CF$_3$; (8) amino (—NH$_2$); (9) alkylamino; (10) dialkylamino (wherein each alkyl group is independently selected), (11) aryl (preferably phenyl) (provided that if this aryl group is optionally substituted with one or more aryl groups these latter aryl groups are not further substituted with aryl groups); (12) aralkoxy (provided that if the aryl moiety of said aralkoxy (i.e., arylalkoxy) group is optionally substituted with one or more aryl groups these latter aryl groups are not further substituted with aryl groups); (13) aryloxy (preferably phenoxy) (provided that if the aryl moiety of said aryloxy group is optionally substituted with one or more aryl groups these latter aryl groups are not further substituted with aryl groups); (14) —S(O)$_a$-aryl, wherein a is 0–2, (provided that if the aryl moiety of said —S(O)$_a$-aryl group is optionally substituted with one or more aryl groups these latter aryl groups are not further substituted with aryl groups); (15) —COOR$^{15}$, wherein said R$^{15}$ represents H, alkyl, aryl (provided that if said aryl moiety is optionally substituted with one or more aryl containing groups these latter aryl containing groups are not further substituted with aryl containing groups), or aralkyl (e.g., benzyl) (provided that if said aryl moiety of said aralkyl group is optionally substituted with one or more aryl containing groups these latter aryl containing groups are not further substituted with aryl containing groups); and (16) —NO$_2$; preferably, said optional substituents are independently selected from the group consisting of: (1) halo; (2) —CF$_3$; (3) alkyl, preferably —(C$_1$ to C$_6$)alkyl; (4) alkoxy, preferably —(C$_1$ to C$_6$)alkoxy (5) —OCF$_3$, (6) —NH$_2$, and (7) —CN;

(CO) or C(O): represents the group

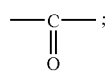

cycloalkyl: represents a cyclic alkyl group of 3 to 10 carbon atoms, and preferably 3 to 8 carbon atoms, said cycloalkyl group being optionally substituted with one or more (e.g., 1, 2 or 3) substituents independently selected from the group consisting of: (1) halo; (2) —OH; (3) —O(alkyl), preferably —O((C$_1$–C$_6$)alkyl), and most preferably —OCH$_3$; (4) —NH$_2$; (5) —NH(alkyl), preferably —NH((C$_1$–C$_6$)alkyl), and most preferably —NHCH$_3$; (6) —N(alkyl)$_2$ wherein each alkyl group is independently selected, preferably —N((C$_1$–C$_6$)alkyl)$_2$ wherein each alkyl group is independently selected, and most preferably —N(CH$_3$)$_2$; and (7) —S(alkyl), preferably —S((C$_1$–C$_6$)alkyl), and most preferably —SCH$_3$;

DCM represents: dichloromethane;

DEAD represents: diethylazodicarboxylate;

DMF: represents dimethylformamide;

EDCI represents: 1-(3-dimethylaminopropyl)-3-ethylcarbodiimide;

Et$_2$O represents: diethyl ether;

EtOAc represents: ethyl acetate;

halo represents: fluoro, chloro, bromo and iodo;

heteroaryl: represents a monocyclic, bicyclic or tricyclic group comprising at least one heteroatom (e.g., 1, 2 or 3) independently selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., triazolyl, imidazolyl, thienyl, furanyl, quinolyl, isoquinolyl, benzofuranyl, benzimidazolyl, benzopyranyl, benzothienyl, thiazolyl, indolyl, naphthyridinyl, pyridyl (e.g., 2-, 3- or 4-pyridyl) or pyridyl N-oxide (e.g., 2-, 3- or 4-pyridyl N-oxide), wherein pyridyl N-oxide can be represented as:

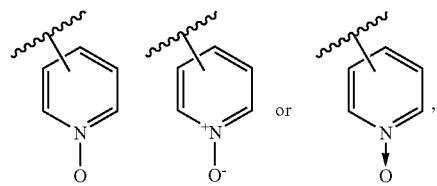

and with all available substitutable carbon and heteroatoms of the cyclic group being intended as possible points of attachment of the heteroaryl group, said cyclic group being optionally substituted with one or more (e.g., 1, 2 or 3) groups independently selected from the group consisting of: (1) halo; (2) alkyl (preferably —(C$_1$ to C$_6$)alkyl); (3) aryl; (4) aralkyl; (5) hydroxy (6) alkoxy (preferably —(C$_1$ to C$_6$)alkoxy); (7) phenoxy, (8) —NO$_2$; (9) —CF$_3$; (10) —OCF$_3$; (11) —CN; (12) amino (—NH$_2$); (13) alkylamino, (14) dialkylamino wherein each alkyl group is independently selected;(15) —COOR$^{15}$ (wherein R$^{15}$ is as defined above); and heteroaryl (provided that if this heteroaryl group, as defined above, is optionally substituted with one or more heteroaryl groups these latter heteroaryl groups are not further substituted with heteroaryl groups); preferably said optional substituents are selected from the group consisting of: (1) halo; (2) —CF$_3$; (3) alkyl, most preferably —(C$_1$ to C$_6$)alkyl; (4) alkoxy, most preferably —(C$_1$ to C$_6$)alkoxy; (5) —OCF$_3$; (6) —NH$_2$; and (7) —CN;

heteroaralkyl (heteroarylalkyl): represents a heteroaryl group, as defined above, bound to an alkyl group, as defined above, wherein said heteroaralkyl group is bound by the alkyl moiety to a part of a molecule (e.g., the alkyl moiety is bound to a part of a compound of this invention);

heterocycloalkyl: represents a cycloalkyl ring as defined above, having one or more (e.g., 1, 2 or 3) heteroatoms independently selected from: O, S, or —NR$^{16}$— wherein R16 is selected from: H, alkyl, aryl, heteroaryl, aralkyl (e.g., ar(C$_1$ to C$_6$)alkyl), or heteroaralkyl (e.g., heteroar(C$_1$ to C$_6$)alkyl), preferred heterocycloalkyl rings are piperidinyl, piperazinyl, morpholinyl, and pyrrolidinyl;

MeOH represents: methanol;
OTBDMS represents: t-butyldimethylsilyloxy (or t-butyldimethylsilyl ether);
OTBDPS represents: t-butyldiphenylsilyloxy (or t-butyldiphenylsilyl ether);
Ph represents: phenyl;
HOBT represents: 1-hydroxybenzotriazole;
TBAF represents: tetrabutylammonium fluoride;
TBDMSCl represents: t-butyldimethylsilyl chloride
TBDPSCl: represents t-butyldiphenylsilylchloride;
TFA: represents trifluroacetic acid;
THF: represents tetrahydrofuran; and
TMS represents: trimethylsilane.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. For example, "one or more" or "at least one" can mean 1 to 6 moieties, and generally 1 to 4 moieties, and usually 1 to 3 moieties.

The term "effective amount" or "therapeutically effective amount" as used in the methods, pharmaceutical compositions, claims and elsewhere of this invention means a therapeutically effective amount to achieve the desired therapeutic effect in a suitable patient.

Those skilled in the art will appreciate that the term "neurodegenerative disease" has its commonly accepted medical meaning and describes diseases and conditions resulting from abnormal function of neurons, including neuronal death and abnormal release of neurotransmitters or neurotoxic substances. In this instance it also includes all diseases resulting from abnormal levels of beta amyloid protein. Examples of such diseases include, but are not limited to, Alzheimer's disease, age-related dementia, cerebral or systemic amyloidosis, hereditary cerebral hemorrhage with amyloidosis, and Down's syndrome.

Lines drawn into the ring systems indicate that the indicated bond may be attached to any of the substitutable ring carbon atoms.

As well known in the art, a bond drawn from a particular atom wherein no moiety is depicted at the terminal end of the bond indicates a methyl group bound through that bond to the atom. For example:

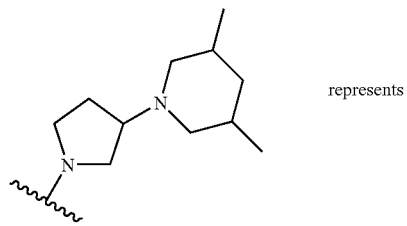 represents

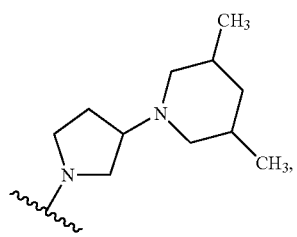

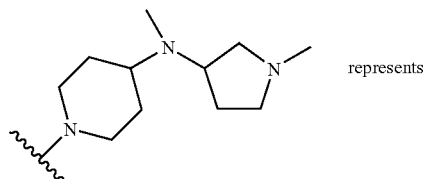 represents

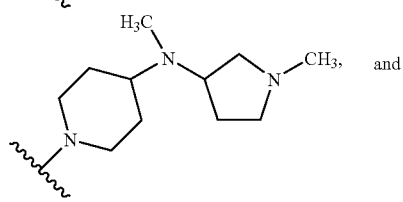 and

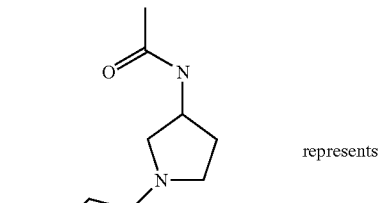 represents

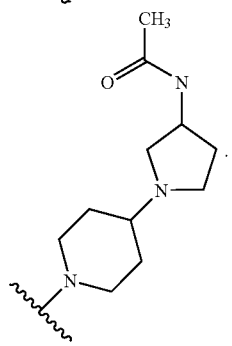

Certain compounds of the invention may exist in different isomeric (e.g., enantiomers and diastereoisomers) forms. The invention contemplates all such isomers both in pure form and in admixture, including racemic mixtures. Enol forms are also included.

The compounds of the invention can be administered as racemic mixtures or enantiomerically pure compounds.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Referring to formula I, examples of Z in the moiety

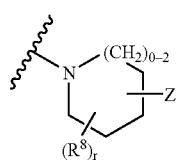

(i)

include, but are not limited to:

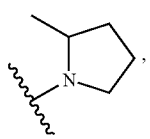

(j)

-continued

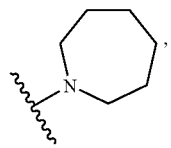

(k)

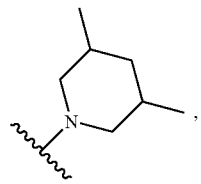

(l)

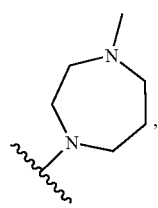

(m)

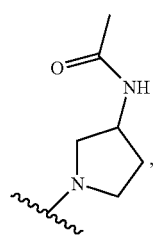

(n)

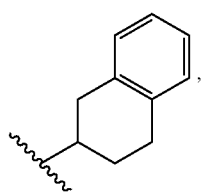

(o)

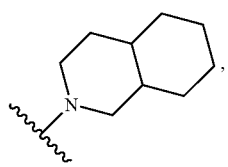

(p)

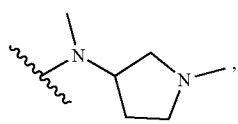

(q)

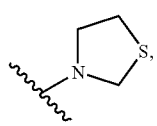

(r)

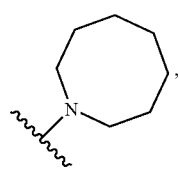

(s)

-continued
(t) 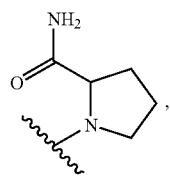
(u) 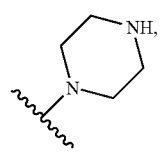
(v) 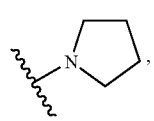
(w) 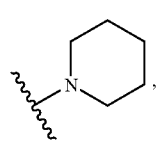
(x) 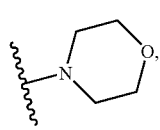
(y) 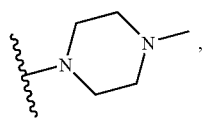
(z) 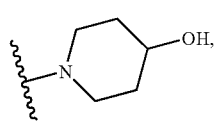
(aa) 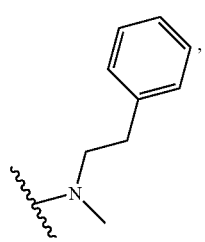
(ab) 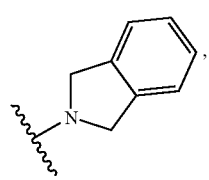
(ac) 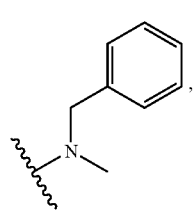
-continued
(ad) 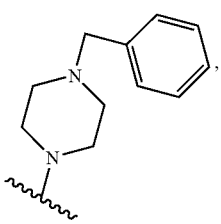
(ae) 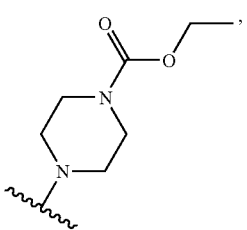
(af) 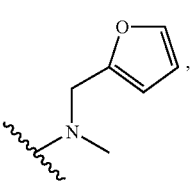
(ag) 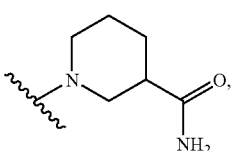
(ah) 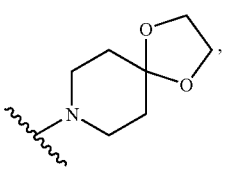
(ai) 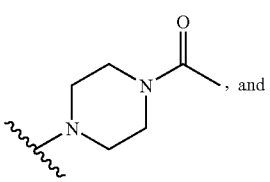
and
(aj) 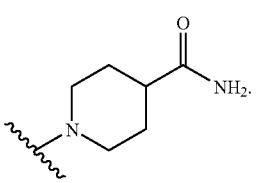
Referring to formula I, examples of the Y group in —X—C(O)—Y— or —X—CO—Y— include, but are not limited to:

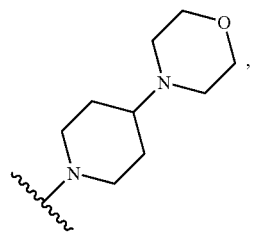 (ak)
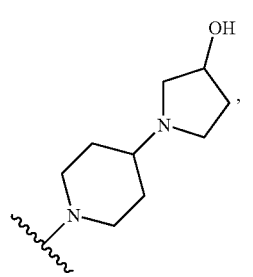 (al)
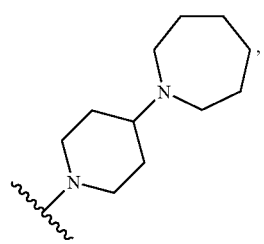 (am)
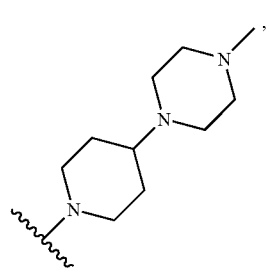 (an)
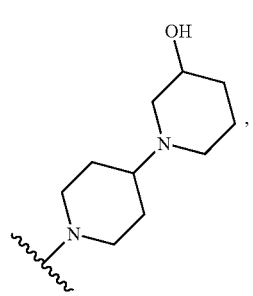 (ao)
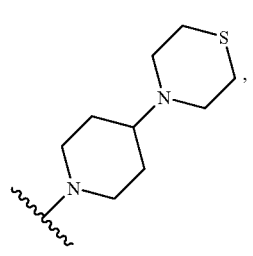 (ap)
-continued
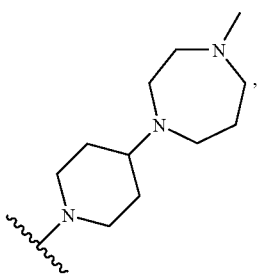 (aq)
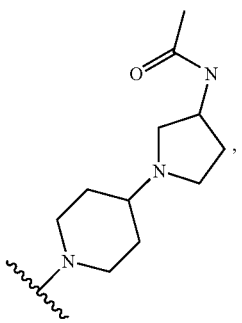 (ar)
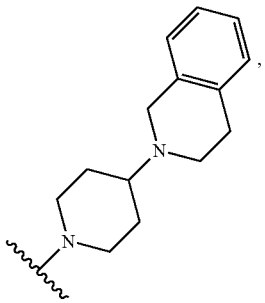 (as)
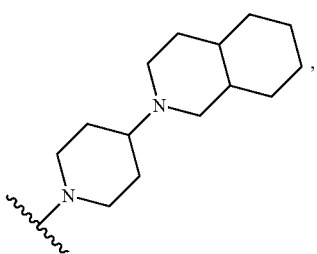 (at)
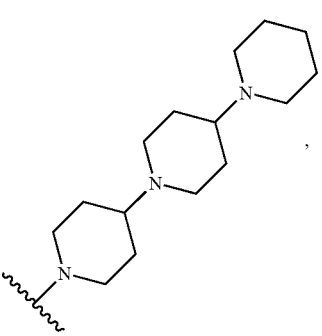 (au)

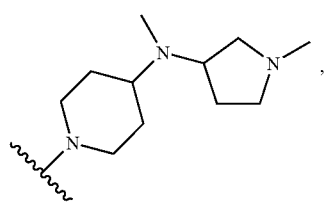 (av)
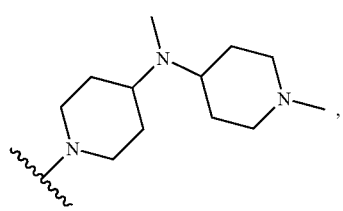 (aw)
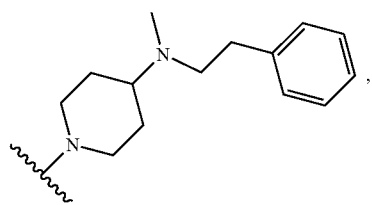 (ax)
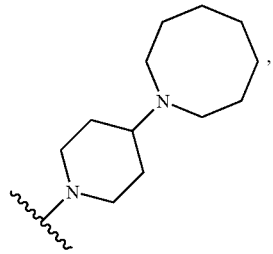 (ay)
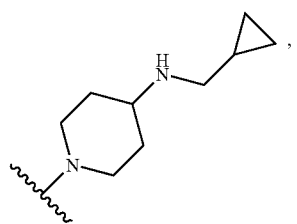 (bc)
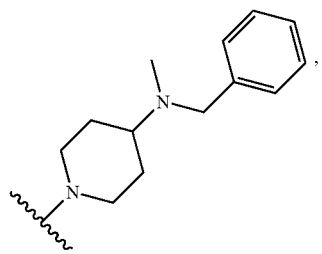 (bd)
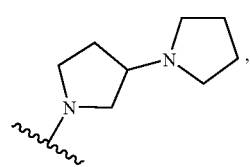 (be)
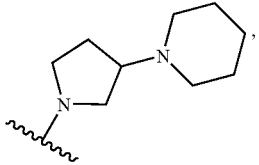 (bf)
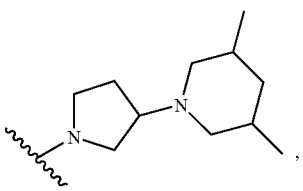 (bg)
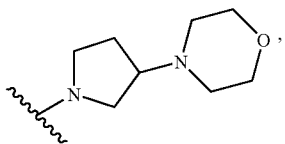 (bh)
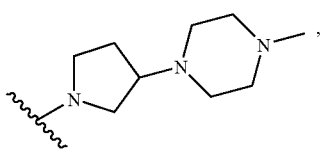 (bi)
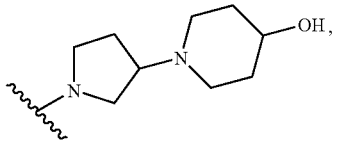 (bj)
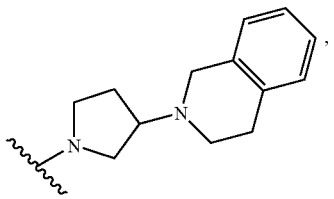 (bk)
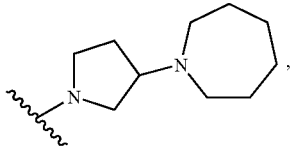 (bl)
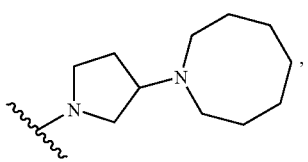 (bm)

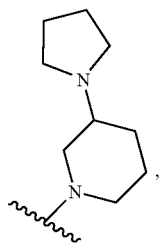
(bn)
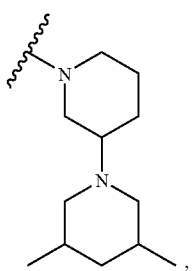
(bo)
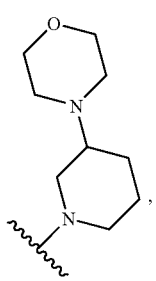
(bp)
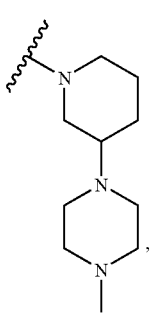
(bq)
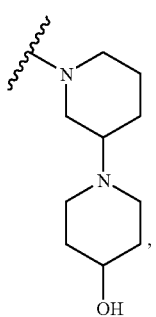
(br)
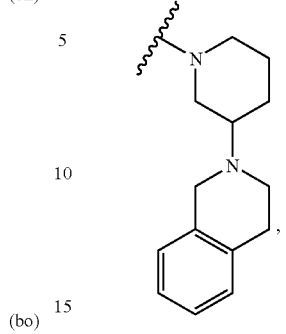
(bs)
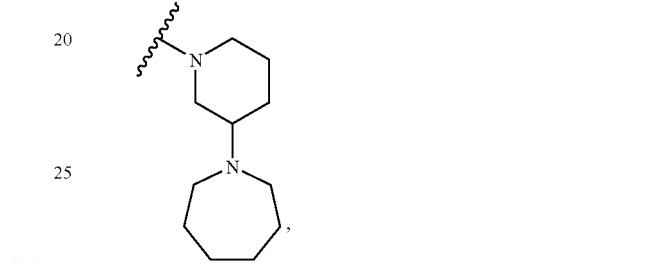
(bt)
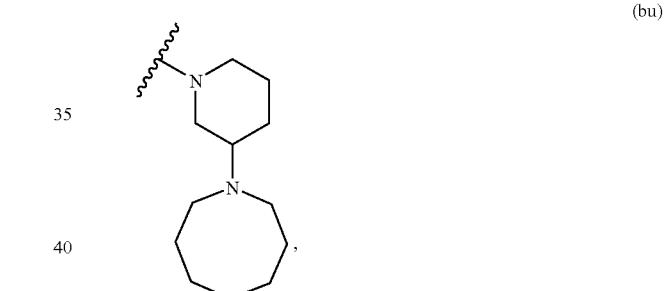
(bu)
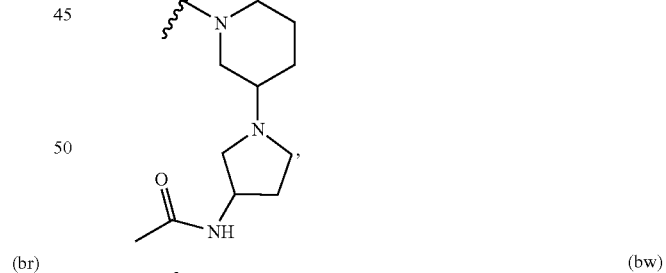
(bv)
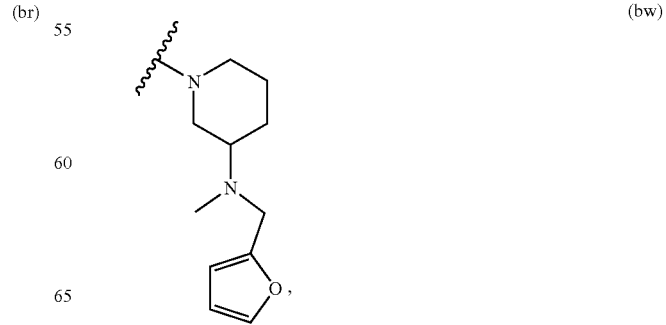
(bw)

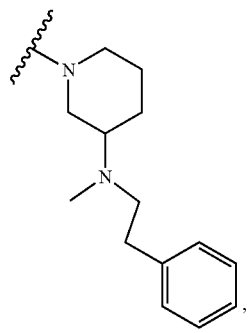
(bx)
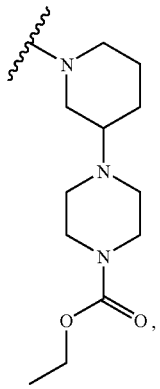
(cb)
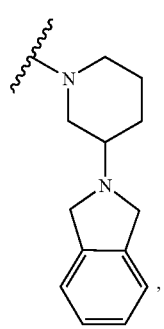
(by)
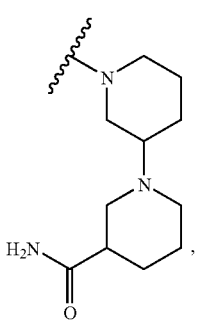
(cc)
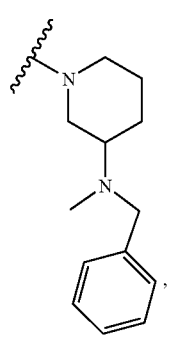
(bz)
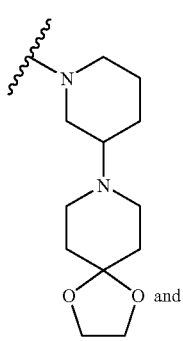
and
(cd)
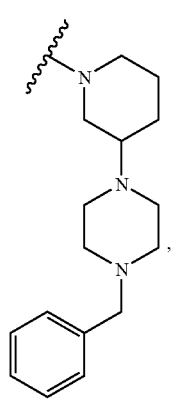
(ca)
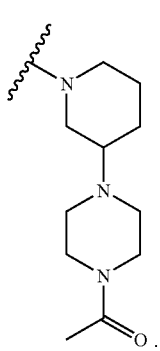
.
(ce)

Preferably R¹ is aryl substituted with one or more (e.g., 1–3) R⁵ groups, most preferably phenyl substituted with one or more (e.g., 1–3) R⁵ groups, and more preferably phenyl substituted with one or more (e.g., 1–3) halo atoms, and still more preferably phenyl substituted with one halo atom, and even still more preferably phenyl substituted with chloro (e.g., p-chlorophenyl).

Preferably n is 0 or 1, o is 0 or 1, and m is 1, 2 or 3, such that m+n+o is 3, and most preferably n and o are independently 0 and m is 3.

Preferably, p is 0 or 1, and most preferably 0.

Preferably, r is 0 or 1, and most preferably 1.

Preferably, s is 0.

Preferably, R² is —XC(O)Y, —(C₁–C₆)alkylene-XC(O)Y, —CH(C₁–C₂alkyl)-X—C(O)—Y (e.g., —CH(CH₃)—X—C(O)—Y), or —C(C₁–C₂alkyl)₂-X—C(O)—Y wherein each alkyl is the same or different, —(C₂–C₆)cycloalkylene-XC(O)Y, most preferably —(C₁–C₆)alkylene-X(CO)Y or —(C₂–C₆)cycloalkylene-XC(O)Y, more preferably —(C₁–C₆)alkylene-X(CO)Y or —(C₂–C₆)cycloalkylene-XC(O)Y wherein X is —O— or —NH—, still more preferably —(C₁–C₆)alkylene-X(CO)Y or —(C₂–C₆)cycloalkylene-XC(O)Y wherein X is —O—, yet more preferably —CH₂—X—C(O)—Y or

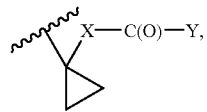

still yet more preferably —CH₂—X—C(O)—Y or

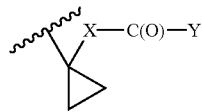

wherein X is —O— or —NH—, and even still more preferably —CH₂—X—C(O)—Y

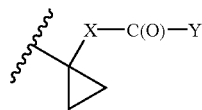

or wherein X is —O—.

Preferably, R³ is H.

Preferably, R⁸ is H or —(C₁–C₆)alkyl, and most preferably H or methyl

Preferably, R⁹ is H, —(C₁–C₆)alkyl (e.g., methyl), —(C₁–C₆)alkyl substituted with 1 to 4 —OH groups (e.g., —(CH₂)₂OH), —(C₁–C₆)alkyl-O—(C₁–C₆)alkyl-OH (e.g., 2-(2-hydroxyethoxy)ethyl), (C₃–C₈)cycloalkyl, or heteroaryl, and most preferably H, methyl, cyclohexyl, 2-pyridyl, 2-hydroxyethyl or 2-(2-hydroxyethoxy)ethyl;

Preferably, R¹⁰ is H or —(C₁–C₆)alkyl, most preferably H or methyl, more preferably H.

Preferably, R¹¹ is selected from the group consisting of: —(C₁–C₆)alkyl (most preferably methyl or ethyl), (C₃–C₈)-cycloalkyl (most preferably cyclopropyl), aryl (most preferably phenyl), aryl(C₁–C₆)alkyl (most preferably benzyl or —(CH₂)₂phenyl) and —(C₁–C₆)alkoxyalkyl (most preferably —CH₂OCH₃).

Preferably, X is —NH— or —O—, and most preferably —O—.

Preferably Y is —NR⁶R⁷, or Y is selected from the group consisting of:

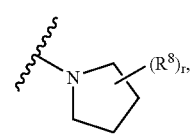

(c)

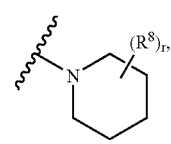

(d)

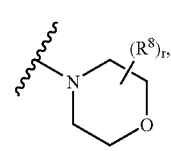

(e)

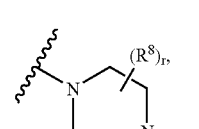

(f)

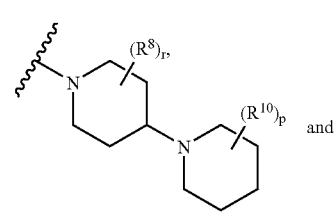

(g)

and

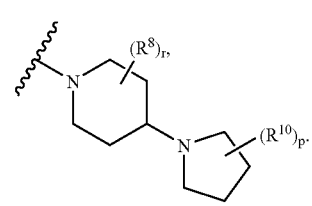

(h)

Most preferably, Y is selected from the group consisting of:
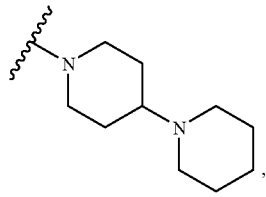 (bd)
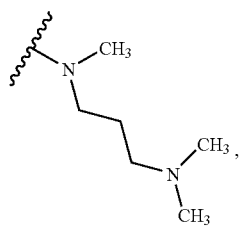 (be)
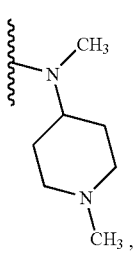 (bf)
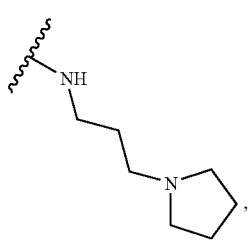 (bg)
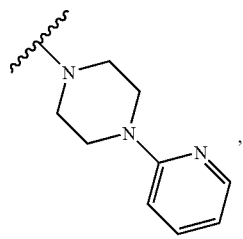 (bh)
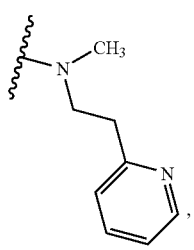 (bi)
-continued
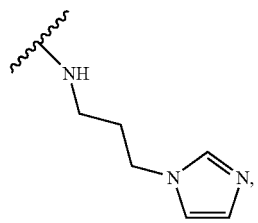 (bj)
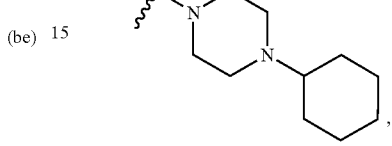 (bk)
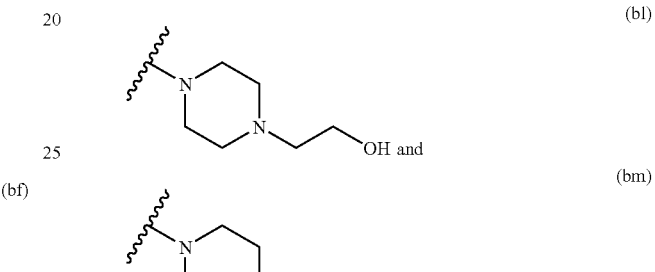 (bl)
OH and
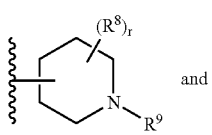 (bm)
Preferably, $R^6$ and $R^7$ are independently selected from the group consisting of: H, methyl, ethyl, $—(C_3–C_8)$cycloalkyl, -aryl$(C_1–C_6)$alkyl, 4-pyridylmethyl,
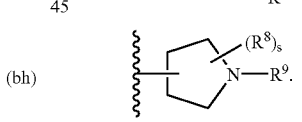 (a)
and
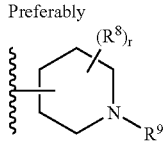 (b)
Preferably
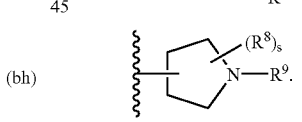 (a)
is a group of the formula:
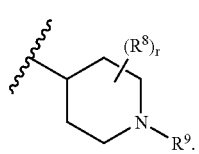 (a1)

-continued

Preferably

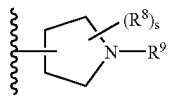

is a group of the formula:

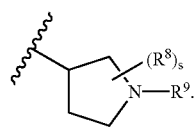

Thus, in one embodiment of the invention:

$R^1$ is aryl substituted with one or more $R^5$ groups, preferably phenyl substituted with one or more $R^5$ groups, and most preferably phenyl substituted with one or more halo atoms, and more preferably phenyl substituted with one halo atom, and still more preferably phenyl substituted with chloro (e.g., p-chlorophenyl);

n and o are 0 or 1, and m is 1, 2 or 3, such that m+n+o is 3, and preferably n and o are 0 and m is 3;

p is 0 or 1, and preferably 0;

r is 0 or 1, and preferably 1;

s is 0;

$R^2$ is —XC(O)Y, —$(C_1-C_6)$alkylene-XC(O)Y, —$(C_2-C_6)$ cycloalkylene-XC(O)Y —CH($C_1-C_2$alkyl)-X—C(O)—Y (e.g., —CH(CH$_3$)—X—C(O)—Y), or —C($C_1-C_2$alkyl)$_2$-X—C(O)—Y wherein each alkyl is the same or different, preferably —$(C_1-C_6)$alkylene-X(CO)Y, or —$(C_2-C_6)$cycloalkylene-X(CO), most preferably —$(C_1-C_6)$alkylene-X(CO)Y or —$(C_1-C_6)$cycloalkylene-X(CO)Y, wherein X is —O— or —NH—, more preferably —$(C_1-C_6)$alkylene-X(CO)Y or —$(C_1-C_6)$cycloalkylene-X(CO)Y, wherein X is —O—, still more preferably —CH$_2$—X—C(O)—Y or

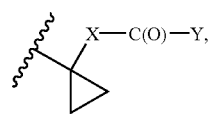

yet still more preferably —CH$_2$—X—C(O)—Y or

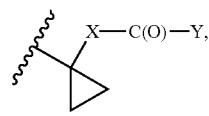

wherein X is —O— or —NH—, and even still more preferably —CH$_2$—X—C(O)—Y or

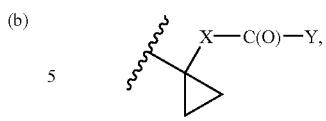

wherein X is —O—;

$R^3$ is H;

$R^8$ is H or —$(C_1-C_6)$alkyl, and preferably H or methyl;

$R^9$ is H, —$(C_1-C_6)$alkyl (e.g., methyl), —$(C_1-C_6)$alkyl substituted with 1 to 4 —OH groups (e.g., —(CH$_2$)$_2$OH), —$(C_1-C_6)$alkyl-O—$(C_1-C_6)$alkyl-OH (e.g., 2-(2-hydroxyethoxy)ethyl), $(C_3-C_8)$cycloalkyl, or heteroaryl, and preferably H, methyl, cyclohexyl, 2-pyridyl, 2-hydroxyethyl or 2-(2-hydroxyethoxy)ethyl;

$R^{10}$ is H or —$(C_1-C_6)$alkyl, preferably H or methyl, and most preferably H; and $R^{11}$ is selected from the group consisting of: —$(C_1-C_6)$ alkyl (most preferably methyl or ethyl), $(C_3-C_8)$-cycloalkyl (most preferably cyclopropyl), aryl (most preferably phenyl), aryl$(C_1-C_6)$alkyl (most preferably benzyl or —(CH$_2$)$_2$phenyl) and —$(C_1-C_6)$alkoxyalkyl (most preferably —CH$_2$OCH$_3$); and the remaining substituents are as defined for formula I.

In another embodiment of the invention:

$R^1$ is aryl substituted with one or more $R^5$ groups, preferably phenyl substituted with one or more $R^5$ groups, and most preferably phenyl substituted with one or more halo atoms, and more preferably phenyl substituted with one halo atom, and still more preferably phenyl substituted with chloro (e.g., p-chlorophenyl);

n and o are 0 or 1, and m is 1, 2 or 3, such that m+n+o are 3, and preferably n and o are 0 and m is 3;

p is 0 or 1, and preferably 0;

r is 0 or 1, and preferably 1;

s is 0;

$R^2$ is —XC(O)Y, —$(C_1-C_6)$alkylene-XC(O)Y, —$(C_1-C_6)$ cycloalkylene-X(CO)Y, —CH($C_1-C_2$alkyl)-X—C(O)—Y (e.g., —CH(CH$_3$)—X—C(O)—Y), or —C($C_1-C_2$alkyl)$_2$-X—C(O)—Y wherein each alkyl is the same or different, preferably —$(C_1-C_6)$alkylene-X(CO)Y or —$(C_2-C_6)$cycloalkylene-X(CO), and most preferably —CH$_2$—X—C(O)—Y or

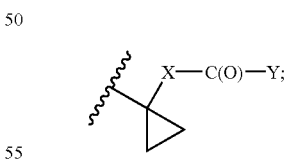

$R^3$ is H;

$R^8$ is H or —$(C_1-C_6)$alkyl, and preferably H or methyl;

$R^9$ is H, —$(C_1-C_6)$alkyl (e.g., methyl), —$(C_1-C_6)$alkyl substituted with 1 to 4 —OH groups (e.g., —(CH$_2$)$_2$OH), —$(C_1-C_6)$alkyl-O—$(C_1-C_6)$alkyl-OH (e.g., 2-(2-hydroxyethoxy)ethyl), $(C_3-C_8)$cycloalkyl, or heteroaryl, and preferably H, methyl, cyclohexyl, 2-pyridyl, 2-hydroxyethyl or 2-(2-hydroxyethoxy)ethyl;

$R^{10}$ is H or —$(C_1-C_6)$alkyl, preferably H or methyl, and most preferably H;

X is —O—;
Y is —NR⁶R⁷; or
Y is selected from the group consisting of:

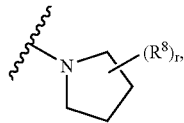
(c)

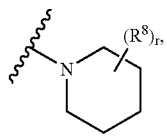
(d)

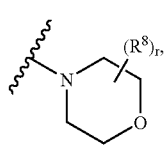
(e)

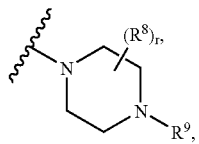
(f)

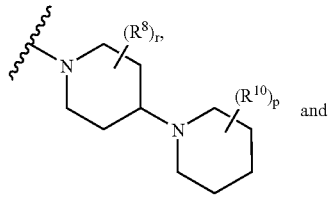
(g)

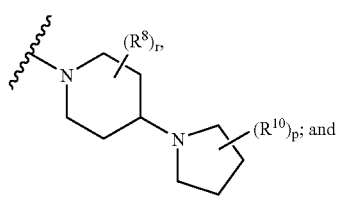
(h)

R¹¹ is selected from the group consisting of: —(C₁–C₆) alkyl (most preferably methyl or ethyl), (C₃–C₈)-cycloalkyl (most preferably cyclopropyl) aryl (most preferably phenyl), aryl(C₁–C₆)alkyl (most preferably benzyl or —(CH₂)₂phenyl) and —(C₁–C₆)alkoxyalkyl (most preferably —CH₂OCH₃); and
the remaining substituents are as defined for formula 1.
In another embodiment of this invention:
R¹ is aryl substituted with one or more R⁵ groups, preferably phenyl substituted with one or more R⁵ groups, and most preferably phenyl substituted with one or more halo atoms, and more preferably phenyl substituted with one halo atom, and still more preferably phenyl substituted with chloro (e.g., p-chlorophenyl);
n is 0 or 1, o is 0 or 1, and m is 1, 2 or 3, such that m+n+o is 3, and preferably n is 0, o is 0, and m is 3;
p is 0 or 1, and preferably 0;
r is 0 or 1, and preferably 1;
s is 0;
R² is —XC(O)Y, —(C₁–C₆)alkylene-XC(O)Y, —CH(C₁–C₂alkyl)-X—C(O)—Y (e.g., —CH(CH₃)—X—C(O)—Y), or —C(C₁–C₂alkyl)₂-X—C(O)—Y wherein each alkyl is the same or different, preferably —(C₁–C₆)alkylene-X(CO)Y, and most preferably —CH₂—X—C(O)—Y or —(C₂–C₆)cycloalkylene-X—C(O)—Y—;
R³ is H;
R⁸ is H or —(C₁–C₆)alkyl, and preferably H or methyl;
R⁹ is H, —(C₁–C₆)alkyl (e.g., methyl), —(C₁–C₆)alkyl substituted with 1 to 4 —OH groups (e.g., —(CH₂)₂OH), —(C₁–C₆)alkyl-O—(C₁–C₆)alkyl-OH (e.g., 2-(2-hydroxyethoxy)ethyl), (C₃–C₈)cycloalkyl, or heteroaryl, and most preferably H, methyl, cyclohexyl, 2-pyridyl, 2-hydroxyethyl or 2-(2-hydroxyethoxy)ethyl;
R¹⁰ is H or —(C₁–C₆)alkyl, preferably H or methyl, and more preferably H;
X is —O—;
Y is —NR⁶R⁷; or
Y is selected from the group consisting of:

(c)

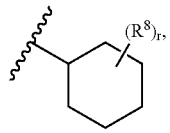
(d)

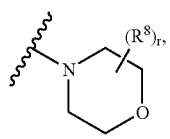
(e)

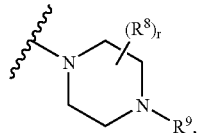
(f)

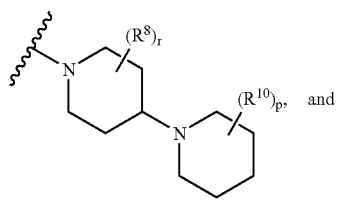
(g)

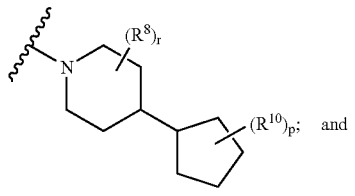
(h)

$R^6$ and $R^7$ are independently selected from the group consisting of: H, methyl, ethyl, —$(C_3$–$C_8)$cycloalkyl, -aryl$(C_1$–$C_6)$alkyl, 4-pyridylmethyl,

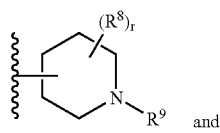

(a)

and

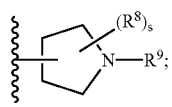

(b)

$R^{11}$ is selected from the group consisting of: —$(C_1$–$C_6)$ alkyl (preferably methyl or ethyl), $(C_3$–$C_8)$-cycloalkyl (preferably cyclopropyl), aryl (preferably phenyl), aryl $(C_1$–$C_6)$alkyl (preferably benzyl or —$(CH_2)_2$phenyl), and —$(C_1$–$C_6)$alkoxyalkyl (preferably —$CH_2OCH_3$); and the remaining substituents are as defined for formula I.

Representative compounds of the invention include but are not limited to the compounds of Examples 1–29, 31–33, 35–48, 50–61, 63–67, 67A-67BS, 68, 69, 71–74, 74A, 74B, 74C, 75, 76, 78–83, 85–99, 101–159, 159A, 159B, 159C, 160, 160A–160AA, 161, 161A–161G, 162, 162A, 162B, 162C, 164, 164A, 164B, 164C, 165–167, 167A, 167B, 167C, 168, 168A, 169, 169A–169D, 170, 170A–170AD, 171–173, 173A–173T, and 174.

Preferred compounds of the invention are the compounds of Examples 7, 61, 67B, 67E, 67N, 67P, 67U, 67AG, 67AT, 67AW, 67AY, 67BA, 67BD, 67BE, 67 67BH, 67BL, 73, 160B, 160K, 161, 161A, 161E, 161F, 173, 173A, 173B, 173C, 173 173G, 1731, 173J, 173K, 173L, 173N. Most preferred compounds are the compounds of Examples 7, 61, 67-B, 67-AT, 67-BG, 73, 161-A, 173, 173-A, 173-C, 173-E, 173-J, 173-N.

Compounds of formula I can be prepared by various methods well known to those skilled in the art, and by the methods described below.

Method 1

In Method 1, compounds of formula I having the structure Ia are prepared.

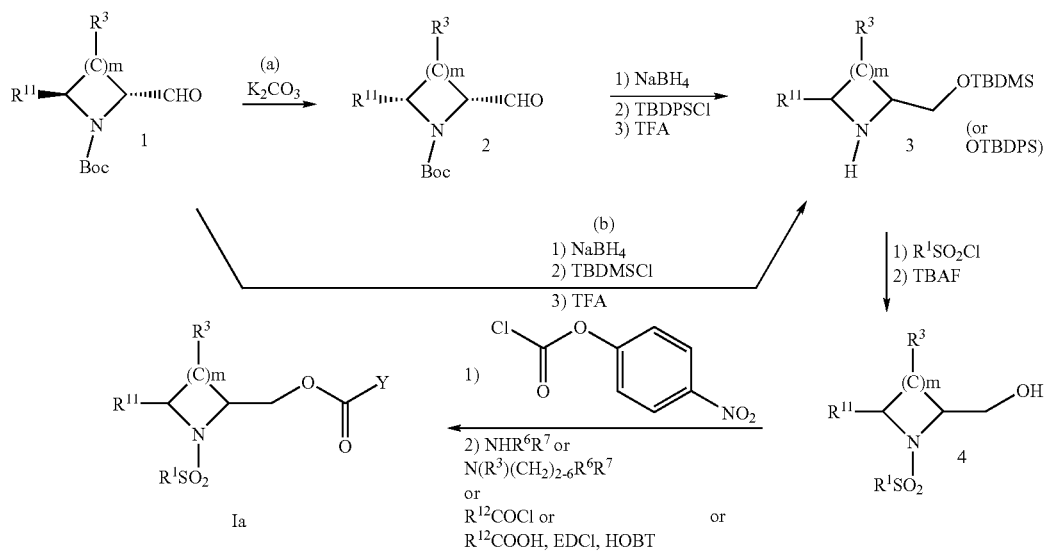

In method 1, $R^{12}$ represents the Y substituents defined above in paragraphs (3) to (18) of the definition of Y. When the reagents $R^{12}$COCl or $R^{12}$COOH are used in Method 1, then Y in formula Ia represents $R^{12}$.

In Method 1, a trans-substituted N-Boc-cyclic amine 2-carboxaldehyde 1 is epimerized to the corresponding cis isomer using a mild base such as potassium carbonate (path a). The cis geometry is retained in all subsequent steps. Alternatively, the epimerization step can be omitted to yield trans products (path b). Aldehyde 2 is reduced using a reducing agent such as sodium borohydride. The alcohol is protected using a typical protecting group such as a t-butyldiphenylsilyl ether, and the boc group is removed under acidic conditions to give 3. The cyclic amine is converted to a sulfonamide by reaction with a sulfonyl halide, and the alcohol protecting group is removed under standard conditions to give 4. Alcohol 4 can be converted to a variety of compounds of type Ia using methods well-known to those skilled in the art. For example, carbamates can be prepared by reaction of 4 with 4-nitrophenylchloroformate followed by reaction of the resulting carbonate with a primary or secondary amine. Alternatively, esters can be prepared by reaction of 4 with either an acid halide of a carboxylic acid in the presence of a suitable coupling reagent such as EDCl and HOBT.

Starting material of formula 1 in Method 1 are known in the art or can be prepared as described below.

Method 2

In Method 2, compounds of formula I having the structure Ib are prepared.

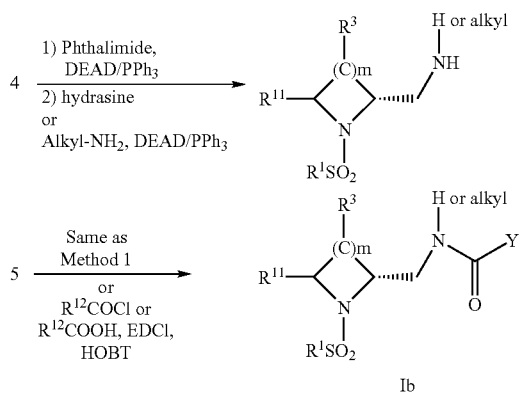

In Method 2, $R^{12}$ is as defined in Method 1

In Method 2, alcohol 4 from method 1 converted to the corresponding primary or secondary amine under a variety of conditions, such as by reaction with phthalimide under Mitsunobu conditions followed by treatment with hydrazine or by reaction with a primary amine under Mitsunobu conditions. The resulting amine is converted to ureas or to amides Ib using the same procedures described for carbamates and esters in Method 1.

Methods 3-A and 3-B

In Methods 3-A and 3-B, compounds of formula I having the structure Ic are prepared.

Method 3-A

In Method 3-A, 2,6-dibromopyridine is reacted with a boronic acid derivative $R^{11}B(OH)_2$ (most preferably an aryl or vinyl boronic acid) in the presence of a palladium catalyst. The resulting 6-substituted 2-bromopyridine is formylated by treatment with an alkyl lithium such as n-butyllithium followed by treatment with a formylating agent such as dimethylformamide to give 7-A. This product is hydrogenated to give alcohol 8 (where any unsaturation in $R^{11}$ may also have been reduced). Alcohol 8 can be converted to compounds of formula Ic using the procedures previously described.

Method 3-B

In Method 3-B, 6-bromopicolinic acid 6-B is converted to its methyl ester under standard conditions followed by reaction with a boronic acid derivative $R^{11}B(OH)_2$ (most preferably an aryl or vinyl boronic acid) in the presence of a palladium catalyst to give 7-B. This is then hydrogenated using a suitable catalyst such as platinum oxide, preferably in the presence of acetic acid, then reduced with a hydride reagent such as lithium aluminum hydride to give alcohol 8. Alcohol 8 can be converted to compounds of formula Ic using the procedures previously described.

Method 4

In Method 4, compounds of formula I having the structure Id are prepared wherein $R^{11}$ in 9 and Id represents alkyl having at least two carbons, arylalkyl, or heteroarylalkyl.

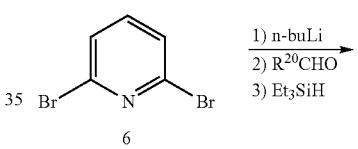

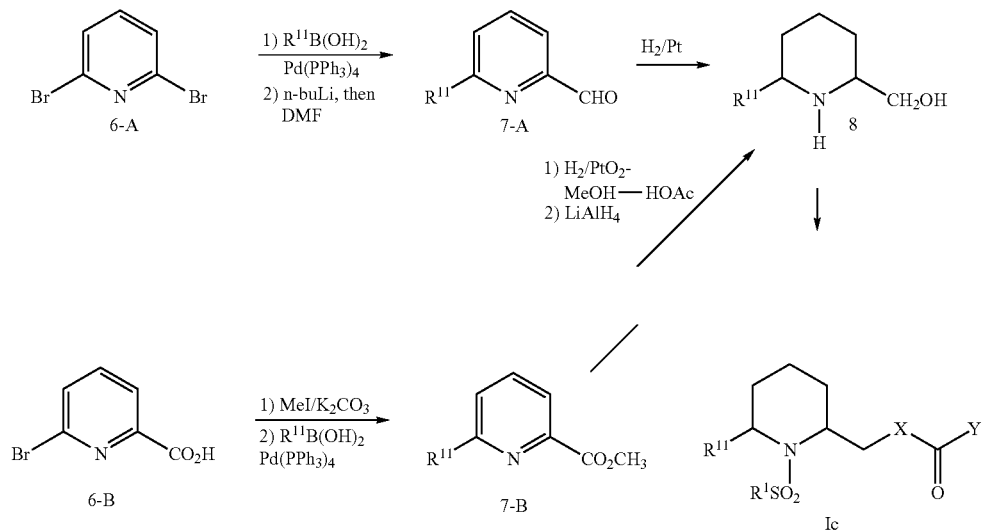

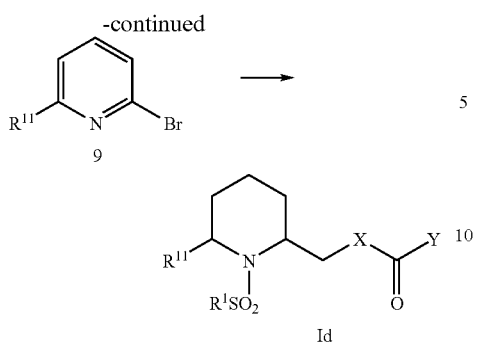

In Method 4, $R^{20}$ represents alkyl, unsubstituted aryl, substituted aryl, unsubstituted arylalkyl, substituted arylalkyl, unsubstituted heteroaryl, substituted heteroaryl, unsubstituted heteroarylalkyl, or substituted heteroarylalkyl, wherein these groups are as defined for $R^{11}$ above.

In Method 4, 2,6-dibromopyridine is mono-metallated under a variety of conditions, such as treatment with an alkyllithium at about −78° C. or by treatment with a lithium trialkylmagnesiumate complex at −10 to 0° C. The resulting organometallic derivative is reacted with an aldeyde $R^{20}$CHO, and the product is deoxygenated under a variety of conditions, such as by treatment with triethylsilane, to give 9. Compound 9 is formylated and the resulting formyl derivative converted compounds of type Id using the procedures previously described.

Method 5

In Method 5, compounds of formula I having the structure Ie are prepared wherein $R^{11}$ in 10 and Ie represents alkyl having at least three carbons, arylalkyl wherein said alkyl moiety has at least two carbons, or heteroarylalkyl wherein said alkyl moiety has at least two carbons.

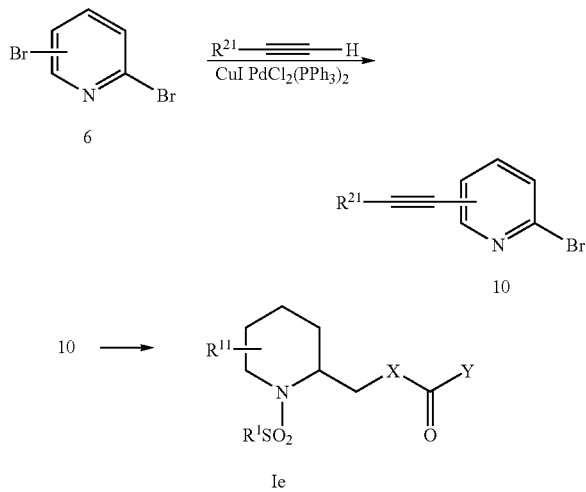

In Method 5, $R^{21}$ represents alkyl, unsubstituted aryl, substituted aryl, unsubstituted arylalkyl, substituted arylalkyl, unsubstituted heteroaryl, substituted heteroaryl, unsubstituted heteroarylalkyl, or substituted heteroarylalkyl, wherein these groups are as defined for $R^{11}$ above.

In Method 5, 2,6-dibromopyridine is coupled with a mono-substituted alkyne in the presence of a catalyst such as PdCl$_2$(PPh$_3$)$_4$/CuI. The resulting product is formylated, hydrogenated, and converted to compounds Ie using the procedures previously described.

Method 6

In Method 6, compounds of formula I having the structure Ie are prepared wherein $R^{11}$ in 12 and If represents alkyl having at least three carbons, arylalkyl wherein said alkyl moiety has at least two carbons, or heteroarylalkyl wherein said alkyl moiety has at least two carbons.

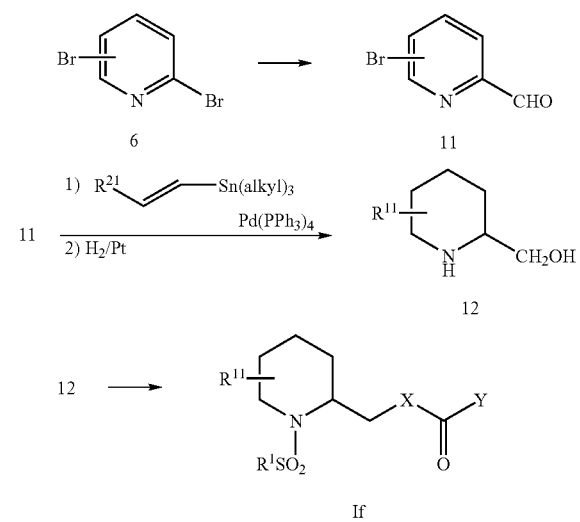

In Method 6, $R^{21}$ represents alkyl, unsubstituted aryl, substituted aryl, unsubstituted arylalkyl, substituted arylalkyl, unsubstituted heteroaryl, substituted heteroaryl, unsubstituted heteroarylalkyl, or substituted heteroarylalkyl, wherein these groups are as defined for $R^{11}$ above.

In Method 6, 2,6-dibromopyridine is mono-metallated as previously described and the resulting organometallic is reacted with a formylating agent such as DMF to give 11. This compound is reacted with a vinyl tin reagent in the presence of a catalyst such as Pd(PPh$_3$)$_4$, and the resulting product is hydrogenated to give 12. Compound 12 is converted to compounds If as previously described.

Method 7

In Method 7, compounds of formula I having the structure Ig are prepared.

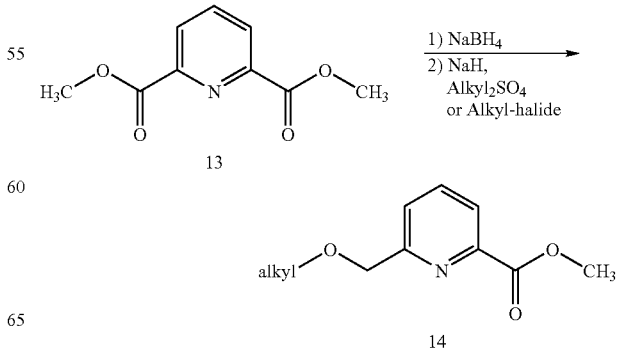

-continued

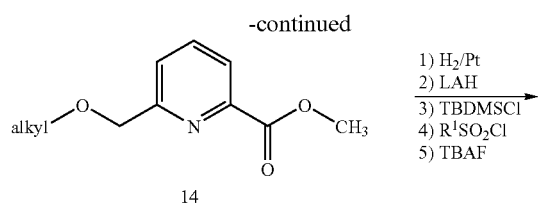

borohydride, and the resulting monohydroxymethyl derivative is treated with an alkylating agent such as an alkyl halide or alkylsulfonate to give 14. This is hydrogenated over a catalyst such as platinum oxide, and then reacted with a reducing agent such as lithium aluminum hydride to provide an intermediate cyclic amino alcohol. The alcohol function is protected using a typical protecting group such as a t-butyldimethylsilyl ether, the cyclic amine is converted to a sulfonamide by reaction with a sulfonyl halide, and the alcohol protecting group is removed under standard conditions to give 15. Compound 15 is converted to compounds of type Ig using the methods previously described.

Method 8

In Method 8, compounds of formula I having the structure Ih are prepared.

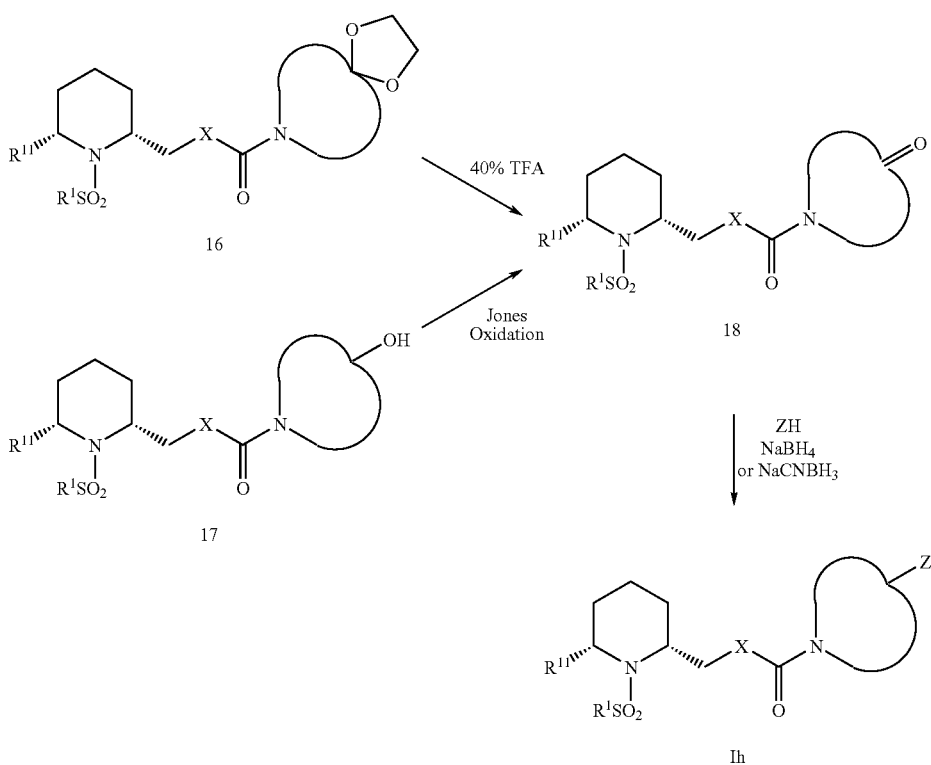

In Method 8, ketal 16 or alcohol 17 are prepared using the procedures described in Method 1 and Method 2. These are converted to the corresponding ketone by either acid hydrolysis of 16 or by oxidation of 17. The ketone is converted to compounds of type Ih by reaction with a primary or secondary amine in the presence of a reducing agent such as sodium borohyride, sodium cyanoborohydride, sodium triacetoxyborohydride, or polymer-bound derivatives thereof.

Method 9

In Method 9, compounds of formula I having the structure Ii and Ij are prepared.

-continued

15 → 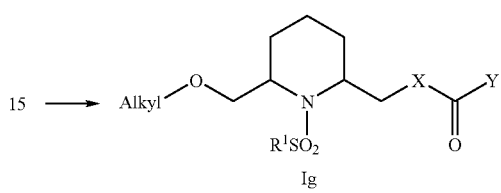

In Method 7, pyridine-2,6-dicarboxylic acid dimethyl ester is reacted with a reducing agent such as sodium

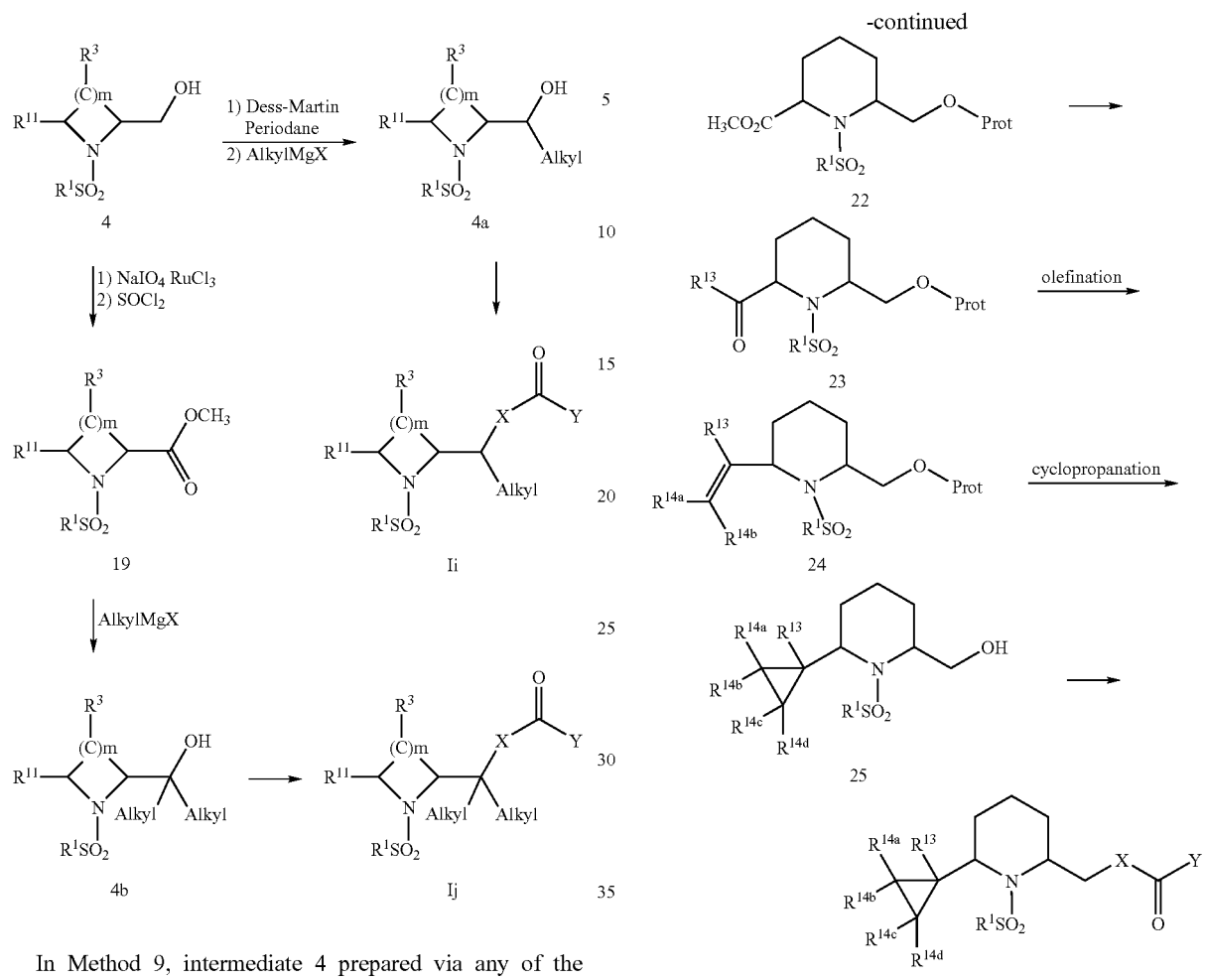

In Method 9, intermediate 4 prepared via any of the methods previously described can be oxidized to an aldehyde using a variety of well-known reagents such as Dess-Martin Periodane. The aldehyde is then treated with an alkylmetal reagent such as a Grignard reagent, an alkyllithium reagent, or an alkylzinc reagent to give alcohol 4a. Intermediate 4a can be converted to compounds of type Ii using the procedures described in Methods 1 through 8. Alternatively, 4 can be converted to ester 19 and then treated with a Grignard reagent to give 4b. This is converted to compounds of type Ij as previously described.

Compounds of type 1k are prepared according to Method 10.

Method 10:

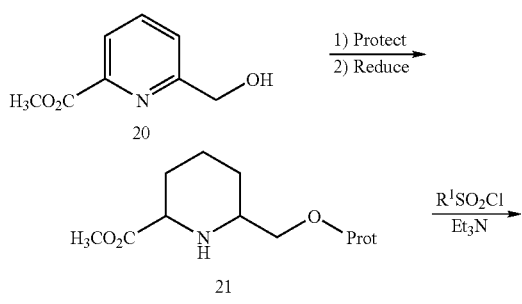

Ester 20 is protected with a suitable protecting group (Prot) such as t-butyldimethylsilyl ether, and the pyridine is reduced by well-known methods such as by treatment with hydrogen gas in the presence of a catalyst such as platinum oxide in a solvent such as ethanol or ether, to give piperidine 21. This is sulfonylated by treatment with a sulfonyl halide in the presence of a base such as triethylamine to give 22. Using well-known methods, the ester of 22 can be converted to 23, where $R^{13}$ is H or alkyl. For instance, 22 can be reduced to the corresponding aldehyde (23, $R^{13}$=H) by treatment with DIBAL. The aldehyde can be treated with a Grignard reagent followed by oxidation to give a ketone (23, $R^{13} \neq$H). Compound 23 can be converted to olefin 24 using well-known methods such as by treatment with a alkyl phosphonium ylide. Olefin 24 can be converted to cyclopropane 25 by well-known methods, for instance, by treatment with a dihalomethane such as diiodomethane in the presence of dialkylzinc and optionally in the presence of trifluoroacetic acid, by treatment with an alkyl or substituted alkyldiazo compound in the presence of a metal such as rhodium chloride, or by treatment of an alkyl halide or substituted alkyl halide with a base such as potassium hydroxide. In the above example, $R^{14a}$, $R^{14b}$, and $R^{14c}$=H, alkyl, aryl, halo, —OH, —O(alkyl), —NH$_2$, —N(H)alkyl, N(alkyl)$_2$, or C(O)Oalkyl.

Compound 25 can be converted to compounds of type Ik using the methods previously described.

Compounds of type 11 are prepared as described in method 11.

Method 11:

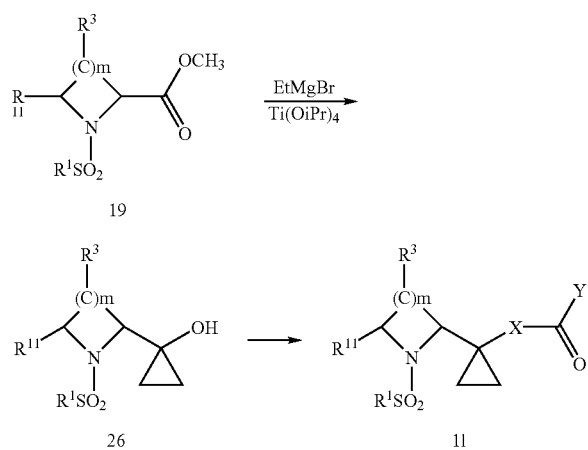

Intermediate 19 of method 9 is treated with ethylmagnesium bromide in the presence of Ti(OiPr)$_4$ to give cyclopropanol 26, which is converted to compounds of type 11 as previously described.

Compounds of type 1m, wherein $R^{11}$ is a heteroaryl moiety can be made by several methods as shown below.

Method 12:

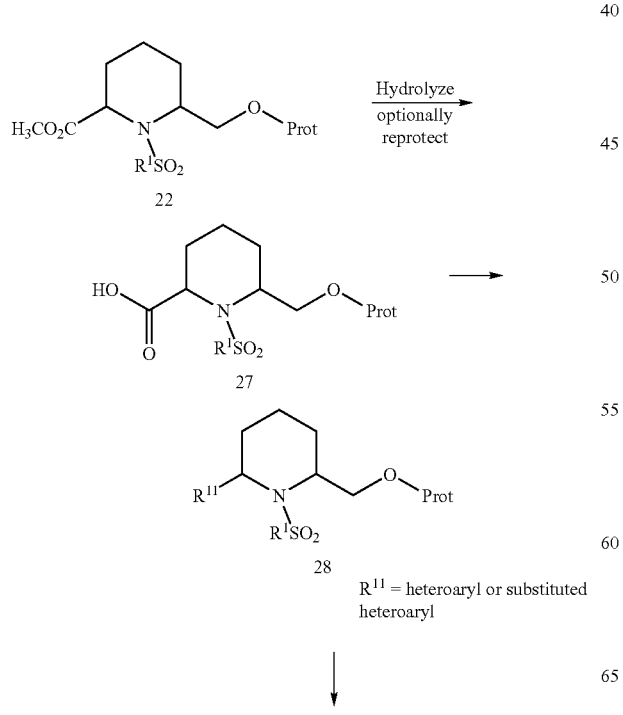

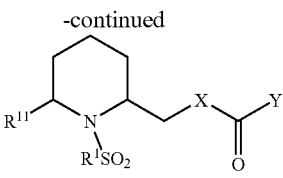

Intermediate 22 from method 10 can be hydrolyzed and, optionally as needed, reprotected to give acid 27. This acid can be transformed to a variety of heteroaryl moieties using methods well-known to those skilled in the art. For instance, coupling with 2-aminoethanol followed by oxidation and dehydrative cyclization according to the method of Morwick et al (*Organic Letters* 2002, 2665) gives 28 where $R^{11}$=2-oxazolyl. Compounds of type 28 can be transformed into compounds of type 1m using the methods described earlier.

Method 13:

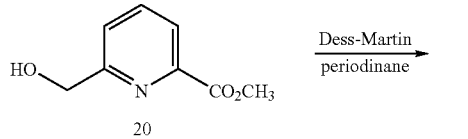

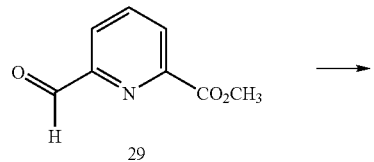

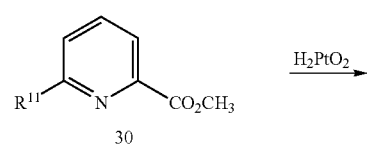

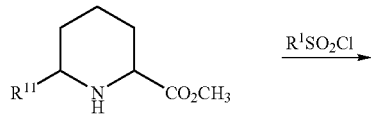

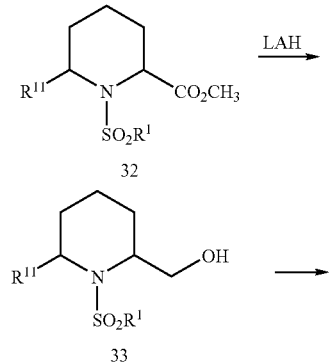

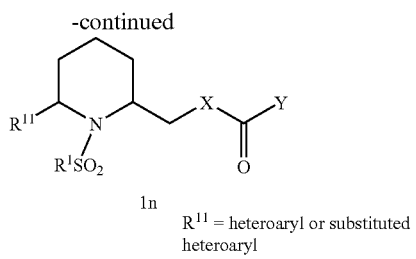

R[11] = heteroaryl or substituted heteroaryl

Intermediate 20 from method 10 can be oxidized to aldehyde 29 using, for instance, Dess-Martin periodinane. Aldeyde 29 can be transformed into a variety of intermediates 30 where R[11] is heteroaryl using well-known methods. For instance, treatment of 29 with glyoxal and ammonia gives 30 where R[11] is 2-imidazolyl. Intermediate 30 can be reduced to piperidine 31 and sulfonylated to give 32 as previously described, and the ester of 32 can be reduced to alcohol 33 using, for instance, lithium aluminum hydride. Intermediate 33 can be transformed to compounds 1n as previously described.

Chiral compounds of this invention can be resolved by chromatography over a chiral stationary phase as described in the examples.

The invention disclosed herein is exemplified by the following examples which should not be construed as limiting the scope of the invention. Alternative mechanistic pathways and analogous structures within the scope of the invention may be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% $CH_3CN$, 5 min—95% $CH_3CN$, 7 min—95% $CH_3CN$, 7.5 min—10% $CH_3CN$, 9 min—stop. The retention time and observed parent ion are given.

EXAMPLE 1

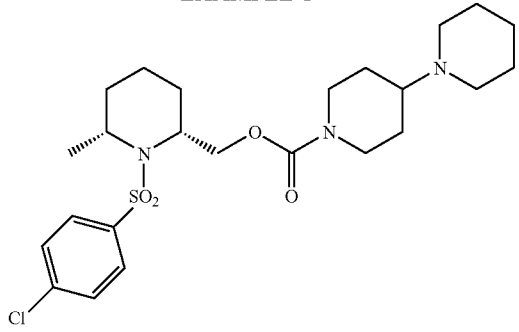

Step 1

Racemic trans 1-(tert-butoxycarbonyl)-2-formyl-6-methyl-piperidine was obtained as described in S. Chackalamannil, R. J. Davies, Y. Wang, T. Asberom, D. Doller, J. Wong, D. Leone and A. T. McPhail, *J. Org. Chem.* 1999, 64, 1932–1940. A solution of 5.44 g of this aldehyde was stirred in 100 mL of methanol with 6.0 g of $K_2CO_3$ overnight. Solids were filtered out, and the residue was concentrated. The mixture was redissolved in DCM, washed with water, dried over $Na_2SO_4$, concentrated and purified chromatographically using 7% ethyl acetate in hexanes as solvent to furnish 3.2 g of product.

Step 2 a) To a solution of 3.21 g (14.1 mmol) of the product of Step 1 in 20.0 mL of THF at 0° C. was added 534 mg (14.1 mmol) of sodium borohydride. The mixture was stirred for 1.5 h, quenched with saturated $NaHCO_3$, extracted with ether, dried over $Na_2SO_4$ and freed from solvent in vacuo to give 3.08 g of crude alcohol.

b) The crude alcohol from step 2 was dissolved in 20.0 mL of DMF and treated with 1.83 g (27 mmol) of imidazole and 4.79 g (17.5 mmol) of TBDPSCl. The mixture was stirred overnight, diluted with DCM, washed with water, dried over $Na_2SO_4$, and solvent was evaporated. The product was purified by chromatography to furnish 4.67 g of TBDPS ether.

c) A solution of 4.67 g of TBDPS ether in 15 mL of DCM was cooled to 0° C. and treated with a mixture containing 30 mL of 99% TFA and 70 mL of DCM. Cooling was removed and the mixture was stirred for 1.5 h. Volatiles were evaporated, the residue was re-evaporated with DCM, re-dissolved in DCM, washed with saturated $NaHCO_3$, dried over $Na_2SO_4$, concentrated and passed through a silica gel plug using 5% MeOH in DCM as solvent to yield 3.50 g of product.

Step 3 a) A mixture of 3.50 g (9.53 mmol) of the product of Step 2, 3.02 g of 4-chlorobenzenesulfonyl chloride and 1.92 g (19.06 mmol) of triethylamine in 20.0 mL of DCM was stirred over a period of 48 h. The reaction was washed with saturated $NaHCO_3$, dried over $Na_2SO_4$, concentrated and purified by chromatography using 10% ethyl acetate in hexanes as solvent to obtain 4.66 g of sulfonamide.

b) The resulting sulfonamide (4.66 g, 8.61 mmol) was dissolved in 50.0 mL of THF and treated with 17.2 mL (17.2 mmol) of 1M TBAF/THF solution. The mixture was stirred over 1.5 h, poured into water, extracted with ethyl acetate and DCM. The combined organic phases were dried over $Na_2SO_4$, concentrated and purified by chromatography using gradient of 10–30% ethyl acetate in hexanes as solvent to furnish 2.39 g of product.

Step 4 a) To a mixture of 712 mg (2.3 mmol) of the product of step 3, and 370 mg (4.6 mmol) of pyridine in 10 mL of DCM at 0° C. was added a solution of 4-nitrophenylchlorocarbonate in 5 mL of DCM. The mixture was stirred overnight at ambient temperature, treated with an additional 0.17 mL of pyridine and 100 mg of 4-nitrophenylchlorocarbonate and stirred for additional 5 h. The mixture was diluted with DCM, washed with water, dried over $Na_2SO_4$, purified by chromatography using 20% ethyl acetate in hexanes as solvent to furnish 860 mg of 4-nitrophenylcarbonate.

b) To a solution of 20 mg of the above product in 0.5 mL of DMF was added 20 mg of 4-(1-piperidino)piperidine. The mixture was allowed to stand overnight, diluted with DCM, washed with 1M NaOH, dried over $Na_2SO_4$ and purified by prep. TLC (5% MeOH/DCM) to furnish 17 mg of the desired product. 1H NMR ($CDCl_3$, 300 MHz) δ 7.75 (2H, d, J=8.5 Hz), 7.45 (2H, d, J=8.5 Hz), 4.33–4.20 (4H, m), 4.11–4.00 (2H, m), 2.74 (2H, wide), 2.48–2.34 (5H, ser. m.), 1.80–1.22 (16H, ser. m.), 1.30 (3H, d, J=7.1 Hz); MS (ES) m/e 498.1 (M+H)$^+$.

Following procedures similar to those in Example 1, the compounds in Table 1 were prepared.
TABLE 1
| EX. No. | COMPOUND | Mass Spec |
|---|---|---|
| 2 | 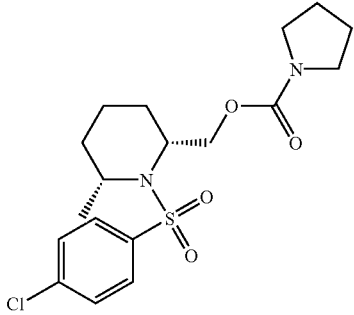 | 401.1 |
| 3 | 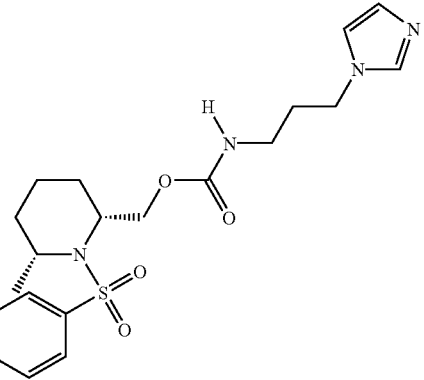 | 455.1 |
| 4 | 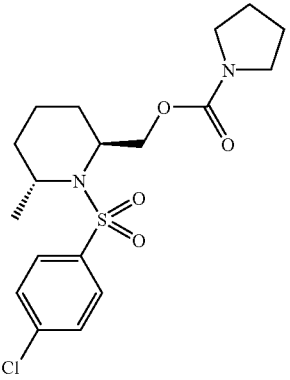 | 401.1 |

TABLE 1-continued
| EX. No. | COMPOUND | Mass Spec |
|---|---|---|
| 5 | 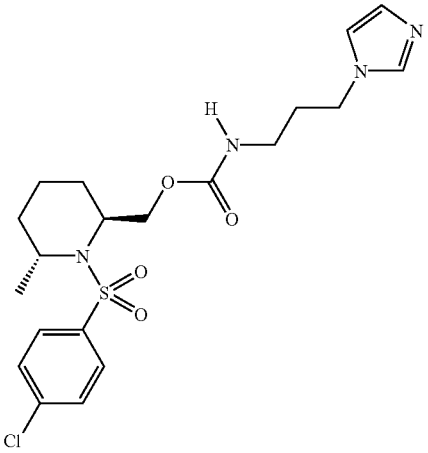 | 455.1 |
| 6 | 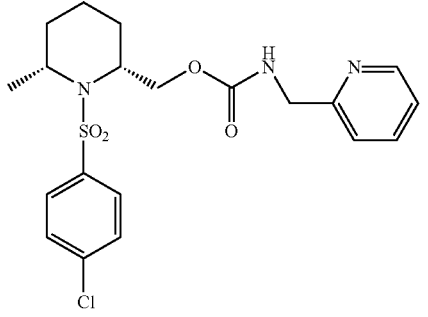 | 438.1 |
| 7 | 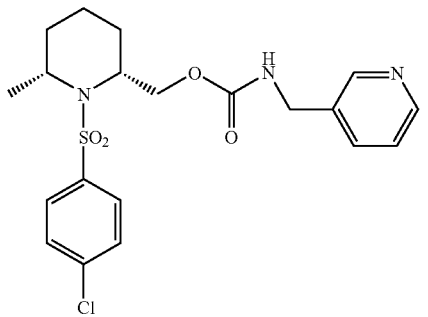 | 438.1 |
| 8 | 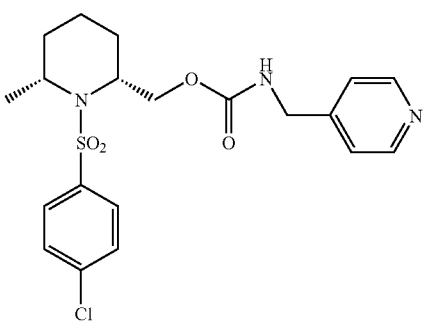 | 438.1 |

TABLE 1-continued

| EX. No. | COMPOUND | Mass Spec |
|---|---|---|
| 9 | | 466.1 |
| 10 | | 452.1 |
| 11 | | 452.1 |
| 12 | | 452.1 |

TABLE 1-continued

| EX. No. | COMPOUND | Mass Spec |
|---|---|---|
| 13 | | 466.1 |
| 14 | | 446.1 |
| 15 | | 446.1 |
| 16 | | 443.1 |

TABLE 1-continued

| EX. No. | COMPOUND | Mass Spec |
|---|---|---|
| 17 | | 490.1 |
| 18 | | 441.1 |
| 19 | | 477.1 |
| 20 | | 491.1 |

TABLE 1-continued

| EX. No. | COMPOUND | Mass Spec |
|---|---|---|
| 21 | | 405.1 |
| 22 | | 491.1 |
| 23 | | 458.1 |
| 24 | | 466.1 |
| 25 | | 460.1 |

TABLE 1-continued

| EX. No. | COMPOUND | Mass Spec |
|---|---|---|
| 26 | | 493.1 |
| 27 | | 504.1 |
| 28 | | 469.1 |
| 29 | | 469.1 |

EXAMPLE 31

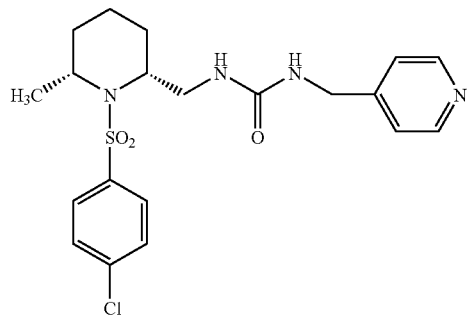

Step 1 a) To a mixture of the product of Example 1, step 3 (425 mg, 1.40 mmol), 308 mg (2.09 mmol) of phthalimide, and 917 mg (3.49 mmol) of triphenylphosphine, was added with stirring 609 mg (3.49 mmol) of DEAD. The mixture was stirred overnight, concentrated in vacuo and purified by column chromatography using 20% ethyl acetate in hexanes. The resulting material was dissolved in 15.0 ml of 1:1 mixture of methanol and DCM and treated with 2 mL of hydrazine, The mixture was stirred over 48 h, partitioned between 1M NaOH solution and DCM, organic phase was washed with 1M NaOH solution to furnish 475 mg of amine.

Step 2

The product of step 1 was transformed to the desired product as described in Example 1, Step 4, using 4-aminomethylpyridine as the amine. 1H NMR (CDCl3 300 MHz) δ 8.56 (2H, d, J=5.5 Hz), 7.71 (2H, d, J=8.2 Hz), 7.48 (2H, d, J=8.2 Hz), 7.29 (2H, d, J=5.5 Hz), 5.14 (2H, m), 4.45 (2H, d, J=6.0 Hz), 4.13 (1H, m), 3.97 (1H, m), 3.53 (1H, m), 3.33 (1H, m), 1.85–1.19 (6H, ser. m.), 1.33 (3H, d, J=7.1 Hz); MS (ES) m/e 437.1 (M+H)+.

Following procedures similar to those in Example 31, the compounds in Table 2 were prepared.

TABLE 2

| EX. No. | COMPOUND | Mass Spec |
|---|---|---|
| 32 | | 437.1 |
| 33 | | 437.1 |
| 35 | | 465.1 |
| 36 | | 451.1 |
| 37 | | 451.1 |

TABLE 2-continued
| EX. No. | COMPOUND | Mass Spec |
|---|---|---|
| 38 | 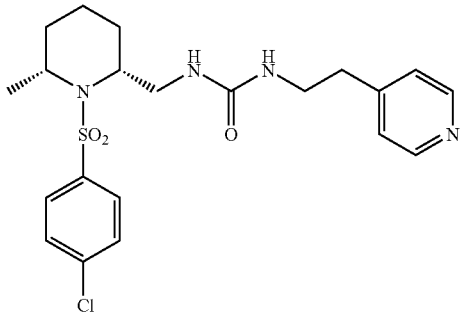 | 451.1 |
| 39 | 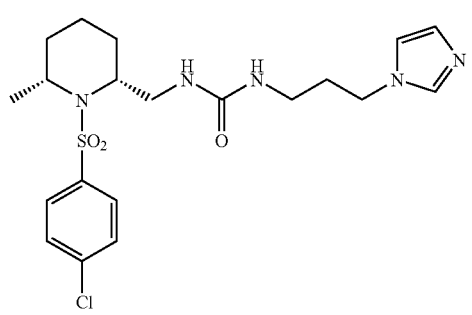 | 454.1 |
| 40 | 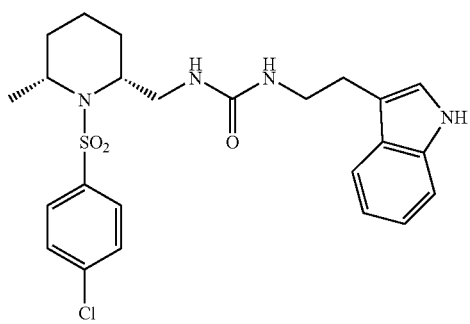 | 489.1 |
| 41 | 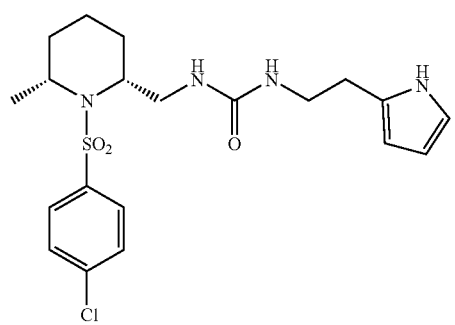 | 440.1 |
| 42 | 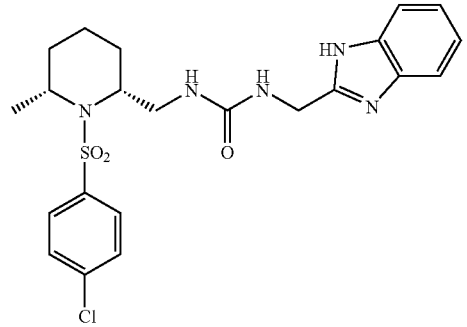 | 476.1 |
| 43 | 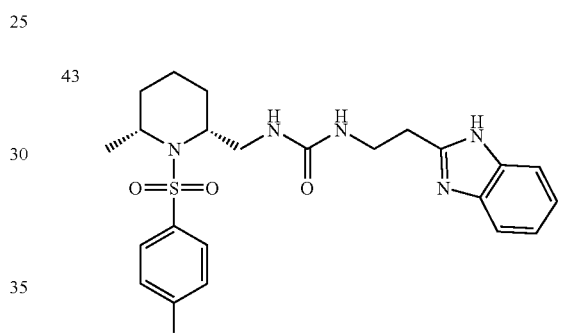 | 490.1 |
EXAMPLE 44
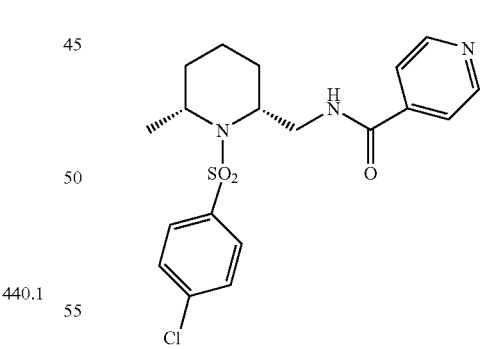
The product of Example 31 step 1 was converted to the title compound by reaction with isonicotinic acid using EDCl and HOBT as coupling reagents, according to the method known in the art. 1H NMR (CDCl3 300 MHz) δ 8.75 (2H, d, J=5.8 Hz), 7.78–7.74 (4H, m), 7.50 (2H, d, J=8.7 Hz), 4.27–4.13 (2H, ser. m), 3.89 (1H, m), 3.39 (1H, dt, J=13.0, 4.3 Hz), 1.81–1.22 (7H, ser. m), 1.35 (3H, d, J=7.3 Hz), MS (ES) m/e 408.1 (M+H)$^+$.

Following procedures similar to those in Example 44, the compounds in Table 3 were prepared.

TABLE 3

| EX. No. | COMPOUND | Mass Spec |
|---|---|---|
| 45 | (structure) | 422.1 |
| 46 | (structure) | 422.1 |
| 47 | (structure) | 416.1 |
| 48 | (structure) | 450.1 |

TABLE 3-continued

| EX. No. | COMPOUND | Mass Spec |
|---|---|---|
| 50 | (structure) | 446.1 |
| 51 | (structure) | 474.1 |
| 52 | (structure) | 458.1 |

EXAMPLE 53

Preparation A: cis (6-Phenyl-piperidin-2-yl)-methanol:

Step 1

(a) To a mixture of 600 mg (2.5 mmol) of 2,6-dibromopyridine in 15 mL of toluene was added a mixture of 150 mg (1.27 mmol) of phenylboronic acid in 5 mL of methanol, 86 mg (0.075 mmol) of Pd(PPh$_3$)$_4$ and 15 mL of 2 m Na$_2$CO$_3$. The mixture was refluxed overnight, cooled, extracted with ethyl acetate, dried and 2-bromo-6-phenylpyridine isolated chromatographically from unreacted 2,6-dibromopyridine and 2,6-diphenylpyridine.

(b) To a solution of 7.2 g (31.03 mmol) of 2-bromo-6-phenylpyridine in 50 mL of THF at −78° C. was added drop-wise 13.5 mL (31 mmol) of 2.3 M n-BuLi in hexanes followed by 10 mL of DMF. The mixture was stirred in the cold for 30 min, quenched with saturated NaHCO$_3$, extracted with ethyl acetate, dried, concentrated, and purified by chromatography using a gradient of 3–5% of ethyl acetate in hexanes to provide 2.02 g of product Step 2

To a solution of 2 g of the product of step 1 in 20 mL of MeOH was added 5 mL of AcOH and 300 mg of PtO$_2$. The mixture was hydrogenated under a balloon. The progress of the reaction was followed by taking NMR spectra of worked-up portions. After overnight stirring another portion of 300 mg of PtO$_2$ was added and hydrogenation continued for additional 24 h. Catalyst was filtered out, volatiles evaporated, residue re-dissolved in DCM and washed with 1M NaOH solution, saturated NaHCO$_3$, dried, and evaporated. Column chromatography yielded 1.30 g of cis (6-phenyl-piperidin-2-yl)-methanol and 200 mg of cis (6-cyclohexyl-piperidin-2-yl)-methanol.

Preparation B: Alternate synthesis of cis (6-phenyl-piperidin-2-yl)-methanol:

Step 1

Treat 6-bromopicolinic acid (1.99 g) in DMF (10 mL) with potassium carbonate (1.40 g) and then methyl iodide (4 mL) at room temperature for 20 h. Dilute the reaction mixture with dichloromethane (60 mL) and filter. Extract the filtrate with brine (twice), dry (MgSO$_4$), and concentrate in vacuo to give methyl 6-Bromopicolinate pale yellow solid (1.75 g).

Step 2

Heat methyl 6-bromopicolinate (0.75 g), phenylboronic acid (0.61 g), tetrakis(triphenylphosphine)palladium (0.19 g) and potassium carbonate (0.75 g) in toluene (20 mL) and methanol (4.5 mL) under reflux for 1 hr. Cool the reaction mixture, dilute with dichloromethane, and filter. Wash the filtrate with water. Concentrate the dried (K$_2$CO$_3$) organic solution in vacuo to give an amber residue (0.81 g). Chromatograph this residue on silica gel plates (8, 1000☐) using hexane:ethyl acetate 3:1 as eluant to give methyl 6-phenylpicolinate as a colorless oil (0.55 g).

Step 3

Under a hydrogen atmosphere, stir methyl 6-phenylpicolinate (0.55 g) in MeOH (30 mL) and glacial acetic acid (15 mL) in the presence of platinum oxide (0.150 g) for 5 hr. Purge the reaction mixture with nitrogen. Filter and then concentrate the reaction mixture in vacuo to give a yellow oil (0.77 g). Chromatograph this oil on silica gel plates (8, 1000☐) using hexane:ethyl acetate 3:1 eluant to give methyl 6-phenylpipecolinate as a colorless oil (0.23 g).

Step 4

Treat methyl 6-phenylipecolinate (0.23 g) in THF (15 mL) with 1M lithium aluminum hydride in ether (10 mL) at room temperature for 2 h. Quench the reaction mixture with EtOAc, the add MgSO$_4$ and filter. Concentrate the filtrate to give a residue. Chromatograph the residue on silica gel plates (2, 1000 m) using EtOAc:hexane 1:1 as eluant to give (6-phenyl-piperidin-2-yl)-methanol as a white solid (0.06 g).

Preparation C:

Step 1

(a) At 0° C., to a solution of 1.29 g (6.77 mmol) of cis (6-phenyl-piperidin-2-yl)-methanol from Preparation A or Preparation B in 20.0 mL of DCM was added 1.90 mL (13.6 mmol) of triethylamine and 1.84 mL (10.1 mL) of trimethylsilyl trifluoromethanesulfonate. The mixture was stirred for 1 h at ambient temperature, washed with saturated NaHCO$_3$, dried over Na$_2$SO$_4$ and volatiles were evaporated.

(b) The residue was re-dissolved in DCM, treated with 1.90 mL (13.5 mmol) of triethylamine and 2.11 g (10.0 mmol) of 4-chlorobenzenesulfonylchloride. The mixture was stirred for 24 h, washed with 1M HCl, saturated NaHCO$_3$, and concentrated.

(c) To insure cleavage of TMS ether, the material was dissolved in methanol (5 mL), treated with 1 mL of 1M HCl, stirred for 30 min, and concentrated. The residue was chromatographed using 10–20% ethyl acetate in hexanes to furnish 1.45 g of 1-(4-Chloro-benzenesulfonyl)-6-phenyl-piperidin-2-yl]-methanol.

Step 2

The product of Step 1 was converted to the title compound according to Step 4 of Example 1, using N-cyclohexylpiperazine at the last stage as the amine. 1H NMR (CDCl$_3$ 300 MHz) δ 7.86 (2H, d, J=8.2 Hz), 7.57–7.49 (4H, m), 7.36–7.24 (3H, m), 5.24 (1 H, d, J=4.9 Hz), 4.34 (1 H, q, J=6.2 Hz), 3.68 (1 H, dd, J=11.0, 6.5 Hz), 3.58–3.40 (5H, ser. m.), 2.55 (4H, m), 2.37–2.24 (2H, ser. m.), 1.90–1.58 (6H, ser. m.), 1.53–1.36 (3H, ser. m.), 1.30–1.13 (6H, ser. m.); MS (ES) m/e 560.1 (M+H)$^+$.

Following procedures similar to those in Example 53, the compounds in Table 4 were prepared. Cis-(6-cyclohexyl-piperidin-2-yl)-methanol, obtained in Preparation A, step 2, was used in Examples 63–66.

TABLE 4

| EX. No. | COMPOUND | Mass Spec |
|---|---|---|
| 54 | | 517.1 |
| 55 | | 560.1 |
| 56 | | 555.1 |
| 57 | | 520.1 |

TABLE 4-continued

| EX. No. | COMPOUND | Mass Spec |
|---|---|---|
| 58 | | 508.1 |
| 59 | | 528.1 |
| 60 | | 528.1 |
| 61 | | 520.1 |
| 63 | | 523.1 |

TABLE 4-continued

| EX. No. | COMPOUND | Mass Spec |
|---|---|---|
| 64 | | 566.1 |
| 65 | | 526.1 |
| 66 | | 514.1 |
| 67 | | 522.1 |

NMR data is given in Table 5 below for compounds in Table 4:

TABLE 5

| EX. No. | COMPOUND | NMR |
|---|---|---|
| 54 | 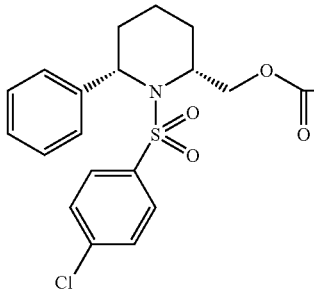 | 1H NMR (CDCl3 300 MHz) δ 7.84(2H, d, J=8.8 Hz), 7.58–7.51(5H, ser.m.), 7.37–7.24(3H, ser.m.), 7.07 (1H, br), 6.96(1H, br), 5.22 (1H, d, J=5.5Hz), 4.91(1H, m), 4.33(1H, m), 4.03(2H, t, J=7.0Hz), 3.75(1H, dd, J=6.0, 11.5Hz), 3.42(1H, dd, J=6.0, 11.5Hz), 3.27–3.17(1H, m), 3.13–3.05(1H, m), 2.34(1H, d, J=14.8Hz), 1.88(2H, m), 1.68–1.19(5H, ser.m.) |
| 55 | 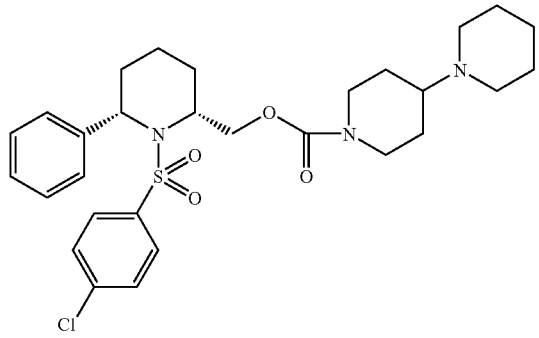 | 1H NMR (CDCl3 300 MHz) δ 7.85(2H, d, J=8.8Hz), 7.57–7.50(4H, ser.m.), 7.36–7.23(3H, ser.m.), 5.24(1H, d, J=4.5Hz), 4.38–4.13(3H, ser.m.), 3.70(1H, dd, J=6.0, 11.0Hz), 3.47(1H, s), 3.42 (1H, dd, J=9.0, 11.0Hz), 2.73(1H, br), 2.53–2.30(5H, ser.m.), 1.94–1.17(16H, ser.m.) |
| 57 | 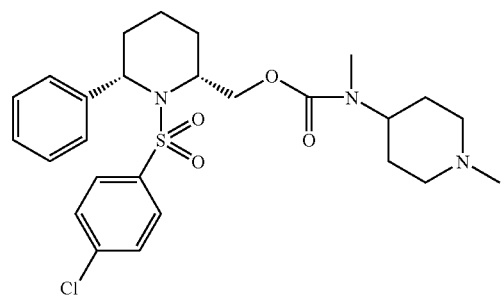 | 1H NMR (CDCl3 300 MHz) δ7.84(2H, d, J=8Hz), 7.59–7.50(4H, m), 7.34–7.26(3H, ser.m.), 5.23(0.5H, br), 5.12 (0.5H, br), 4.59(0.5H, br), 4.47–4.32(1H, m), 4.11 (0.5H, br), 3.71(1H, d, J=10.2Hz), 3.43(2H, t, J=10.5Hz), 3.24(1H, br) |
| 58 | 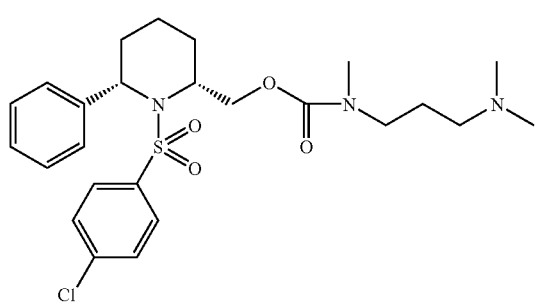 | 1H NMR (CDCl3 300 MHz)δ7.83(2H, d, J=8Hz), 7.63–7.53(4H, ser.m.), 7.38–7.27(3H, ser.m.), 5.18(1H, m), 4.44(1H, m), 3.86–3.62 (3H, ser.m.), 3.56–3.30 (2H, ser.m.), 3.00(3H, s), 2.78 (3H, s), 2.73(3H, s) |

TABLE 5-continued
| EX. No. | COMPOUND | NMR |
|---|---|---|
| 61 | 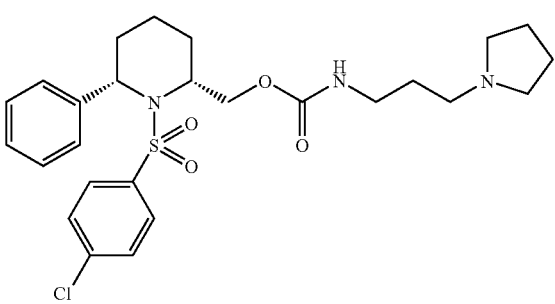 | 1H NMR (CDCl3 300 MHz)δ7.84(2H, d, J=8.7Hz), 7.56–7.51(4H, ser.m), 7.38 (2H, t, J=7.3Hz), 7.29(1H, d, J=7.3Hz), 5.66(1H, m), 5.20(1H, d, J=5.1Hz), 4.35 (1H, m), 3.70(1H, dd, J=11.2, 7.0Hz), 3.45–3.0 (3H, ser.m), 3.27–2.96(5H, ser.m), 2.30(1H, d, J=14.0 Hz), 2.04–1.2(12H, ser.m) |
| 64 | 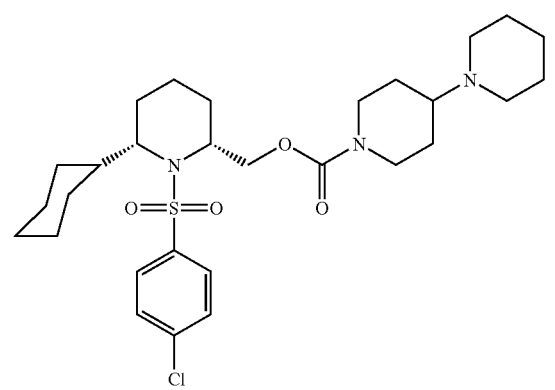 | 1H NMR (CDCl3 300 MHz) δ 7.78(2H, d, J=8.5Hz), 7.47(2H, d, J=8.5Hz), 4.29–4.08(5H, ser.m.), 3.68(1H, m), 2.76(2H, m), 2.5–2.35 (5H, ser.m.), 2.10(1H, d, J=12.6Hz), 1.85–0.77(26H, ser.m.) |
| 67 | 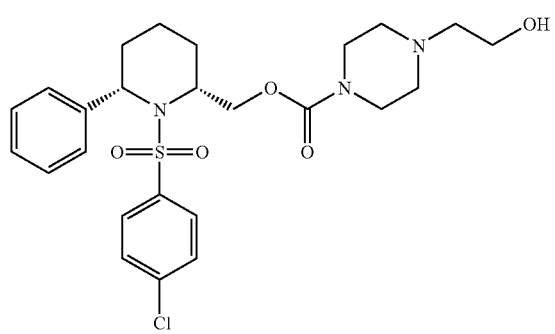 | 1H NMR (CDCl3 300 MHz) δ 7.85(2H, d), 7.57–7.50(4H, ser.m.), 7.37–7.24(3H, ser.m.), 5.24(1H, d, J=4.5 Hz), 4.35(1H, m), 3.72(1H, dd, J=11.0, 6.0Hz), 3.64 (2H, t, J=5.2Hz), 3.60–3.45 (4H, ser.m.), 3.43(1H, dd, J=11.0, 9.3Hz), 2.61–2.46 (6H, ser.m.), 2.35(1H, d, J=14.3Hz), 1.73–1.18(6H, ser.m.) |

Also prepared were the following compounds:

| Compound No. | Structure | Retention Time (minutes) | Observed Mass |
|---|---|---|---|
| 67-A | [Alpha]$^{20}_D$ = +51.40 | 5.38 | 578.1 |
| 67-B | [Alpha]$^{20}_D$ = −56.95 | 5.38 | 578.1 |
| 67-C | 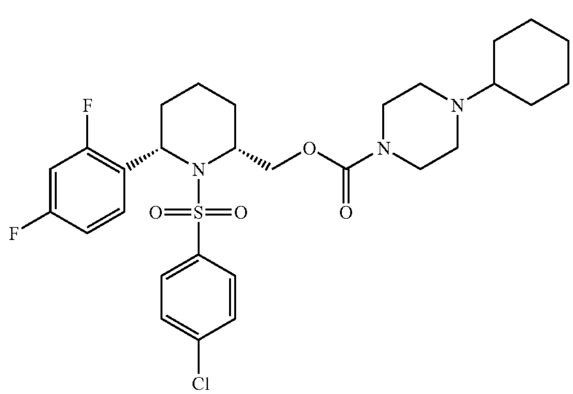 | 5.52 | 596.1 |

-continued

| Compound No. | Structure | Retention Time (minutes) | Observed Mass |
|---|---|---|---|
| 67-D | 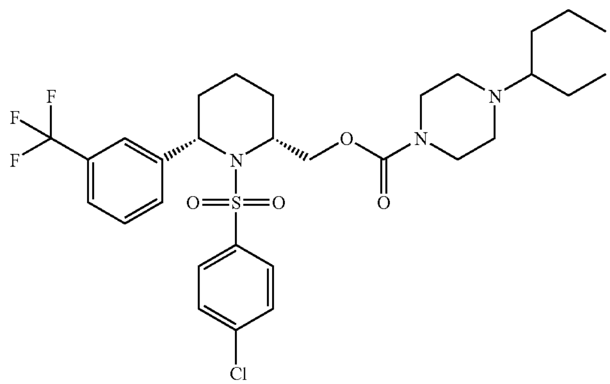 | 5.68 | 628.1 |
| 67-E | 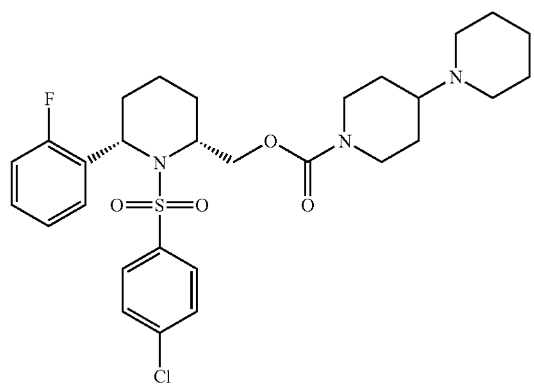 | 5.42 | 578.1 |
| 67-F | 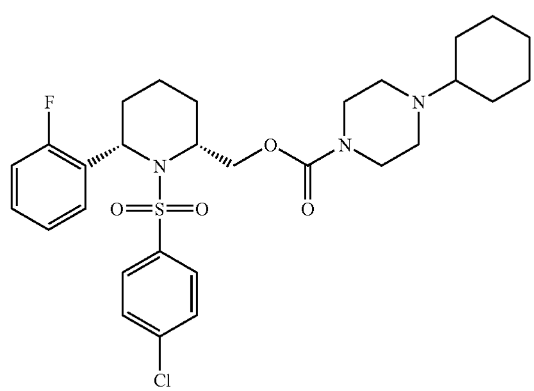 | 5.48 | 578.1 |
| 67-G | 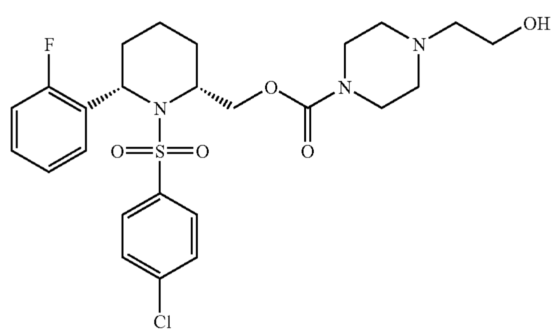 | 4.83 | 540.1 |

-continued

| Compound No. | Structure | Retention Time (minutes) | Observed Mass |
|---|---|---|---|
| 67-H | 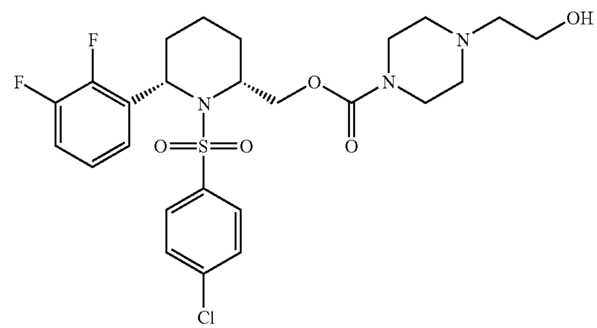 | 4.75 | 558.1 |
| 67-I | 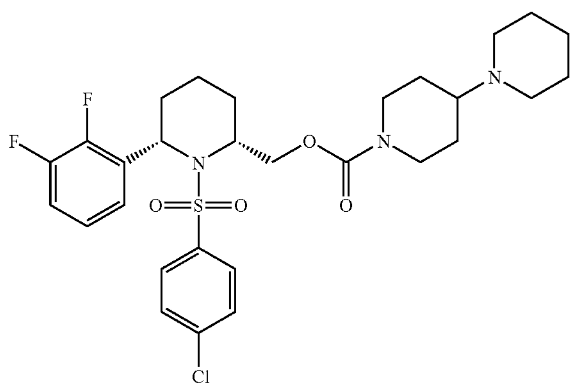 | 5.42 | 596.1 |
| 67-J | 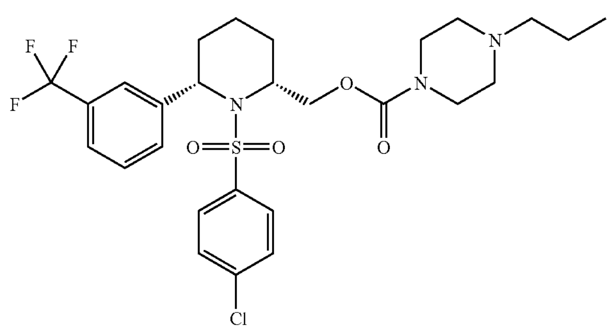 | 5.18 | 590.1 |
| 67-K | 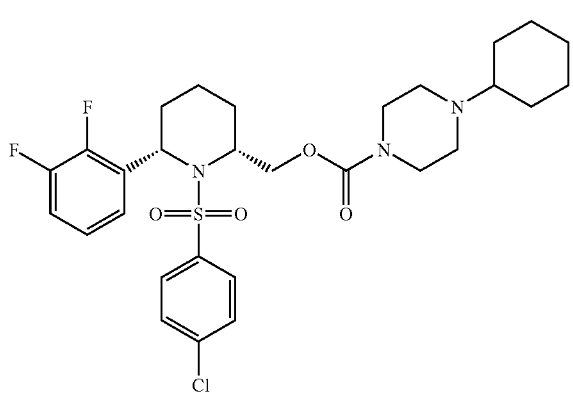 | 5.48 | 596.1 |

| Compound No. | Structure | Retention Time (minutes) | Observed Mass |
|---|---|---|---|
| 67-L | 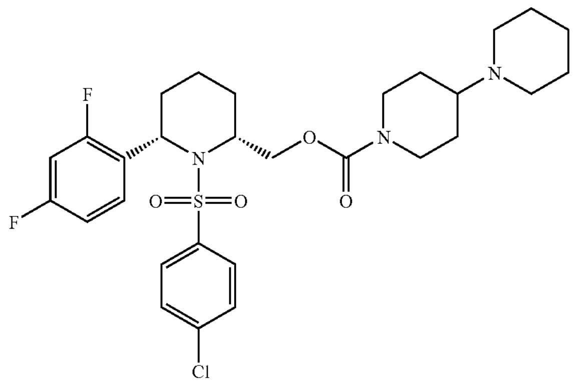 | 5.62 | 596.1 |
| 67-M | 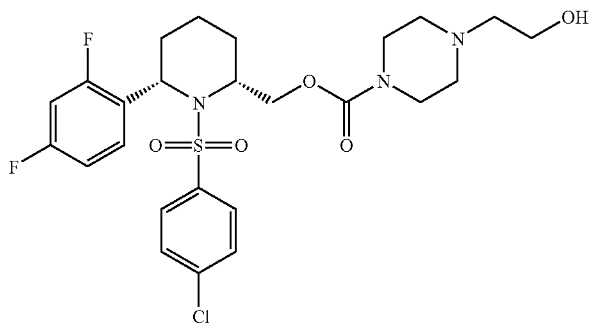 | 4.85 | 558.1 |
| 67-N | 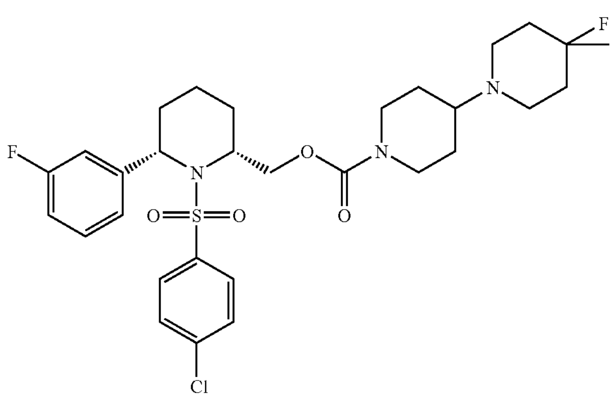 | 5.51 | 614.3 |
| 67-O | 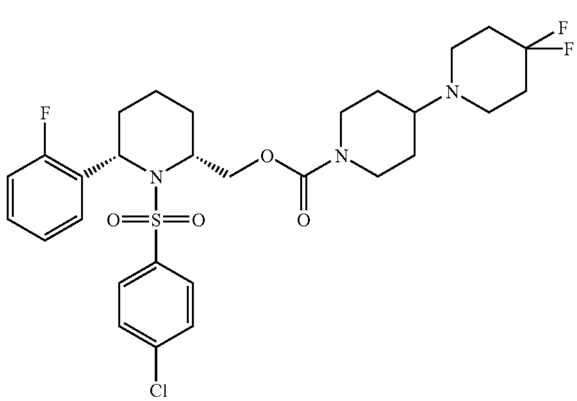 | 5.48 | 614.3 |

-continued

| Compound No. | Structure | Retention Time (minutes) | Observed Mass |
|---|---|---|---|
| 67-P | 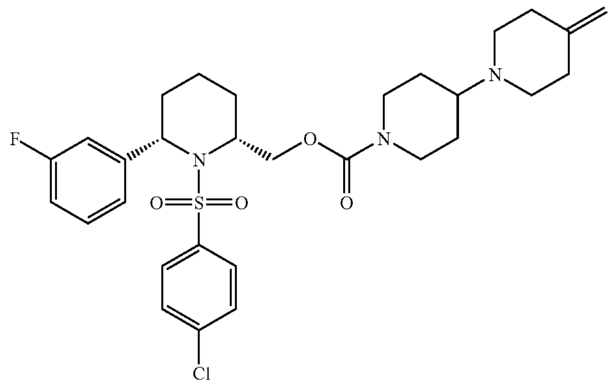 | 5.55 | 590.1 |
| 67-Q | 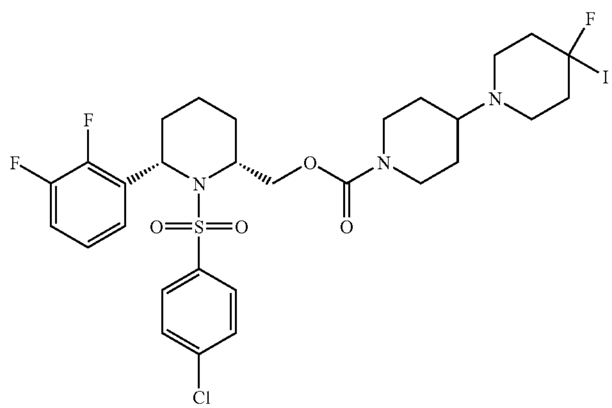 | 5.48 | 632.1 |
| 67-R | 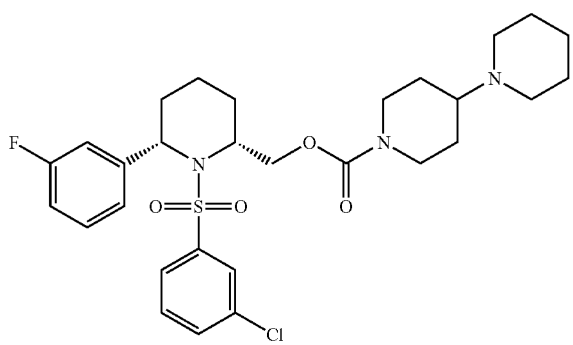 | 5.82 | 578.1 |
| 67-S | 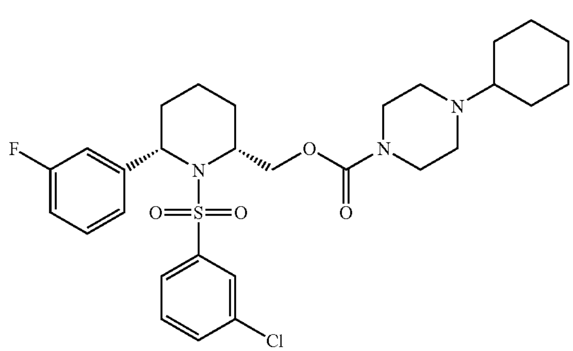 | 5.85 | 578.1 |

-continued

| Compound No. | Structure | Retention Time (minutes) | Observed Mass |
|---|---|---|---|
| 67-T | 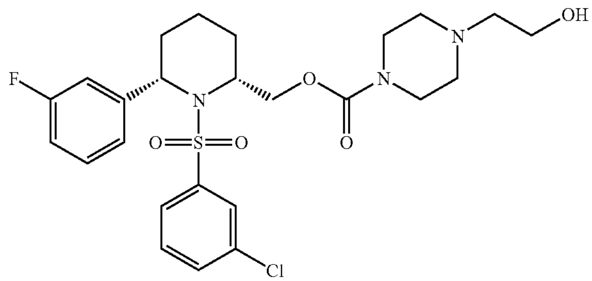 | 5.35 | 540.1 |
| 67-U | 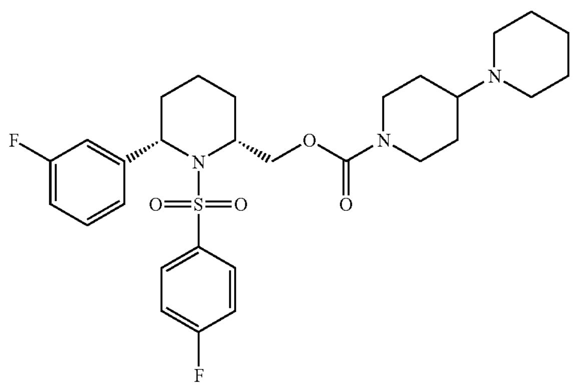 | 5.65 | 562.1 |
| 67-V | 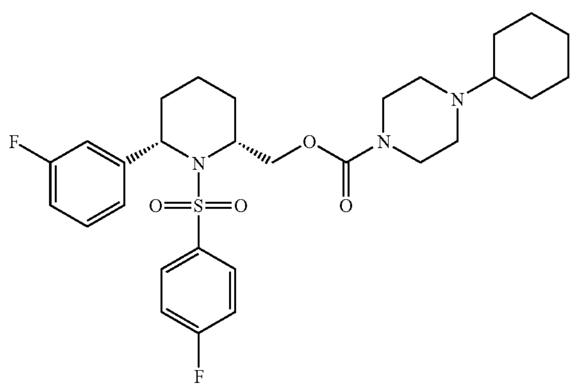 | 5.68 | 562.1 |
| 67-W | 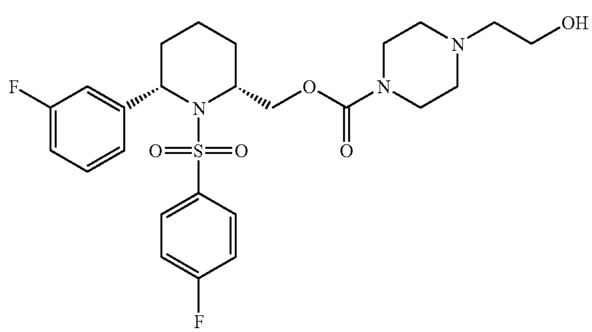 | 5.18 | 524.1 |

-continued

| Compound No. | Structure | Retention Time (minutes) | Observed Mass |
|---|---|---|---|
| 67-X | 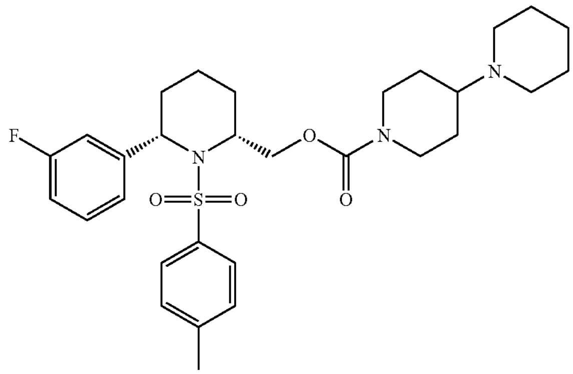 | 5.08 | 558.3 |
| 67-Y | 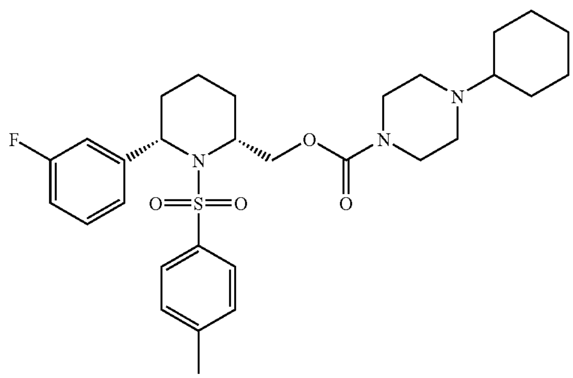 | 5.18 | 558.3 |
| 67-Z | 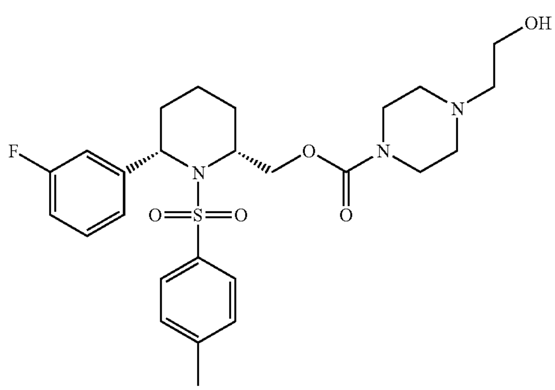 | 4.38 | 520.3 |
| 67-AA | 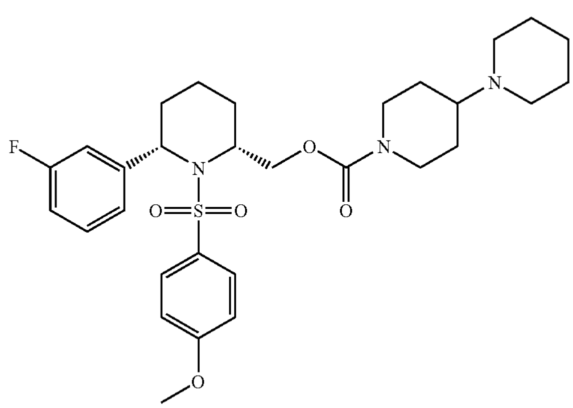 | 5.32 | 574.1 |

-continued

| Compound No. | Structure | Retention Time (minutes) | Observed Mass |
|---|---|---|---|
| 67-AB | 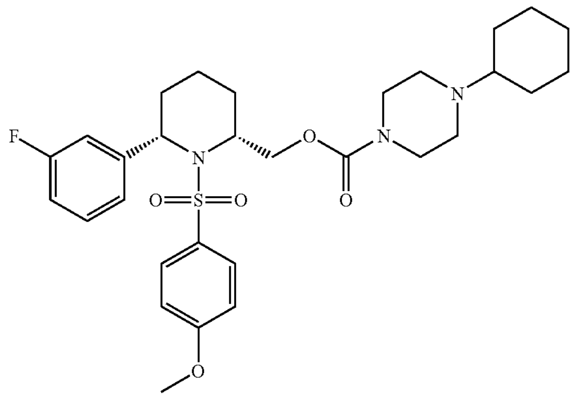 | 5.55 | 574.1 |
| 67-AC | 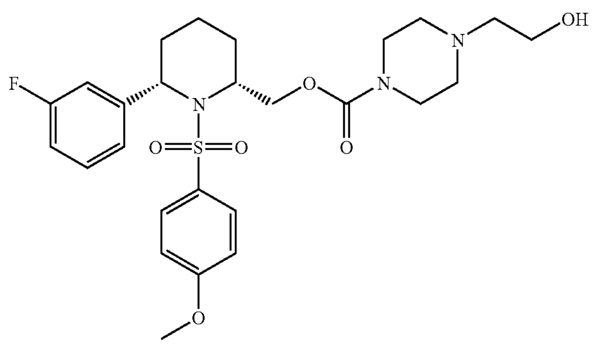 | 4.68 | 536.1 |
| 67-AD | 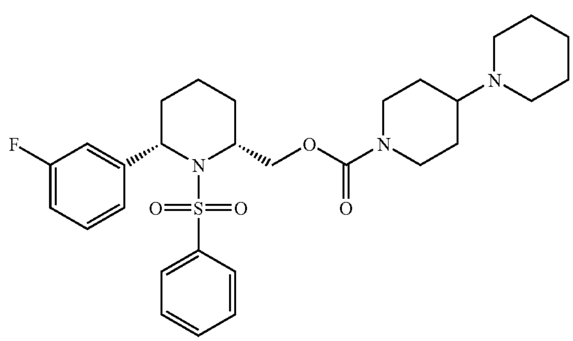 | 5.25 | 544.1 |
| 67-AE | 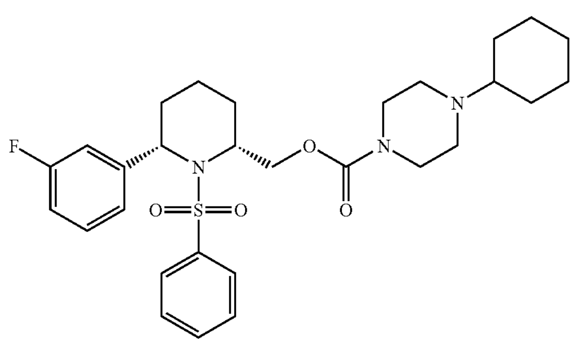 | 5.55 | 544.1 |

-continued

| Compound No. | Structure | Retention Time (minutes) | Observed Mass |
|---|---|---|---|
| 67-AF | 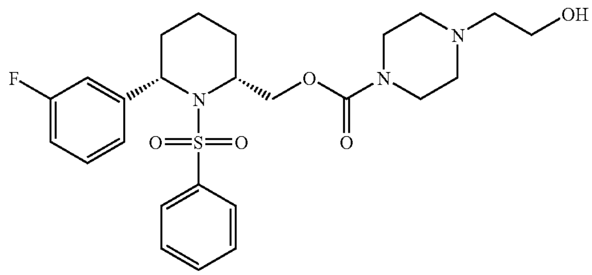 | 4.61 | 506.1 |
| 67-AG | 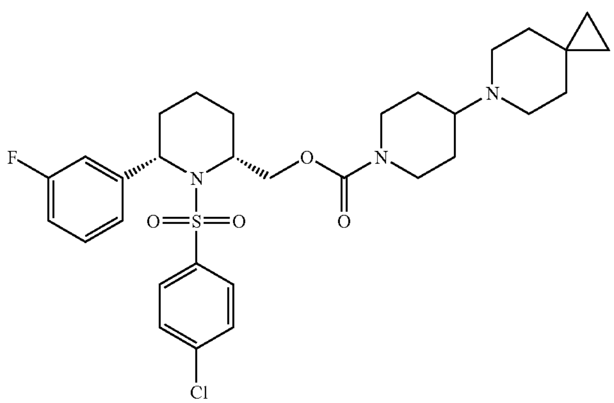 | 5.65 | 608.1 |
| 67-AH | 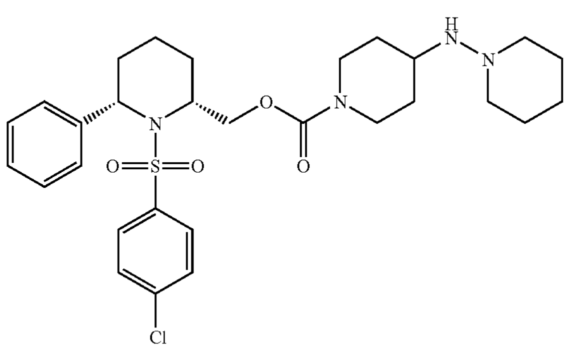 | 5.38 | 575.1 |
| 67-AI | 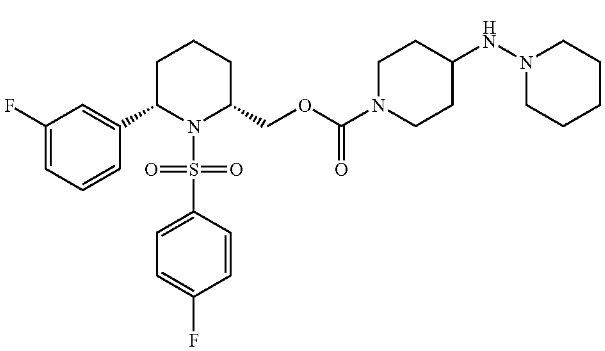 | 5.25 | 577.1 |

-continued

| Compound No. | Structure | Retention Time (minutes) | Observed Mass |
|---|---|---|---|
| 67-AJ | 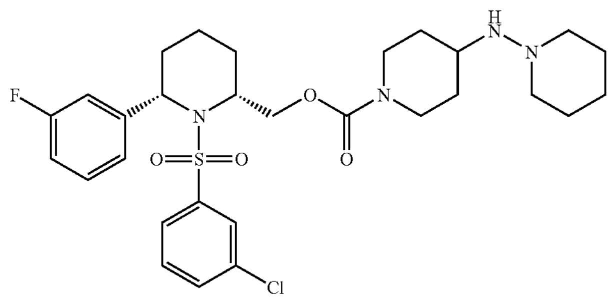 | 5.38 | 593.1 |
| 67-AK | 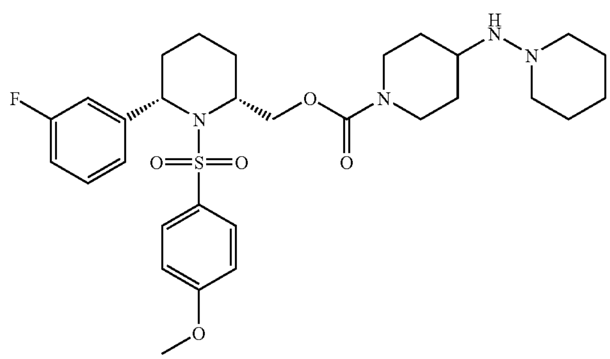 | 5.22 | 589.1 |
| 67-AL | 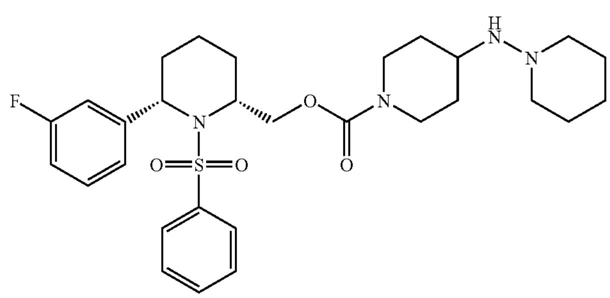 | 5.15 | 559.1 |
| 67-AM | 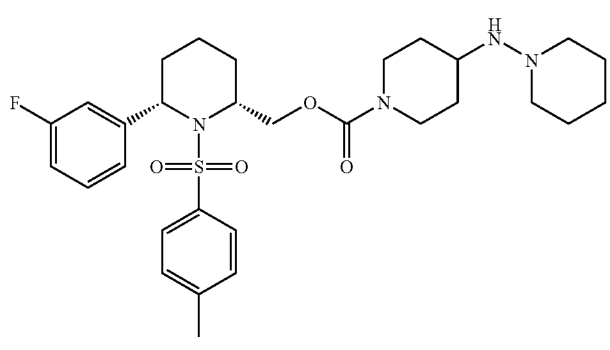 | 5.35 | 573.1 |

-continued

| Compound No. | Structure | Retention Time (minutes) | Observed Mass |
|---|---|---|---|
| 67-AN | 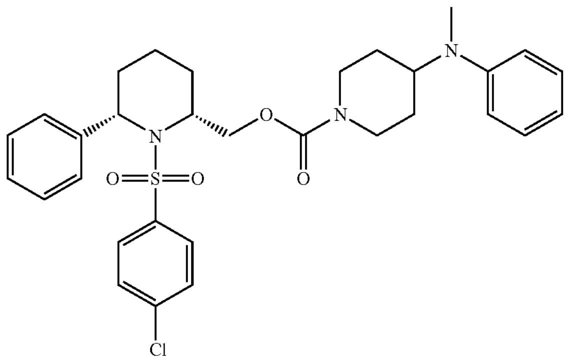 | 5.01 | 582.3 |
| 67-AO | 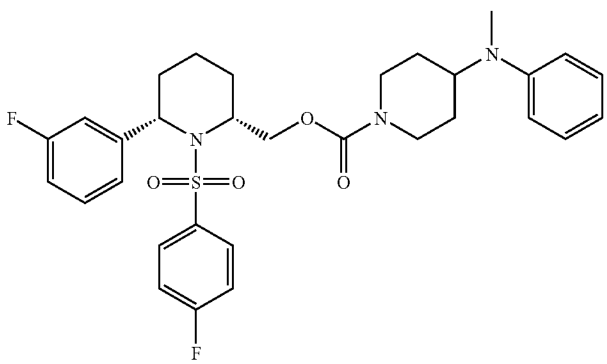 | 4.85 | 584.3 |
| 67-AP | 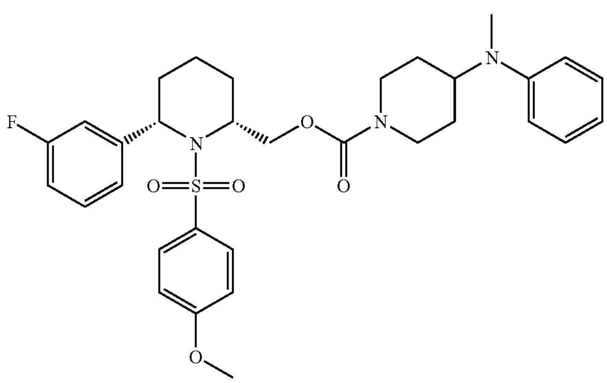 | 4.85 | 596.3 |
| 67-AQ | 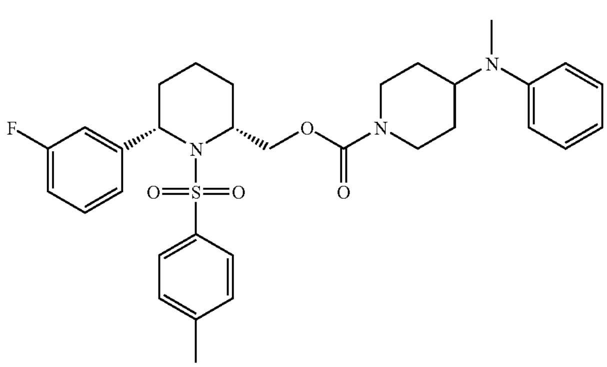 | 5.01 | 580.3 |

-continued

| Compound No. | Structure | Retention Time (minutes) | Observed Mass |
|---|---|---|---|
| 67-AR | 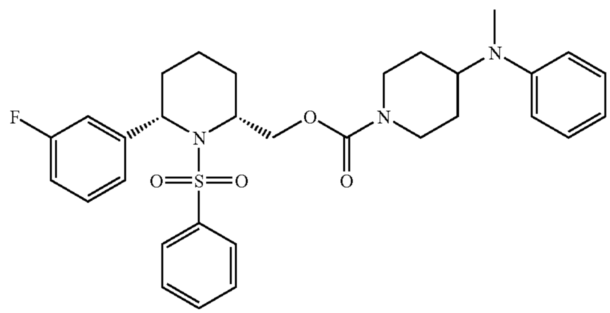 | 4.78 | 566.3 |
| 67-AS | 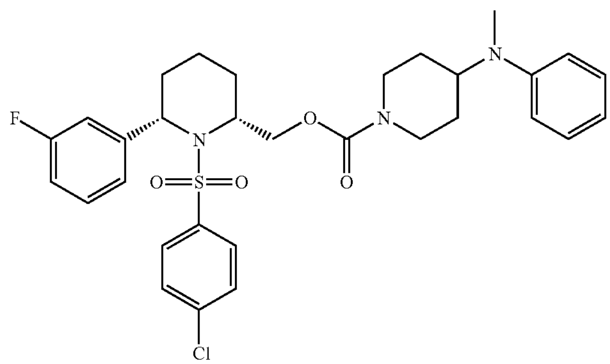 | 5.52 | 600.1 |
| 67-AT | 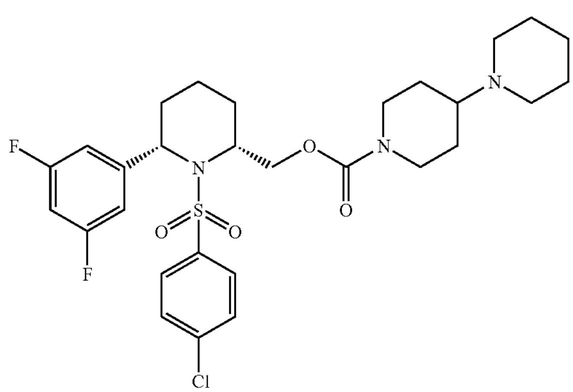 | 5.52 | 596.1 |
| 67-AV | 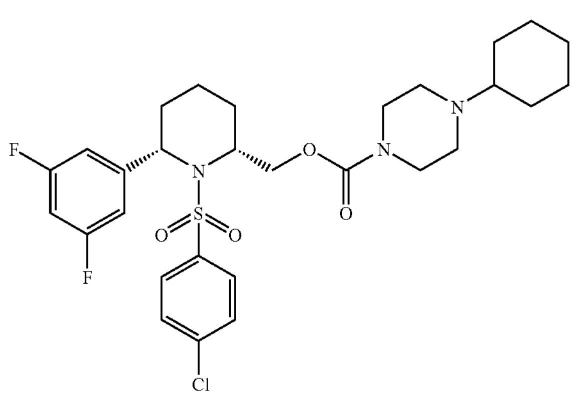 | 5.52 | 596.1 |

| Compound No. | Structure | Retention Time (minutes) | Observed Mass |
|---|---|---|---|
| 67-AW | 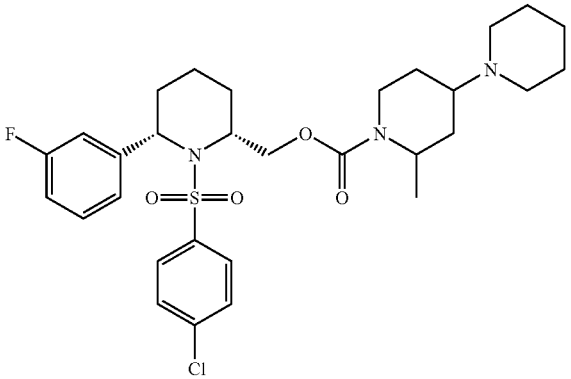 | 5.85 | 578.1 |
| 67-AX | 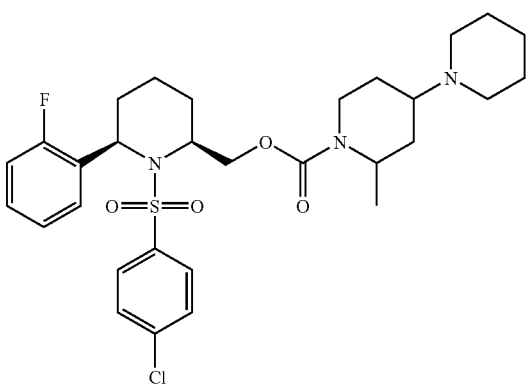 | 5.85 | 578.1 |
| 67-AY | 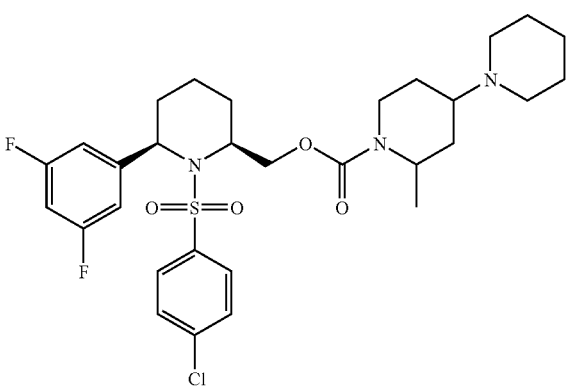 | 5.82 | 596.1 |
| 67-AZ | 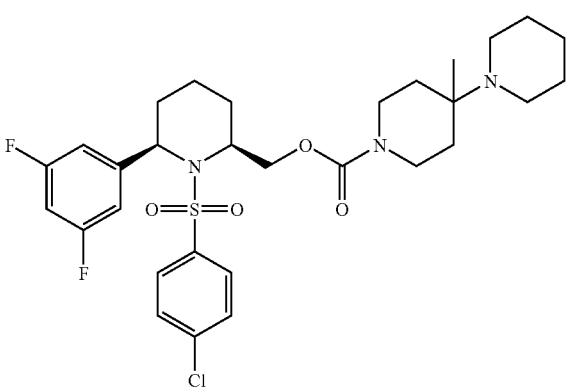 | 5.45 | 610.1 |

-continued

| Compound No. | Structure | Retention Time (minutes) | Observed Mass |
|---|---|---|---|
| 67-BA | 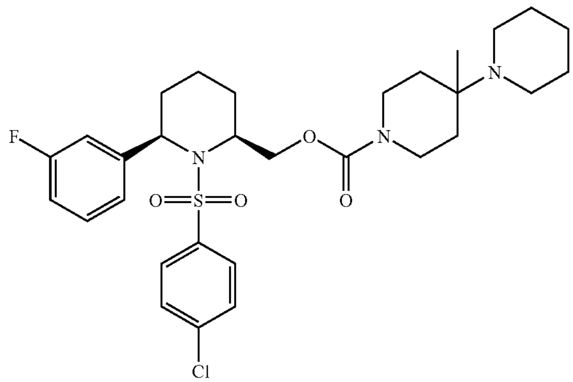 | 5.92 | 592.1 |
| 67-BB | 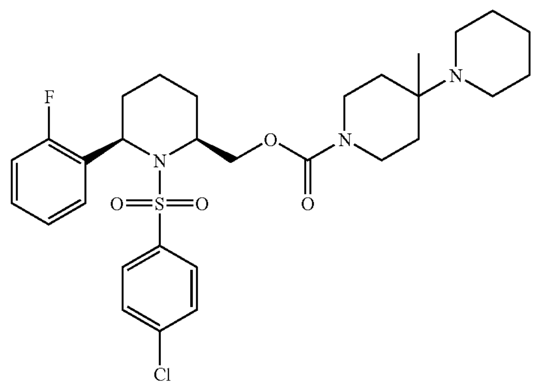 | 5.88 | 592.1 |
| 67-BC | 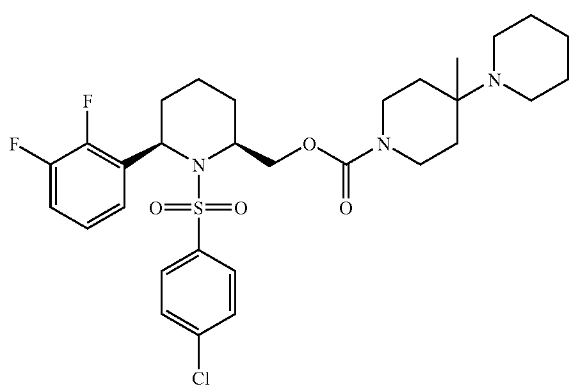 | 5.92 | 610.1 |
| 67-BD | 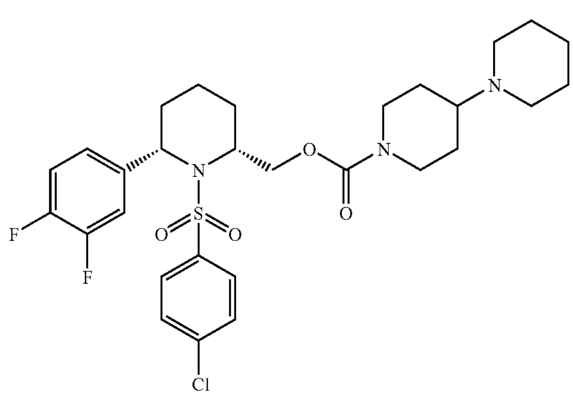 | 5.72 | 596.1 |

-continued

| Compound No. | Structure | Retention Time (minutes) | Observed Mass |
|---|---|---|---|
| 67-BE | 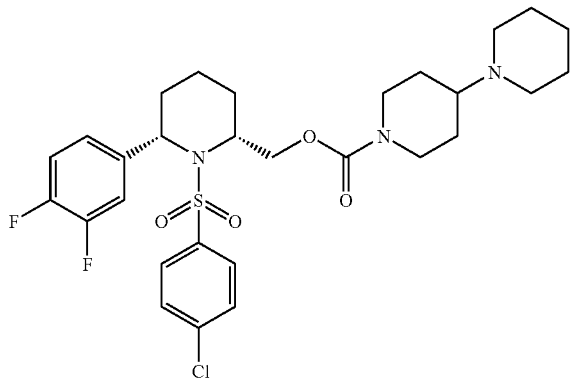 | 5.92 | 592.1 |
| 67-BF | 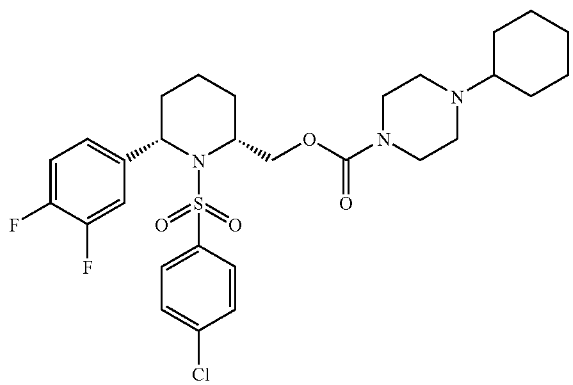 | 5.78 | 596.1 |
| 67-BG | 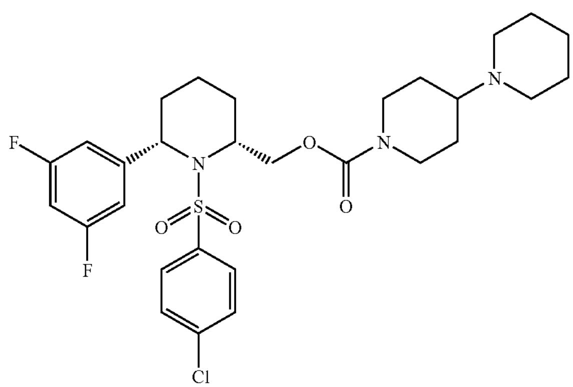 | 5.42 | 596.1 |
| 67-BH | 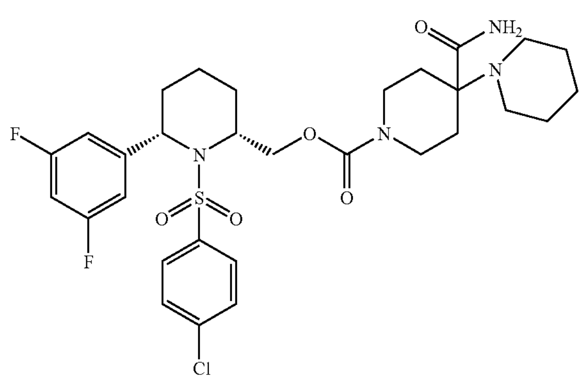 | 5.35 | 639.0 |

-continued

| Compound No. | Structure | Retention Time (minutes) | Observed Mass |
| --- | --- | --- | --- |
| 67-BI | 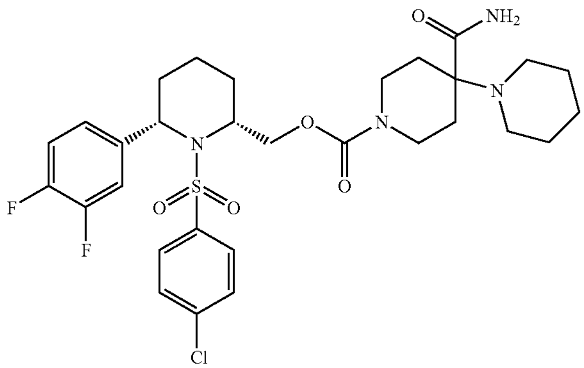 | 5.15 | 639.2 |
| 67-BJ | 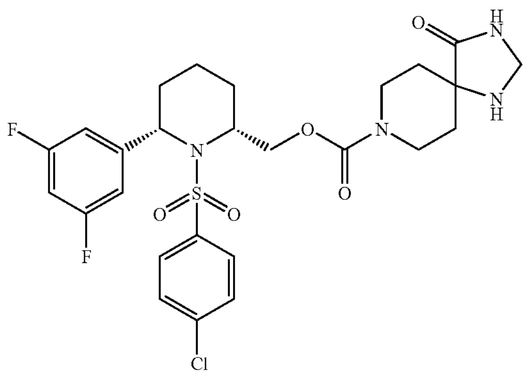 | 4.65 | 583.1 |
| 67-BK | 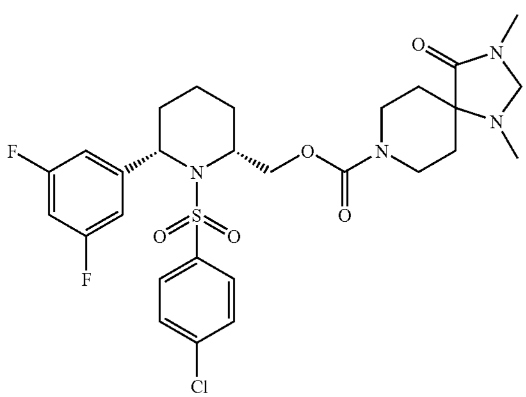 | 5.22 | 611.1 |
| 67-BL | 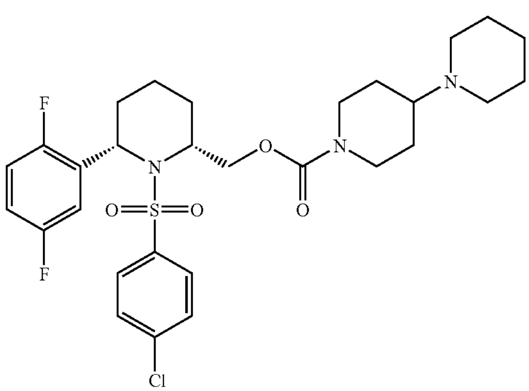 | 5.00 | 596.1 |

-continued

| Compound No. | Structure | Retention Time (minutes) | Observed Mass |
|---|---|---|---|
| 67-BM | 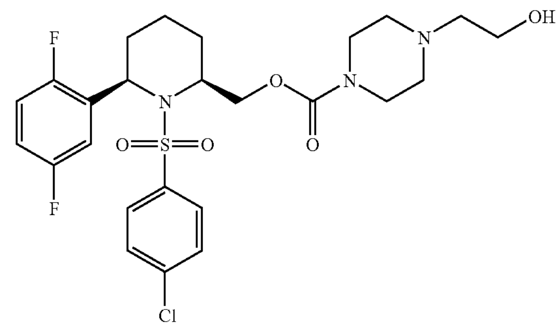 | 4.50 | 558.1 |
| 67-BN | 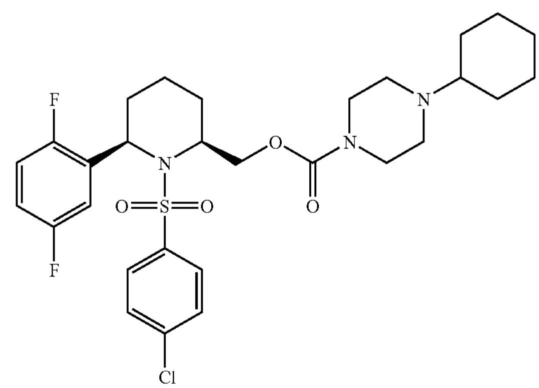 | 5.30 | 596.1 |
| 67-BO | 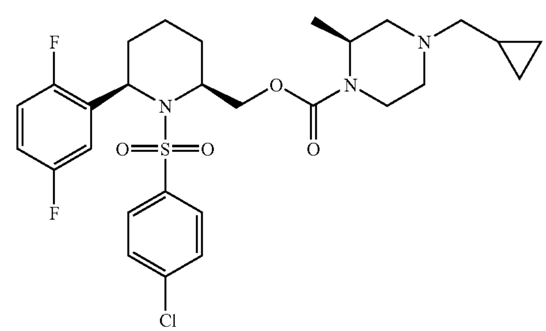 | 5.00 | 582.1 |
| 67-BP | 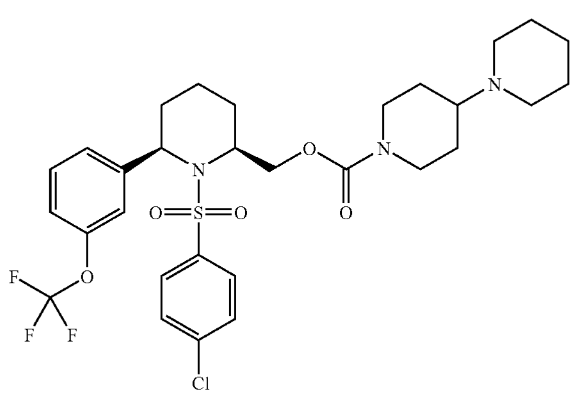 | 5.50 | 644.2 |

-continued

| Compound No. | Structure | Retention Time (minutes) | Observed Mass |
|---|---|---|---|
| 67-BQ | 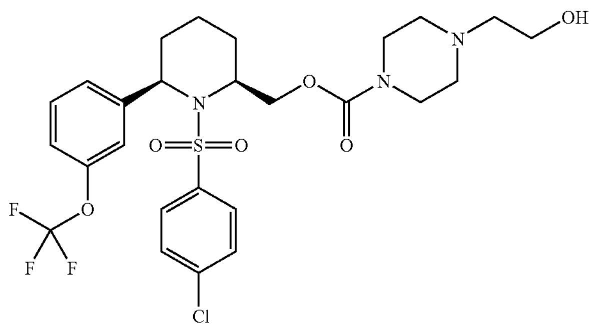 | 5.00 | 606.1 |
| 67-BR | 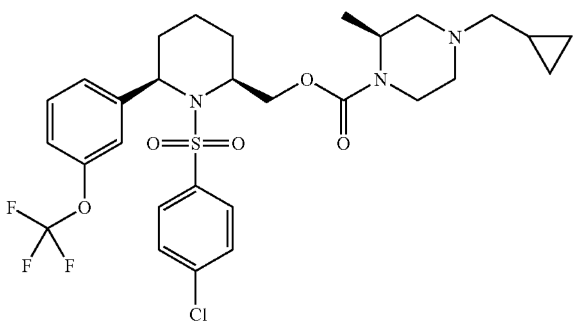 | 5.30 | 631.1 |
| 67-BS | 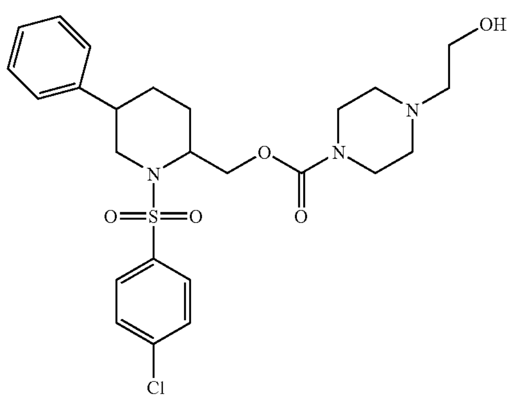 | 4.85 | 522.1 |

EXAMPLE 68

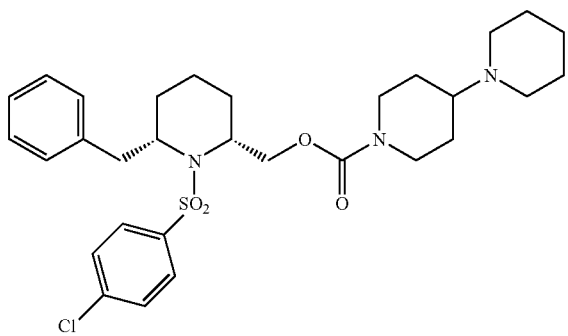

Step 1

(a) A solution of 1.00 g (4.29 mmol) of 2,6-dibromopyridine in a mixture of 20 mL of ether and 20 mL of THF was cooled to −78° C. (becomes turbid due to partial precipitation). To this was added drop-wise 1.86 mL (4.29 mmol) of 2.3 M BuLi, and the reaction was stirred for 5 min.

(b) Benzaldehyde (456 mg, 4.3 mmol) was added drop-wise to the above mixture, and the reaction was stirred in the cold for 15 min, quenched with saturated NaHCO₃, extracted with ethyl acetate, dried, concentrated. The residue was purified by chromatography using a gradient of 10–30% of ethyl acetate in hexane as solvent to give 0.85 g of oily product.

(c) A mixture of the above product, 5 ml of triethylsilane, 5 mL of TFA and 5 mL of DCM was heated at reflux over a period of 36 h. After evaporating most of the volatiles, the residue was redissolved in DCM, washed with 1M NaOH, dried, concentrated, and purified by chromatography using 5% ethyl acetate in hexanes. Obtained 0.55 g of the product.

Step 2

The product of step 1 was converted to the target compound using conditions described in Example 53, Preparations A and C. 1H NMR (CDCl3 300 MHz) δ 7.75 (2H, d, J=8.8 Hz), 7.44 (2H, d, J=8.8 Hz), 7.33–7.19 (5H, ser. m.), 4.42–4.22 (4H, ser. m.), 4.14 (1H, m), 3.98 (1H, m), 3.09 (1H, dd, J=12.0, 2.7 Hz), 2.90 (1H, t, J=12.0 Hz), 2.78 (2H, br), 2.51–2.37 (5H, ser. m.), 1.84–1.27 (16H, ser. m.); MS (ES) m/e 574.1 (M+H)+.

Following procedures similar to Example 68 the compounds in Table 6 were prepared.

TABLE 6

| EX No. | COMPOUND | Mass Spec |
|---|---|---|
| 69 | | 531.1 |
| 71 | | 534.1 |
| 72 | | 522.1 |
| 73 | | 534.1 |

TABLE 6-continued
| EX No. | COMPOUND | Mass Spec |
|---|---|---|
| 74 | 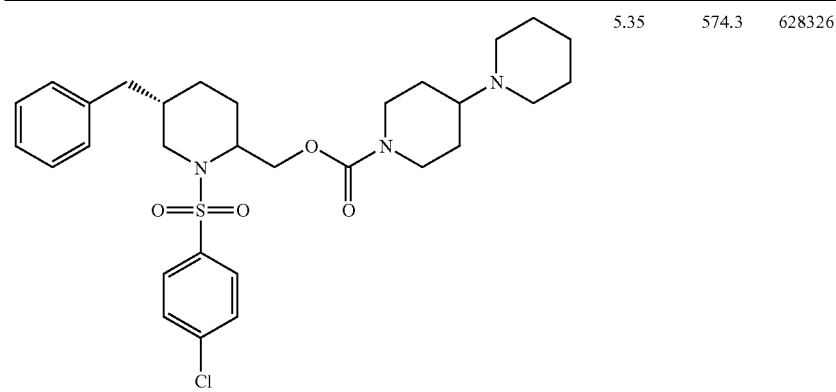 | 574.1 |
Also prepared were the following compounds:
| | Retention Time (minutes) | Observed Mass | |
|---|---|---|---|
| 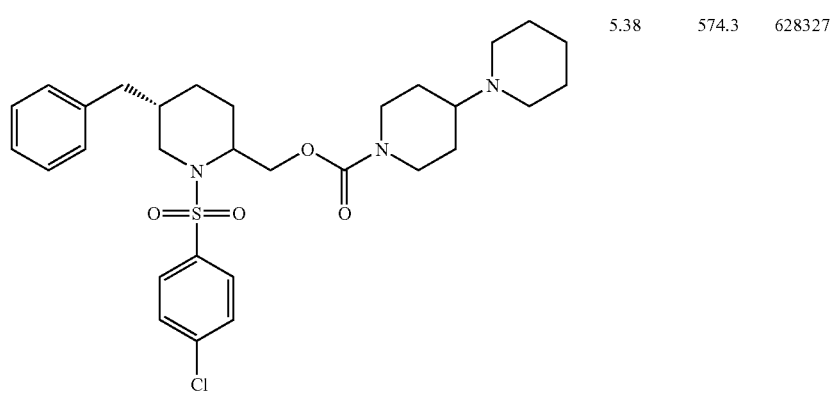 | 5.35 | 574.3 | 628326 |
| | 5.38 | 574.3 | 628327 |

| | Retention Time (minutes) | Observed Mass | |
|---|---|---|---|
| 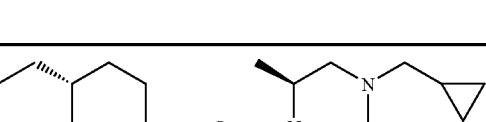 | 5.05 | 560.3 | 629247 |

EXAMPLE 75

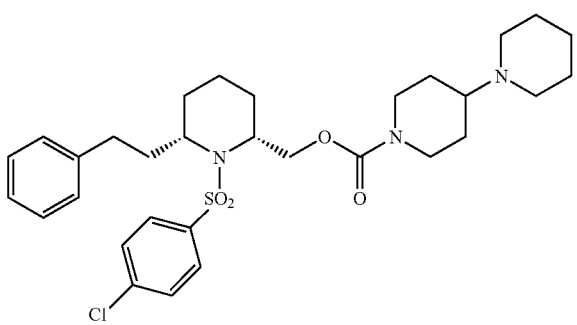

Step 1

To a solution of 5.0 g (21.4 mmol) of 2,6-dibromopyridine in 50.0 mL of DCM was added 5.6 mL (40 mmol) of triethylamine, 701 mg (1 mmol) of Pd(PPh$_3$)$_4$Cl$_2$, 95 mg (0.5 mmol) of CuI, and a mixture of phenylacetylene in 20.0 mL of DCM. The dark mixture was stirred overnight, washed with concentrated ammonium hydroxide, dried, concentrated, and chromatographed. Fractions containing the desired product of mono-substitution of bromine were identified by MS (m/z=258.1), yield 2.41 g.

Step 2

The product of step 1 was converted to the target compound using conditions described in Example 53, Preparations A and C. $^1$H NMR (CDCl3 300 MHz) δ 7.73 (2H, d, J=8.8 Hz), 7.45 (2H, d, J=8.8 Hz), 7.31–7.16 (5H, ser. m.), 4.30 (4H, m), 4.13 (1H, m), 3.97 (1H, m), 2.73 (4H, m), 2.42 (5H, m), 2.04 (1H, m), 1.78–1.15 (17H, ser. m.); MS (ES) m/e 588.1 (M+H)$^+$.

Following procedures similar to those of Example 75 the compounds in Table 7 were prepared.

TABLE 7

| EX No. | COMPOUND | Mass Spec |
|---|---|---|
| 76 | (structure shown) | 545.1 |

TABLE 7-continued

| EX No. | COMPOUND | Mass Spec |
|---|---|---|
| 78 | | 548.1 |
| 79 | | 536.1 |
| 80 | | 548.1 |
| 81 | | 588.1 |

EXAMPLE 82

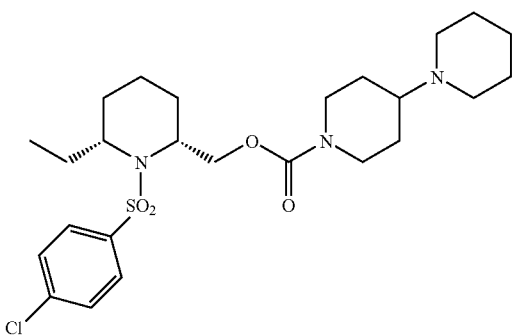

Step 1

To a solution of 5.0 g (21.2 mmol) of 2,6-dibromopyridine in THF at −78° C. was added 9.2 mL (21 mmol) of 2.3 M solution of n-BuLi in hexanes, followed by 2.3 mL (30 mmol) of DMF. The mixture was stirred for 45 min in the cold, quenched with saturated $NaHCO_3$, extracted with ethyl acetate and the product purified by column chromatography (3% ethyl acetate in hexanes) to furnish 1.13 g of 2-bromo-6-formylpyridine.

Step 2

(a) A mixture containing 750 mg (4.05 mmol) of product of step 1, 1.41 g (4.46 mmol) of vinyltributyltin, 231 mg (0.2 mmol) of $Pd(PPh_3)_4$, and 5.0 mL of DMF was heated for 12 h at 90° C. The volatiles were evaporated, and the residue purified by chromatography (3–5% ethyl acetate in hexanes) to furnish 360 mg of 2-formyl-6-vilylpyridine.

(b) The above product was hydrogenated at 50 psi over catalytic $PtO_2$ using 1:3 mixture of AcOH and MeOH as solvent to furnish 87 mg of reduced product

Step 3

The product of step 2 was converted to the target compound using conditions described in Example 53, Preparations C. $^1$H NMR (CDCl3 300 MHz) δ 7.77 (2H, d, J=8 Hz), 7.47 (2H, d, J=8 Hz), 4.29–4.22 (4H, ser. m.), 4.05 (1H, m), 3.79 (1H, m), 2.77 (2H, br), 2.50–2.37 (5H, ser. m.), 1.83–1.70 (6H, ser. m.), 1.62–1.10 (12H, ser. m.), 0.96 (3H, t, J=7.3 Hz); MS (ES) m/e 512.1 $(M+H)^+$.

Following procedures similar to those of Example 82 the compounds in Table 8 were prepared.

TABLE 8

| EX No. | COMPOUND | Mass Spec |
|---|---|---|
| 83 | | 469.1 |
| 85 | | 472.1 |
| 86 | | 472.1 |

TABLE 8-continued

| EX No. | COMPOUND | Mass Spec |
|---|---|---|
| 87 | | 512.1 |

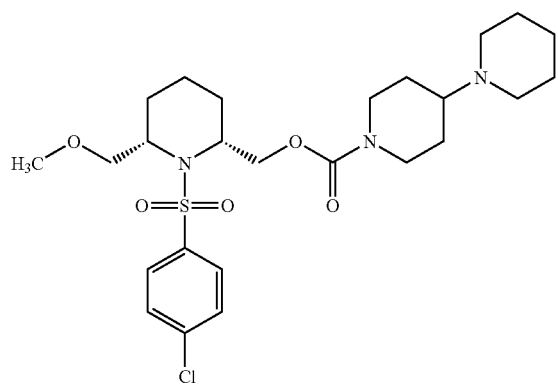

EXAMPLE 88

Step 1

To a solution of 2,6-pyridinedicarboxylate methyl ester (19.52 g; 100 mmol) in ice-cooled anhydrous methanol (300 ml) is added sodium borohydride (3.03 g; 80 mmol) portionwise then the reaction is stirred 30 min at room temperature. Another 1.0 g of sodium borohydride is added to the mixture and the reaction is stirred an additional 30 minutes. After concentration, the crude is diluted with water and $CH_2Cl_2$ and extracted with $CH_2Cl_2$. Combined organic layers are dried over $Na_2SO_4$, concentrated, and the residue is subjected to flash-chromatography over silica gel (eluting $CH_2Cl_2$/MeOH 95:5) to give 11.09 g (66%) of alcohol, as a white solid, Step 2

To a solution of alcohol (9.00 g; 53.8 mmol) in anhydrous THF (200 mL) at 0° C. is added NaH 60% in mineral oil (2.60 g; 64.6 mmol) followed by dimethylsulfate (6.60 ml; 70 mmol) and the reaction is stirred 2 h at 35° C. After concentration, the crude is diluted with water and extracted with $CH_2Cl_2$. Combined organic layers are dried over Na2SO4, concentrated, and the residue is subjected to flash-chromatography over silica gel (eluting CH2Cl2/MeOH 95:5). The purified product is dissolved in $CH_2Cl_2$/MeOH, treated with an excess of 1 N HCl in Et2O and concentrated to provide 11.5 g (98%) of pyridine intermediate, as a hydrochloride salt.

Step 3

A mixture of pyridine intermediate (11.50 g; 52.8 mmol) and platinum (IV) oxide (1 g) in ethanol is hydrogenated 16 h at 40 psi, filtered over Celite and concentrated to provide 11.60 g of crude piperidine amine, as a white solid.

Step 4

To a suspension of piperidine amine (11.60 g; 52.1 mmol) in anhydrous THF (50 ml) at 0° C. is slowly added lithium aluminum hydride 1 N in THF (200 ml; 200 mmol), then the reaction is allowed to warm to room temperature and stirred an additional 1 h. The reaction is quenched with an excess of AcOEt, diluted with 0.5 N aqueous NaOH solution, and extracted with AcOEt and $CH_2Cl_2$. Combined organic layers are dried over $Na_2SO_4$ and concentrated to provide 8.3 g of crude piperidine alcohol, as an oil.

Step 5

A solution of piperidine alcohol (8.3 g; 52.1 mmol), tert-butyldimethylsilyl chloride (8.6 g; 57.3 mmol) and triethylamine (8.7 ml; 62.5 mmol) in anhydrous 1,2-dichloroethane (100 ml) is stirred 16 h at 60° C. The reaction mixture is diluted with 0.5 N aqueous NaOH solution and extracted with $CH_2Cl_2$. Combined organic layers are dried over $Na_2SO_4$, concentrated, and the residue is subjected to flash-chromatography over silica gel (eluting $CH_2Cl_2$/AcOEt 95:5 to 70:30) to provide 5.0 g (35%) of O-protected piperidine, as an oil.

Step 6

A solution of O-protected piperidine (2.50 g; 9.14 mmol), 4-chlorobenzenesulfonyl chloride (2.90 g; 13.7 mmol) and triethylamine (1.53 ml; 11 mmol) in anhydrous 1,2-dichloroethane (25 ml) is stirred 3 h at 60° C. then overnight at room temperature. The reaction mixture is diluted with 0.5 N aqueous NaOH solution and extracted with CH2Cl2. Combined organic layers are dried over $Na_2SO_4$, concentrated, and the residue is subjected to flash-chromatography over silica gel (eluting $CH_2Cl_2$) to provide 3.72 g (90%) of O-protected sulfonamide, as an oil.

Step 7

To a solution of O-protected sulfonamide (3.70 g; 8.3 mmol) in anhydrous THF (50 ml) is added TBAF 1 N in THF (16.6 ml; 16.6 mmol) and the reaction is stirred overnight at room temperature. After concentration, the crude is diluted with 5% NaHCO$_3$ aqueous solution and extracted with CH$_2$Cl$_2$. Combined organic layers are dried over Na$_2$SO$_4$, concentrated, and the residue is subjected to flash-chromatography over silica gel (eluting CH2Cl2) to give 2.50 g (93%) of sulfonamide alcohol, as an oil: $^1$H-NMR (300 MHz, CDCl$_3$) δ 7.79 (d, J=8.8 Hz, 2H), 7.47 (d, J=8.8 Hz, 2H), 4.24 (m, 1 H), 4.09 (m, 1H), 3.40–3.70 (m, 4H), 3.37 (s, 3H), 1.40–1.70 (m, 3H), 1.20–1.40 (m, 3H); HRMS (MH$^+$) 334.0883.

Step 8

To a solution of sulfonamide alcohol (2.50 g; 7.50 mmol) and p-nitrophenyl chloroformate (1.70 g; 8.25 mmol) in anhydrous THF (30 ml) is slowly added triethylamine (1.20 ml; 8.25 mmol) and the reaction is stirred overnight at room temperature. After concentration, the residue is subjected to flash-chromatography over silica gel (eluting Hexanes/AcOEt 90:10) to give 3.70 g (99%) of sulfonamide p-nitrophenylcarbonate, as a foam.

Step 9

A solution of sulfonamide p-nitrophenylcarbonate (50 mg; 0.10 mmol) and 4-piperidinopiperidine (84 mg; 0.50 mmol) in 1,2-dichloroethane (1 ml) is stirred overnight at room temperature. The reaction mixture is diluted with 0.5 N aqueous NaOH solution and CH$_2$Cl$_2$ and the organic layer is directly subjected to preparative chromatography over silica gel (eluting CH2Cl2) then treated with dry 1 N HCl in Et$_2$O to provide 7 mg of product: $^1$ H-NMR (300 MHz, CDCl$_3$) δ 7.76 (d, J=8.8 Hz, 2H), 7.46 (d, J=8.8 Hz, 2H), 4.15–4.35 (m, 4H), 3.85–4.00 (m, 2H), 3.40–3.55 (m, 3H), 3.34 (s, 3H), 2.65–2.90 (m, 2H), 2.10–2.60 (m, 6H), 1.80–1.90 (brd, 2H), 1.00–1.80 (m, 12H); HRMS (MH$^+$): 528.2305.

Following the procedures similar to those in Example 88 the compounds in Table 9 were prepared.

TABLE 9

| EX No. | COMPOUND | High Res. Mass Spec |
|---|---|---|
| 89 | | 476.1985 |
| 90 | | 490.1776 |
| 91 | | 485.1630 |

TABLE 9-continued

| EX No. | COMPOUND | High Res. Mass Spec |
|---|---|---|
| 92 | | 523.1792 |
| 93 | | 460.1440 |
| 94 | | 462.1656 |
| 95 | | 488.1989 |

TABLE 9-continued
| EX No. | COMPOUND | High Res. Mass Spec |
|---|---|---|
| 96 | 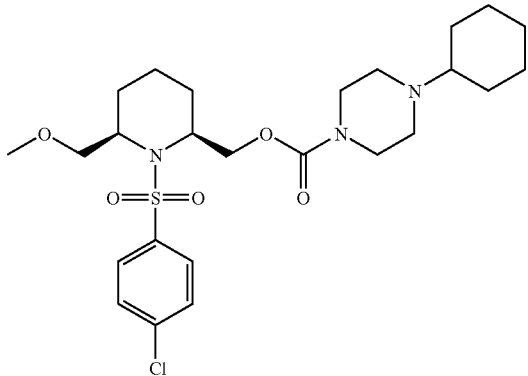 | 528.2304 |
| 97 | 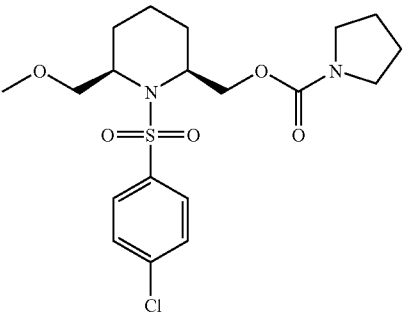 | 431.1413 |
| 98 | 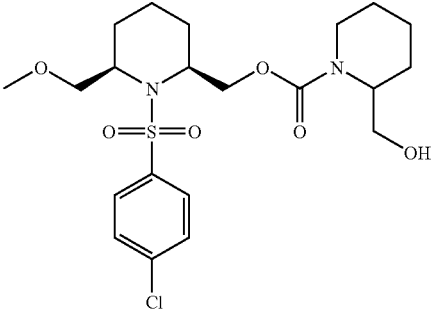 | 475.1661 |
| 99 | 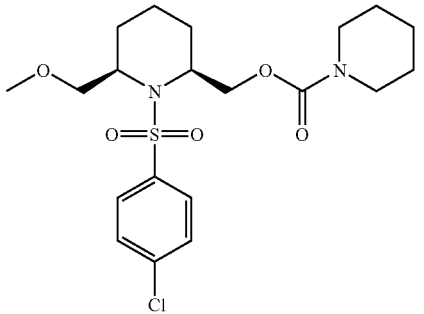 | 445.1568 |

TABLE 9-continued

| EX No. | COMPOUND | High Res. Mass Spec |
|---|---|---|
| 101 | (structure) | 496.1679 |
| 102 | (structure) | 488.1986 |
| 103 | (structure) | 460.1677 |
| 104 | (structure) | 334.0883 |

NMR data for compounds in Table 9 is given in Table 10.
TABLE 10
| EX No. | COMPOUND | NMR (δ) |
|---|---|---|
| 92 | 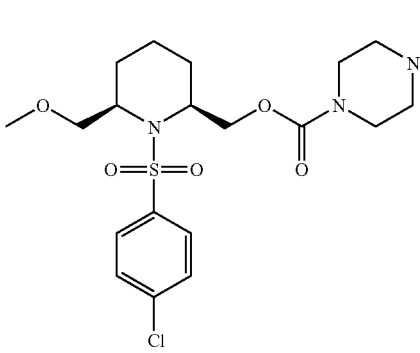 | 8.19 (d, J = 3.9 Hz, 1H), 7.77 (d, J = 8.8 Hz, 2H), 7.40–7.55 (m, 3H), 6.60–6.75 (m, 2H), 4.20–4.35 (m, 2H). 3.95–4.05 (m, 2H), 3.40–3.75 (m, 10H), 3.35 (s, 3H), 1.50–1.80 (m, 3H), 1.05–1.40 (m, 3H) |
| 94 | 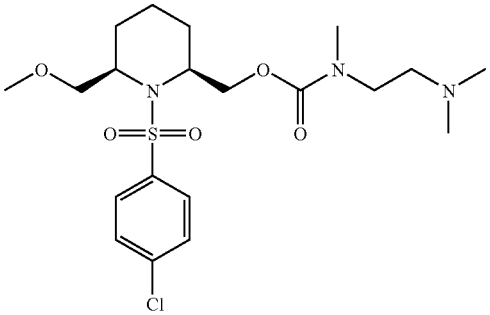 | 7.78 (d, J = 8.8 Hz, 2H), 7.46 (d, J = 8.8 Hz, 2H), 4.15–4.35 (m, 2H), 3.90–4.05 (m, 2H), 3.35–3.60 (m, 4H), 3.35 (s, 3H), 2.96 (s, 3H), 2.45–2.60 (m, 2H), 2.31 (s, 3H), 2.28 (s, 3H), 1.45–1.80 (m, 3H), 1.20–1.40 (m, 2H), 1.13 (m, 1H) |
| 96 | 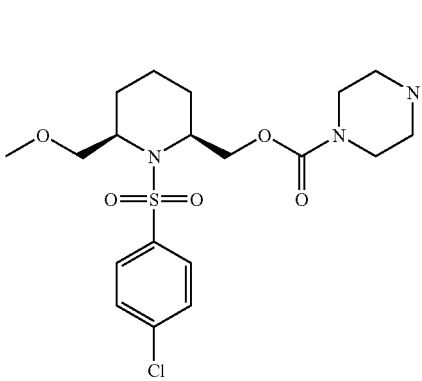 | 7.76 (d, J = 8.8 Hz, 2H), 7.46 (d, J = 8.8 Hz, 2H), 4.15–4.35 (m, 2H), 3.90–4.00 (m, 2H), 3.40–3.60 (m, 6H), 3.34 (s, 3H), 2.45–2.65 (m, 4H), 2.29 (m, 1H), 1.45–1.90 (m, 6H), 1.00–1.40 (m, 10H) |
| 100 | 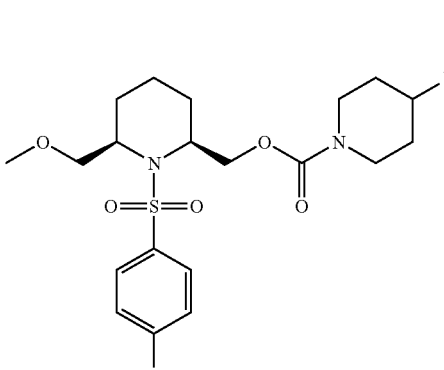 | 7.76 (d, J = 8.8 Hz, 2H), 7.46 (d, J = 8.8 Hz, 2H), 4.15–4.35 (m, 4H), 3.85–4.00 (m, 2H), 3.40–3.55 (m, 3H), 3.34 (s, 3H), 2.65–2.90 (m, 2H), 2.10–2.60 (m, 6H), 1.80–1.90 (br d, 2H), 1.00–1.80 (m, 12H) |

TABLE 10-continued

| EX No. | COMPOUND | NMR (δ) |
|---|---|---|
| 104 | 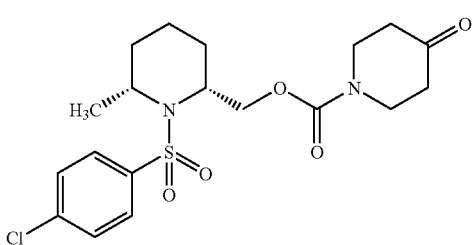 | 7.79 (d, J = 8.8 Hz, 2H), 7.47 (d, J = 8.8 Hz, 2H), 4.24 (m, 1H), 4.09 (m, 1H), 3.40–3.70 (m, 4H), 3.37 (s, 3H), 1.40–1.70 (m, 3H), 1.20–1.40 (m, 3H) |

EXAMPLE 105

Preparation A

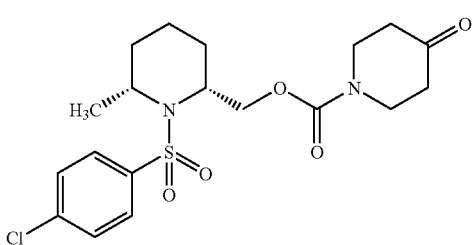

Step 1

Treat the 4-nitrophenylcarbonate product of Example 1, step 4-a (1.26 g) in methanol (50 mL) with 1,4-dioxa-8-azaspiro[4.5]decane (0.76 mL) and stir the resulting mixture at room temperature for 66 h. Concentrate the reaction mixture in vacuo and partition the residue between ethyl acetate/10% sodium hydroxide solution. Extract the ethyl acetate (EtOAc) solution with water, and then brine. Concentrate the dried (MgSO4) EtOAc solution in vacuo to give a pale yellow oil (1.26 g). Chromatograph this oil on silica gel plates (8, 1000□) using EtOAc:hexane 1:3 as eluant (two elutions) to give the title compound, as a colorless oil (1.11 g).

Step 2

To the product of step 1 (1.10 g) in dichloromethane (20 mL), add 40% trifluoroacetic acid (TFA) in water (8 mL), and stir the resulting mixture for 4 hr. Add additional 40% TFA in water (6 mL). After 2 h, add 40% TFA in water (3 ml). Stir the resulting mixture at room temperature for 18 hr. Separate the reaction mixture. Partition the dichloromethane solution water and then sodium bicarbonate solution. Concentrate the dried (MgSO$_4$) dichloromethane solution in vacuo to give a colorless foam. Chromatograph this foam on silica gel plates (8, 1000□) using EtOAc:hexane 1:3 as eluant to give the title compound (0.80 g).

Preparation B

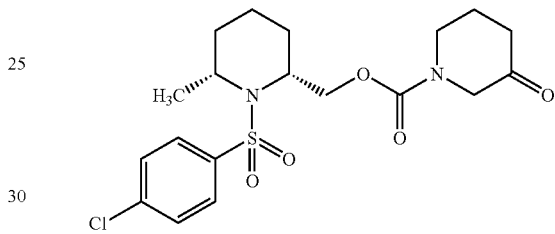

Step 1

Treat the 4-nitrophenylcarbonate product of Example 1, step 4-a (0.100 g) in methanol (55 mL) with 3-hydroxypiperidine (0.060 g, liberated from the hydrochloride salt) and stir the resulting mixture at room temperature for 24 h. Concentrate the reaction mixture in vacuo and partition the residue between ethyl acetate/10% sodium hydroxide solution. Extract the ethyl acetate (EtOAc) solution with water, and then brine. Concentrate the dried (MgSO$_4$) EtOAc solution in vacuo to give the title compound, as a colorless oil (0.10 g).

Step 2

Treat the product from step 1, in acetone (5 mL) with Jones Reagent (0.40 mL) for 40 min at room temperature. Quench the reaction mixture with MeOH (2 mL), filter, and dilute with dichloromethane. Extract the organic mixture with brine. Concentrate the dried (MgSO4) solution in vacuo to a residue (0.070 g). Chromatograph this residue on silica gel plates (1, 1000□) using EtOAc:hexane 1:3 as eluant to give the title compound (0.040 g).

Preparation C

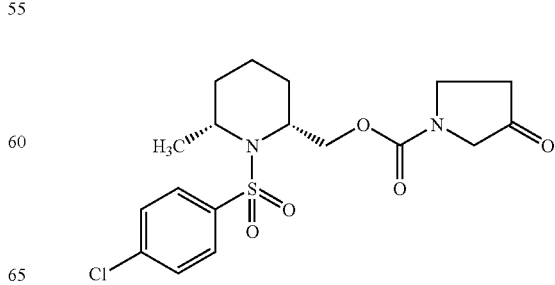

Follow essentially the same procedure as Preparation B, except start with 3-hydroxypyrrolidine (0.060 g) to give the title compound (0.030 g).

Preparation D

Following the procedure described below, the compounds in Table 11 are prepared from the appropriate ketones and amines. The ketones and amines used will be apparent to those skilled in the art from the compounds in Table 11.

Using Bohdan Miniblocks (6 mL cartridge), dispense ketones from Preparation A, B or C (0.010 g) in MeOH: AcOH 9:1 (1 mL). Add amines (1.2 equiv) followed by MP-cyanoborohydride resin (~2 equiv, 20 to 30 mg., 2.37 mmol/g, Argonaut). Shake the resulting mixture at room temperature for 20 hr. Add PS-isocyanate resin (50–60 mg, 4 equiv. 1.44 mmol/1 g, Argonaut). After 4h, add additional PS-isocyanate resin (90–100 mg) and leave shaking overnight. Filter from Bohdan block to block and wash the residue with MeOH (1 mL). Add MP-TsOH resin (~4 equiv., 1.46 mmol/mg, Argonaut) to filtrate followed by dichloroethane (1 mL). Shake for 2–4 hr. Drain and wash with MeOH (1 mL, 3 times). Add 2M $NH_3$/MeOH (1.5 mL), shake for 30 min. Drain into vials. Add 2M $NH_3$/MeOH (2 mL) and shake for 10 min. and drain. Remove the solvent in to give the products in Table 11.

TABLE 11

| EX No. | COMPOUND | Mass Spec |
|---|---|---|
| 106 | | 498 |
| 107 | | 500 |
| 108 | | 500 |

TABLE 11-continued

| EX No. | COMPOUND | Mass Spec |
|---|---|---|
| 109 | | 512 |
| 110 | | 513 |
| 111 | | 514 |

TABLE 11-continued

| EX No. | COMPOUND | Mass Spec |
|---|---|---|
| 112 | | 516 |
| 113 | | 526 |
| 114 | | 527 |

TABLE 11-continued
| EX No. | COMPOUND | Mass Spec |
|---|---|---|
| 115 | 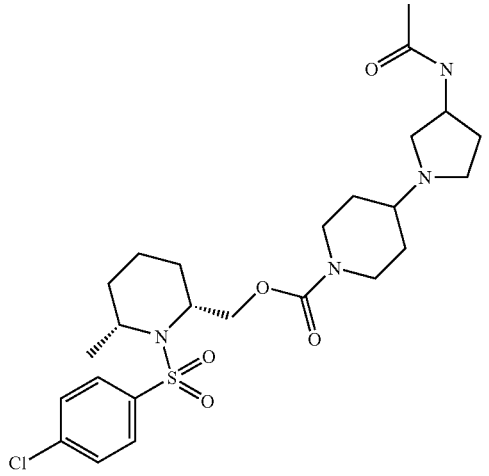 | 541 |
| 116 | 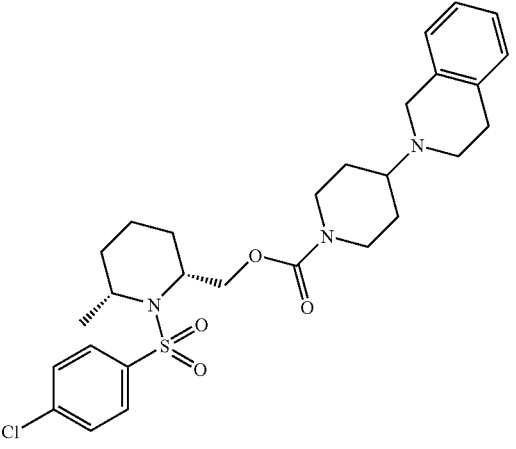 | 546 |
| 117 | 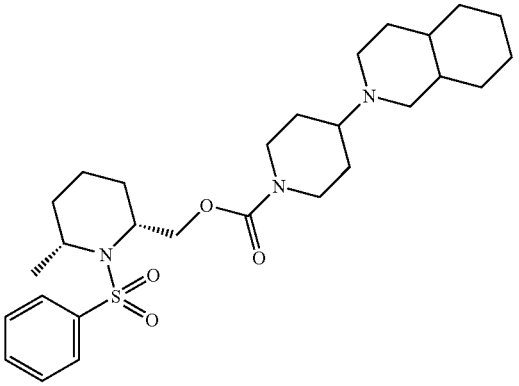 | 552 |

TABLE 11-continued

| EX No. | COMPOUND | Mass Spec |
|---|---|---|
| 118 | | 581 |
| 119 | | 527 |
| 120 | | 541 |
| 121 | | 548 |

TABLE 11-continued

| EX No. | COMPOUND | Mass Spec |
|---|---|---|
| 122 | | 484 |
| 123 | | 502 |
| 124 | | 526 |
| 125 | | 527 |

TABLE 11-continued
| EX No. | COMPOUND | Mass Spec |
|---|---|---|
| 126 | 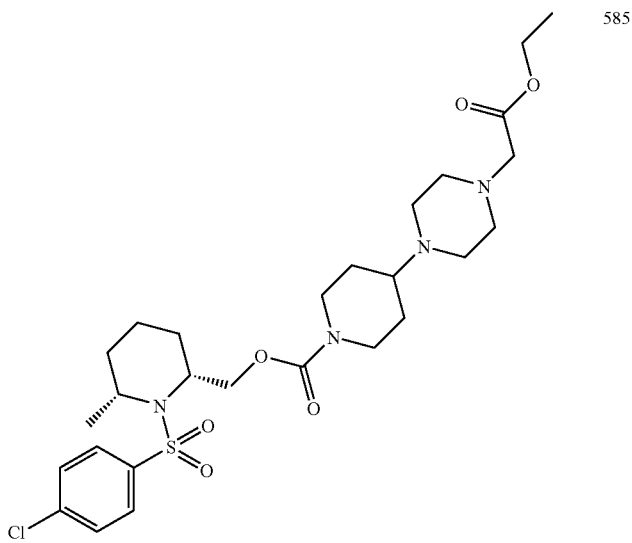 | 585 |
| 127 | 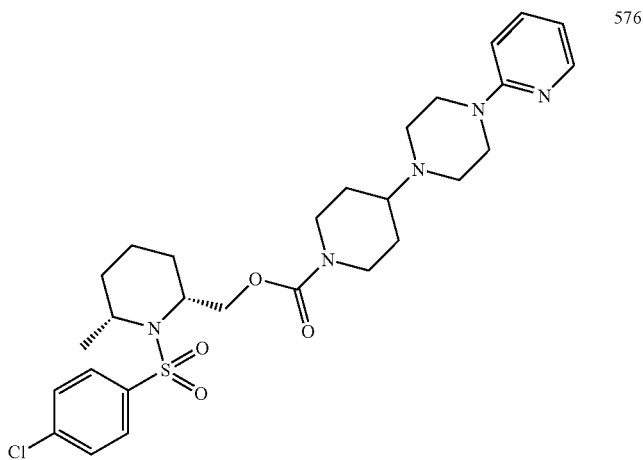 | 576 |
| 128 | 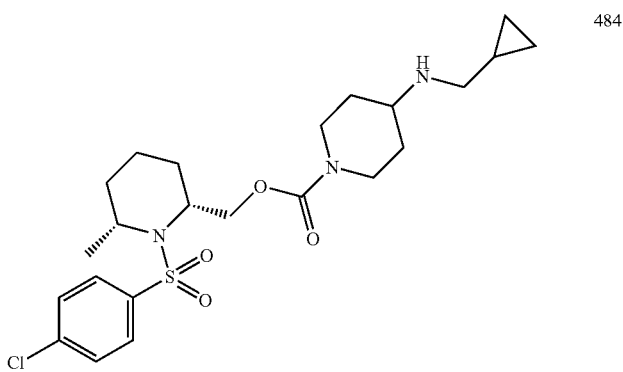 | 484 |

TABLE 11-continued

| EX No. | COMPOUND | Mass Spec |
|---|---|---|
| 129 | | 534 |
| 130 | | 498 |
| 131 | | 470 |
| 132 | | 484 |

TABLE 11-continued

| EX No. | COMPOUND | Mass Spec |
|---|---|---|
| 133 | | 512 |
| 134 | | 486 |
| 135 | | 499 |
| 136 | | 500 |

TABLE 11-continued

| EX No. | COMPOUND | Mass Spec |
|---|---|---|
| 137 | | 532 |
| 138 | | 498 |
| 139 | | 512 |
| 140 | | 464 |

TABLE 11-continued

| EX No. | COMPOUND | Mass Spec |
|---|---|---|
| 141 | | 526 |
| 142 | | 500 |
| 143 | | 513 |
| 144 | | 514 |

TABLE 11-continued
| EX No. | COMPOUND | Mass Spec |
|---|---|---|
| 145 | 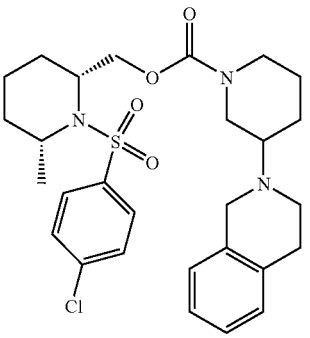 | 546 |
| 146 | 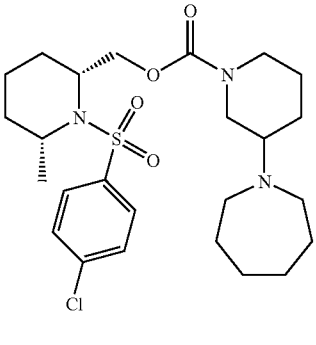 | 512 |
| 147 | 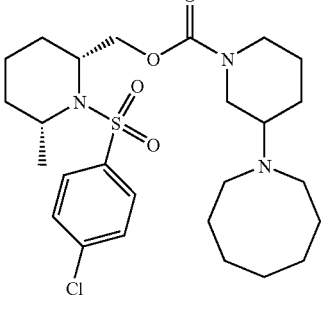 | 526 |
| 148 | 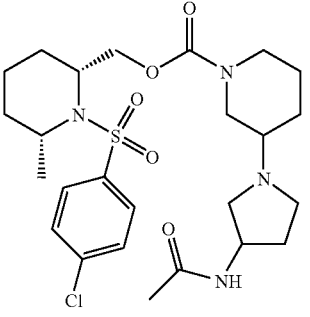 | 541 |

TABLE 11-continued
| EX No. | COMPOUND | Mass Spec |
|---|---|---|
| 149 | 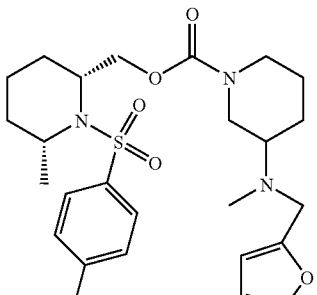 | 524 |
| 150 | 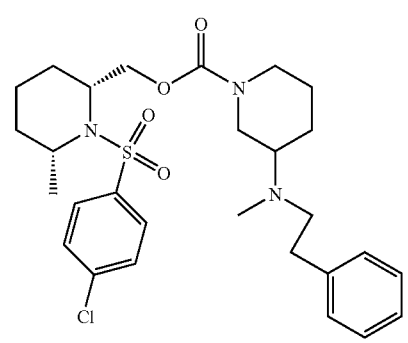 | 548 |
| 151 | 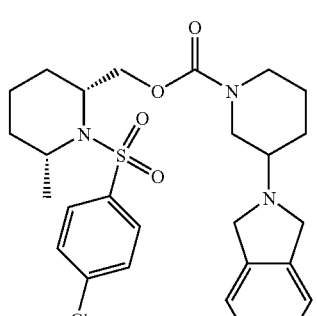 | 532 |
| 152 | 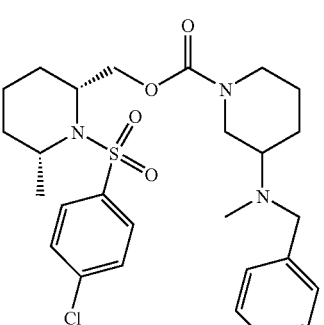 | 534 |

TABLE 11-continued

| EX No. | COMPOUND | Mass Spec |
|---|---|---|
| 153 | | 589 |
| 154 | | 571 |
| 155 | | 541 |
| 156 | | 556 |

TABLE 11-continued

| EX No. | COMPOUND | Mass Spec |
|---|---|---|
| 157 | 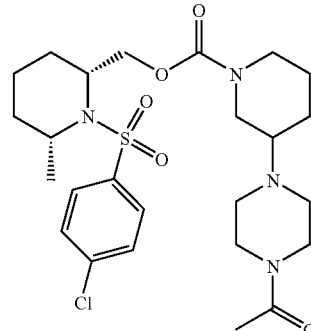 | 541 |
| 158 | 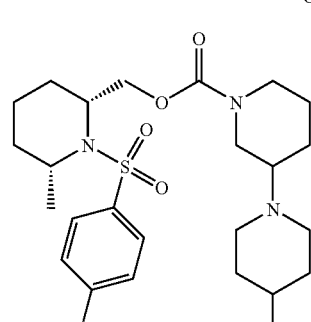 | 541 |

EXAMPLE 159

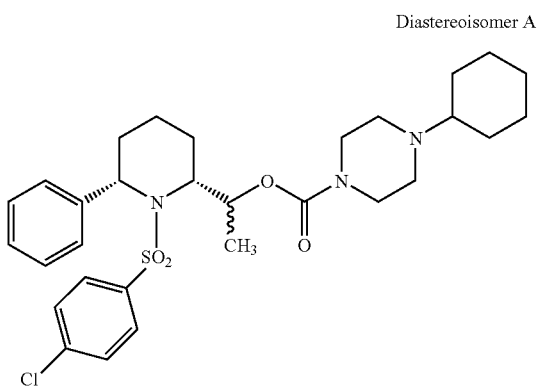

Diastereoisomer A

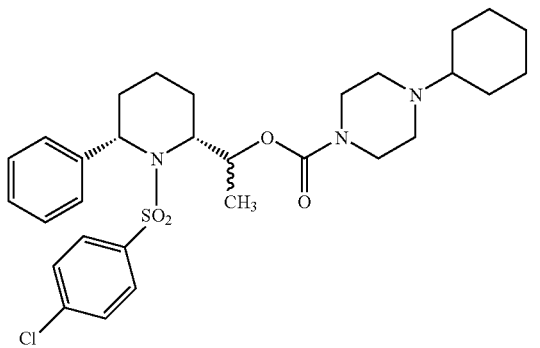

Diastereoisomer B

Step 1

To a solution of the 1-(4-chloro-benzenesulfonyl)-6-phenyl-piperidin-2-yl-methanol prepared according to Example 53 Preparation C Step 1 (300 mg; 0.82 mmol) in DCM (8 ml) was added Dess-Martin periodinane (850 mg; 2.0 mmol) followed by sodium bicarbonate (100 mg) and two drops of water. The mixture was stirred overnight at room temperature, then quenched with $Et_2O$ (20 mL), saturated $NaHCO_3$ and sodium thiosulfite (2.0 g) for 20 minutes. The reaction was extracted with $Et_2O$, dried over $Na_2SO_4$ and concentrated to provide 232 mg (78%) of 1-(4-chloro-benzenesulfonyl)-6-phenyl-piperidine-2-carbaldehyde as an oil.

Step 2

To a solution of the product of step 1 (232 mg; 0.64 mmol) in THF (6 mL) at 0° C. was added methyl magnesium bromide solution 3 N in $Et_2O$ (0.27 mL; 0.83 mmol) and the reaction was allowed to warm to room temperature for 1 h. The mixture was poured into saturated ammonium chloride, extracted with DCM, and dried over $Na_2SO_4$. After concentration of the solvents, the residue was purified by chromatography over silica gel (eluting Hexanes/EtOAc 8:2) to give 240 mg (100%) of 1-[1-(4-chloro-benzenesulfonyl)-6-phenyl-piperidin-2-yl]-ethanol as a ca 4.5:1 mixture of diastereoisomers.

Step 3

The product of Step 2 was converted to the title compounds according to Step 4 of Example 1, using N-cyclohexylpiperazine at the last stage as the amine. The diastereoisomers were separated at the last stage by chromatography on silica gel (eluting Hexanes/EtOAc 8:2) to provide, in order of elution:

(i) Diastereoisomer A: $^1$H-NMR (300 MHz, CDCl$_3$) δ 7.86 (d, J=6.0 Hz, 2H), 7.60 (d, J=6.0 Hz, 2H), 7.53 (d, J=6.0 Hz, 2H), 7.30–7.45 (m, 2H), 7.20–7.30 (m, 1H), 5.25 (d, J=4.5 Hz, 2H), 4.35–4.50 (m, 1H), 3.90–4.00 (m, 1H), 3.20–3.50 (m, 4H), 2.15–2.60 (m, 5H) 1.70–2.05 (m, 5H), 1.50–1.65 (m, 2H), 1.00–1.45 (m, 9H), 0.99 (d, J=4.5 Hz, 2H); HRMS (MH$^+$) 574.2500.

(ii) Diastereoisomer B: $^1$H-NMR (300 MHz, CDCl$_3$) δ 7.84 (d, J=6.0 Hz, 2H), 7.45–7.60 (m, 4H), 7.25–7.40 (m, 3H), 5.23 (m, 1H), 4.30–4.45 (m, 1H), 4.05–4.20 (m, 1H), 3.30–3.70 (m, 4H), 2.20–2.70 (m, 5H), 1.75–2.00 (m, 5H), 1.05–1.70 (m, 14H); HRMS (MH$^+$) 574.2512.

Some compounds prepared are shown below:

layers were dried over Na2SO4 and concentrated, and the crude was purified by flash-chromatography over silica gel (eluting DCM/AcOEt 7:3 to 1:1) to afford 4.72 g (72%) of 1-tert-butoxycarbonyl-4-[1-(4,4-ethylenedioxypiperidino)]piperidine.

Step 2:

To 1-tert-butoxycarbonyl-4-[1-(4,4-ethylenedioxy)piperidino]piperidine (200 mg, 061 mmol) in DCM (10 mL) was added TFA (1.5 mL), and the reaction was stirred 1 h 30. The reaction was treated with 1 N NaOH until pH>12 and extracted with DCM and AcOEt. The combined organic layers were dried over Na2SO4 and concentrated to provide 100 mg (75%) of 4-[1-(4,4-ethylenedioxypiperidino)]piperidine.

Preparation P-2: Preparation of 4-[1-(4-methoxyiminopiperidino)]piperidine:

Step 1:

To a solution of 4-piperidonemethoxime (150 mg, 1.17 mmol) in DCE (5 mL) was added 1-tert-butoxycarbonyl-4-

| Compound No. | Structure | Retention Time (minutes) | Observed Mass |
|---|---|---|---|
| 159-A | 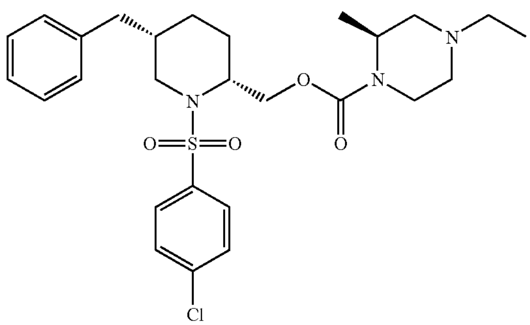 | 5.10 | 546.1 |
| 159-B | 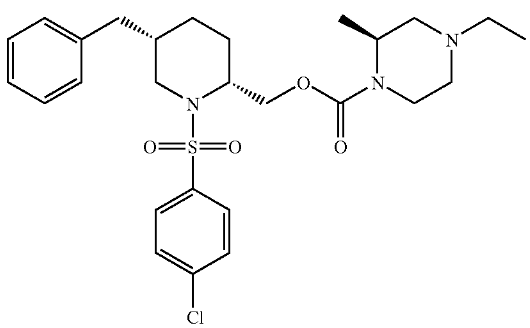 | 5.10 | 546.1 |

Preparations P-1 to P-4 describe preparation of intermediates used in several procedures.

Preparation P-1: Preparation of 4-[1-(4,4-ethylenedioxypiperidino)]piperidine;

Step 1:

A solution of 1-tert-butoxycarbonyl-4-piperidone (3.98 g, 20 mmol), 4-piperidoneethyleneketal (3.15 g, 22 mmol), sodium triacetoxyborohydride (4.66 g, 22 mmol), sodium sulfate (15 g) and acetic acid (300 μL) in DCE (15 mL) was stirred 2 days at RT. The solution was quenched with an excess of MeOH for 15 min then treated with diluted NaOH and extracted with DCM and AcOEt. The combined organic piperidone (350 mg, 1.75 mmol) and the reaction was stirred 1 h at RT. Sodium triacetoxyborohydride (500 mg, 2.34 mmol) was added, followed by AcOH (20 μl), and the reaction was stirred 2 days at RT. The solution was quenched with an excess of MeOH for 15 min then treated with 5% NaHCO3 and extracted with DCM and AcOEt. The combined organic layers were dried over Na$_2$SO$_4$ and concentrated to provide 500 mg of crude 1-tert-butoxycarbonyl-4-[1-(4-methoxyiminopiperidino]piperidine.

Step 2:

A solution of 1-tert-butoxycarbonyl-4-[1-(4-methoxyiminopiperidino)]piperidine (50 mg, 0.16 mmol) in DCM (2 mL) was treated with TFA (0.2 mL) and stirred at RT for 30 min. The reaction was concentrated, diluted with 1 N NaOH, and extracted with DCM and AcOEt. The combined organic layers were dried over Na2SO4 and concentrated to provide 50 mg (100%) of crude 4-[1-(4-methoxyiminopiperidino)] piperidine that could be used without purification in the next step.

Preparation P-3: Preparation of cis-3-methyl-4-(1-piperidino)piperidine:

Step 1:

To a solution of 1-benzyl-3-methylpiperidone (5.0 g, 24.6 mmol) in DCE was added piperidine (2.6 ml, 27.06 mmol) followed by Ti(OiPr)4 (8.8 ml, 29.52 mmol). The reaction was stirred at RT for 8 h, NaBH₃(CN) was added slowly and the mixture was then stirred 2 days at RT. The solution was quenched with an excess of MeOH for 15 min, treated with diluted NaOH, extracted with DCM and AcOEt, and the combined organic layers were dried over Na2SO4 and concentrated. Purification of a sample by flash-chromatography over silica gel (eluting hexanes/AcOEt 9:1 to 1:1) afforded 1.7 g of cis-1-benzyl-3-methyl-4-(1-piperidino)piperidine.

Step 2:

A solution of cis-1-benzyl-3-methyl-4-(1-piperidino)piperidine (1.7 g, 6.2 mmol), ammonium formate (6.3 g, 100 mmol) and palladium hydroxide on charcoal (1 g, 7.1 mmol) in MeOH (20 mL) was heated at reflux for 4 h. The final solution was filtered over Celite, rinsing with MeOH then concentrated. The residue was diluted with saturated NaHCO3, extracted with DCM and AcOEt, and combined organic layers were dried over Na2SO4 and concentrated to give 580 mg (52%) of cis-3-methyl-4-(1-piperidino)piperidine.

Preparation P4: Preparation of 2'-Methyl-[1,4']bipiperidine:

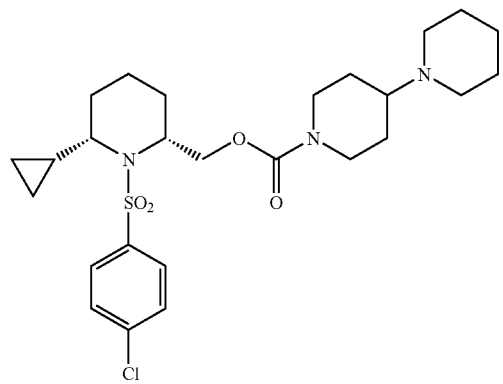

Compound 2: To a solution of 1'-tert-Butoxycarbonyl-[1,4']-Bipiperidine 1 (5.1 g, 19.0 mmol), TMEDA (19 ml) in dry Et₂O (40 ml) at −78° C. is slowly added a solution of sec-butyllithium (19.0 ml, 24.7 mmol, 1.3 M in cyclohexanes) over a period of 30 min. The mixture is stirred at −78° C. for 3 hr, and then is treated with a solution of Dimethylsulfate (3.6 g, 28.5 mmol) in Et₂O (5 ml). The cooling bath is removed and the reaction mixture is stirred at ambient temperature for 16 hr. After cooling to 0° C., the reaction mixture is quenched with water, extracted with Et₂O (5×100 ml), and the combined ether layers is dried over K₂CO₃. The solvent is removed in vacuo and the residue is purified on silica gel chromatography (eluting 40% ethyl acetate in hexane) to give 2.51 g of 1'-tert-Butoxycarbonyl-2'-methyl-[1,4']-Bipiperidine, 2.

Compound 3: To a stirring solution of compound 2 (1.5 g, 5.3 mmol) in DCM (10 ml) is added TFA, and the mixture is stirred at room temperature for 2 hr. After removing the volatiles, the residue is diluted with DCM, basified with 30% NH₄OH to pH 8 and the layer are separated. The organic phase is dried over MgSO₄ and concentrated to give 730 mg of 2'-Methyl-[1,4']bipiperidinyl. Specific examples are shown below:

EXAMPLE 160:

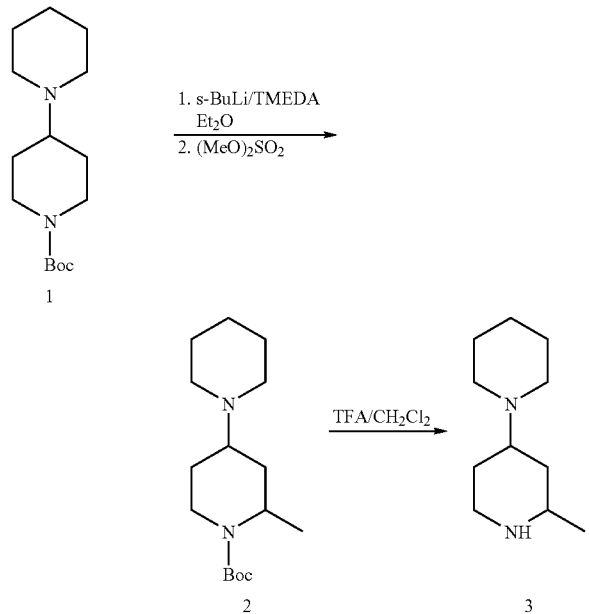

Step 1:

a) To a solution of 2-hydroxymethyl-6-(methoxycarbonyl)pyridine (44.5 g, 0.266 mol) in DCE (500 mL) was added triethylamine (44 mL, 0.31 mol) followed by TBSCl (44 g, 0.29 mol) and the reaction was heated at 70° C. for 4 h, then concentrated. The residue was directly purified by flash chromatography over silica gel (eluting hexane to hexane/AcOEt 1:1) to give 68.8 g (92%) of O-protected pyridine ester.

b) A solution of O-protected pyridine ester (68 g, 0.241 mmol) and platinum(IV) oxide (6 g, 0.026 mol) in MeOH (500 mL) and AcOH (50 ml) was hydrogenated 2 h at 40 psi. The final solution was filtered over Celite, rinsing with MeOH then concentrated. The residue was diluted with 1 N NaOH, extracted with DCM and AcOEt, and combined organic layers were dried over Na2SO4 and concentrated to provide 66 g (97%) of O-protected piperidine ester.

Step 2:

To a solution of O-protected piperidine ester (63 g, 0.22 mol) in DCE (500 mL) was added triethylamine (100 mL, 0.66 mol) then, slowly, 4-chlorobenzenesulfonyl chloride (93 g, 0.44 mol) and the reaction was heated at 40° C. overnight. The final mixture was concentrated and directly purified by flash chromatography over silica gel (eluting hexane to hexane/AcOEt 9:1) to afford 89 g (88%) of O-protected sulfonamide ester.

Step 3:

a) To a solution of O-protected sulfonamide ester (20.0 g, 43.3 mmol) in DCM (200 mL) at −78° C. was slowly added DIBAH 1 N in THF (45 ml, 45 mmol) and the reaction was stirred 1 h at this temperature. The reaction was then quenched with saturated sodium tartrate in water, warmed to room temperature, and diluted with DCM. Celite was added, the mixture was stirred 30 min and filtered. The solution was extracted with DCM and AcOEt and combined organic layers were dried over $Na_2SO_4$ and concentrated. The residue was purified by flash chromatography over silica gel (eluting hexane to hexane/AcOEt 1:1) to afford 15 g (80%) of O-protected sulfonamide aldehyde.

b) To a suspension of methyltriphenylphosphonium bromide (2.6 g, 7.2 mmol) in THF (25 mL) at −78° C. was added n-BuLi 2.5 N in hexanes (2.7 ml, 6.9 mmol). The solution was warmed to −20° C. for 30 min then treated with O-protected sulfonamide aldehyde (2.6 g, 6.0 mmol) dissolved in THF (25 mL). The reaction was allowed to warm to room temperature for 1 h then concentrated. The residue was taken up in saturated NaHCO3, extracted with DCM and AcOEt and combined organic layers were dried over $Na_2SO_4$ and concentrated. The residue was purified by flash chromatography over silica gel (eluting hexane to hexane/AcOEt 8:2) to give 2.1 g (85%) of O-protected sulfonamide alkene.

Step 4 a) To diethylzinc 1 N in hexanes (48.4 ml, 48.4 mmol) at 0° C. was added DCM (20 mL) followed by TFA (3.7 ml, 48.4 mmol) and the solution was stirred 5 min at this temperature Diiodomethane (3.9 ml, 48.4 mmol) was then added followed 5 min later, by O-protected sulfonamide alkene (5.2 g, 12.1 mmol) in DCM (40 mL). The reaction was allowed to warm to room temperature for 2 h, diluted with water and extracted with DCM and AcOEt Combined organic layers were dried over Na2SO4 and concentrated to give 5.7 g (100%) of O-protected cyclopropyl sulfonamide.

b) O-protected cyclopropyl sulfonamide (5.4 g, 12.1 mmol) was treated with TBAF following the conditions described in Example 1 Step 3-b to afford, after flash chromatography over silica gel (eluting hexane/AcOEt 9:1 to hexane/AcOEt 4:6), 4.0 g (100%) of cyclopropyl sulfonamide alcohol.

Optional Step 4-R: Optional Resolution of Cyclopropyl Sulfonamide Alcohol:

Cyclopropyl sulfonamide alcohol (0.75 g) was resolved by HPLC on Chiracel OJ column (eluting hexane/isopropanol 95:5) to afford, in order of elution, 276 mg of enantiomer A and 296 mg of enantiomer B, both as oils.

Step 5

The product of step 4 was converted to the title compound according to conditions similar to the ones described in Step 4 of Example 1, using 4-(1-piperidino)piperidine at the last stage as the amine. $^1$H-NMR (300 MHz, $CDCl_3$) δ 7.74 (d, J=8.4 Hz, 2H), 7.45 (d, J=8.4 Hz, 2H), 4.10–4.40 (m, 5H), 3.24 (m, 1H), 2.40–2.90 (m, 7H), 1.05–1.90 (m, 17H), 0.70 (m, 1H), 0.59 (m, 2H), 0.25 (m, 1H); HRMS ($MH^+$) 524.2356.

Following procedures similar to those in Example 160, the following compounds were prepared:

| Compound No. | Structure | Retention Time (minutes) | Observed Mass |
|---|---|---|---|
| 160-A | 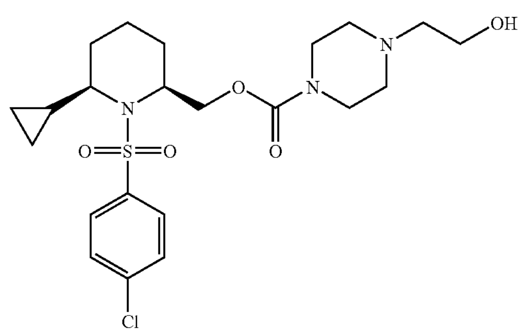 | 4.60 | 486.1 |
| 160-B | 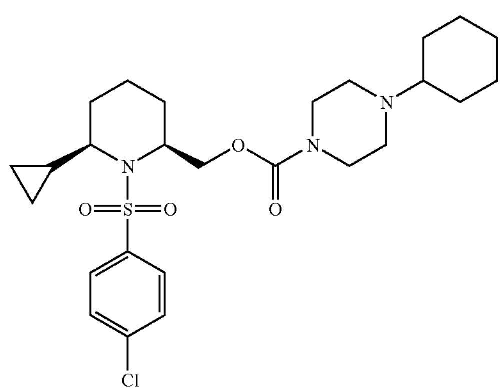 | 5.00 | 524.1 |

| Compound No. | Structure | Retention Time (minutes) | Observed Mass |
|---|---|---|---|
| 160-C | 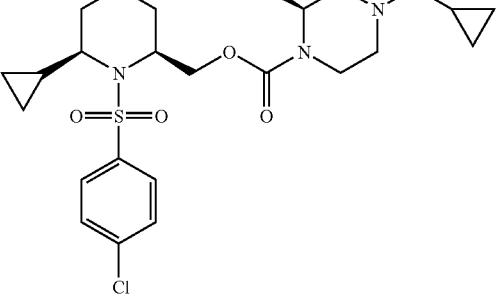 | 5.30 | 510.1 |
| 160-D | 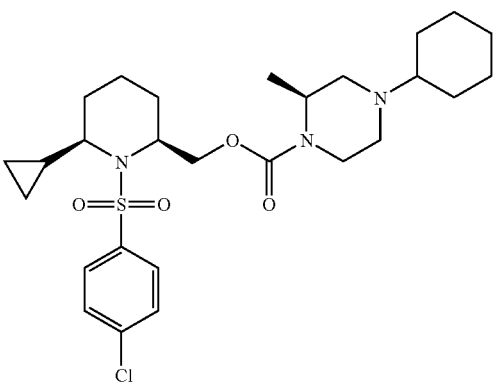 | 5.40 | 538.1 |
| 160-E | 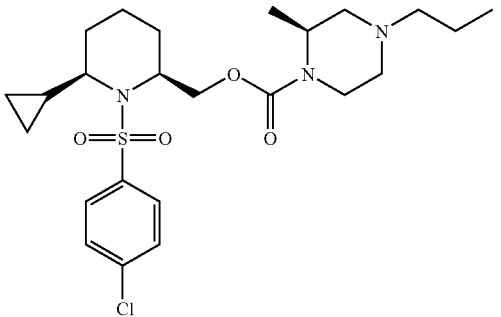 | 5.30 | 498.1 |
| 160-F | 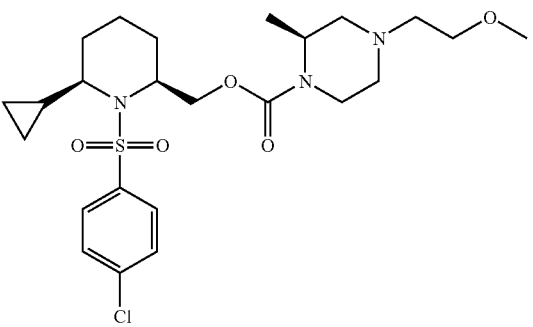 | 5.40 | 514.1 |

-continued

| Compound No. | Structure | Retention Time (minutes) | Observed Mass |
|---|---|---|---|
| 160-G | 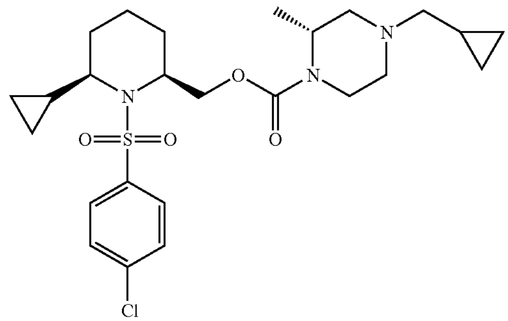 | 5.30 | 510.1 |
| 160-H | 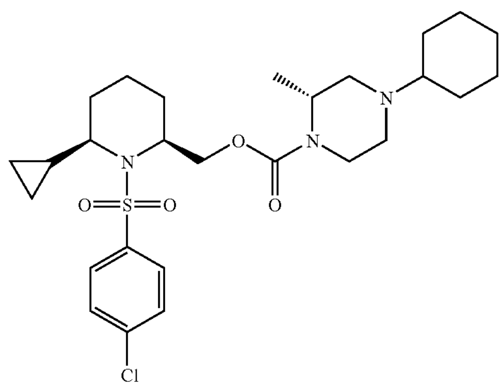 | 5.50 | 538.1 |
| 160-I | 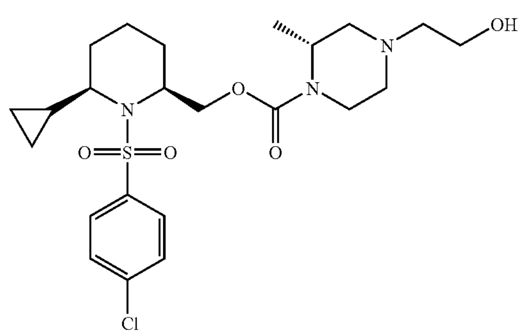 | 5.00 | 500.1 |
| 160-J | 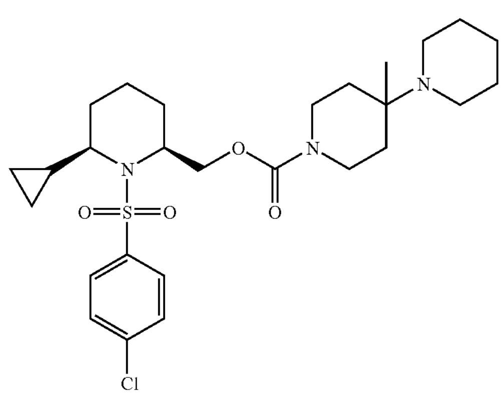 | 5.70 | 538.1 |

-continued

| Compound No. | Structure | Retention Time (minutes) | Observed Mass |
|---|---|---|---|
| 160-K | 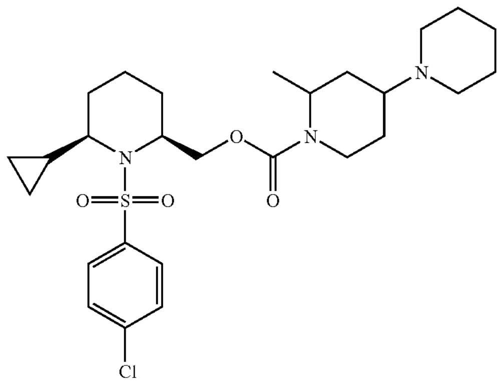 | 5.90 | 538.1 |
| 160-L | 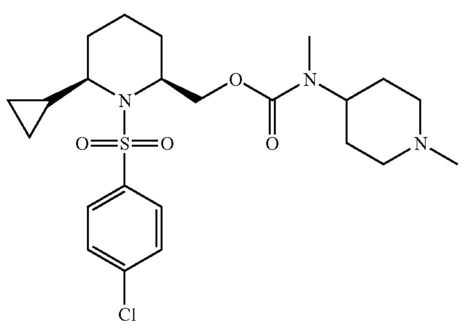 | 4.50 | 484.1 |
| 160-M | 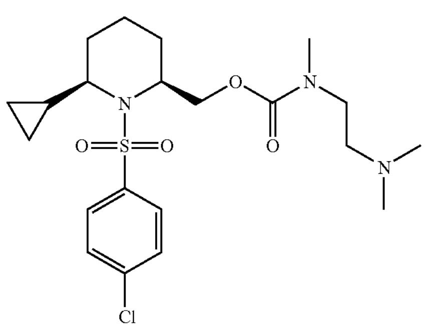 | 4.70 | 458.3 |
| 160-N | 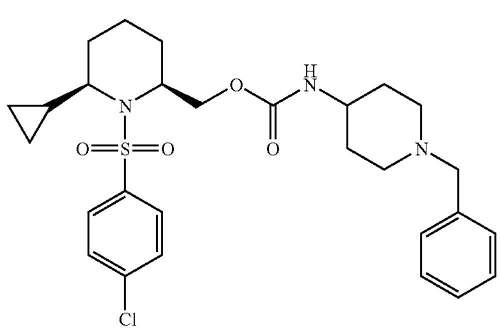 | 4.80 | 546.3 |

-continued

| Compound No. | Structure | Retention Time (minutes) | Observed Mass |
|---|---|---|---|
| 160-O | 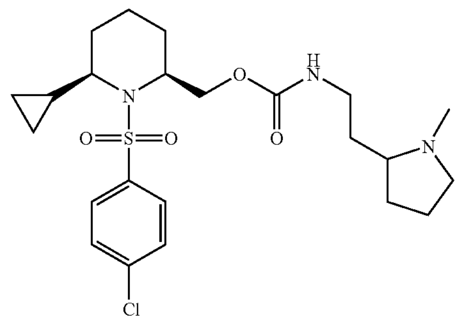 | 4.60 | 484.3 |
| 160-P | 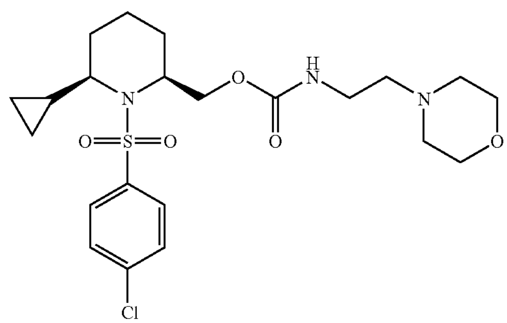 | 4.30 | 486.3 |
| 160-Q | 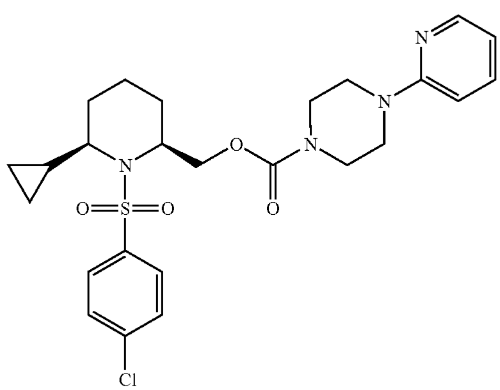 | 4.80 | 519.3 |
| 160-R | 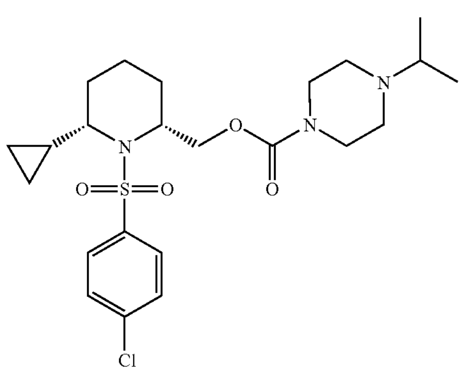 | 5.00 | 484.1 |

| Compound No. | Structure | Retention Time (minutes) | Observed Mass |
|---|---|---|---|
| 160-S | 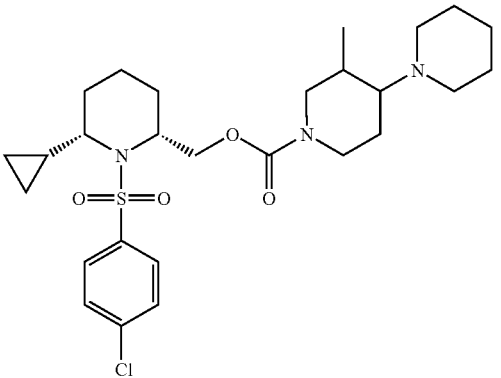 | 5.30 | 538.1 |
| 160-T | 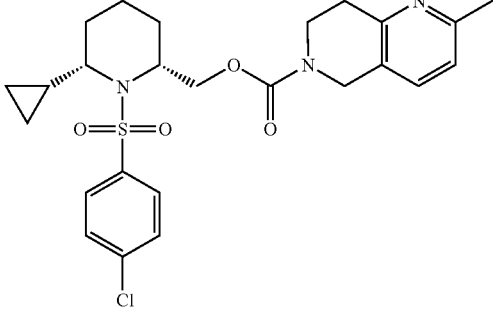 | 5.10 | 504.1 |
| 160-U | 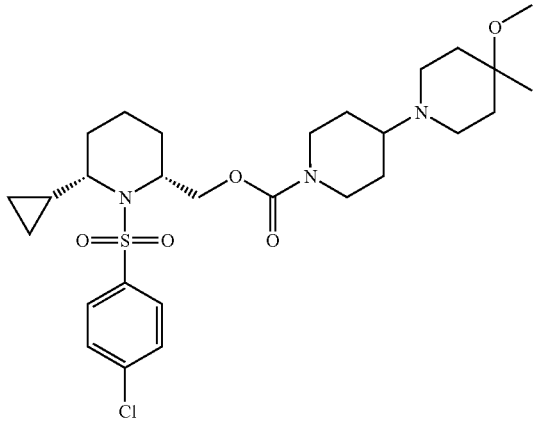 | 5.60 | 582.1 |
| 160-V | 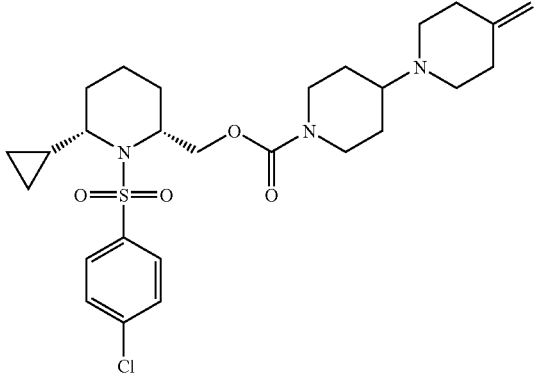 | 4.90 | 567.1 |

| Compound No. | Structure | Retention Time (minutes) | Observed Mass |
|---|---|---|---|
| 160-W | 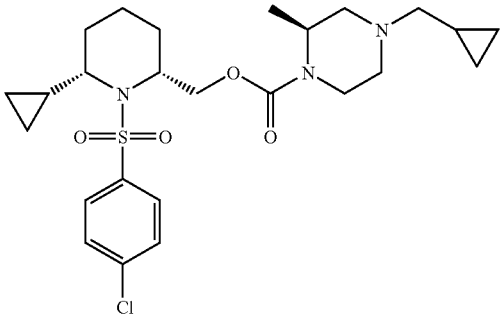 | 4.70 | 510.3 |
| 160-X | 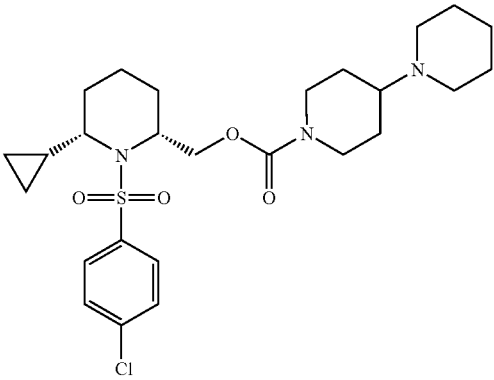 | 5.10 | 526.1 |
| 160-Y | 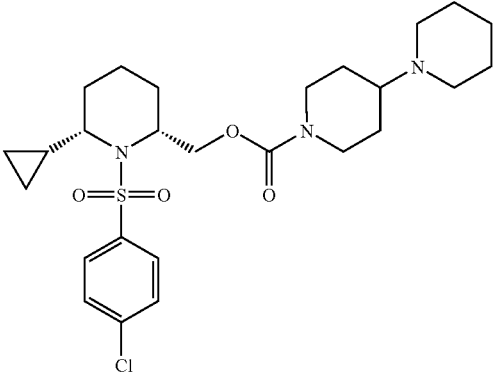 | 5.00 | 526.1 |

| Compound No. | Structure | Retention Time (minutes) | Observed Mass |
|---|---|---|---|
| 160-Z | 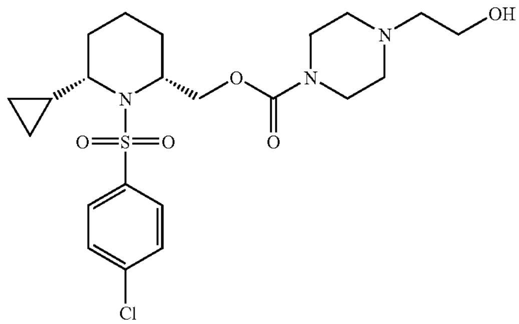 | 4.50 | 486.1 |
| 160-AA | 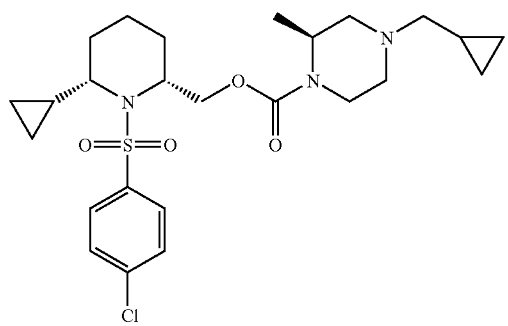 | 4.60 | 510.3 |

EXAMPLE 161

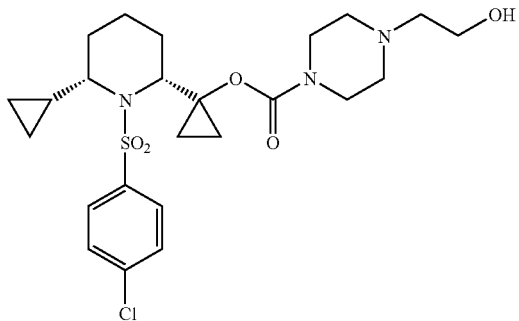

Step 1:

a) To a solution of cyclopropyl sulfonamide alcohol product of Example 160 Step 4-b (4.8 g, 14.5 mmol) in AcOEt (25 mL), acetonitrile (25 mL) and water (50 mL) was added sodium periodate (9.3 g, 43.5 mmol) followed by RuCl3.nH2O (100 mg). The reaction was stirred at RT for 2 hr, filtered over Celite, and extracted with AcOEt. Combined organic layers were dried over Na2SO4 and concentrated to provide 4.55 g (90%) of cyclopropyl sulfonamide acid.

b) A solution of cyclopropyl sulfonamide acid (4.55 g, 13.2 mmol) in MeOH (100 mL) was treated with thionyl chloride (2 ml, 26.5 mmol) at RT slowly then the solution was heated to reflux for 2 hr. The reaction was concentrated, diluted with saturated NaHCO3, extracted with DCM and AcOEt and combined organic layers were dried over Na2SO4 and concentrated. The residue was purified by flash chromatography over silica gel (eluting hexane to hexane/AcOEt 1:1) to afford 3.0 g (64%) of cyclopropyl sulfonamide ester.

Step 2:

To a solution of cyclopropyl sulfonamide ester (600 mg, 1.7 mmol) in THF (10 mL) was added Ti(OiPr)4 (0.1 ml, 0.34 mmol), then the reaction was cooled to 10° C. and slowly treated with EtMgBr 3 N in ether (1.7 ml, 5.1 mmol) over 30–40 min. The mixture was stirred another 30 min at 10° C., then treated with saturated NH4Cl at this temperature, and extracted with DCM and AcOEt. Combined organic layers were dried over Na2SO4, concentrated, and the residue was purified by flash chromatography over silica gel (eluting hexane to hexane/AcOEt 1:1) to yield 370 mg (61%) of cyclopropyl sulfonamide cyclopropylalcohol.

Step 3:

The product of step 2 was converted to the title compound according to conditions similar to the ones described in Step 4 of Example 1, using 1-(2-hydroxyethyl)piperazine at the last stage as the amine. $^1$H-NMR (300 MHz, CDCl$_3$) δ 7.69 (d, J=8.8 Hz, 2H), 7.42 (d, J=8.8 Hz, 2H), 4.56 (d, J=6.6 Hz, 1H), 3.30–3.75 (m, 6H), 3.01 (m, 1H), 2.30–2.65 (m, 6H), 1.40–1.70 (m, 4H), 0.95–1.25 (m, 8H), 0.73 (m, 1H), 0.58 (m, 2H), 0.23 (m, 1H); HRMS (MH$^+$) 512.1992.

Following procedures similar to those in Example 161 the following compounds were prepared:

| Compound No. | Structure | Retention Time (minutes) | Observed Mass |
|---|---|---|---|
| 161-A | 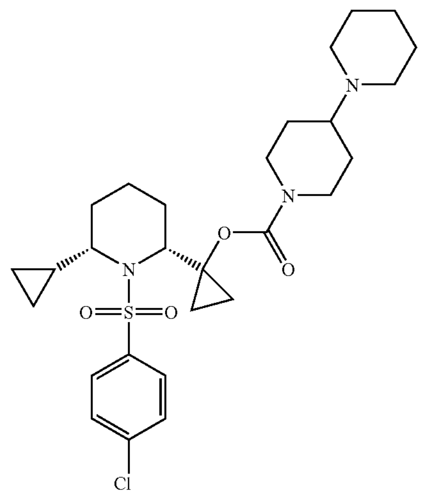 | 4.60 | 550.3 |
| 161-B | 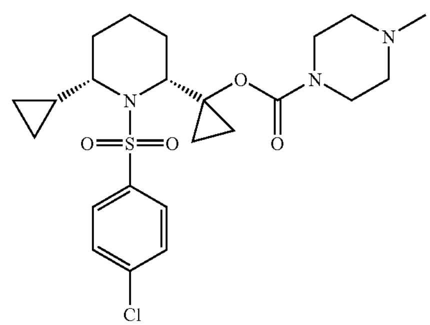 | 4.40 | 482.3 |
| 161-C | 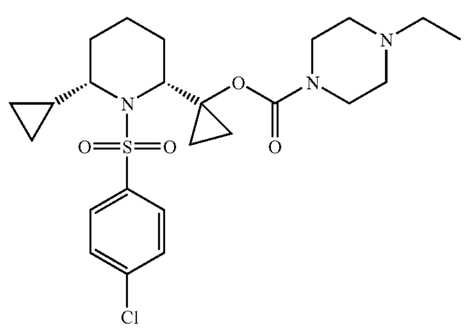 | 4.40 | 496.3 |
| 161-D | 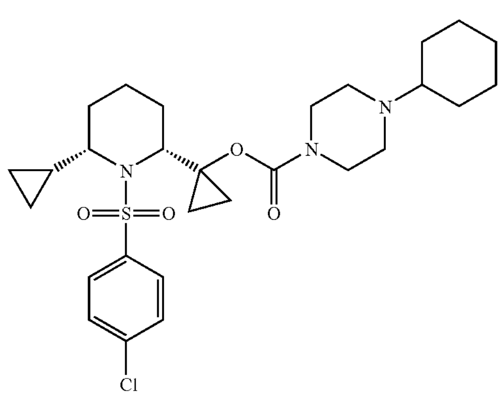 | 4.90 | 550.3 |

-continued

| Compound No. | Structure | Retention Time (minutes) | Observed Mass |
|---|---|---|---|
| 161-E | 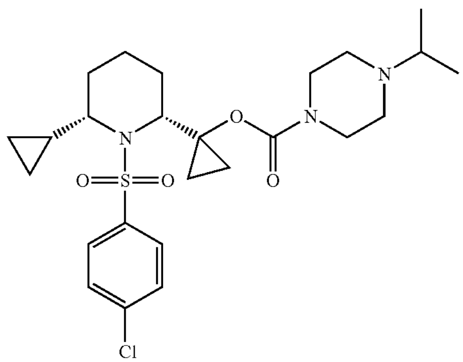 | 4.60 | 510.3 |
| 161-F | 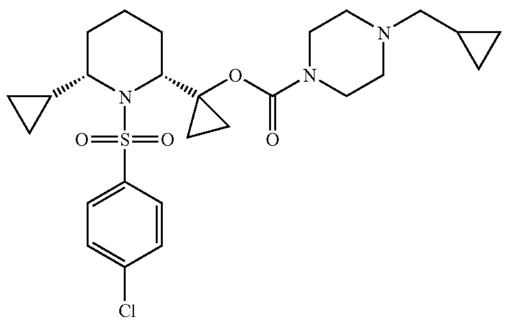 | 4.90 | 522.1 |
| 161-G | 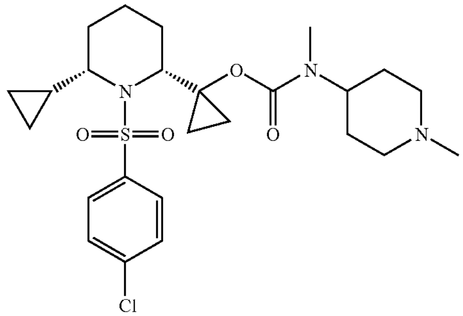 | 4.80 | 510.3 |

EXAMPLE 162

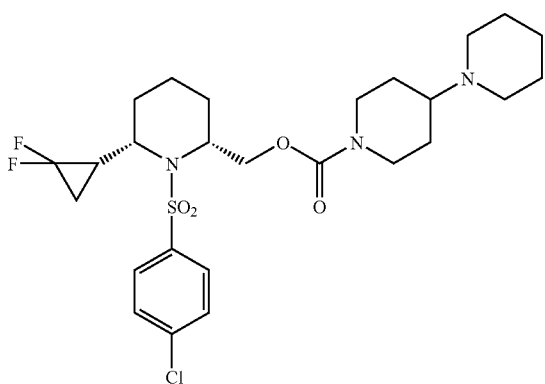

Step 1:

To a solution of O-protected sulfonamide alkene product of Example 160 Step 3-b (480 mg, 1.12 mmol) and sodium fluoride (1 mg) in toluene (0.2 mL) at 100° C. was added FSO2CF2COOTMS (700 mg, 2.8 mmol) over 1 h and the reaction was stirred an additional 2 h at this temperature. The final mixture was concentrated and purified over silica gel (eluting hexane/AcOEt 9:1) to afford 338 mg of starting material and 65 mg (41% based on recovery) of O-protected difluorocyclopropyl sulfonamide.

Step 2:

The product of step 1 was converted to the title compound according to conditions similar to the ones described in Example 1 Step 3-b and Step 4, using 4-(1-piperidino) piperidine at the last stage as the amine. $^1$H-NMR (300 MHz, CDCl$_3$) δ 7.78 (d, J=8.4 Hz, 2H) 7.46 (d, J=8.4 Hz, 2H), 3.90–4.35 (m, 6H), 3.47 (s, 1H), 2.60–2.80 (m, 2H), 2.35–2.60 (m, 5H), 1.70–2.05 (m, 5H), 1.20–1.70 (m, 12H), 1.06 (m, 1H); HRMS (MH$^+$) 560.2153.

Following procedures similar to those in Example 162 the following compounds were prepared.

| Compound No. | Structure | Retention Time (minutes) | Observed Mass |
|---|---|---|---|
| 162-A | 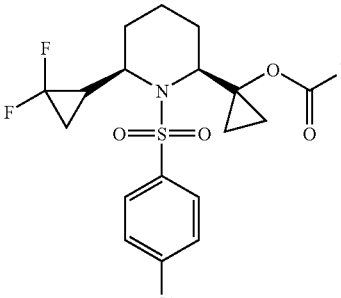 | 4.10 | 522.3 |
| 162-B | 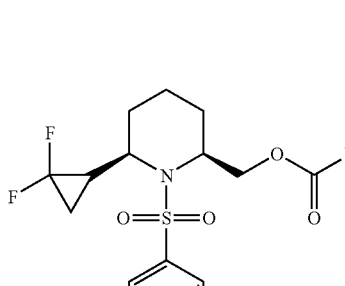 | 4.90 | 560.3 |

EXAMPLE 163

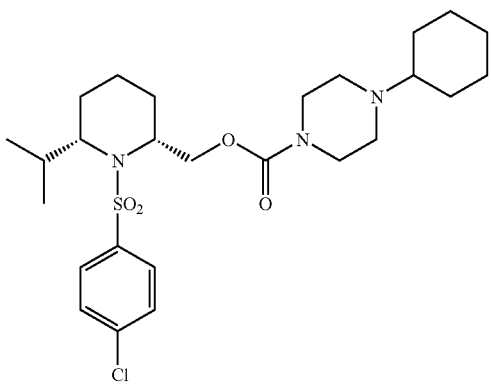

Step 1:

a) To a solution of O-protected pyridine ester product from Example 160 Step 1-a (10.0 g, 36 mmol) in THF (140 mL) at 0° C. was slowly added MeMgBr 3 N in ether (30 ml, 90 mmol), and the reaction was warmed to RT and stirred 1 h. The final mixture was poured into 1 N NaOH and DCM to which was added Celite, stirred, and filtered. The aqueous layer was extracted with DCM and AcOEt, combined organic layers were dried over Na2SO4 and concentrated, and the residue was purified by flash chromatography over silica gel (eluting hexane/AcOEt 8:2) to give 3.0 g (30%) of O-protected pyridine dimethylcarbinol.

b) To a solution of O-protected pyridine dimethylcarbinol (3.0 g, 10.6 mmol) in THF (50 mL) at −78° C. was added n-BuLi 2.5 N in hexanes (4.7 ml, 11.7 mmol) followed, 1 min later, by phenylthionochloroformate (2.76 g, 16.0 mmol). The reaction was stirred at −78° C. for 40 min, then allowed to warm to RT and stirred 4 h. The final mixture was treated with saturated NaHCO3, extracted with DCM and AcOEt and combined organic layers were dried over Na2SO4 and concentrated. Purification of the residue by flash chromatography over silica gel (eluting hexane to DCM) afforded 1.5 g of O-protected pyridine propene as well as 1.8 g of starting O-protected pyridine dimethylcarbinol.

Step 2:

a) A solution of O-protected pyridine propene (1.5 g, 5.7 mmol) and platinum(IV) oxide (258 mg) in MeOH (20 mL) and AcOH (4 ml) was hydrogenated 6 h at 40 psi. The final solution was filtered over Celite, rinsing with MeOH then concentrated. The residue was diluted with 1 N NaOH, extracted with DCM and AcOEt, and combined organic layers were dried over Na2SO4 and concentrated. The residue was quickly passed through a plug of silica gel (eluting hexanes/AcOEt 8:2) to provide 1.0 g (65%) of O-protected isopropyl piperidine.

b) A solution of O-protected isopropyl piperidine (0.82 g, 3.0 mmol), 4-chlorobenzenesulfonyl chloride (1.2 g, 6.0 mmol) and pyridine (10 mL) in DCE (10 mL) was heated at 60° C. overnight. The final mixture was concentrated and directly purified by flash chromatography over silica gel (eluting hexane to DCM) to afford 0.42 g (32%) of O-protected isopropyl sulfonamide.

Step 3:

The product of step 2 was converted to the title compound according to conditions similar to the ones described in Example 1 Step 3-b and Step 4, using 1-cyclohexylpiperazine at the last stage as the amine. $^1$H-NMR (300 MHz, CDCl$_3$) δ 7.77 (d, J=8.8 Hz, 2H), 7.47 (d, J=8.8 Hz, 2H), 4.05–4.30 (m, 3H), 3.40–3.70 (m, 5H), 2.53 (br s, 4H), 2.27 (m, 1H), 1.35–2.00 (m, 10H), 0.95–1.35 (m, 10H), 0.91 (dm J=6.6 Hz, 3H), HRMS (MH$^+$) 526.2501.

Following procedures similar to those in Example 163 the following compounds were prepared.

| Compound No. | Structure | Retention Time (minutes) | Observed Mass |
|---|---|---|---|
| 163-A | 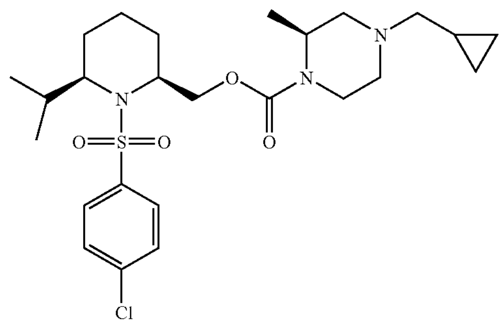 | 5.40 | 512.1 |
| 163-B | 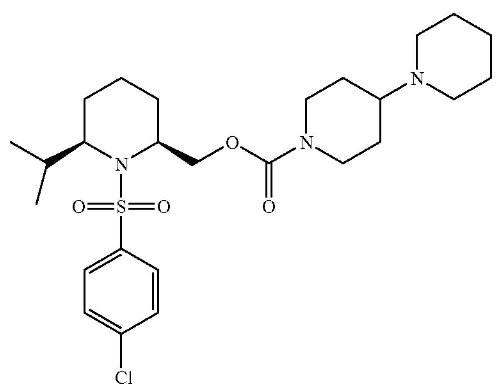 | 5.60 | 526.1 |
| 163-C | 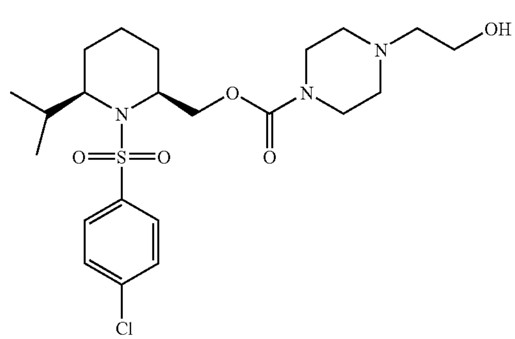 | 5.10 | 488.1 |

EXAMPLE 164

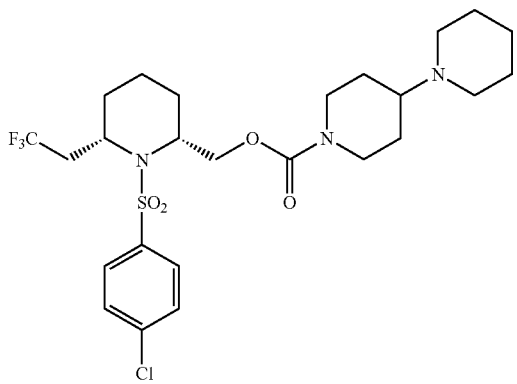

Step 1:

a) To a solution of O-protected pyridine ester product from Example 160 Step 1-a (45.75 g, 0.16 mol) in DCM (500 mL) at −40° C. was slowly added DIBAH 1 N in hexane (211 ml, 0.21 mmol) and the reaction was stirred 1 h at this temperature. The reaction was then quenched with an excess of acetone, then treated with sodium fluoride (25 g) solution in water (100 mL) for 30 min. The final mixture was filtered over Celite, extracted with DCM and AcOEt and combined organic layers were dried over Na2SO4 and concentrated. The residue was purified by flash chromatography over silica gel (eluting hexane/AcOEt 8:2) to afford 27.2 g (68%) of O-protected pyridine aldehyde.

b) To a solution of O-protected pyridine aldehyde (5.0 g, 19.9 mmol) and TBAF 1 N in THF (1.5 mL, 1.5 mmol) in THF (60 mL) at 0° C. was slowly trifluoromethyltrimethylsilane (3.4 mL, 20.9 mmol) and the reaction was allowed to warm to RT overnight. The reaction was diluted with water and DCM, extracted with DCM, dried over Na2SO4 and concentrated. The residue was purified by flash chromatography over silica gel (eluting hexane/AcOEt 8:2) to afford 1.5 g (24%) of O-protected pyridine trifluoroethyl alcohol.

Step 2:

a) To a solution of O-protected pyridine trifluoroethyl alcohol (1.8 g, 5.6 mmol) in THF (30 mL) at −78° C. was added n-BuLi 2.5 N in hexanes (2.5 ml, 6.2 mmol) followed, 1 min later, by phenylthionochloroformate (1.45 g, 8.4 mmol). The reaction was stirred at −78° C. for 40 min, then allowed to warm to RT and stirred an additional 1 h. The final mixture was then diluted with saturated NaHCO3, extracted with DCM and AcOEt and combined organic layers were dried over Na2SO4 and concentrated. Purification of the residue by flash chromatography over silica gel (eluting DCM/hexane 1:1) afforded 2.3 g (92%) of O-protected pyridine trifluoroethyl thionocarbonate.

b) To a solution of O-protected pyridine trifluoroethyl thionocarbonate (2.3 g, 5.0 mmol) in toluene (60 mL) was added tributyltin hydride (3.0 mL, 10.5 mmol) followed by 2,2'-azobisisobutyronitrile (265 mg, 1.6 mmol) and the reaction was heated under reflux for 5 h. After concentration of the solvent, the residue was purified by flash chromatography over silica gel (eluting hexane to DCM/hexane 1:1) to give 1.3 g (86%) of O-protected trifluoroethyl pyridine.

Step 3:

a) A solution of O-protected trifluoroethyl pyridine (1.3 g, 4.3 mmol) and platinum(IV) oxide (100 mg) in MeOH (50 mL) and AcOH (5 ml) was hydrogenated overnight at 50 psi. The final solution was filtered over Celite, rinsing with MeOH then concentrated. The residue was diluted with 1 N NaOH, extracted with DCM and AcOEt, and combined organic layers were dried over Na2SO4 and concentrated to provide 1.13 g (84%) of O-protected trifluoroethyl piperidine.

b) To a solution of O-protected trifluoroethyl piperidine (1.13 g, 3.6 mmol) in DCE (15 mL) was added triethylamine (0.6 mL, 4.3 mmol) then 4-chlorobenzenesulfonyl chloride (1.13 g, 5.4 mmol) and the reaction was heated at reflux overnight. The final mixture was concentrated and directly purified by flash chromatography over silica gel (eluting hexane to DCM) to afford 0.67 g (38%) of O-protected trifluoroethyl sulfonamide.

Step 4:

The product of step 3 was converted to the title compound according to conditions similar to the ones described in Example 1 Step 3-b and Step 4, using 4-(1-piperidino)piperidine at the last stag as the amine. $^1$H-NMR (300 Mhz, CDCl$_3$) δ 7.77 (d, J=8.3 Hz, 2H), 7.48 (d, J=8.3 Hz, 2H), 4.10–4.45 (m, 5H), 3.99 (m, 1H), 2.40–2.95 (m, 9H), 1.20–2.00 (m, 16H); HRMS (MH$^+$) 566.2075.

Following procedures similar to those in Example 164, the following compounds were prepared.

| Compound No. | Structure | Retention Time (minutes) | Observed Mass |
|---|---|---|---|
| 164-A | 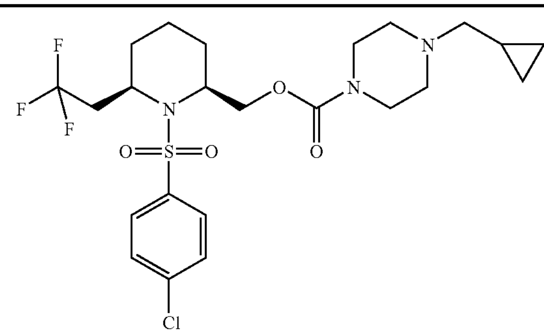 | 5.00 | 538.1 |

| Compound No. | Structure | Retention Time (minutes) | Observed Mass |
|---|---|---|---|
| 164-B | 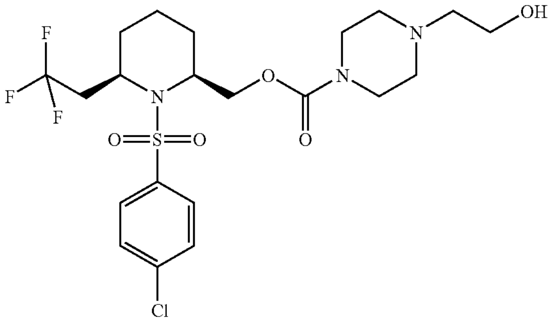 | 4.60 | 528.1 |
| 164-C | 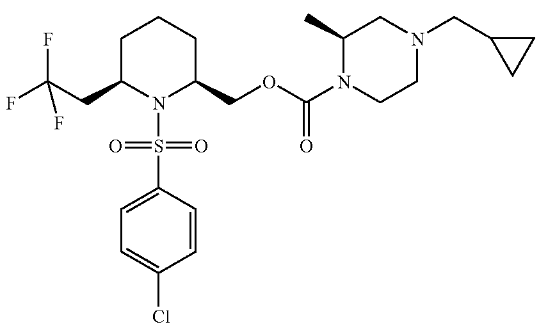 | 4.90 | 552.1 |
EXAMPLE 165
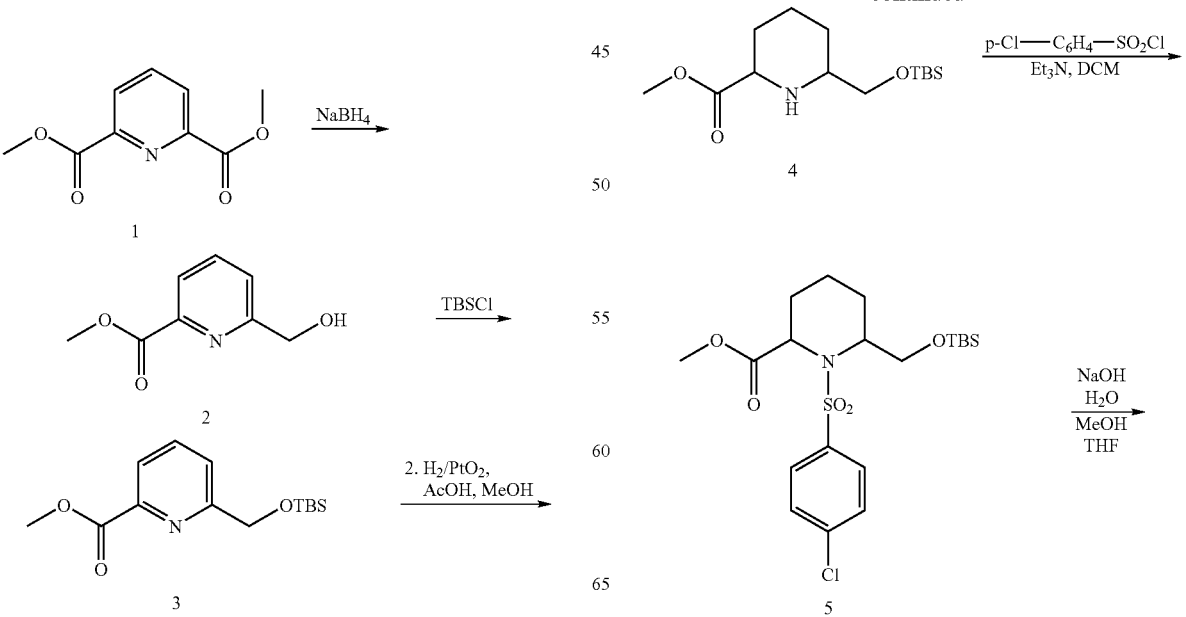

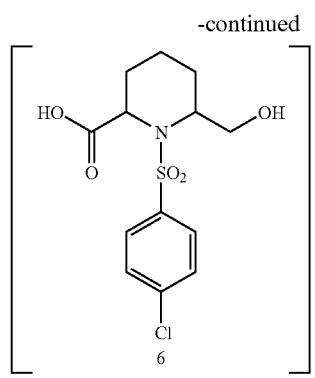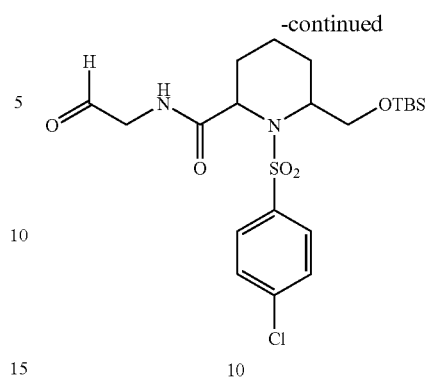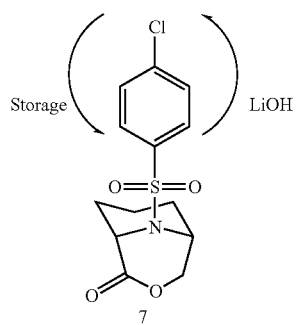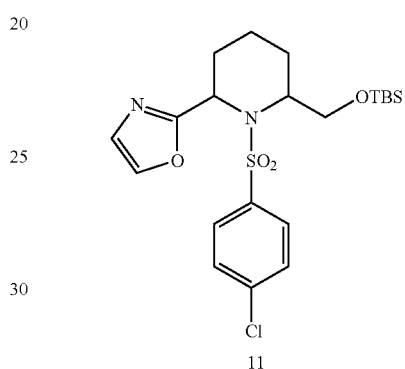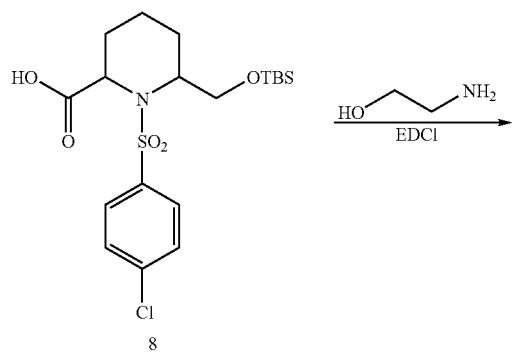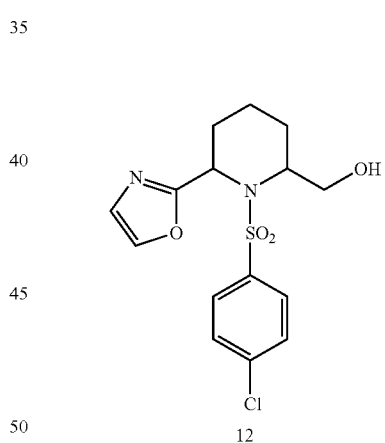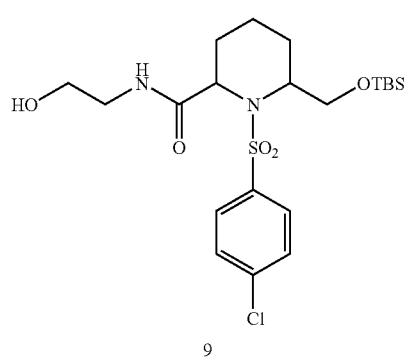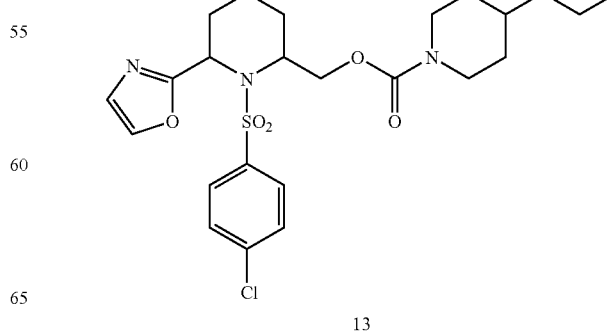

Step 1: Compound 2 is prepared as described in Example 88, Step 1.

Step 2: A mixture of 1.396 g (8.35 mmol) of Compound 2 and 1.137 g (19.71 mmol) of imidazole in 10 ml of DMF was treated with 1.210 g (9.18 mmol) of TBSCl. After overnight stirring, the mixture was diluted with DCM, washed with water, dried over sodium sulfate and concentrated. The product was purified by chromatography using 10% ethyl acetate in hexanes as solvent to furnish 1.65 g of Compound 3.

Step 3: Compound 3 (4.0 g) was hydrogenated at 50 psi using 200 mg of $PtO_2$ as catalyst and a mixture of 20 ml of methanol and 20 ml of acetic acid as solvent over a period of 12 h. The reaction vessel was flushed with nitrogen, catalyst was filtered out and volatiles were evaporated. The residue was re-dissolved in DCM, washed with sat. $NaHCO_3$, aqueous phase was re-extracted with DCM, combined organic phase was dried over sodium sulfate and concentrated to furnish 3.77 g of Compound 4.

Step 4: A mixture of 3.77 g (13.13 mmol) of Compound 4, 7.4 ml (52.6 mmol) of triethylamine and 5.54 g (26.26 mmol) of 4-chlorobenzenesulfonyl chloride in 60 ml of DCM was stirred over 7 days. The mixture was diluted with DCM, washed with water, dried over sodium sulfate and concentrated. The product was purified by chromatography using 5–15% of ethyl acetate in hexanes as solvent to furnish 4.99 g of Compound 5.

Step 5: A mixture of 150 mg of Compound 5, 5 ml of methanol, 5 ml of THF and 5.0 ml of 1 M aqueous NaOH was refluxed overnight. The mixture was cooled, DCM (100 ml) and 1 M HCl were added so that pH was adjusted to ~3. Organic layer was separated, aqueous phase was extracted with DCM. Combined organic phase was dried over sodium sulfate and concentrated to furnish 90 mg of unstable Compound 6, which had a tendency to dehydrate on storage to provide Compound 7. In order to regenerate Compound 6 from Compound 7, the following procedure was used:

A mixture of 500 mg of Compound 7, 4.0 ml of THF, 0.7 ml of water and 72 mg of LiOH was vigorously stirred overnight. Reaction mixture was diluted with ethyl acetate and pH was adjusted to ~3 with 1 M HCl. Organic layer was separated, aqueous phase was extracted with DCM. Combined organic phase was dried over sodium sulfate and concentrated to furnish 310 mg of unstable Compound 6.

Step 6: Stirred overnight a mixture of 310 mg (0.931 mmol) of freshly prepared Compound 6, 349 mg (2.33 mmol) of TBSCl, 272 mg (4 mmol) of imidazole and 5 ml of DMF. The mixture was diluted with DCM, partitioned with citric acid, aqueous phase was re-extracted with DCM. Combined organic phase was dried over sodium sulfate and concentrated. The product was purified by chromatography using 30% of ethyl acetate in hexanes as solvent to furnish 350 mg of Compound 8.

Step 7: To a mixture of 350 mg (0.783 mmol) of Compound 8, 95 mg (1.56 mmol) of ethanolamine in 5 ml of DMF was added 211 mg (1.56 mmol) of HOBt, 300 mg (1.56 mmol) of EDCl, and 0.218 ml (1.56 mmol) of triethylamine. The turbid mixture was stirred overnight, diluted with DCM, washed with water, dried over sodium sulfate and concentrated. The product was purified by chromatography using 40% of ethyl acetate in hexanes as solvent to furnish 138 mg of Compound 9.

Step 8. To a solution of 138 mg (0.2816 mmol) of Compound 9 in 2 ml of DCM was added 238 mg (0.563 mmol) of Dess-Martin periodinane. The mixture was stirred over a period of 1 h, diluted with DCM, washed with sat. $NaHCO_3$, dried over sodium sulfate and concentrated. The product was purified by chromatography using 40% of ethyl acetate in hexanes as solvent to furnish 110 mg of Compound 10.

Step 9. To a mixture of 80 mg (0.1638 mmol) of Compound 10 in 3 ml of acetonitrile was added 194 mg (0.82 mmol) of hexachloroethane, 0.23 ml (1.64 mmol) of triethylamine followed by 215 mg (0.82 mmol) of triphenylphosphine. (The latter reagent dissolved gradually, then a new precipitate forms after 10 min of stirring). The mixture was stirred overnight and Compound 11 (56 mg) was isolated by prep. TLC chromatography using 20% ethyl acetate in hexanes as solvent.

Step 10. A mixture of 56 mg (0.119 mmol) of Compound 11 in 1.5 ml of THF was treated with 0.24 ml (0.24 mmol) of 1M TBAF solution in THF. The reaction mixture was stirred for 1 h, poured into water, extracted with DCM, organic phase was dried over sodium sulfate and concentrated to furnish 50 mg of crude Compound 12, which was used without further purification.

Step 11. Compound 13 was prepared from Compound 12 using procedures similar to Example 1, Step 4(a) and 4(b), except that step 4(a) was modified so that a 2:1 mixture of THF and acetonitrile was used as solvent instead of DCM.

$^1$H NMR (CDCl$_3$, 400 MHz) δ 7.86 (2H, d, J=8.8 Hz), 7 63 (1H, s), 7.51 (2H, d, J=8.8 Hz), 7.09 (1H, s), 5.32 (1H, d, J=5.0 Hz), 4.25 (1H, m), 4.14 (1H, br), 3.73 (1H, t, J=9.0 Hz), 3.58 (1H, t, J=9.0 Hz), 2.70 (2H, m). 2.52–2.33 (6H, ser. m.), 2.0–1.2 (16H, ser. m.); MS (ES) m/e 552.1 (M+H)$^+$.

EXAMPLE 166

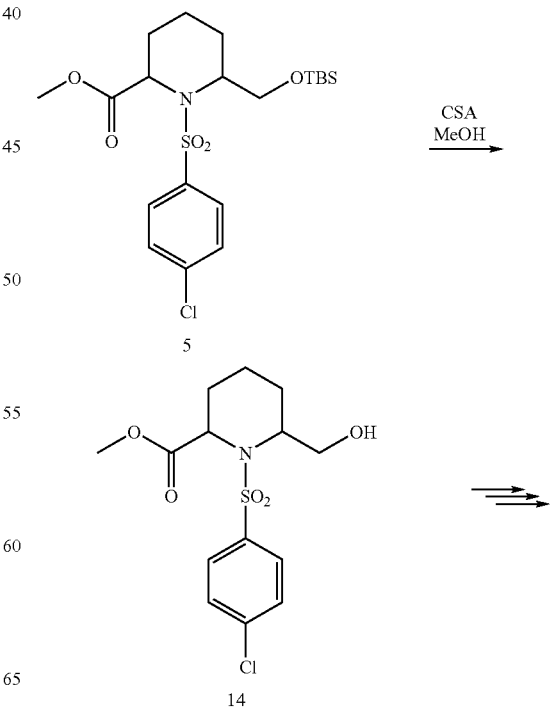

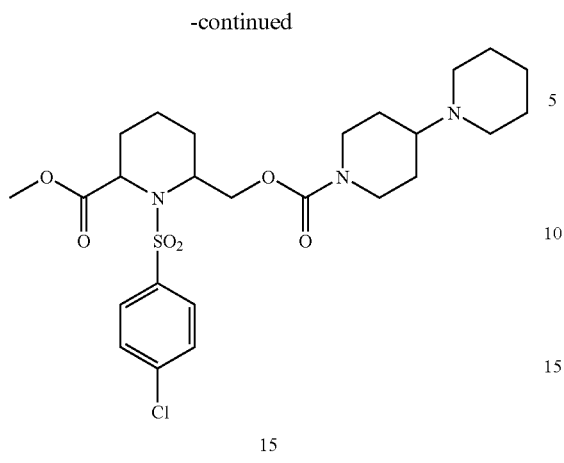

Step 1: A mixture of 480 mg (1.04 mmol) of Compound 5, 10 ml of MeOH and 1 ml of DCM was warmed with a heat gun till dissolution was complete. Cooled to r.t., added 48 mg of CSA. Stirred for 1.5 h, diluted with DCM, washed with sat. NaHCO$_3$, dried over sodium sulfate and concentrated. The product was purified by chromatography using 30% of ethyl acetate in hexanes as solvent to furnish 320 mg of Compound 14.

Step 2. Compound 15 was prepared from Compound 14 using procedures similar to Example 1, Step 4(a) and 4(b), except that step 4(a) was modified so that a 2:1 mixture of THF and acetonitrile was used as solvent instead of DCM.

$^1$H NMR (CDCl$_3$ 400 MHz) δ 7.86 (2H, d, J=8.8 Hz), 7.63 (1H, s), 7.51 (2H, d, J=8.8 Hz), 7.09 (1H, s), 5.32 (1H, d, J=5.0 Hz), 4.25 (1H, m), 4.14 (1H, br), 3.73 (1H, t, J=9.0 Hz), 3.58 (1H, t, J=9.0 Hz), 2.70 (2H, m), 2.52–2.33 (6H, ser. m.), 2.0–1.2 (16H, ser. m.); MS (ES) m/e 542.3 (M$^+$).

EXAMPLE 167

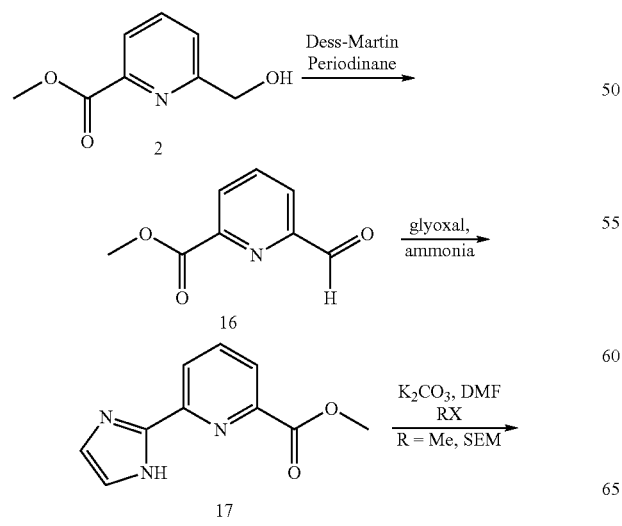

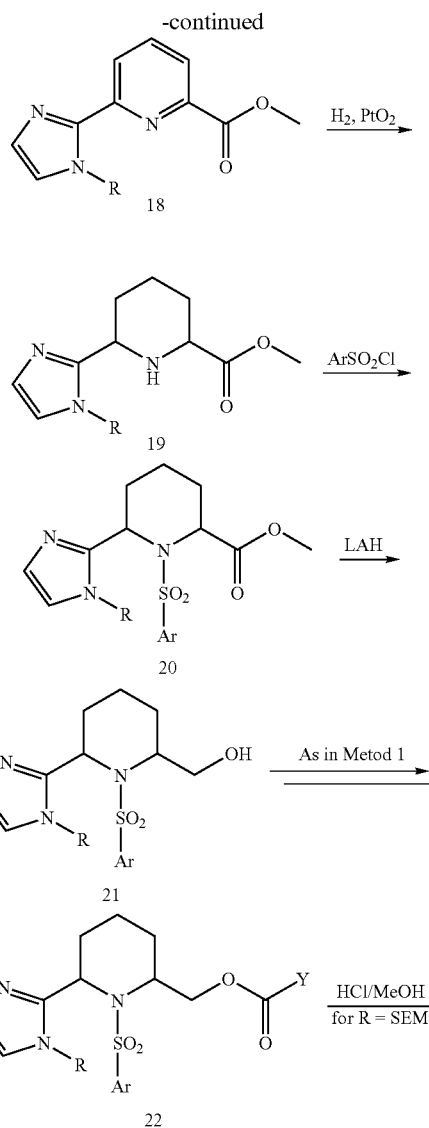

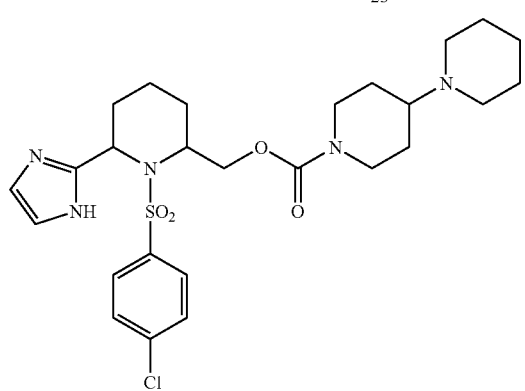

Step 1: Compound 2 was oxidized with Dess-Martin Periodinane using procedure similar to the one used in preparation of Compound 10.

Step 2: To a solution of 3.1 g (18.8 mmol) of Compound 16 in 95 ml of MeOH was added 7.9 g (37.5 mmol) of glyoxal trimer dihydrate followed by slow addition of 24.1 ml of 7 N ammonia/methanol solution. Work-up involved evaporation of volatiles and partitioning the residue between water and DCM. The aqueous phase was extracted with DCM, combined organic phase dried to yield 81.6 g of compound 17.

Step 3: To a solution of 250 mg (1.19 mmol) of Compound 17 in 7 ml of DMF was added 412.8 mg (2.99 mmol) of $K_2CO_3$ followed by 0.422 ml (2.4 mmol) of SEMCl. The mixture was stirred overnight, partitioned between water and DCM, aqueous phase was re-extracted with DCM, combined organic phase was dried over sodium sulfate, concentrated and purified chromatographically to furnish 230 mg of Compound 18.

Step 4: A mixture of 230 mg (0.69 mmol) of Compound 18, 40 mg of $PtO_2$, 10 ml of MeOH and 5 ml of AcOH was hydrogenated at 55 psi over a period of 15 hrs. The catalyst was filtered out, volatiles evaporated, residue dissolved in DCM and washed with sat. $NaHCO_3$, aqueous phase was re-extracted with DCM, combined organic phase was dried over sodium sulfate and concentrated to furnish Compound 19.

Step 5: Compound 20 was prepared from compound 19 using the procedure similar to the procedure used for the preparation of compound 5 in step 4 of example 165.

Step 6: Compound 21 was prepared from Compound 20 by reduction with LAH using the procedure described in Example 53, Preparation B, Step 4

Step 7: Compound 22 was prepared from Compound 21 using procedures similar to Example 1, Step 4(a) and 4(b), except that step 4(a) was modified so that a 2:1 mixture of THF and acetonitrile was used as solvent instead of DCM.

Step 8: A solution of compound 22 in 3M HCl/EtOH was refluxed for 3 hours, concentrated, partitioned between DCM and 15% aq. NaOH, aqueous phase was re-extracted with DCM, combined organic phase was dried over sodium sulfate, concentrated and purified chromatographically using 8% MeOH in DCM to furnish Compound 23.

$^1$H NMR (CDCl$_3$ 300 MHz) δ 10 (1H, s), 7.81 (2H, d, J=8.8 Hz), 7.53 (2H, d, J=8.8 Hz), 7.02 (2H, s), 4.48 (1H, d, J=4.8 Hz), 4.49 (1H, m), 4.20 (2H, d, J=12.0 Hz), 3.85 (1H, s), 3.38 (1H, t, J=10.4 Hz), 2.92–2.48 (7H, ser. m.), 2.06–1.17 (16H, ser. m.); MS (ES) m/e 550.1 (M+H)$^+$.

Other compounds prepared by this method:

| Compound No. | Structure | Retention Time (minutes) | Observed Mass |
|---|---|---|---|
| 167-A | 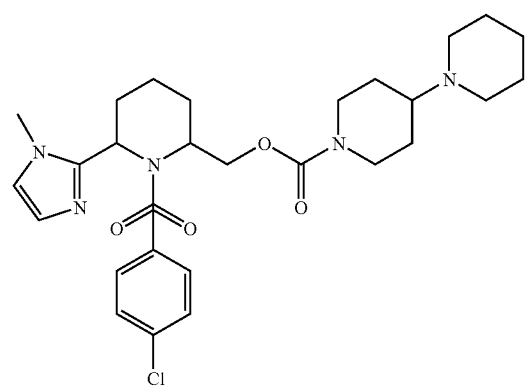 | 3.91 | 564.3 |
| 167-B | 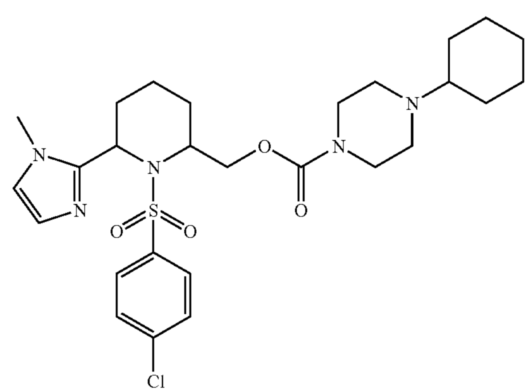 | 4.68 | 564.1 |

| Compound No. | Structure | Retention Time (minutes) | Observed Mass |
|---|---|---|---|
| 167-C | 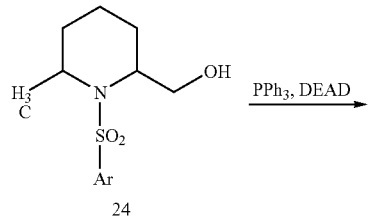 | N/A | N/A |

EXAMPLE 168

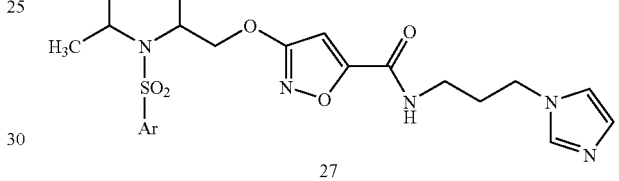

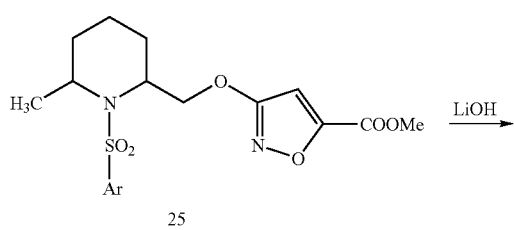

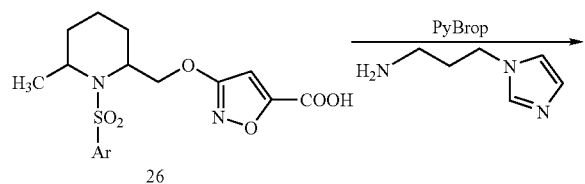

Step 1: To a mixture of 100 mg (0.329 mmol) of Compound 24, prepared as described in Example 1, in 1 ml of THF was added 172 mg (0.658 mmol) of triphenylphosphine and 114 mg (0.658 mmol) of DEAD. The mixture was stirred overnight, concentrated and chromatographed to yield 60 mg of Compound 25.

Step 2: To a solution of 60 mg of Compound 25 in 2 ml of THF was added a solution of 40 mg of LiOH in 0.3 ml of water. The mixture was stirred vigorously over a period of 4 hr, diluted with a few ml of 20% citric acid and extracted with DCM. The organic phase was dried over $Na_2SO_4$ and concentrated, the residue was passed through a silica gel plug using 10% of MeOH in DCM as solvent to yield 40 mg of Compound 26.

Step 3: A solution of 20 mg of Compound 26 in a mixture of 1 ml of DCM and 0.5 ml of DMF was treated with 20 mg of N-(3-aminopropyl)imidazole and 25 mg of PyBrop. The mixture was stirred overnight, washed with water, dried, concentrated and purified chromatographically using 10% of MeOH in DCM to furnish 12 mg of Compound 27.

$^1$H NMR (CDCl$_3$ 300 MHz) δ 7.78 (2H, d, J=8.8 Hz), 7.53 (1H, s), 7.47 (2H, d, J=8.8 Hz), 7.10–6.98 (2H, ser. m.), 6.52 (1H, s), 4.43–4.34 (3H, ser. m.), 4.14 (1H, m), 4.05 (2H, t, J=7.0 Hz), 3.44 (2H, m), 2.12 (3H, m), 1.90–1.20 (6H, ser. m.), 1.28 (3H, d, J=7.1 Hz); MS (ES) m/e 522.1 (M+H)$^+$.

Other compounds prepared by this method:

| Compound No. | Structure | Retention Time (minutes) | Observed Mass |
|---|---|---|---|
| 168-A | 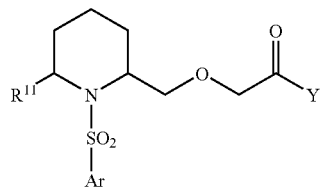 | 5.31 | 429.1 |

EXAMPLE 169

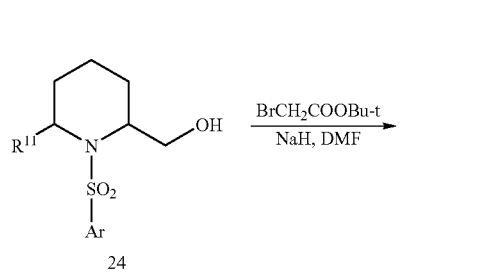

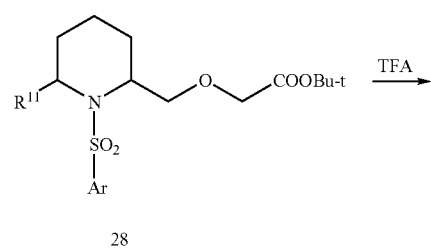

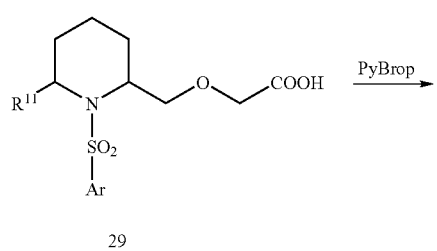

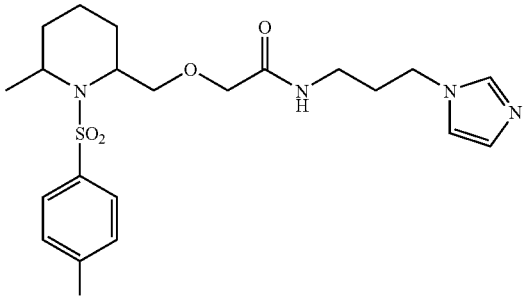

Step 1: To a solution of 100 mg (0.329 mmol) of Compound 24 in 1 ml of DMF was added 26 mg (0.658 mmol) of a 60% dispersion of NaH in mineral oil. The mixture was sonicated for 15 min. 137 mg (0.9 mmol) of t-butyl bromoacetate was added and the mixture was stirred overnight. Reaction was quenched with water, extracted with DCM, concentrated, passed through a silica gel plug using 10% of ethyl acetates in hexanes as solvent to furnish 130 mg of Compound 28.

Step 2: Dissolved 120 mg of compound 28 in 2 ml of DCM. Added 2 ml of TFA. Stirred the mixture for 30 min, evaporated volatiles. Obtained 120 mg of crude acid 29.

Step 3: For the preparation of amide 30 used the procedure described in Example 168 (synthesis of Compound 27).

$^1$H NMR (CDCl$_3$ 300 MHz) δ 7.76 (2H, d, J=8.8 Hz), 7.66 (1H, s), 7.48 (2H, d, J=8.8 Hz), 7.03 (2H, d, J=10.5 Hz), 4.40 (1H, m), 4.12–3.93 (4H, ser. m.), 3.83 (1H, m), 3.71 (1 H, m), 3.52 (1H, m), 3.36 (2H, m), 2.65 (1 H, br), 2.07 (2H, m), 1.66–1.26 (6H, ser. m.), 1.33 (3H, d, J=7.1 Hz); MS (ES) m/e 469.1 (M+H)$^+$.

Other compounds prepared by this method:

| Compound No. | Structure | Retention Time (minutes) | Observed Mass |
|---|---|---|---|
| 169-A | 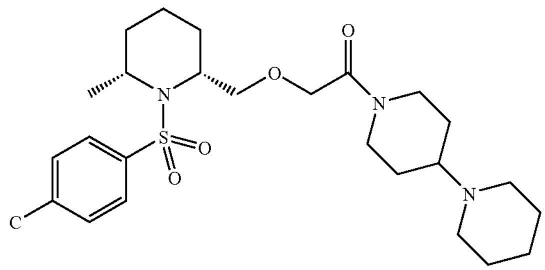 | 4.81 | 512.1 |
| 169-B | 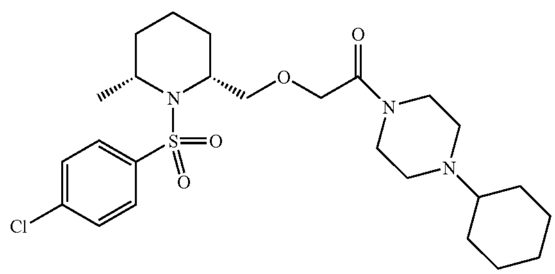 | 4.57 | 512.1 |
| 169-C | 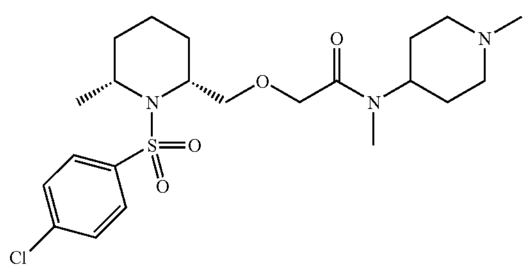 | 4.56 | 472.1 |
| 169-D | 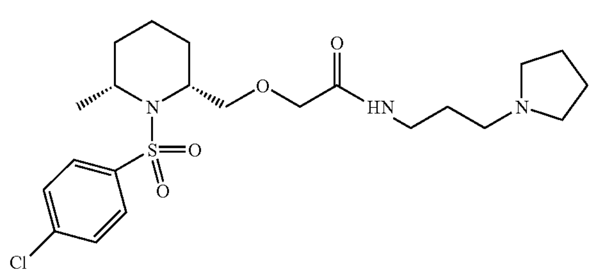 | 4.81 | 472.1 |

EXAMPLE 170

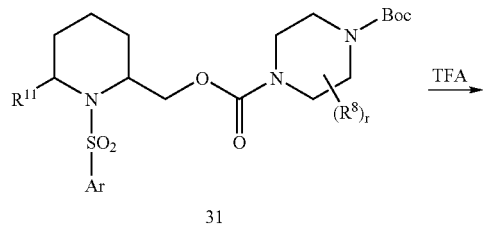

31

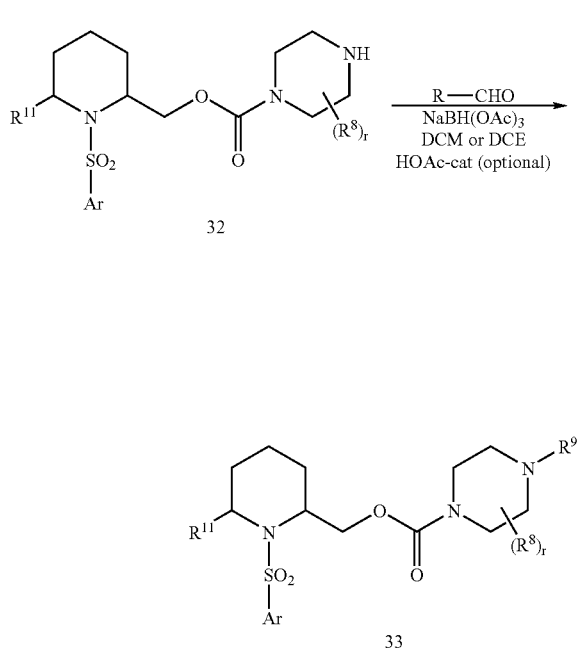

More Specifically

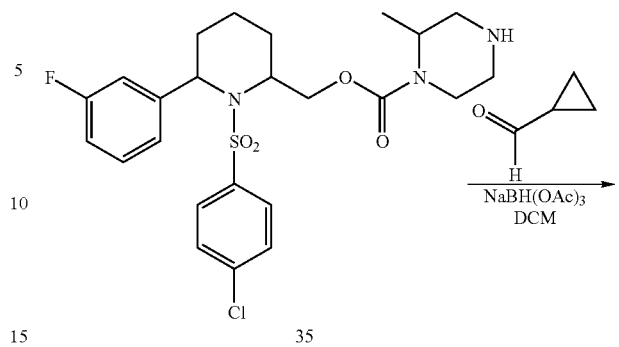

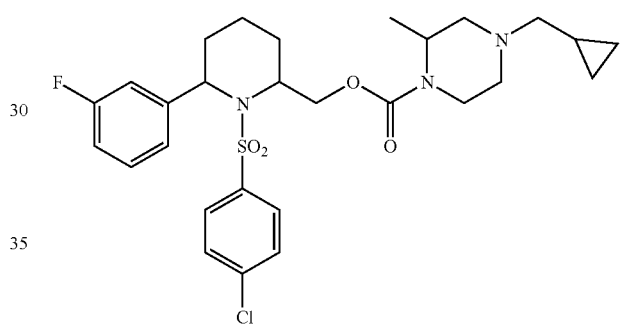

36

Step 1: 120 mg of Compound 34, prepared using procedures described in Example 53, was dissolved in 20 ml of DCM and treated with a pre-mixture of 10 ml of TFA and 1 ml of water. Reaction mixture was stirred over a period of 1 hr, volatiles were evaporated, residue was re-dissolved in DCM and washed with 1M sodium hydroxide. Organic phase was dried over sodium sulfate and concentrated to furnish 90 mg of Compound 35.

Step 2: To a solution of 44 mg (0.0864 mmol) of compound 35 in 2 ml of DCM was added 100 mg of cyclopropylcarboxaldehyde, 55 mg (0.259 mmol) of sodium triacetoxyborohydrate and one drop of acetic acid. The mixture was stirred overnight, diluted with DCM, washed with 1 M sodium hydroxide, dried over sodium sulfate and concentrated. The residue was purified by chromatography using 5% of MeOH in DCM as solvent. $^1$H NMR (CDCl$_3$ 400 MHz) δ 7.85 (2H, m), 7.53 (2H, m), 7.38–7.27 (3H, m), 7.00–6.94 (1H, m), 5.19 (1H, m), 4.42–4.24 (2H, ser. m.), 3.91 (1H, m) 3.76 (1H, m), 3.50–3.38 (1H, m), 3.21 (1H, m), 2.89 (2H, m), 2.33–1.95 (4H, ser. m.), 1.64–1.20 (9H, ser. m., J=7.1 Hz), 0.85 (1H, ser. m.), 0.52 (2H, s), 0.11 (2H, s); MS (ES) m/e 564.1 (M+H)$^+$.

Other compounds prepared are shown below:

| Compound No. | Structure | Retention Time (minutes) | Observed Mass |
|---|---|---|---|
| 170-A | 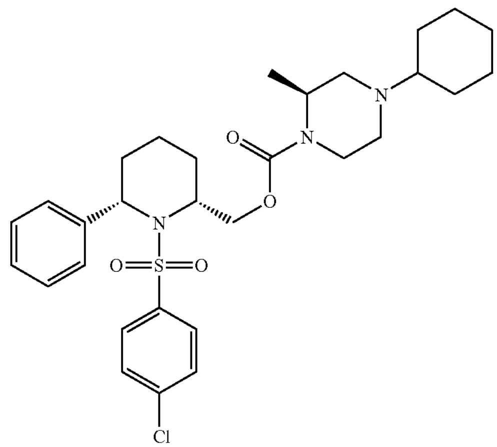 | 5.56 | 574.1 |
| 170-B | 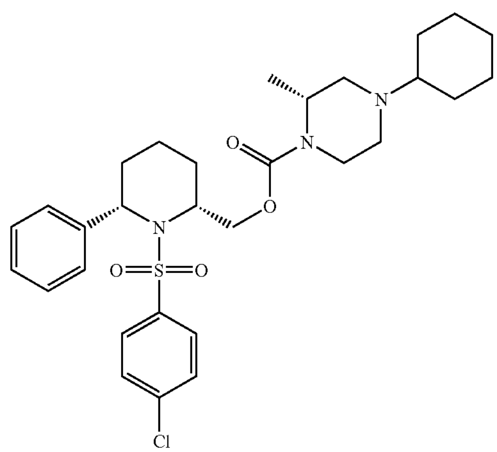 | 5.41 | 575.1 |
| 170-C | 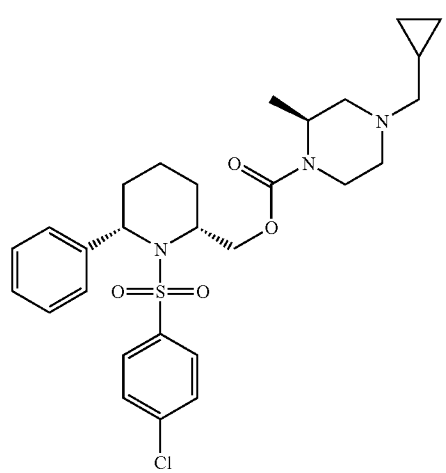 | 5.21 | 546.1 |

-continued

| Compound No. | Structure | Retention Time (minutes) | Observed Mass |
|---|---|---|---|
| 170-D | 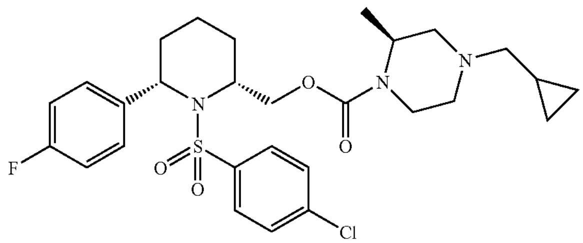 | 5.36 | 564.1 |
| 170-E | 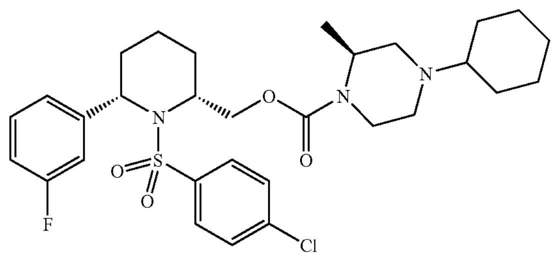 | 5.21 | 592.3 |
| 170-F | 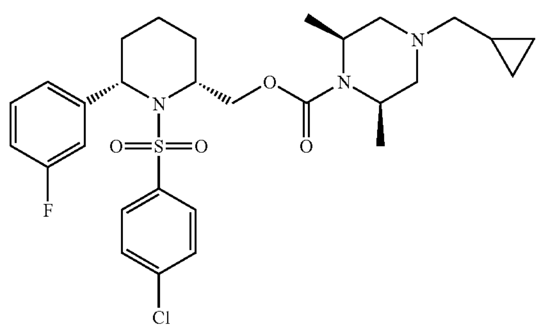 | 5.18 | 578.1 |
| 170-G | 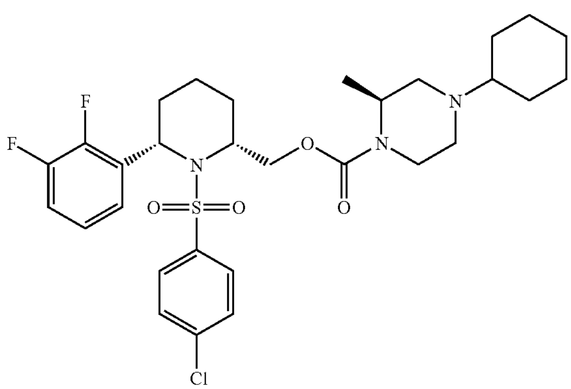 | 5.55 | 610.1 |
| 170-H | 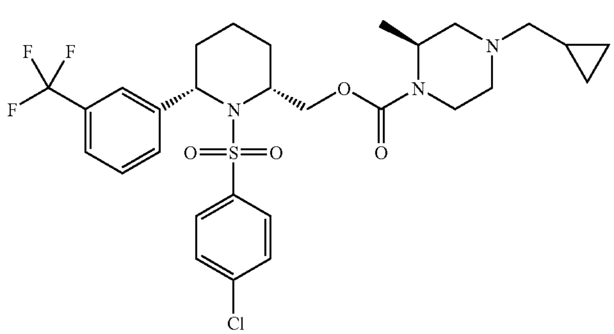 | 5.72 | 614.1 |

-continued

| Compound No. | Structure | Retention Time (minutes) | Observed Mass |
|---|---|---|---|
| 170-I | 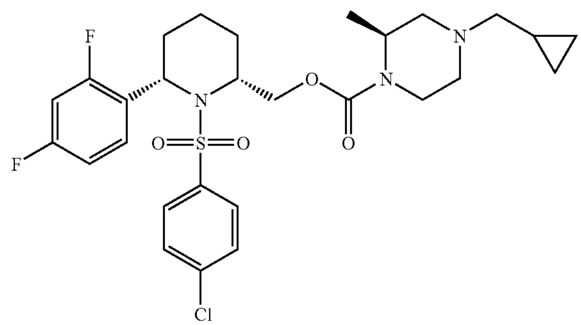 | 5.55 | 582.1 |
| 170-J | 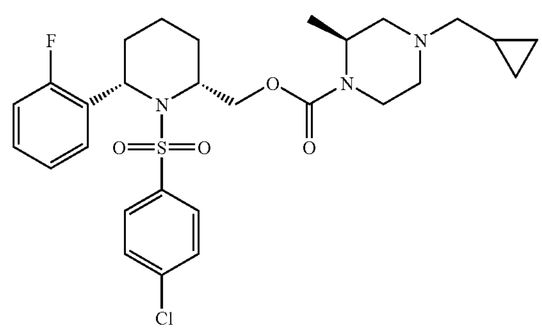 | 5.58 | 564.1 |
| 170-K | 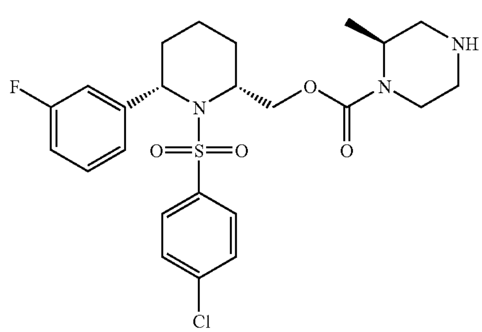 | 5.12 | 510.1 |
| 170-L | 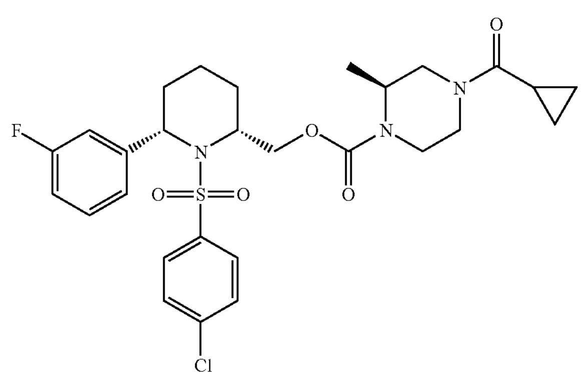 | 5.58 | 578.1 |

-continued

| Compound No. | Structure | Retention Time (minutes) | Observed Mass |
|---|---|---|---|
| 170-M | 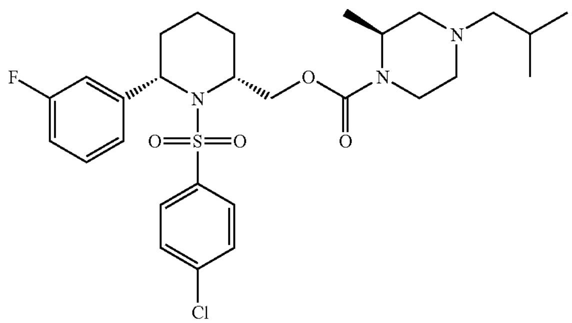 | 5.72 | 566.1 |
| 170-N | 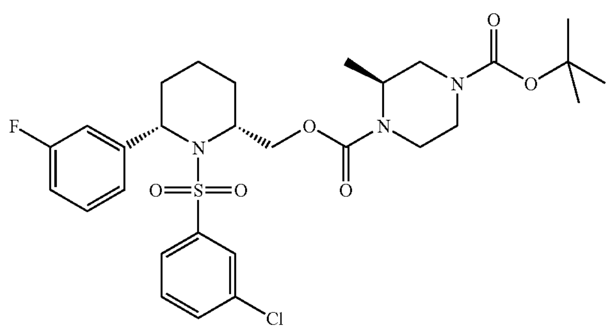 | 6.05 | 610.1 |
| 170-O | 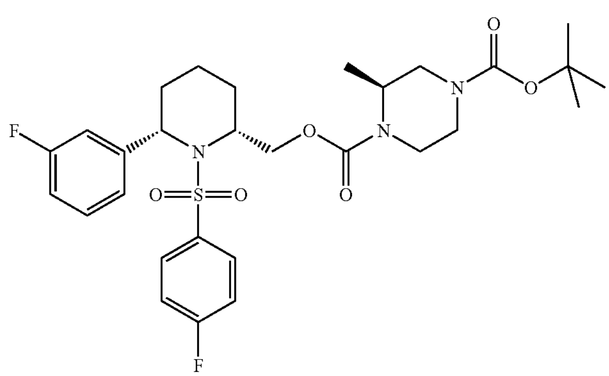 | 6.05 | 594.1 |
| 170-P | 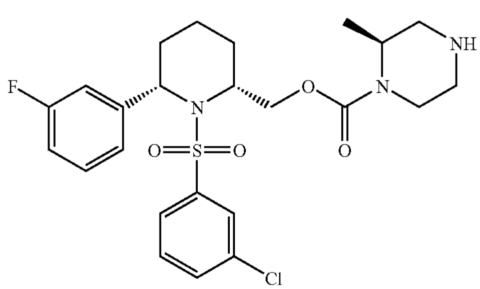 | 5.22 | 510.1 |

-continued

| Compound No. | Structure | Retention Time (minutes) | Observed Mass |
|---|---|---|---|
| 170-Q | 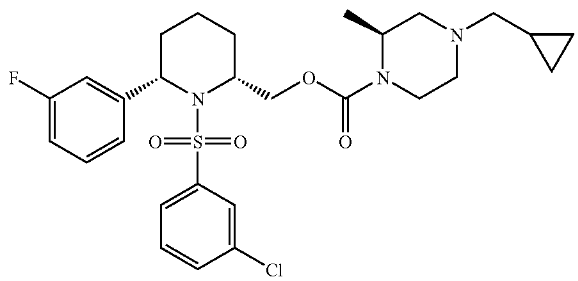 | 4.87 | 564.3 |
| 170-R | 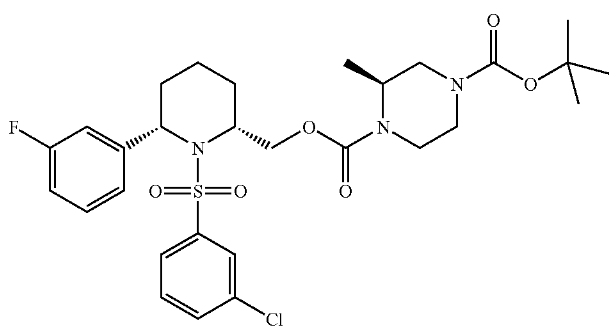 | 5.48 | 590.3 |
| 170-S | 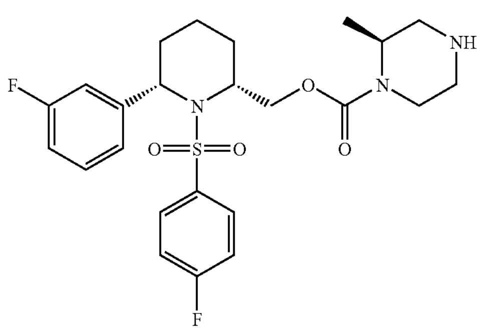 | 4.41 | 494.3 |
| 170-T | 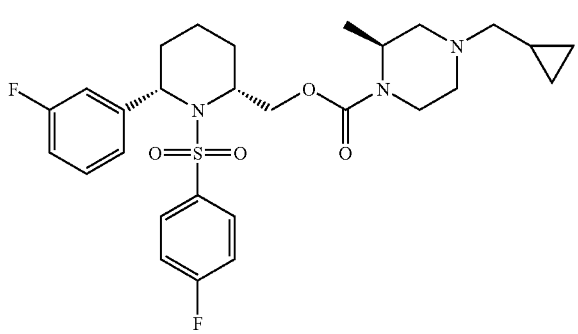 | 4.78 | 548.3 |

-continued

| Compound No. | Structure | Retention Time (minutes) | Observed Mass |
|---|---|---|---|
| 170-U | 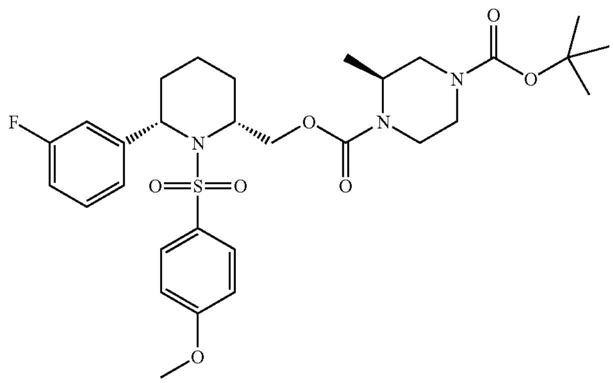 | 5.98 | 606.1 |
| 170-V | 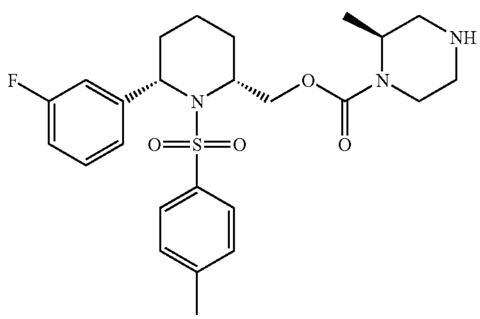 | 4.75 | 490.1 |
| 170-W | 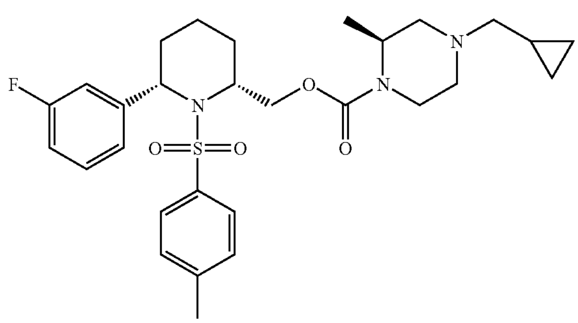 | 5.38 | 544.1 |
| 170-X | 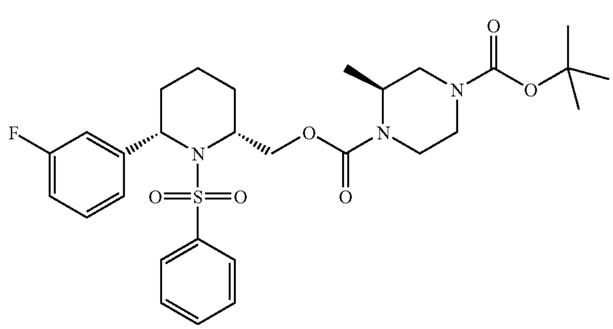 | 5.92 | 576.1 |

-continued

| Compound No. | Structure | Retention Time (minutes) | Observed Mass |
|---|---|---|---|
| 170-Y | 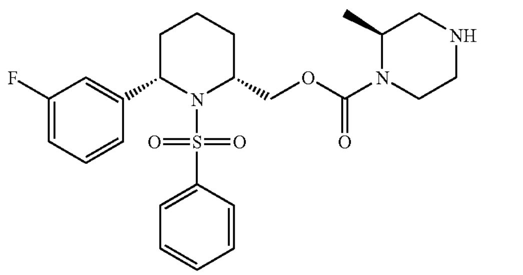 | 4.61 | 476.1 |
| 170-Z | 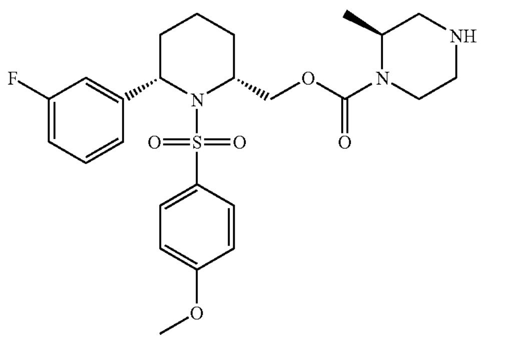 | 4.51 | 506.1 |
| 170-AA | 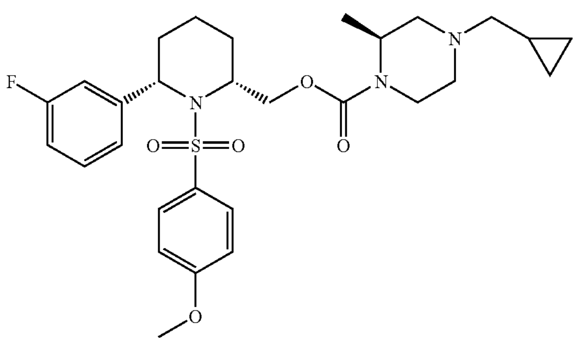 | 5.28 | 560.1 |
| 170-AB | 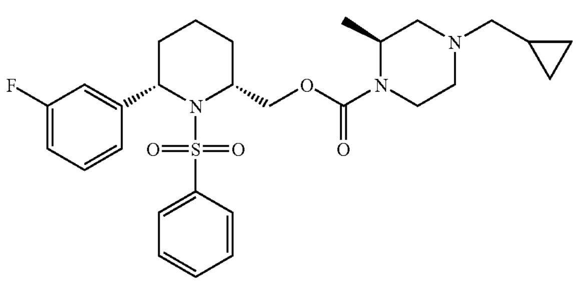 | 5.12 | 531.1 |
| 170-AC | 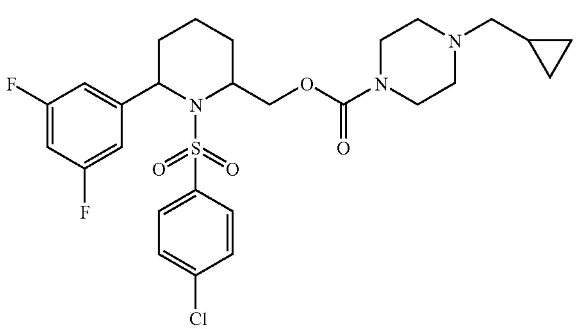 | 5.55 | 568.3 |

-continued
| Compound No. | Structure | Retention Time (minutes) | Observed Mass |
|---|---|---|---|
| 170-AD | 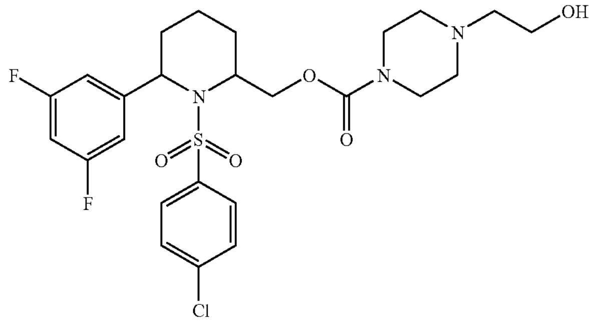 | 5.01 | 558.3 |
EXAMPLE 171
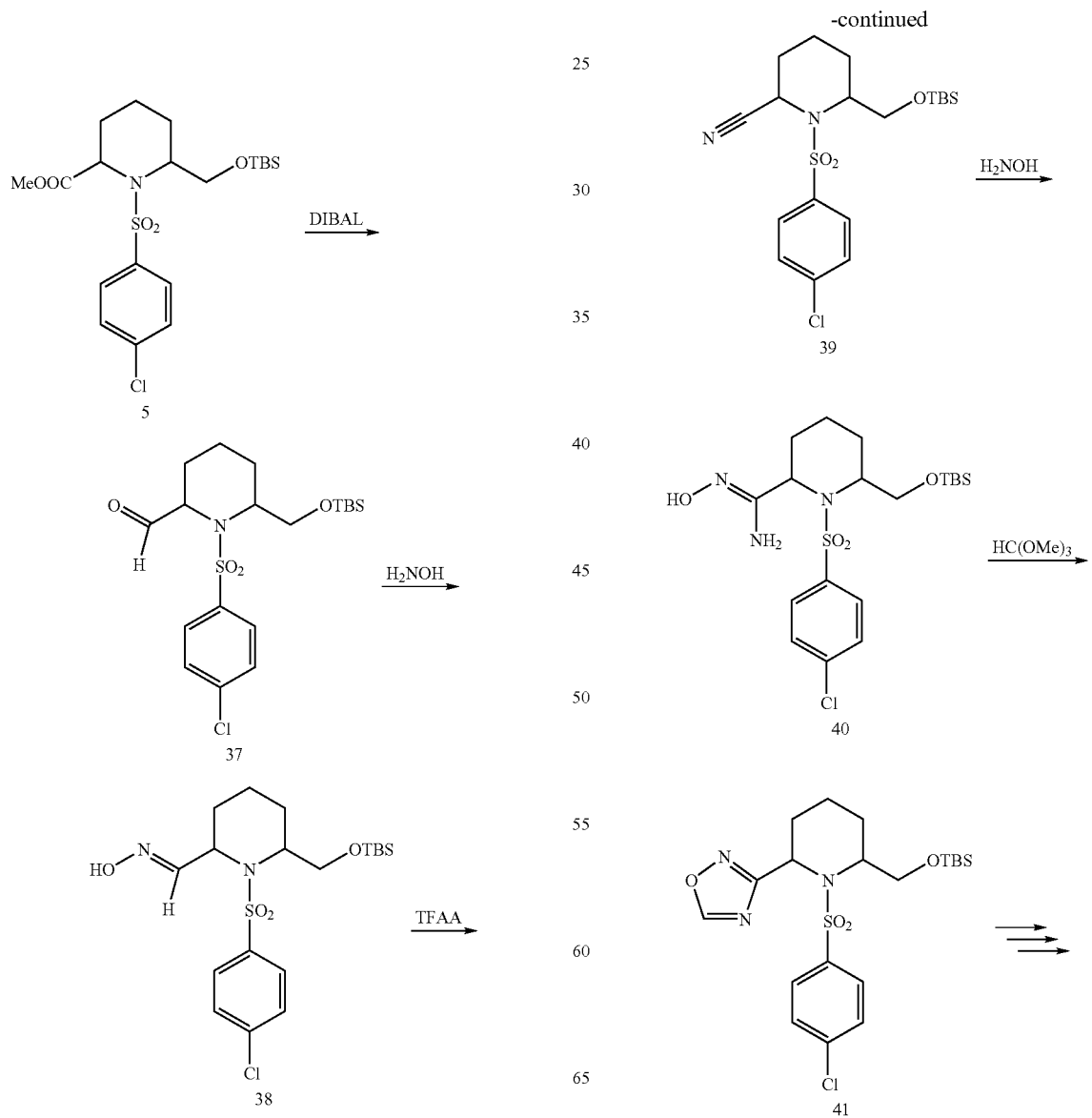

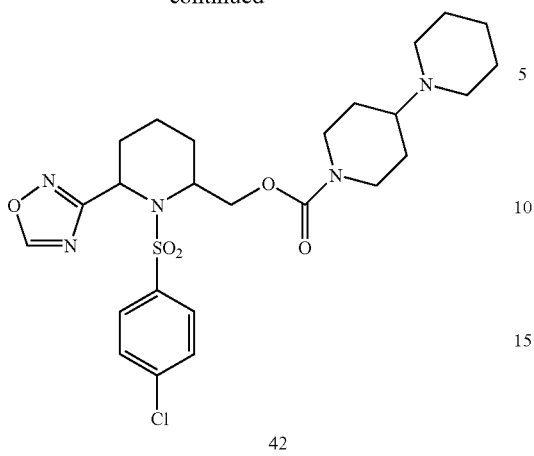

42

Step 1: To a solution of 1.35 g (2.92 mmol) of Compound 5 in 20.0 ml of DCM at −78° C. was added 3.2 ml (3.2 mmol) of 1 M solution of DIBAL in toluene. The mixture was stirred for 5 min, quenched with a 20% aq. sodium potassium tartrate solution, warmed up to room temperature, extracted with DCM, dried over sodium sulfate and concentrated. The product was purified chromatographically using DCM as solvent to furnish 1.06 g of aldehyde 37.

Step 2: A mixture of 3.21 g of aldehyde 37, 3.21 g of hydroxylamine hydrochloride, 8 ml of triethylamine and 50 ml of ethanol was heated briefly with a heat gun to boiling till all components dissolved. The reaction mixture was stirred overnight at r.t., volatiles were evaporated, residue partitioned between DCM and water, aqueous phase was re-extracted with DCM. Combined organic phase was dried over sodium sulfate and concentrated. The product was purified chromatographically using gradient 5 to 20% of ethyl acetate in hexanes as solvent to furnish 1.546 g of oxime 38.

Step 3: To a solution of 1.21 g (2.71 mmol) of oxime 38 in 12 ml of DCM was added 2.18 ml (27 mmol) of pyridine followed by 1.14 g (5.42 mmol) of trifluoroacetic acid. The reaction mixture was stirred for 1 h, washed with water, dried over sodium sulfate and concentrated. The product was purified chromatographically using 10% of ethyl acetate in hexanes as solvent to furnish 1.09 g of nitrile 39.

Step 4: Heated a mixture of 100 mg of nitrile 39, 100 mg of hydroxilamine hydrochloride, 0.1 ml of Hunig's base and 1.0 ml of ethanol at 80° C. for 10 min, removed heating and stirred over 24 h. The reaction mixture was partitioned between water and DCM, organic phase was dried over sodium sulfate and concentrated. The product was purified chromatographically using 30% of ethyl acetate in hexanes as solvent to furnish 90 mg of amidoxime 40.

Step 5: A mixture of 90 mg of amidoxime 40, 3.0 ml of triethylorthoformate, 5 mg of tosic acid hydrate and 0.5 ml of DCM was heated at 100° C. over a period of 40 min. The reaction mixture was partitioned between DCM and sat. sodium bicarbonate, organic phase was dried over sodium sulfate and concentrated. The product was purified chromatographically using 20% of ethyl acetate in hexanes as solvent to furnish 70 mg of oxadiazole 41.

Step 6: Conversion of oxadiazole 41 to compound 42 was carried out according to Steps 1 and 2 of example 166. $^1$H NMR (CDCl$_3$ 300 MHz) δ 8.67 (1H, s), 7.89 (2H, d, J=8.05 Hz), 7.50 (2H, d, J=8.05 Hz), 5.42 (1H, d, J=5.8 Hz), 4.26 (1H, m), 4.12 (2H, m), 3.83 (2H, m), 2.69 (2H, m), 2.48 (4H, m), 2.37 (2H, m), 1.84–1.36 (15H, ser. m.), MS (ES) m/e 552.1 (M+H)$^+$.

EXAMPLE 172

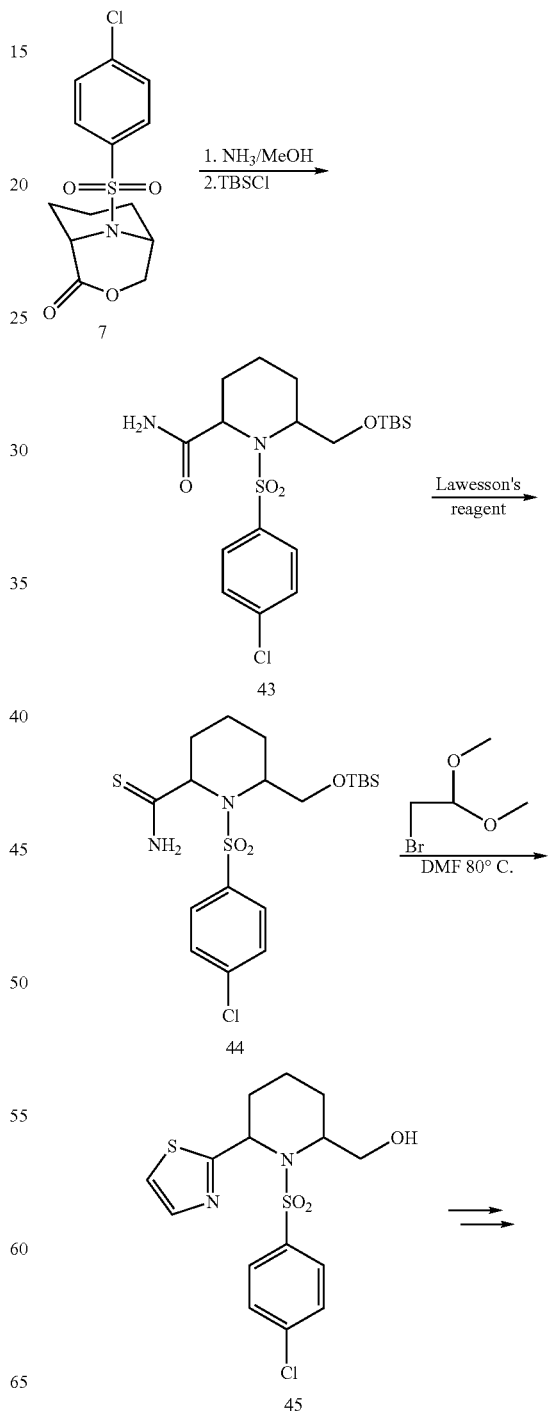

-continued

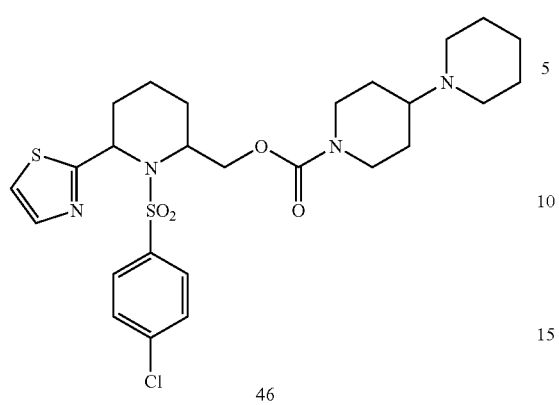

46

Step 1: Stirred a mixture of 1.0 g of compound 7 in 10 ml of 7 M solution of ammonia in methanol over a period of 3 h and evaporated the volatiles. 500 mg of resulting product was dissolved in 5 ml of DMF and treated with 152 mg (2.24 mmol) of imidazole and 218 mg (1.456 mmol) of TBSCl. Reaction mixture was stirred overnight, diluted with DCM, washed with sat. NaHCO$_3$, dried and concentrated. The product was purified chromatographically using 20% of ethyl acetate in hexanes as solvent to furnish 500 mg of amide 43.

Step 2: A mixture of 250 mg (0.56 mmol) of amide 43 and 226 mg (0.56 mmol) of Lawesson's reagent was refluxed in 3 ml of DCM over 8 h. Solvent was evaporated and the product purified by prep. TLC using 30% of ethyl acetate in hexanes as solvent to furnish 70 mg of thioamide 44.

Step 3: Heated a mixture of 70 mg (0.151 mmol) of thioamide 44, 0.5 ml of dimethylacetal of bromoaldehyde in 1 ml of DMF at 80° C. over a period of 5 h. Reaction mixture was partitioned between DCM and sat. NaHCO$_3$, dried and concentrated. The product was purified chromatographically using 30% of ethyl acetate in hexanes as solvent to furnish 25 mg of thiazole 45.

Step 4: Transformation of alcohol 45 to compound 46 was carried out according to Example 1 steps A and B. LCMS m/z=567.1, retention 4.88 min.

$^1$H NMR (CDCl$_3$ 300 MHz) δ 7.86 (2H, d, J=8.8 Hz), 7.68 (1H, d, J=3.3 Hz), 7.52 (2H, d, J=8.8 Hz), 7.37 (1H, d, J=3.3 Hz), 5.35 (1H, d, J=5.5 Hz), 4.36 (1H, m), 4.20 (2H, m), 3.83 (1H, dd, J=6.6, 11.0 Hz), 3.63 (1H, dd, J=8.7, 11.0 Hz), 2.82–2.33 (8H, ser. m.), 1.88–1.20 (15H, ser. m.), MS (ES) m/e 567.1 (M+H)$^+$.

EXAMPLE 173

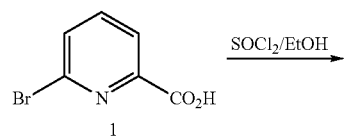

-continued

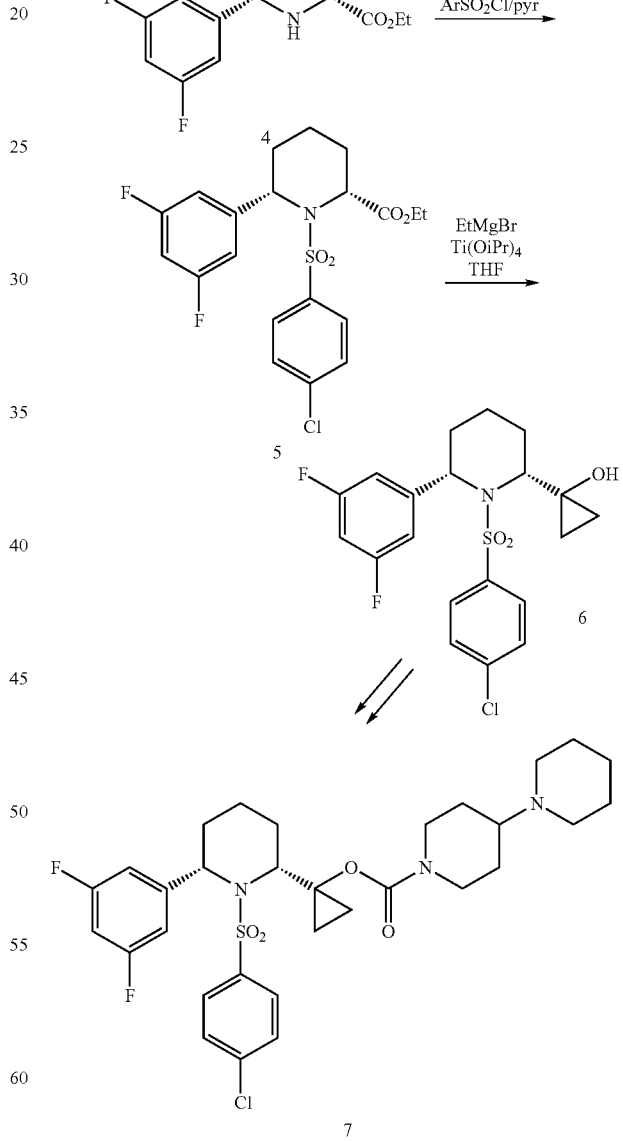

Step 1: To a stirring solution of 6-bromopicolinic acid (14.25 g, 70.3 mmol) in anhydrous ethanol (250 ml) is slowly added thionyl chloride (60 ml) at 5° C. After the addition is completed, remove the ice-bath and stir the mixture at 25°

C. for 3 hr. Evaporate the solvent in vacuo, basify aqueous residue with saturated sodium carbonate, and extract with DCM. Dry the organic phase over Na$_2$SO$_4$ and concentrate to give ethyl 6-bromopicolinate as white solid (15.75 g).

Step 2: Heat ethyl 6-bromopicolinate (15.75 g, 68.5 mmol), 3,5-difluorophenylboronic acid (12.98 g, 82.2 mmol), tetrakis(triphenylphsphine)palladium (7.9 g, 6.85 mmol) and sodium carbonate (18 g) in toluene (160 ml) and methanol (80 ml) under reflux for 16 hr. Cool to room temperature, dilute with DCM, and filter. Wash the filtrate with water, concentrate the dried (Na$_2$SO$_4$) organic solution, and purify the residue chromatographically using 5% ethyl acetate in hexanes to give 10.6 g of the product, as white solid.

Step 3: Under a hydrogen atmosphere, stir a solution of Compound 3 (10.5 g, 39.9 mmol) in methanol (400 ml) and glacial acetic acid (40 ml) in the presence of platinum oxide (1.81 g) for 72 hr. Purge the reaction mixture with nitrogen. Filter and then concentrate the reaction mixture in vacuo. Take up the residue in water, basify with saturated sodium carbonate, and extract with DCM. Dry the organic phase over Na$_2$SO$_4$ and concentrate in vacuo to give light yellow foam (10.7 g).

Step 4: A solution of Compound 4 (10.7 g, 39.7 mmol) in pyridine (100 ml) is treated with 4-chlorobenzenesulfonyl-chloride (16.8 g, 79.5 mmol). The mixture is heated at 60° C. for 4 hr. Cool to room temperature, concentrate in vacuo, and the residue is subjected to flash-chromatography over silica gel (eluting 10% ethyl acetate in hexanes) to provide 14 g of product, as white powder.

Step 5: To a stirring solution of Compound 5 (2.0 g, 4.5 mmol) and titanium isopropoxide (0.41 ml, 1.35 mmol) in terahydrofuran (15 ml) is added a solution of ethylmagnesium bromide (4.5 ml, 13.5 ml, 3M in Et$_2$O) slowly over a period of 1 hr at 5° C., and the stirring is continued for 10 min. The mixture is then poured into cooled (5° C.) 10% aq HCl (45 ml) and the products are extracted with DCM (3×25 ml). The combined DCM extracts are washed with water (25 ml), dried (Na$_2$SO$_4$), and the solvent is removed. The product is obtained by flash-chromatography (eluting 13% ethyl acetate in hexanes) as light yellow oil (1.5 g).

Step 6: The compound was prepared from Compound 6 using procedures similar to Example 1, Step 4(a) and 4(b) except that step 4(a) was modified so that a 2:1 mixture of THF and acetonitrile was used as solvent instead of DCM, and the mixture was heated at 78° C. for 16 hr.

$^1$H NMR (CDCl$_3$, 400 MHz) δ 7.81 (2H, d, J=8.3 Hz), 7.79 (2H, d, J=7.9 Hz), 7.49 (2H, d, J=8.1 Hz), 6.75–6.62 (1H, m), 5.50–4.60 (2H, m), 4.35–3.62 (2H, m), 2.90–2.20 (7H, m), 2.10–0.86 (16H, m), 0.85–0.63 (2H, m), 0.50–0.10 (2H, m); MS (ES) m/e 623.1 (M+H)$^+$.

Compounds prepared via a similar method:

| Compound No. | Structure | Retention Time (minutes) | Observed Mass |
|---|---|---|---|
| 173-A | 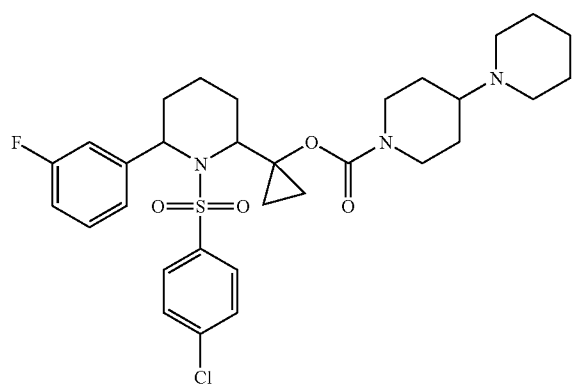 | 5.45 | 604.1 |
| 173-B | 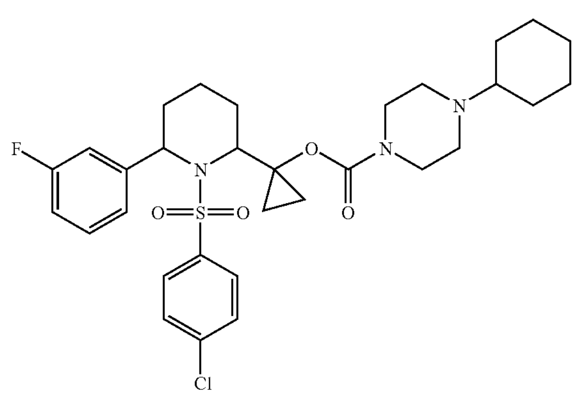 | 5.55 | 604.1 |

-continued

| Compound No. | Structure | Retention Time (minutes) | Observed Mass |
|---|---|---|---|
| 173-C | 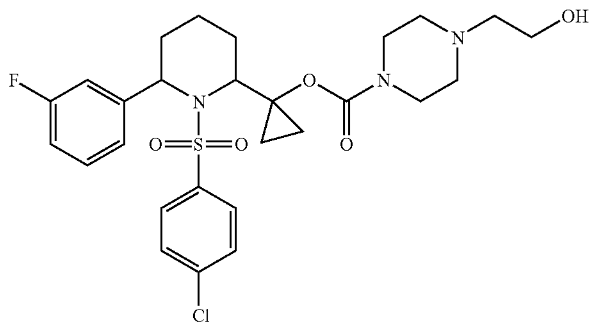 | 4.95 | 566.1 |
| 173-D | 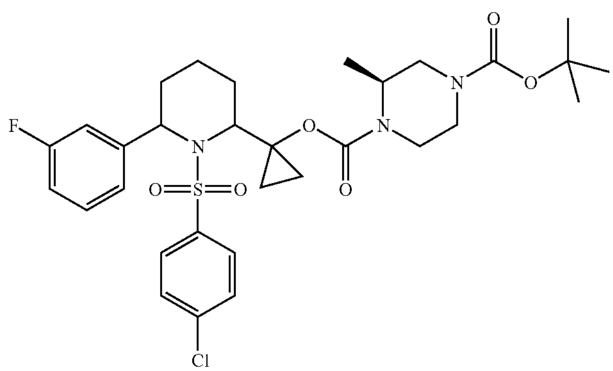 | 5.62 | 636.2 |
| 173-E | 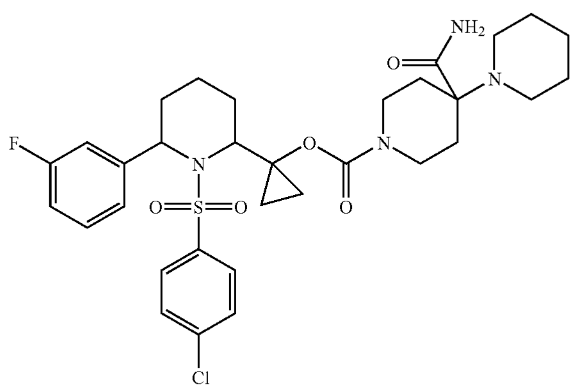 | 4.65 | 647.4 |
| 173-F | 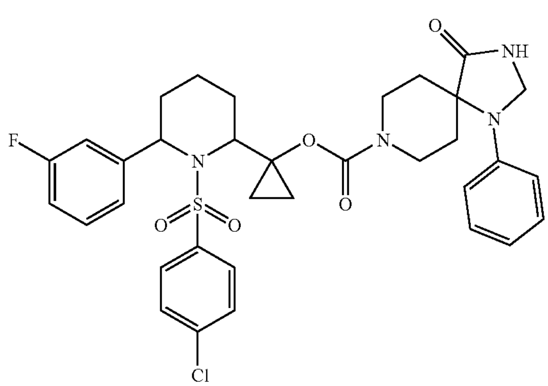 | 5.08 | 667.4 |

-continued

| Compound No. | Structure | Retention Time (minutes) | Observed Mass |
|---|---|---|---|
| 173-G | 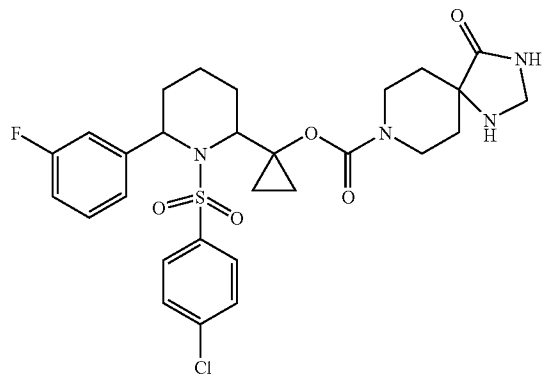 | 4.24 | 591.3 |
| 173-I | 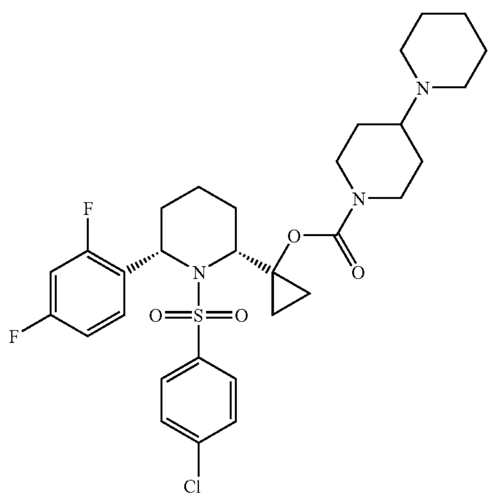 | 5.75 | 622.1 |
| 173-J | 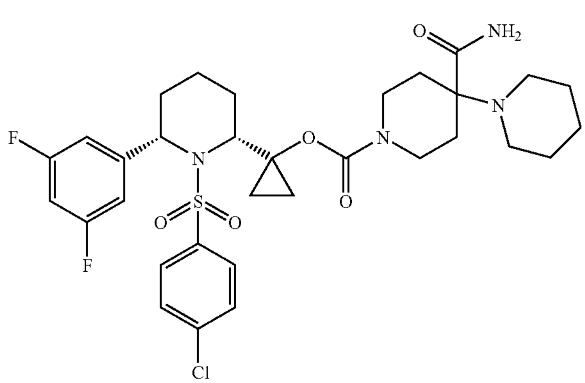 | 5.12 | 665.2 |

-continued

| Compound No. | Structure | Retention Time (minutes) | Observed Mass |
|---|---|---|---|
| 173-K | 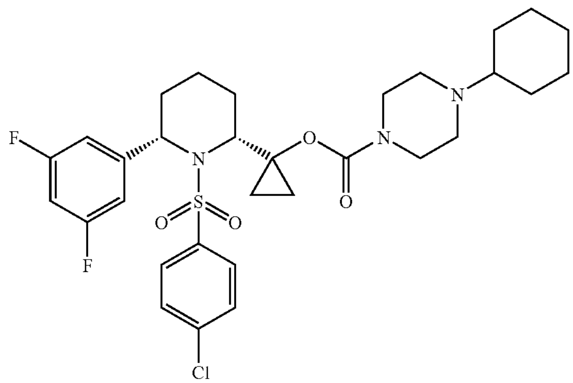 | 5.45 | 622.1 |
| 173-L | 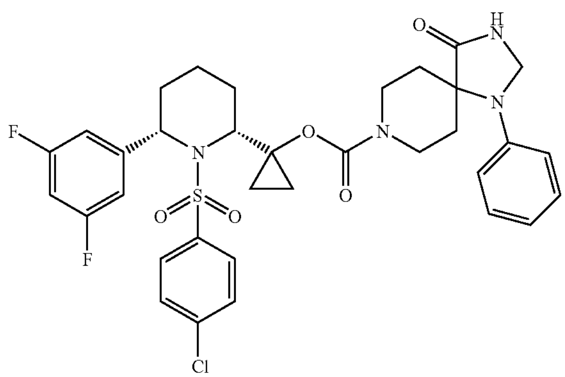 | 5.42 | 685.2 |
| 173-M | 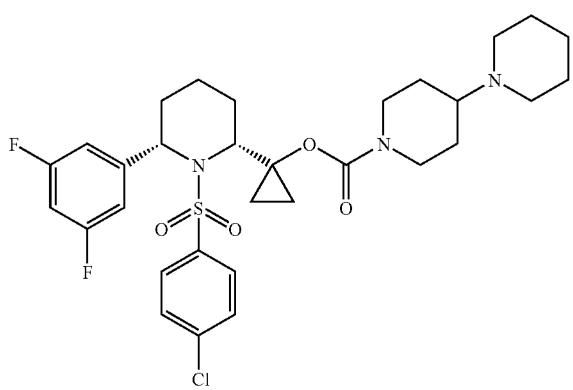 | 5.55 | 622.1 |
| 173-N | 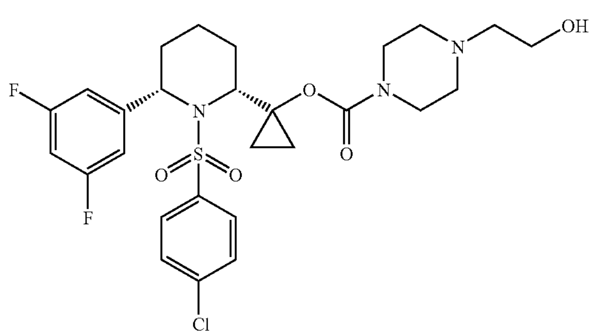 | 5.02 | 584.1 |

-continued

| Compound No. | Structure | Retention Time (minutes) | Observed Mass |
|---|---|---|---|
| 173-O | 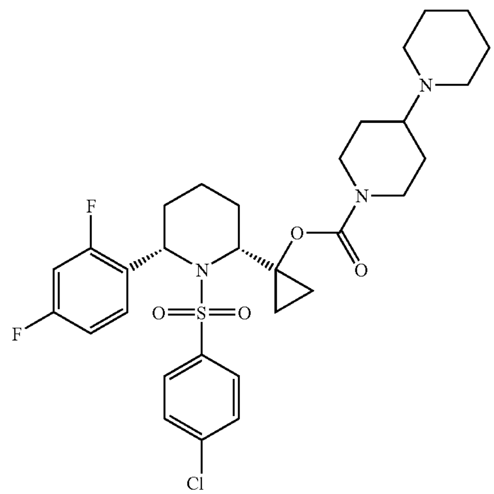 | 5.75 | 622.1 |
| 173-P | 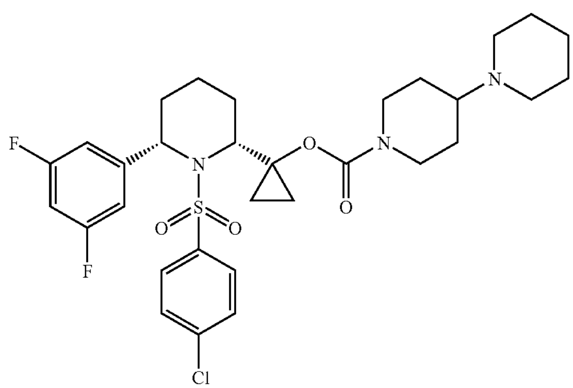 | 5.55 | 622.1 |
| 173-Q | 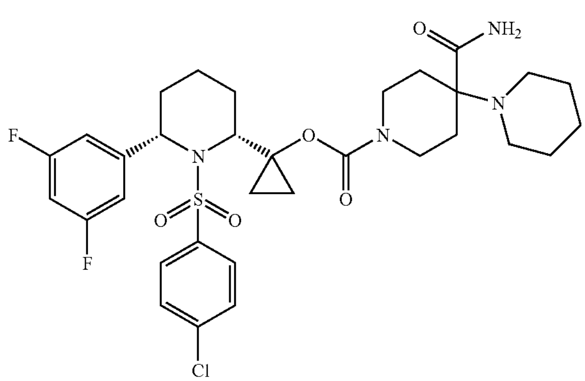 | 5.12 | 665.2 |

-continued
| Compound No. | Structure | Retention Time (minutes) | Observed Mass |
|---|---|---|---|
| 173-R | 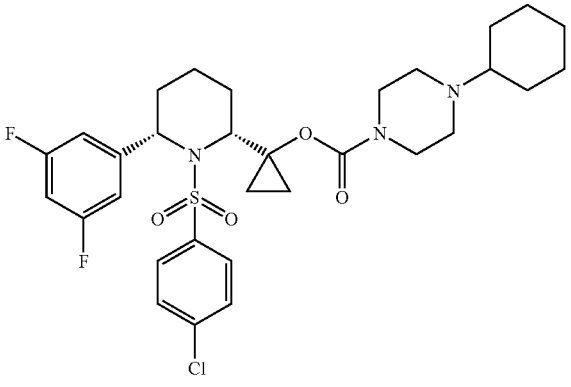 | 5.45 | 622.1 |
| 173-S | 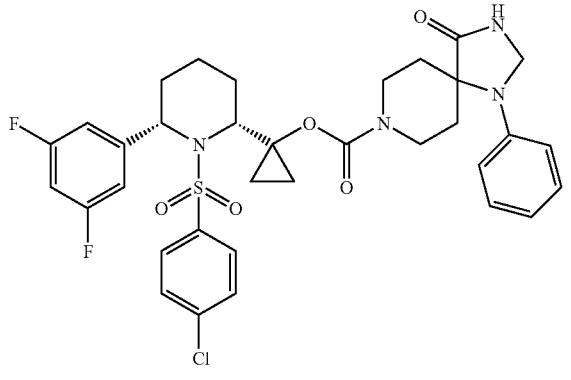 | 5.42 | 685.2 |
| 173-T | 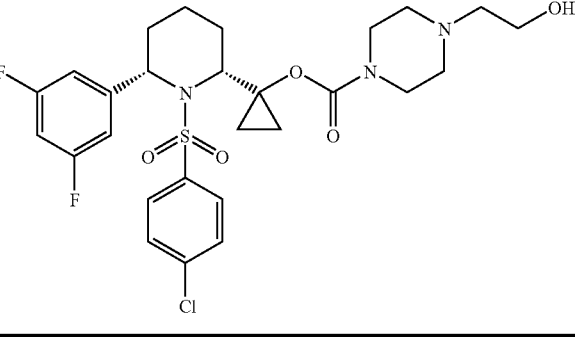 | 5.02 | 584.1 |

EXAMPLE 174

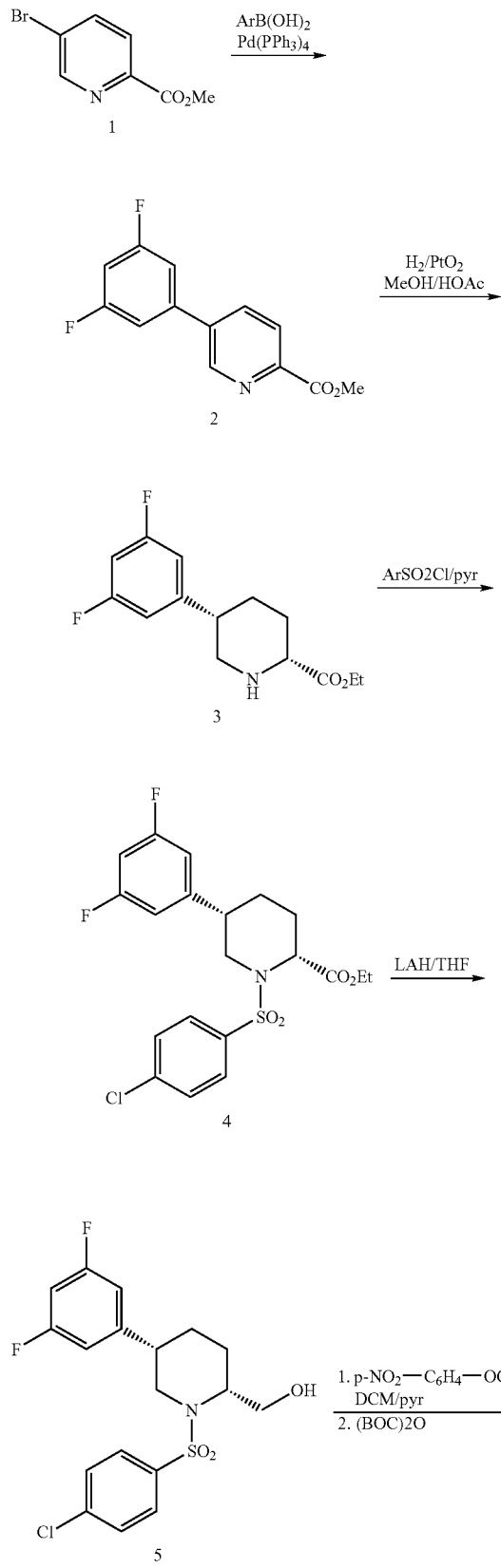

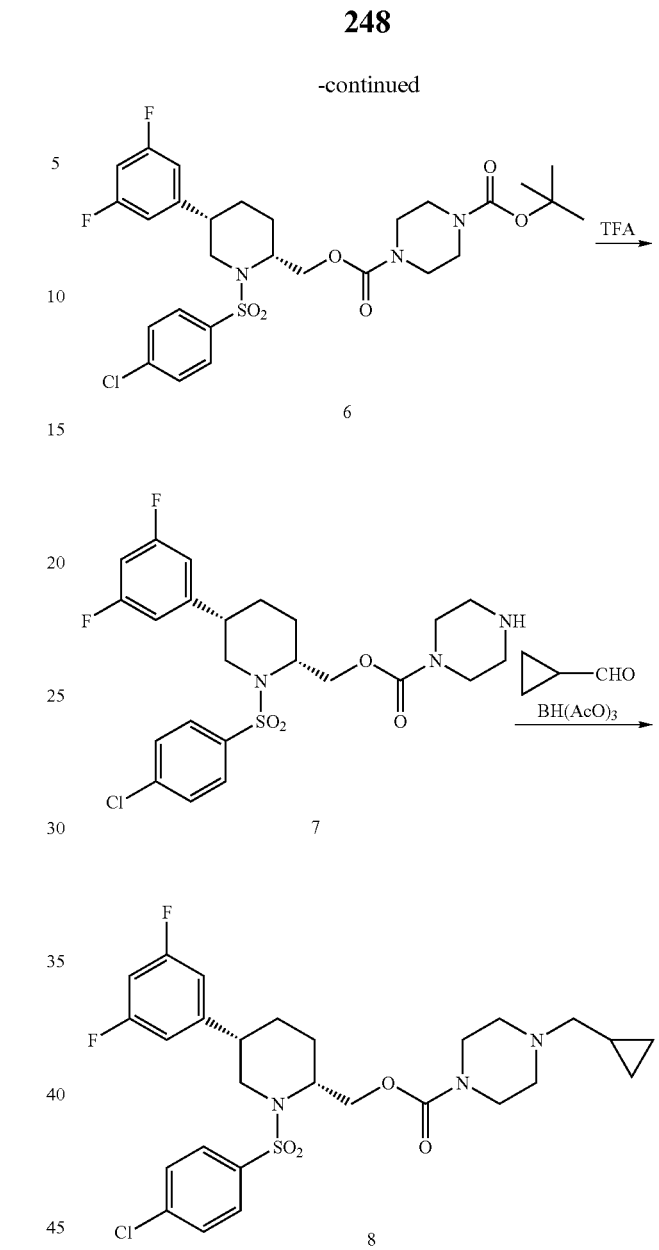

Step 1: Methyl 5-Bromopicolinate 1 was obtained as described in J. J. Song and N. K. Yee, *J. Org. Chem.* 2001, 66, 605–608. A solution of this ester (2.5 g, 11.6 mmol) in a mixture of toluene (160 ml) and ethanol (80 ml) is treated with 3,5-difluorobenzeneboronic acid (2.19 g, 13.9 mmol), tetrakis(triphenyphosphine)palladium (1.34 g, 1.16 mmol) and sodium carbonate (2.5 g). The mixture is heated at reflux for 16 hr. The solvent is removed at reduced pressure. The residue is redissolved in DCM, washed with water, dried over $Na_2SO_4$, concentrated and purified chromatographically using 30% ethyl acetate in hexanes as solvent to furnish 2.17 g of the product.

Step 2: Under a hydrogen atmosphere, stir a solution of Compound 2 (2.3 g, 9.2 mmol) in methanol (90 ml) and glacial acetic acid (10 ml) in the presence of platinum oxide (0.42 g) for 8 hr. Purge the reaction mixture with nitrogen.

Filter and then concentrate the reaction mixture in vacuo. Take up the residue in water, basify with saturated sodium carbonate, and extract with DCM. Dry the organic phase over Na$_2$SO$_4$ and concentrate in vacuo to give light yellow foam (2.3 g).

Step 3: A solution of Compound 3 (2.3 g, 9.2 mmol) in pyridine (20 ml) is treated with 4-chlorobenzenesulfonyl-chloride (3.8 g, 18.5 mmol). The mixture is heated at 60° C. for 16 hr. Cool to room temperature, concentrate in vacuo, and the residue subjected to flash-chromatography over silica gel (eluting 10% ethyl acetate in hexanes) to provide 2.1 g of product, as white powder.

Step 4: To an ice-cold solution of Compound 4 (2.1 g, 4.9 mmol) in THF (15 ml) is slowly added a solution of lithium aluminum hydride (9.8 ml, 1M THF). The cooling bath is removed and the reaction is stirred at ambient temperature for 2 hr. The mixture is quenched sequentially with water (0.4 ml), 15% NaOH (0.4 ml), and water (1.2 ml). The mixture is stirred for 1 hr, filtered, the filtrate dried over Na$_2$SO$_4$, and concentrated to give 1.8 g of the product as yellow solid.

Step 5: This was prepared according to Step 4 of Example 1, using N-Boc piperazine at the last stage as the amine.

Step 6: A solution of Compound 6 (100.0 mg, 0.163 mmol) in DCM (3 ml) is treated with TFA, and the mixture is stirred, at ambient temperature for 2 hr. The mixture is basified with saturated sodium carbonate. extracted with DCM, dried over Na$_2$SO$_4$, and concentrated to afford 72.3 mg of the product, as white powder.

Step 7: To a solution of Compound 7 (50.0 mg, 0.097 mmol) in dichloroethane (2.0 ml) is added cyclopropanecarboxaldehyde (20.0 mg, 0.28 mmol) followed by sodium triacetoxyborohydride (60.0 mg, 0.28 mmol) and one drop of acetic acid. After stirring at ambient temperature for 16 hr, the mixture is diluted with water and basified with saturated sodium carbonate. The crude product is extracted with DCM, washed with water, dried over Na$_2$SO$_4$, and concentrated. The crude was purified by preparative TLC (eluting 95:5:0.5; DCM:MeOH:NH$_4$OH) to furnish 30.0 mg of the product, as white powder. $^1$H NMR (CDCl$_3$, 400 MHz) δ 7.78 (2H, d, J=7.8 Hz), 7.49 (2H, d, J=7.8 Hz), 6.75–6.62 (3H, m), 4.50–4.36 (2H, m), 4.18–4.02 (1H, m), 3.89–3.71 (1H, m), 3.52 (4H, s. br.), 3.08 (1H, t, J=9.0 Hz)), 2.65–2.34 (4H, m), 2.34 (2H, d, J=6.6 Hz), 1.84–1.56 (4H, m), 0.95–0.74 (1H, m), 0.53 (2H, d, J=7.8 Hz), 0.11 (2H, d, J=4.5 Hz); MS (ES) m/e 569.1 (M+H)$^+$.

Assay:

Gamma secretase activity was determined as described by Zhang et al. (*Biochemistry*, 40 (16), 5049–5055, 2001). Activity is expressed either as a percent inhibition or as the concentration of compound producing 50% inhibition of enzyme activity.

Reagents. Antibodies W02, G2–10, and G2–11 were obtained from Dr. Konrad Beyreuther (University of Heidelberg, Heidelberg, Germany). W02 recognizes residues 5–8 of Aβ peptide, while G2–10 and G2–11 recognize the specific C-terminal structure of Aβ 40 and A□ 42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK167 was from Enzyme Systems Products (Livermore, Calif.).

cDNA Constructs, Tissue Culture, and Cell Line Construction. The construct SPC99-Lon, which contains the first 18 residues and the C-terminal 99 amino acids of APP carrying the London mutation, has been described (Zhang, L., Song, L., and Parker, E. (1999) *J. Biol. Chem.* 274, 8966–8972). Upon insertion into the membrane, the 17 amino acid signal peptide is processed, leaving an additional leucine at the N-terminus of Aβ. SPC99-Ion was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for A□ production by inducing C99 expression with 0.1 g/mL tetracycline for 16–20 h and analyzing conditioned media with a sandwich immunoassay (see below). One of the clones, designated as pTRE.15, was used in these studies.

Membrane Preparation. C99 expression in cells was induced with 0.1 g/mL tetracycline for 20 h. The cells were pretreated with 1 M phorbol 12-myristate 13-acetate (PMA) and 1 M brefeldin A (BFA) for 5–6 h at 37 C. before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70 C. before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70 C.

γ-Secretase Reaction and Aβ Analysis. To measure γ-secretase activity, membranes were incubated at 37 C. for 1 h in 50 L of buffer containing 20 mM Hepes (pH 7.0) and 2 mM EDTA. At the end of the incubation, Aβ 40 and Aβ 42 were measured using an electrochemiluminescence (ECL)-based immunoassay. Aβ 40 was identified with antibody pairs TAG-G2-10 and biotin-W02, while Aβ 42 was identified with TAG-G2-11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of γ-secretase activity described were confirmed using more than five independent membrane preparations.

Using the above assay, the compounds of Examples 1–29, 31–33, 35–48, 50–61, 63–67, 67A-67BR, 68, 69, 71–74, 74A, 74B, 74C, 75, 76, 78–83, 85–99, 101–159, 159A, 159B, 159C, 160, 160A–160AA, 161, 161A–161G, 162, 162A, 162B, 162C, 164, 164A, 164B, 164C, 165–167, 167A, 167B, 167C, 168, 168A, 169, 169A–169D, 170, 170A–170AD, 171–173, 173A–173T, and 174 showed IC$_{50}$ within the range of about 0.0002 to about 15 µM. The compounds of Examples 67B, 67E, 67N, 67P, 67U, 67AG, 67AT, 67AW, 67AY, 67BA, 67BD, 67BE, 67BG, 67BH, 67BL, 160B, 160K, 161, 161A, 161E, 161 F, 173, 173A, 173B, 173C, 173E, 173G, 173I, 173J, 173K, 173L and 173N showed IC$_{50}$ within the range of about 0.0002 to about 0.015 µM.

The γ-secretase inhibitory activity of some of the inventive compounds are shown below:

| Example | IC50 (µM) |
|---------|-----------|
| 7-B | .0027 |
| 7-AT | .0038 |
| 7-BG | .0023 |
| 61-A | .0028 |
| 73 | .0002 |
| 73-A | .0007 |
| 73-C | .0018 |
| 73-E | .0027 |
| 73-J | .0008 |
| 73-N | .0024 |

Pharmaceutical compositions can comprise one or more of the compounds of formula I. For preparing pharmaceutical compositions from the compounds described by this invention, inert, pharmaceutically acceptable carriers can be either solid or liquid. Solid form preparations include powders, tablets, dispersible granules, capsules cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in one to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula

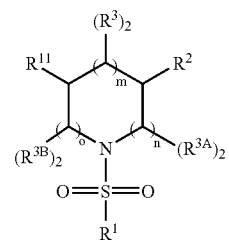

(I)

or a pharmaceutically acceptable salt or solvate thereof, wherein:

(A) $R^1$ is selected from the group consisting of:
  (1) unsubstituted aryl; and
  (2) aryl substituted with one or more $R^5$ groups;
(B) $R^2$ is selected from the group consisting of:
  (1) —X(CO)Y;
  (2) —($C_1$–$C_6$)alkylene-X(CO)Y;
  (3) —($C_0$–$C_6$)alkylene-($C_2$–$C_6$)cycloalkylene-($C_0$–$C_6$)alkylene-X(CO)Y;
  (4) heteroaryl;
  (5) heteroaryl substituted with one or more $R^5$ groups;
(C) Each $R^3$ is independently selected from the group consisting of:
  (1) H, and
  (2) alkyl, and
(D) Each $R^{3A}$ and $R^{3B}$ are independently selected from the group consisting of:
  (1) H; and
  (2) alkyl;
(E) $R^5$ is independently selected from the group consisting of:
  (1) halo;
  (2) —$CF_3$;
  (3) —OH;
  (4) —Oalkyl;
  (5) —$OCF_3$;
  (6) —CN;

(7) —NH$_2$;
(8) —CO$_2$alkyl;
(9) —CONR$^6$R$^7$;
(10) -alkylene-NR$^6$R$^7$;
(11) —NR$^6$COalkyl;
(12) —NR$^6$COaryl;
(13) —NR$^6$COheteroaryl; and
(14) —NR$^6$CONR$^6$R$^7$;

(F) X is selected from the group consisting of:
(1) —O—;
(2) —NH—;
(3) —Nalkyl; and
(4) —Oalkylene;

(G) Y is selected from the group consisting of:
(1) —NR$^6$R$^7$;
(2) —N(R$^3$)(CH$_2$)$_b$NR$^6$R$^7$ wherein b is 2–6;
(3) unsubstituted aryl;
(4) unsubstituted heteroaryl;
(5) -alkyl;
(6) -cycloalkyl,
(7) unsubstituted arylalkyl;
(8) unsubstituted arylcycloalkyl;
(9) unsubstituted heteroarylalkyl;
(10) unsubstituted heteroarylcycloalkyl;
(11) unsubstituted arylheterocycloalkyl;
(12) substituted aryl;
(13) substituted heteroaryl;
(14) substituted arylalkyl;
(15) substituted arylcycloalkyl;
(16) substituted heteroarylalkyl;
(17) substituted heteroarylcycloalkyl; and
(18) substituted arylheterocycloalkyl;

wherein the aryl moiety in said substituted groups (12), (14), (15) and (18) of said Y group, and the heteroaryl moiety in said substituted groups (13), (16), and (17) of said Y group, are substituted with one or more (e.g., 1 to 3) substituents independently selected from the group consisting of:
(a) halo;
(b) —CF$_3$;
(c) —OH;
(d) —Oalkyl;
(e) —OCF$_3$;
(f) —CN;
(g) —NH$_2$;
(h) —CO$_2$(C$_1$–C$_6$)alkyl;
(i) —C(O)NR$^6$R$^7$;
(j) —(C$_1$–C$_6$)alkylene-NR$^6$R$^7$;
(k) —NR$^6$COalkyl;
(l) —NR$^6$COaryl;
(m) —NR$^6$COheteroaryl; and
(n) —NR$^6$CONR$^6$R$^7$;

or Y is selected from the group consisting of:

(c)
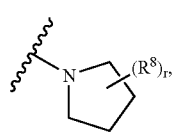

(d)
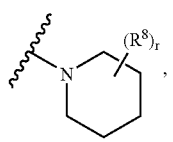

(e)
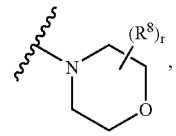

(f)
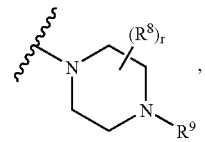

(g)
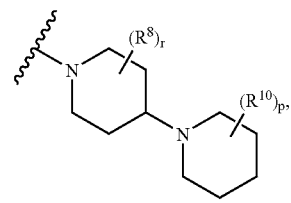

(h)
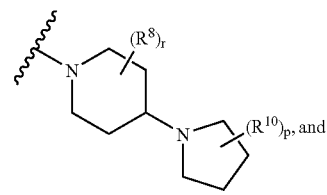

(i)
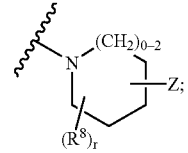

(H) R$^6$ and R$^7$ are independently selected from the group consisting of
(1) H;
(2) alkyl;
(3) cycloalkyl;
(4) arylalkyl;
(5) heteroarylalkyl;

(6)
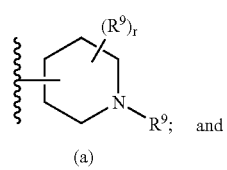
(a)
and (7)
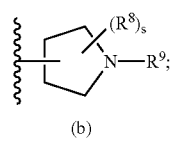
(b)

(I) Each R$^8$ is independently selected from the group consisting of:
(1) alkyl; and
(2) alkyl substituted with 1 to 4 hydroxy groups;

(J) Each R$^9$ is independently selected from the group consisting of:

(1) H;
(2) alkyl;
(3) alkyl substituted with 1 to 4 hydroxy groups;
(4) cycloalkyl;
(5) cycloalkyl substituted with 1 to 4 hydroxy groups;
(6) arylalkyl;
(7) heteroarylalkyl;
(8) —C(O)Oalkyl;
(9) alkylene-O-alkylene-OH;
(10) aryl substituted with one or more $R^5$ groups; and
(11) heteroaryl substituted with one or more $R^5$ groups;
(12) unsubstituted heteroaryl;
(13) unsubstituted aryl; and
(14) -alkylene-C(O)Oalkyl;
(K) Each $R^{10}$ is independently selected from the group consisting of:
(1) H; and
(2) alkyl;
(L) $R^{11}$ is selected from the group consisting of:
(1) unsubstituted aryl;
(2) substituted aryl;
(3) unsubstituted heteroaryl,
(4) alkyl;
(5) cycloalkyl;
(6) unsubstituted arylalkyl;
(7) unsubstituted arylcycloalkyl,
(8) unsubstituted heteroarylalkyl;
(9) unsubstituted heteroarylcycloalkyl;
(10) unsubstituted aryl heterocycloalkyl;
(11) alkoxyalkyl;
(12) substituted heteroaryl;
(13) substituted arylalkyl;
(14) substituted arylcycloalkyl;
(15) substituted heteroarylalkyl;
(16) substituted arylheterocycloalkyl;
wherein the aryl moiety in said substituted groups (2), (13), (14) and (16) of said $R^{11}$ group, and the heteroaryl moiety in said substituted groups (12) and (15) of said $R^{11}$ group, are substituted with one or more (e.g., 1 to 3) substituents independently selected from the group consisting of:
(a) halo;
(b) —$CF_3$;
(c) —OH;
(d) —Oalkyl;
(e) —$OCF_3$;
(f) —CN;
(g) —$NH_2$;
(h) —$CO_2(C_1$–$C_6)$alkyl;
(i) —$CONR^6R^7$;
(j) —$(C_1$–$C_6)$alkylene-$NR^6R^7$;
(k) —$NR^6$COalkyl;
(l) —$NR^6$COaryl;
(m) —$NR^6$COheteroaryl; and
(n) —$NR^6CONR^6R^7$;
(M) m is 0 to 3, and n is 0 to 3, o is 0–3, such that m+n+o is 1, 2, 3 or 4;
(N) p is 0 to 4;
(O) r is 0 to 4;
(P) s is 0 to 3; and
(Q) Z is selected from the group consisting of:
(1) unsubstituted heterocycloalkyl;
(2) substituted heterocycloalkyl;
(3) —$NH_2$;
(4) —NH(alkyl);
(5) —N(alkyl)$_2$ wherein each alkyl is the same or different;
(6) —NH(unsubstituted cycloalkyl);
(7) —NH(substituted cycloalkyl);
(8) —N(alkyl)(unsubstituted cycloalkyl);
(9) —N(alkyl )(substituted cycloalkyl);
(10) —NH(unsubstituted aralkyl);
(11) —NH(substituted aralkyl);
(12) —N(alkyl)(aralkyl);
(13) —NH(unsubstituted heterocycloalkyl);
(14) —NH(substituted heterocycloalkyl);
(15) —N(alkyl)(unsubstituted heterocycloalkyl),
(16) —N(alkyl)(substituted heterocycloalkyl);
(17) —NH(unsubstituted heteroaralkyl);
(18) —NH(substituted heteroaralkyl);
(19) —NH-alkylene-(unsubstituted cycloalkyl);
(20) —NH-alkylene-(substituted cycloalkyl);
(21) —N(alkyl)alkylene-(unsubstituted cycloalkyl);
(22) —N(alkyl)alkylene-(substituted cycloalkyl);
(23) —NHalkylene-(unsubstituted heterocycloalkyl);
(24) —NHalkylene-(substituted heterocycloalkyl);
(25) —N(alkyl)alkylene-(unsubstituted heterocycloalkyl);
(26) —N(alkyl)alkylene-(substituted heterocycloalkyl);
(27) unsubstituted benzofused heterocycloalkyl; and
(28) substituted benzofused heterocycloalkyl;
wherein said substituted heterocycloalkyl moiety of substituents (2), (14), (16), (24), (26) and (27) of group Z, and said substituted cycloalkyl moiety of substituents (7), (9), (20) and (22) of group Z, and said substituted aryl moiety of substituent (11) of group Z, and said substituted heteroaryl moiety of substituent (18) of group Z, are substituted with 1 to 3 groups independently selected from the group consisting of:
(a) alkyl;
(b) —OH;
(c) —Oalkyl;
(d) —O(CO)alkyl;
(e) —O(CO)aryl;
(f) —$NH_2$;
(g) —NH(alkyl);
(h) —N(alkyl)$_2$ wherein each alkyl is the same or different;
(i) —NH(CO)alkyl;
(j) —N(alkyl)(CO)alkyl;
(k) —NH(CO)aryl;
(l) —N(alkyl)(CO)aryl;
(m) —COalkyl;
(n) —COaryl;
(o) —$CONH_2$;
(p) —CONH(alkyl);
(q) —CON(alkyl)$_2$ wherein each alkyl is the same or different;
(r) —COOalkyl;
(s) -alkylene-C(O)Oalkyl;
(t) piperidinyl;
(u) pyrrolidinyl;
(v) 1,1-ethylenedioxy;
(w) aryl;
(x) heteroaryl; and
(y) —O—$CH_2CH_2$—O— wherein both oxygen atoms are bound to the same carbon atom, and provided that the aryl and heteroaryl moieties of said Z group are not substituted with said —O—$CH_2CH_2$—O— group.

2. The compound of claim 1 wherein:
(A) $R^1$ is aryl substituted with one or more $R^5$ groups;
(B) n is 0 or 1 and m is 1, 2 or 3 such that m+n is 3;
(C) p is 0 or 1; and (D) $R^2$ is —X(CO)Y, —($C_1$–$C_6$)alkylene-X(CO)Y or —($C_0$–$C_6$)alkylene-($C_2$–$C_6$)cycloalkylene-($C_0$–$C_6$)alkylene-X(CO)Y.

3. The compound of claim 2 wherein:
(A) $R^1$ is phenyl substituted with one or more $R^5$ groups; and
(B) n is 0 and m is 3.

4. The compound of claim 1, wherein $R^2$ is

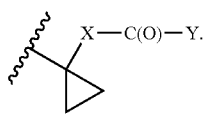

5. The compound of claim 3 wherein $R^1$ is phenyl substituted with one or more halo atoms.

6. The compound of claim 1 wherein:
(A) $R^1$ is aryl substituted with one or more $R^5$ groups;
(B) n is 0 or 1 and m is 1, 2 or 3 such that m+n is 3;
(C) p is 0 or 1;
(D) $R^2$ is —X(CO)Y, —($C_1$–$C_6$)alkylene-X(CO)Y or —($C_0$–$C_6$)alkylene-($C_2$–$C_6$)cycloalkylene-($C_0$–$C_6$)alkylene-X(CO)Y;
(E) X is O;
(F) Y is —$NR^6R^7$; or Y is selected from the group consisting of:

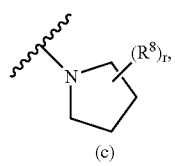 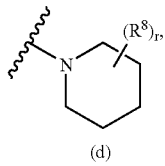
(c) (d)

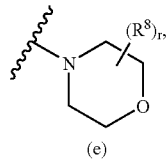 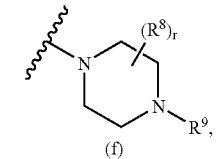
(e) (f)

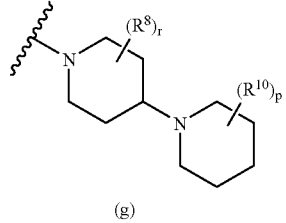
(g)

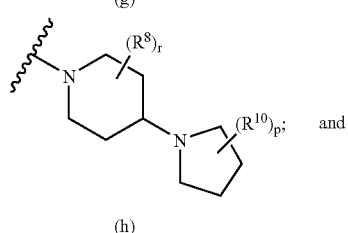
(h)

(G) $R^6$ and $R^7$ are independently selected from the group consisting of: H, methyl, ethyl, —($C_3$–$C_8$)cycloalkyl, -aryl($C_1$–$C_6$)alkyl, 4-pyridyl methyl, and

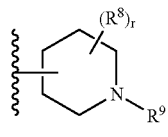 and 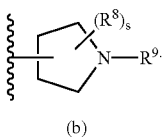
(a) (b)

7. The compound of claim 6 wherein:
(A) $R^1$ is phenyl substituted with one or more $R^5$ groups;
(B) n is 0 and m is 3;
(C) said group

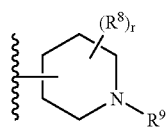
(a)

is a group of the formula:

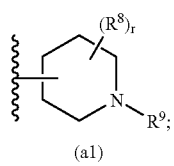
(a1)

(D) said group

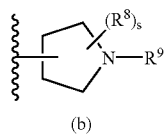
(b)

is a group of the formula:

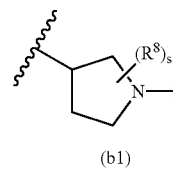
(b1)

(E) $R^{11}$ is selected from the group consisting of: —($C_1$–$C_6$)alkyl, ($C_3$–$C_8$)-cycloalkyl, aryl, aryl($C_1$–$C_6$)alkyl and —($C_1$–$C_6$)alkoxyalkyl.

8. The compound of claim 7 wherein said $R^{11}$ is selected from the group consisting of: methyl, ethyl, cyclohexyl, phenyl, benzyl, —$(CH_2)_2$phenyl, and —$CH_2OCH_3$.

9. The compound of claim 7 wherein $R^1$ is phenyl substituted with one or more halo atoms.

10. The compound of claim 8 wherein $R^{11}$ is phenyl substituted with one or more halo atoms.

11. The compound of claim 6 wherein Y is selected from the group consisting of:

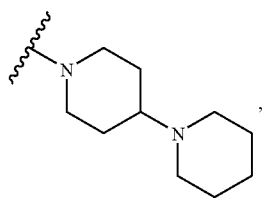 (i)
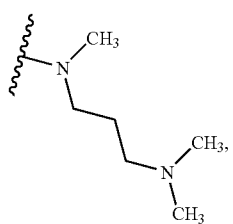 (j)
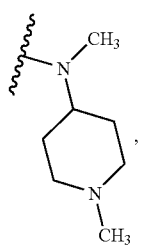 (k)
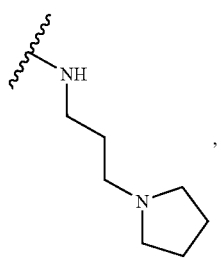 (l)
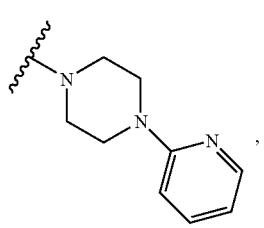 (m)
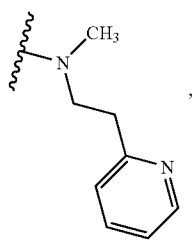 (n)
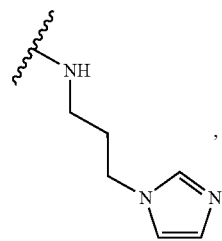 (o)
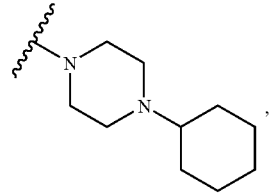 (p)
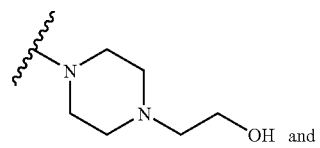 (q)
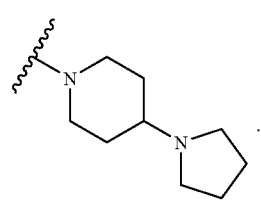 (r)
12. The compound of claim 1 selected from the group consisting of:
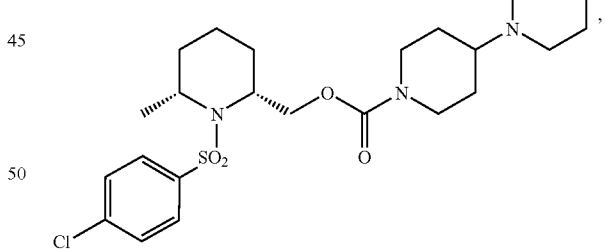
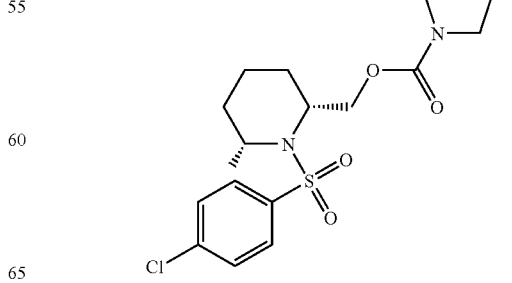

261
-continued
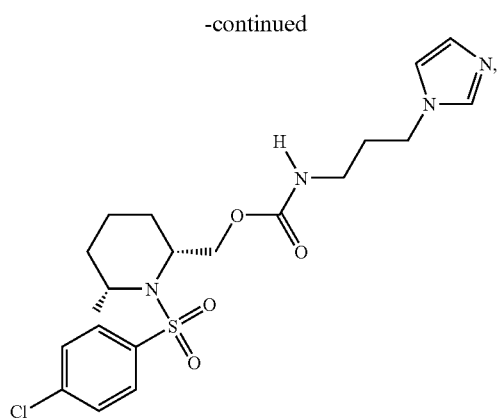
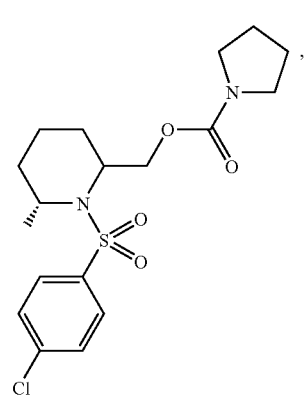
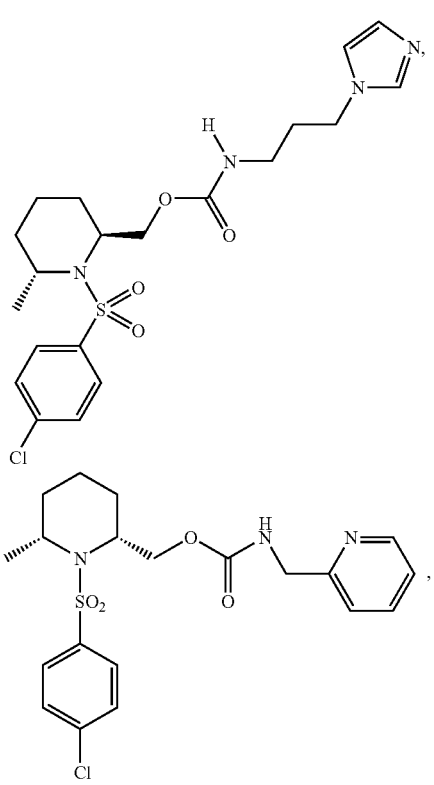
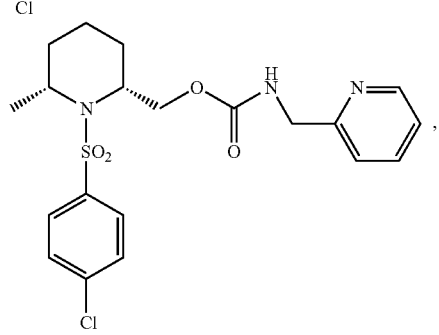
262
-continued
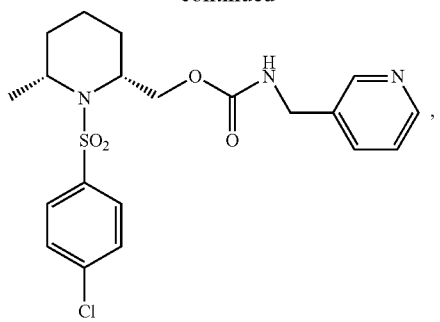
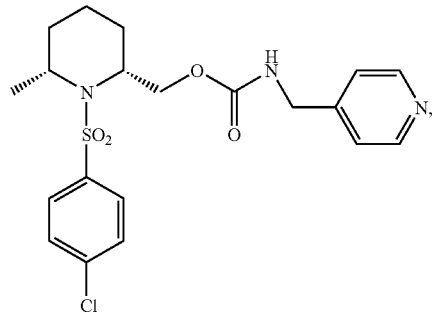
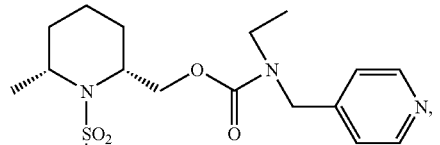
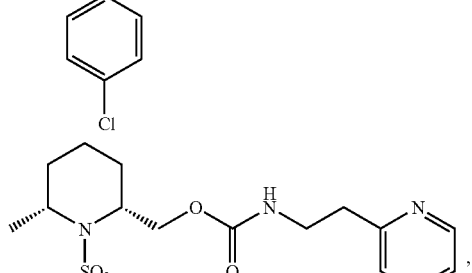
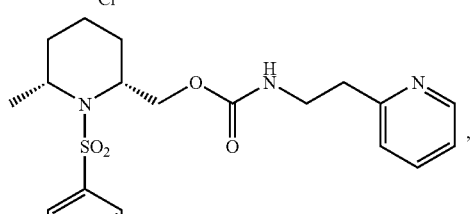
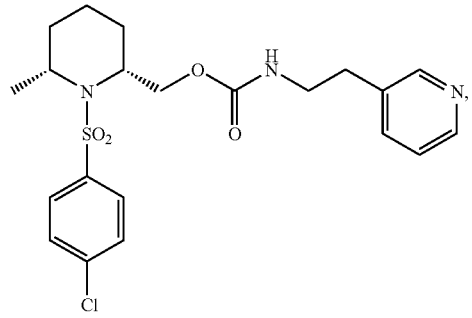

263
-continued
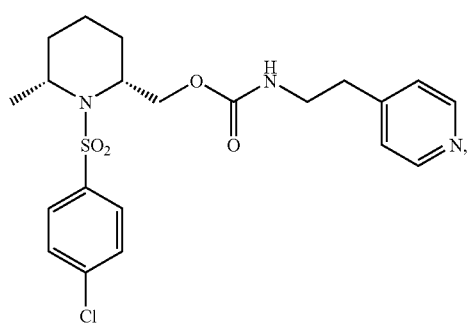
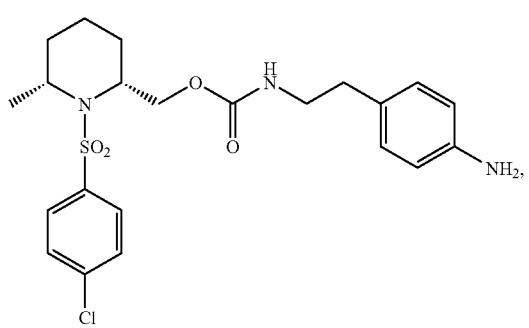
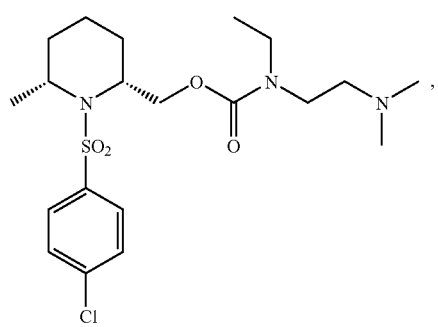
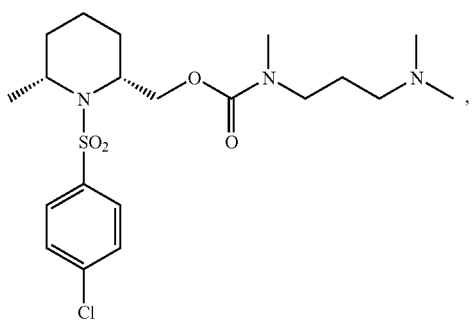
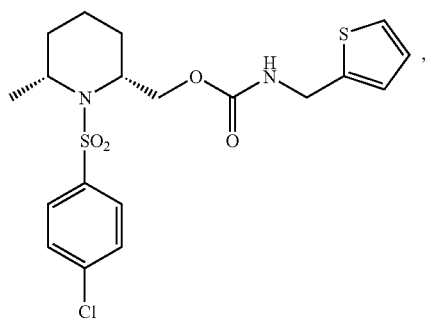
264
-continued
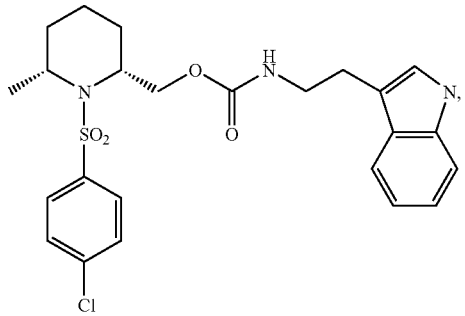
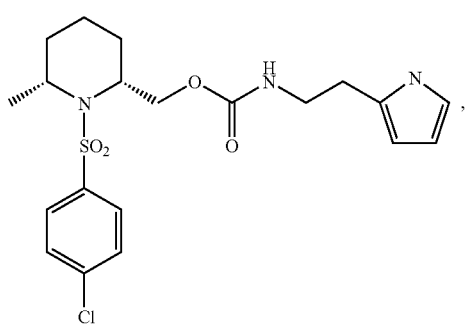
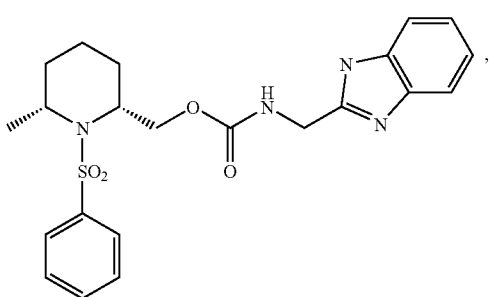
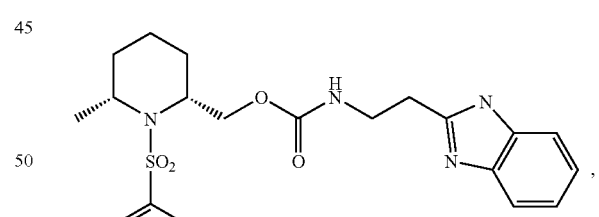
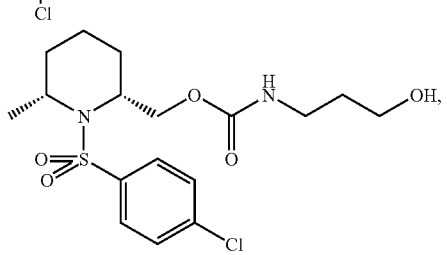

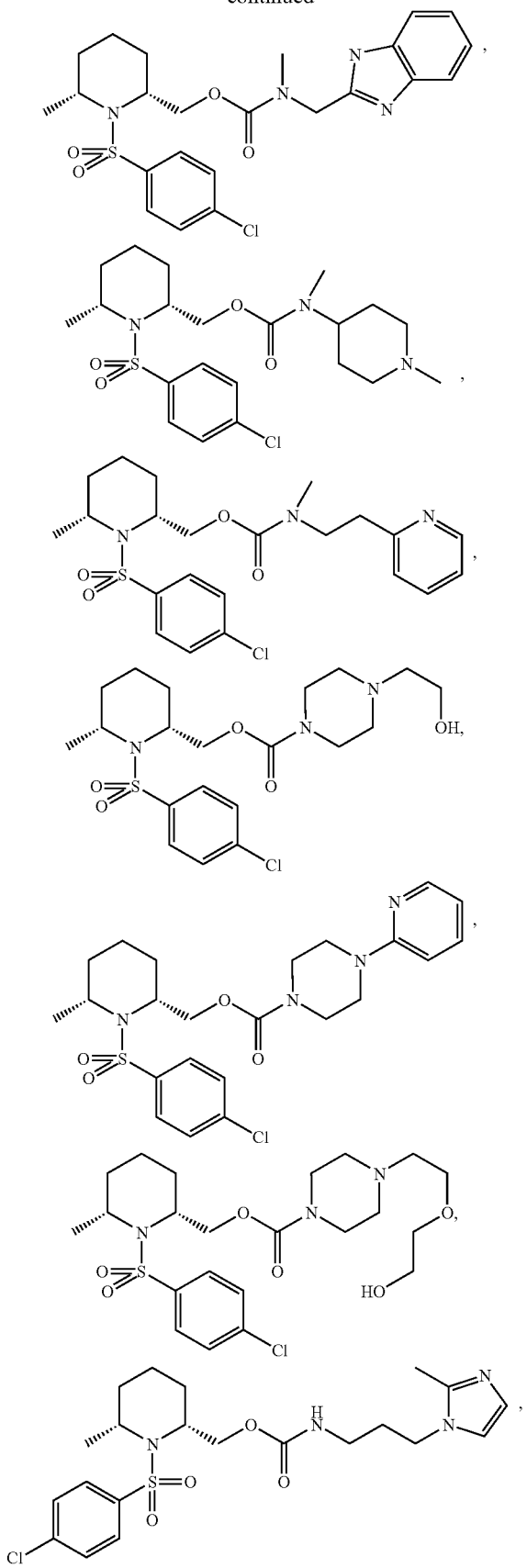
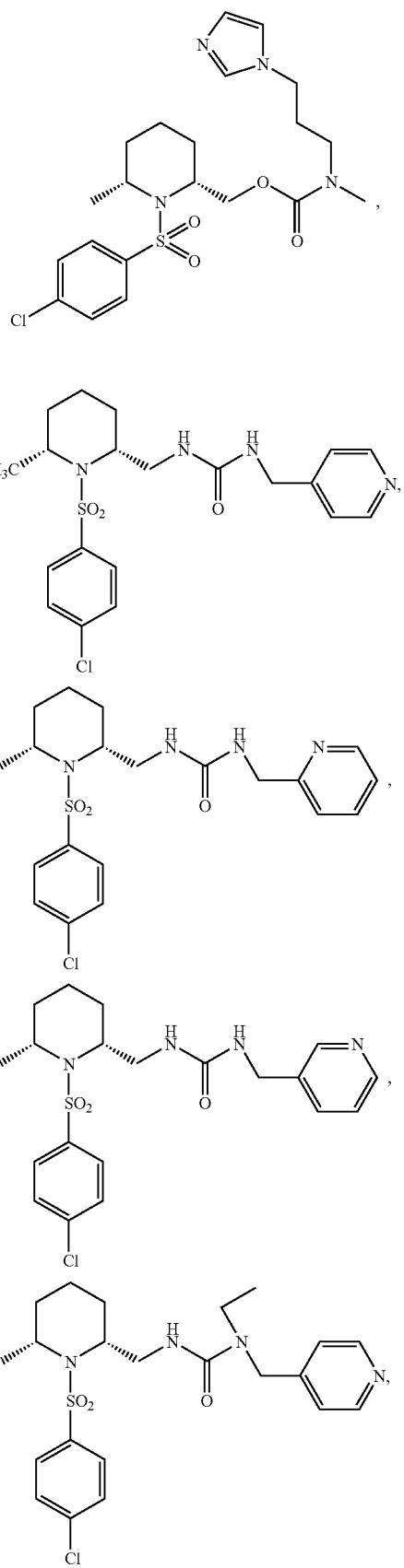

267
-continued
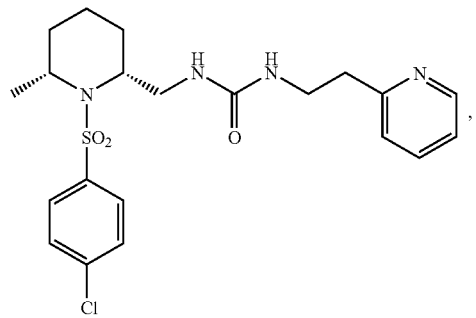
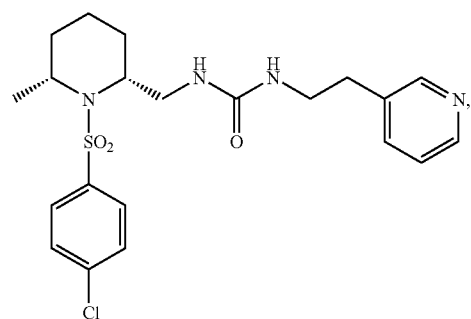
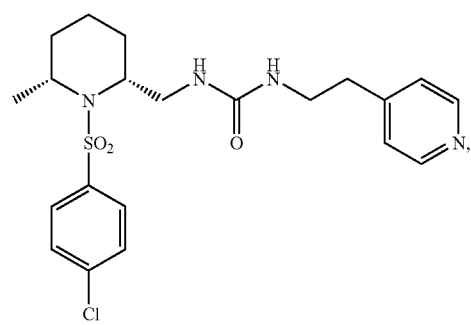
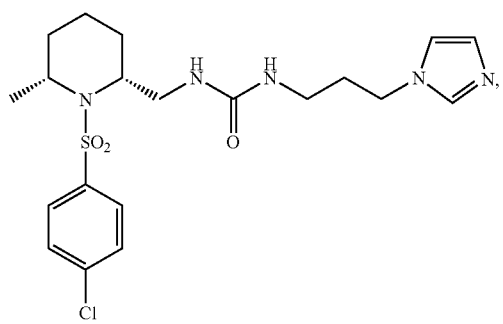
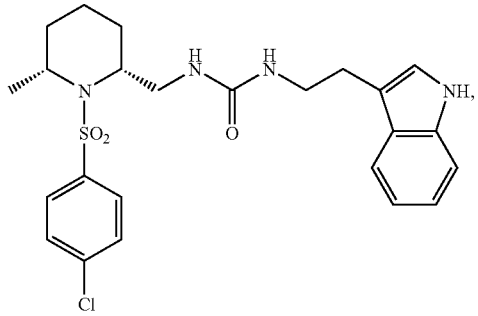
268
-continued
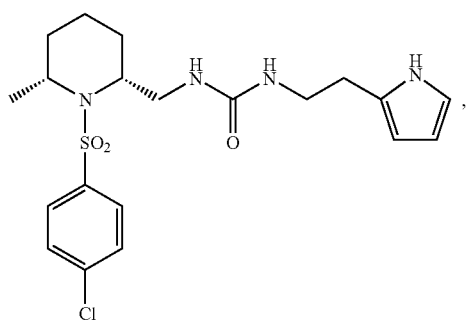
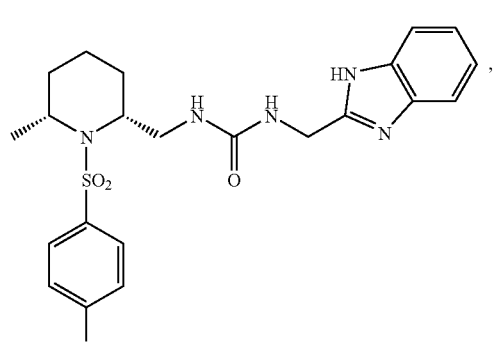
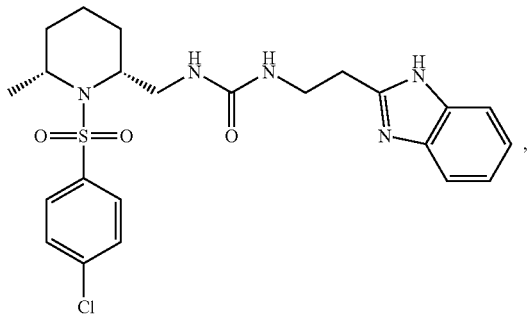
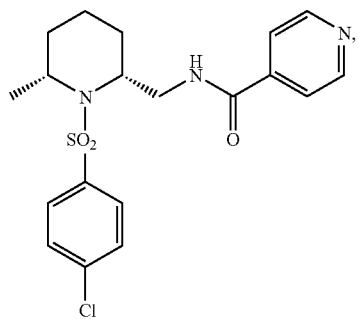
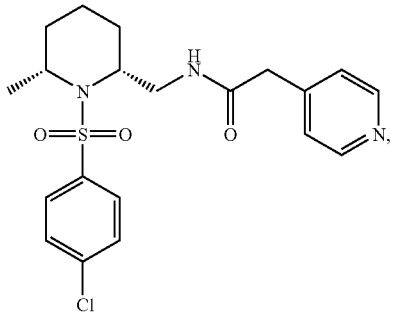

269
-continued
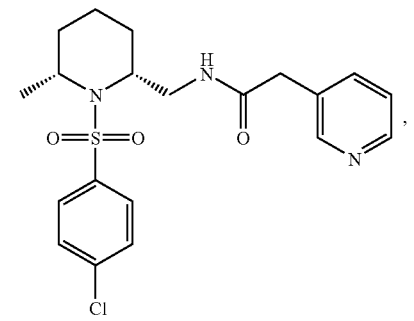
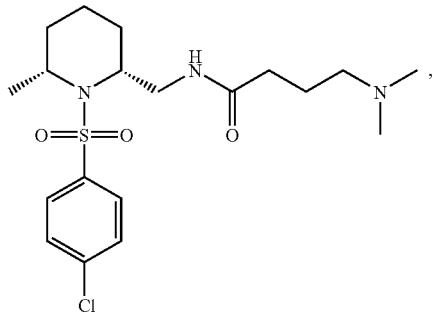
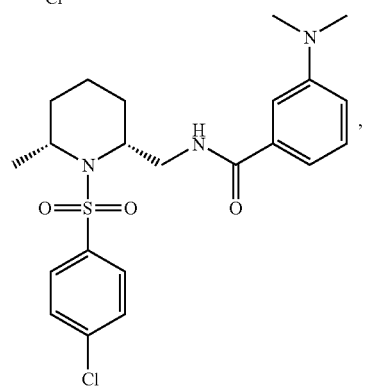
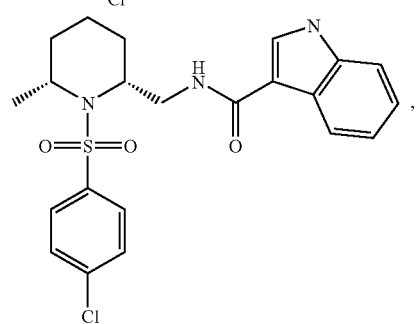
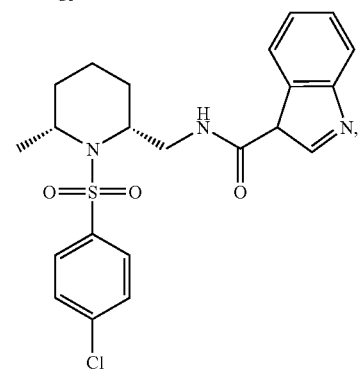
270
-continued
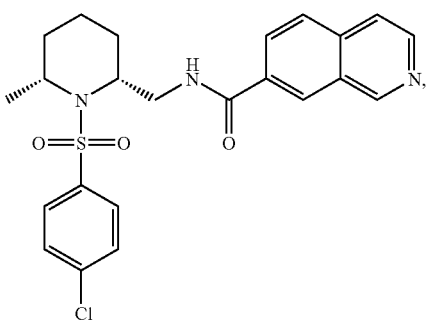
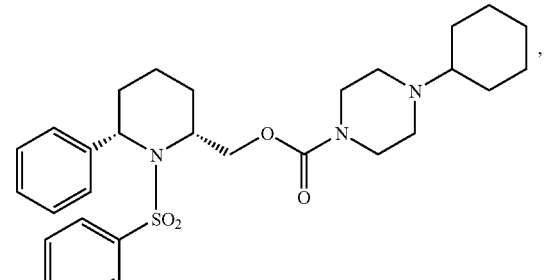
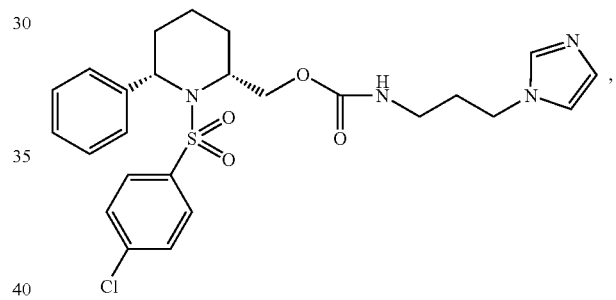
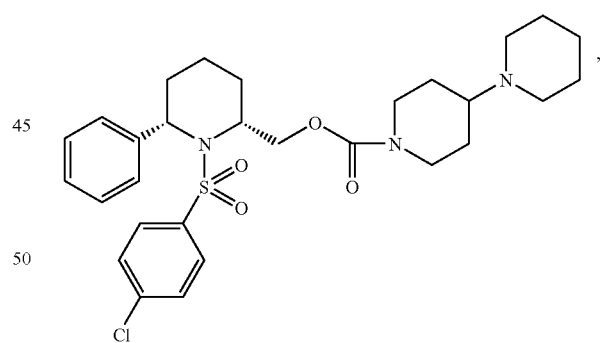
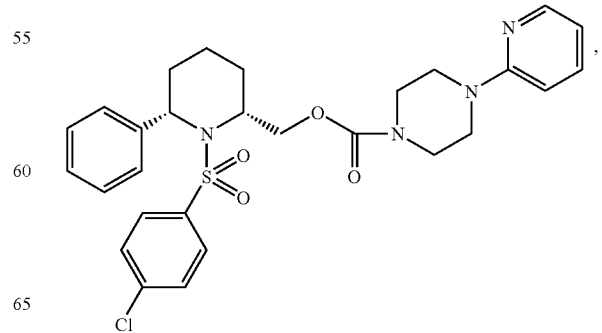

271 272

273
-continued
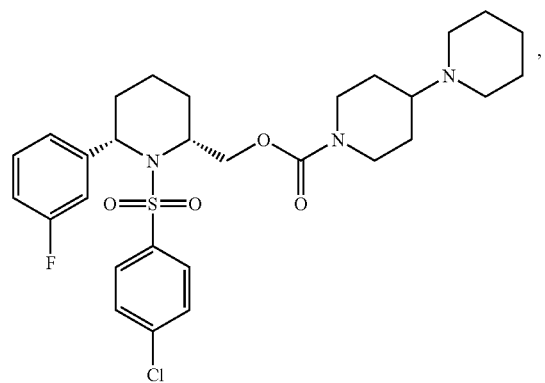
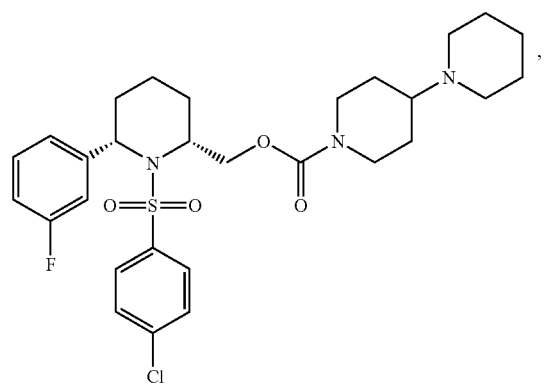
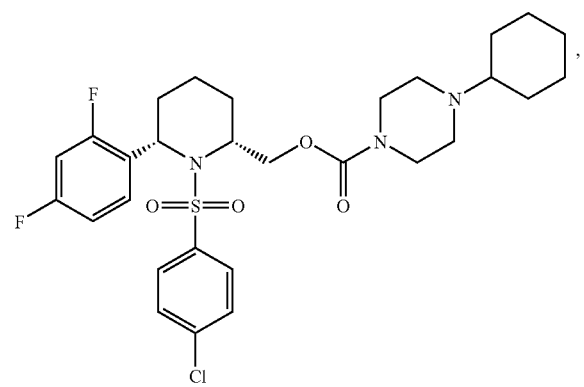
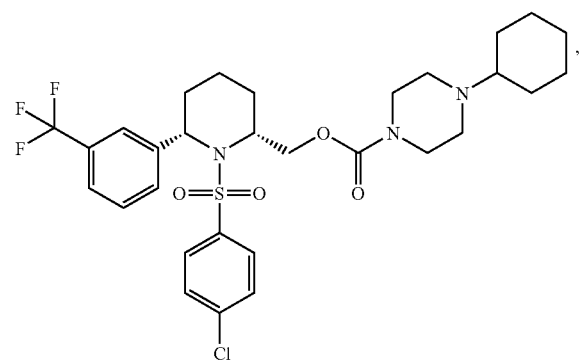
274
-continued
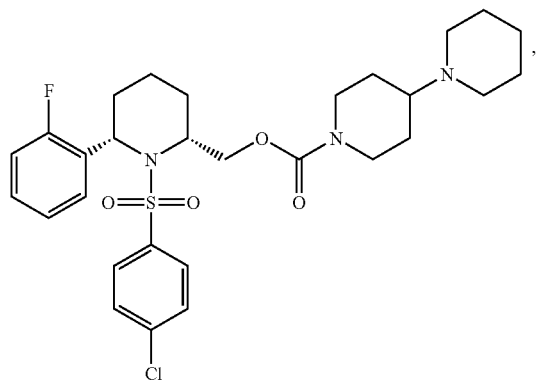
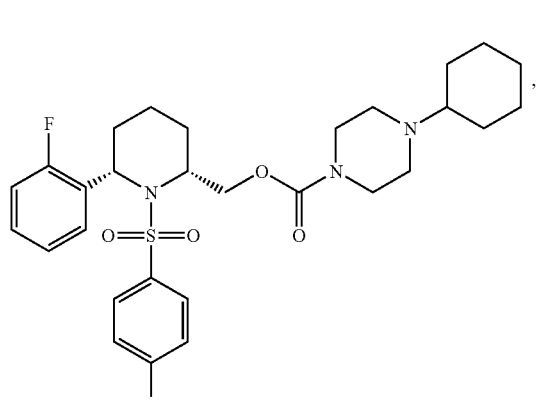
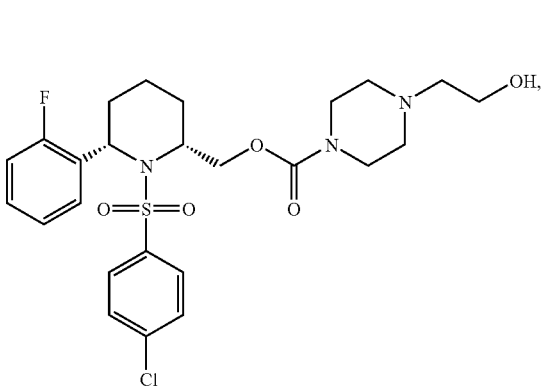
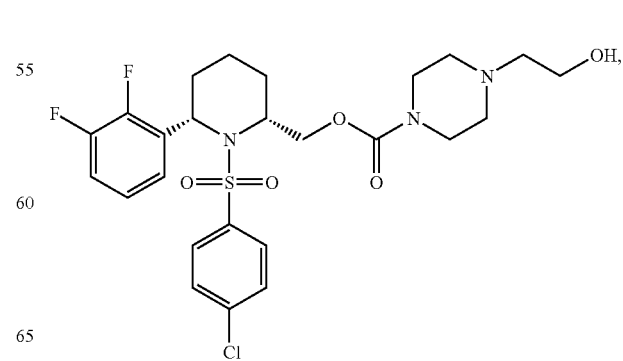

275
-continued
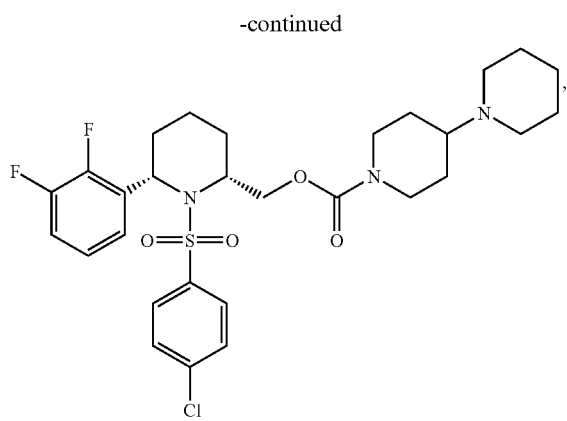
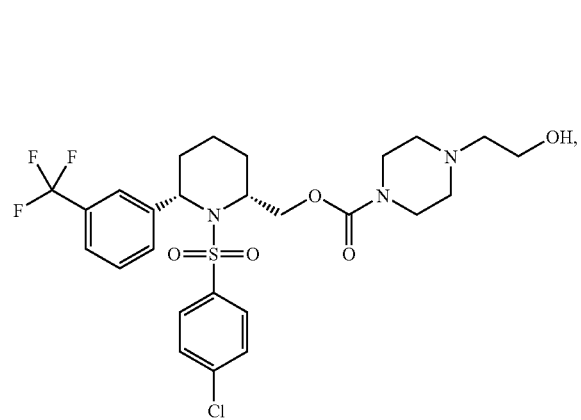
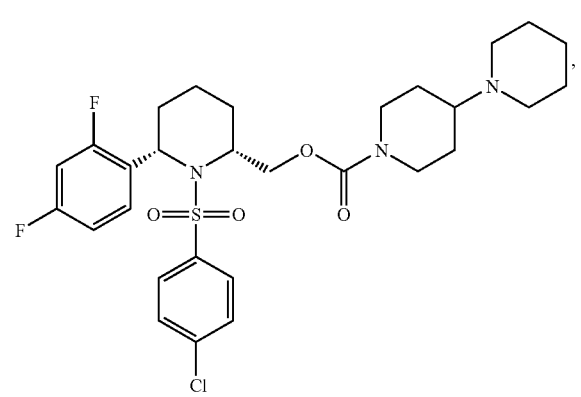
276
-continued
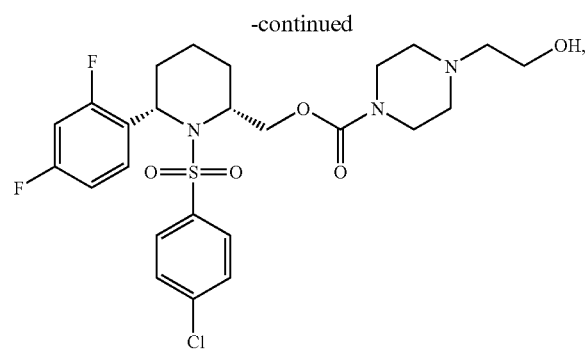
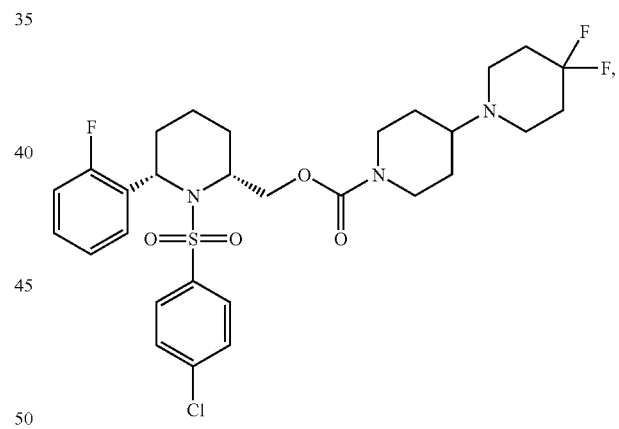
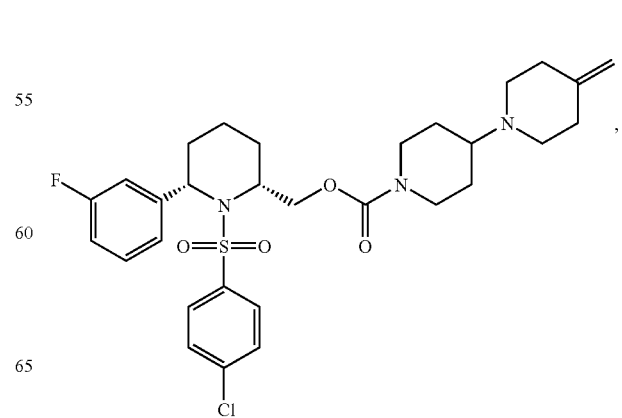

277 278
-continued                    -continued
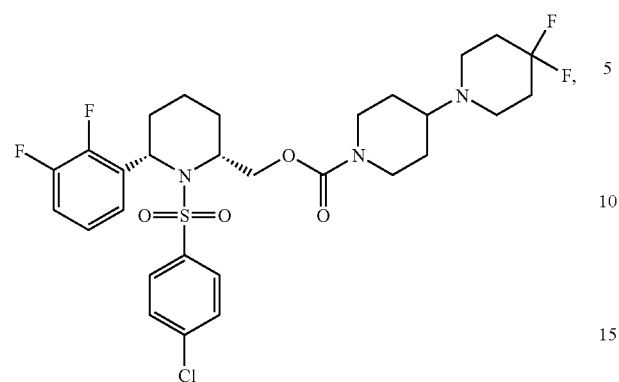
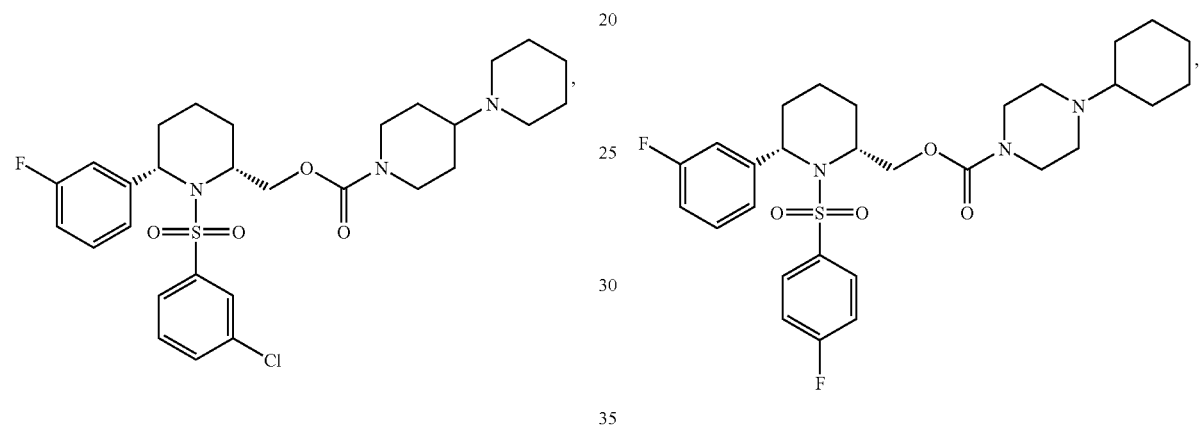
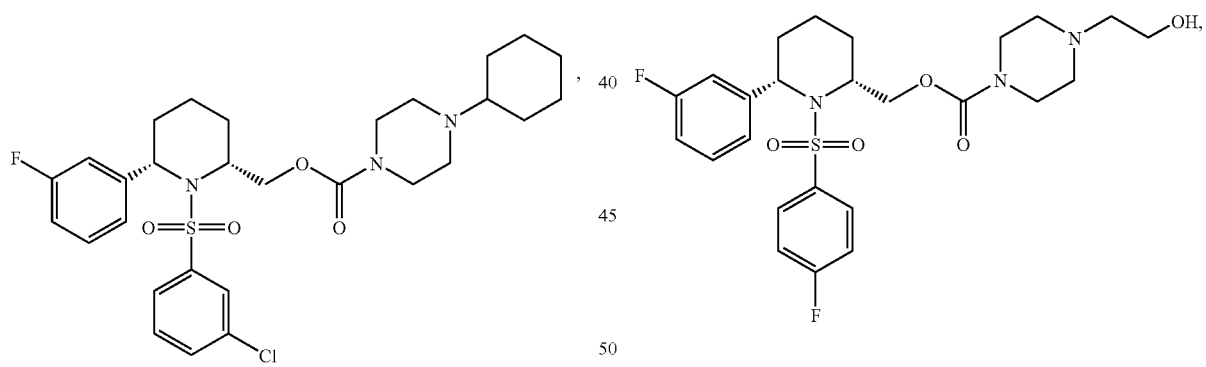
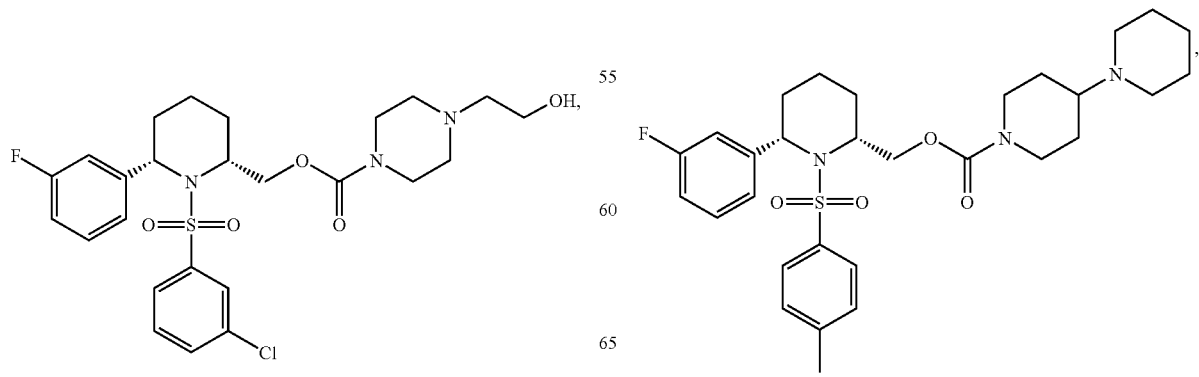

279
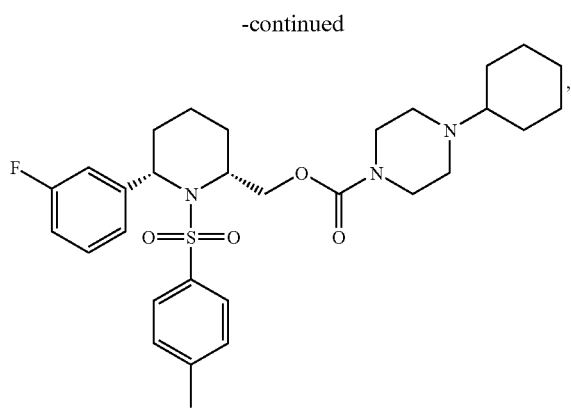
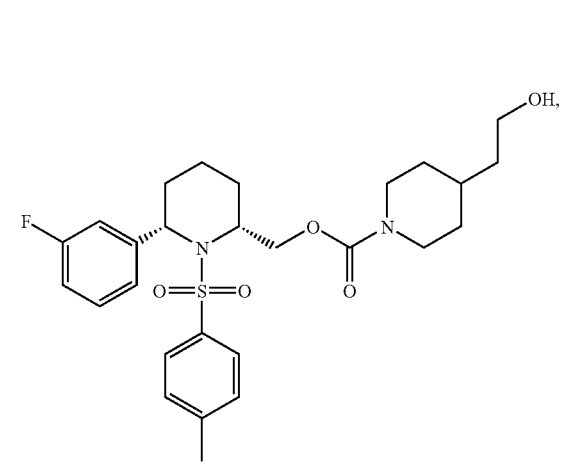
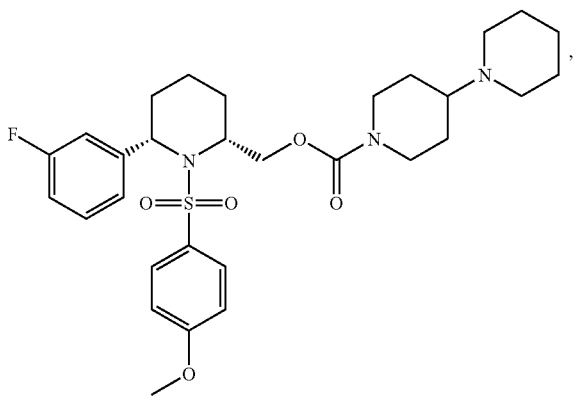
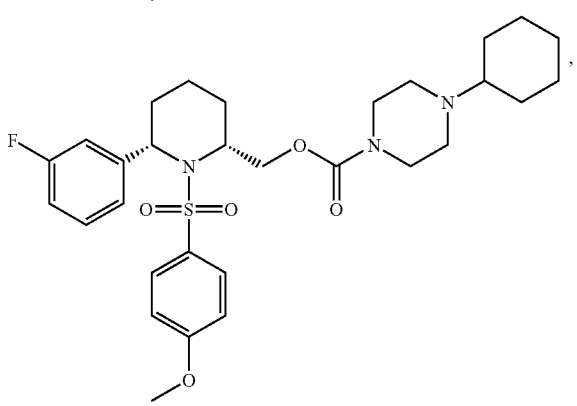
280
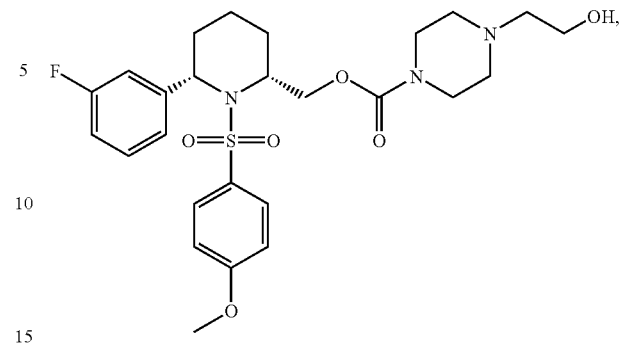
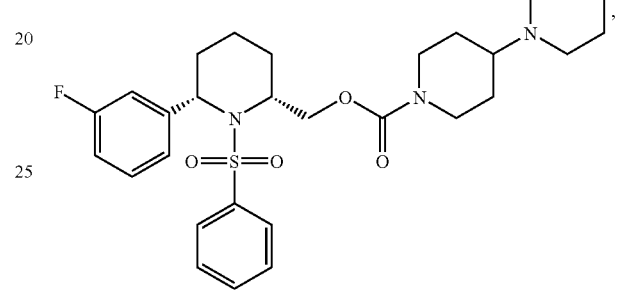
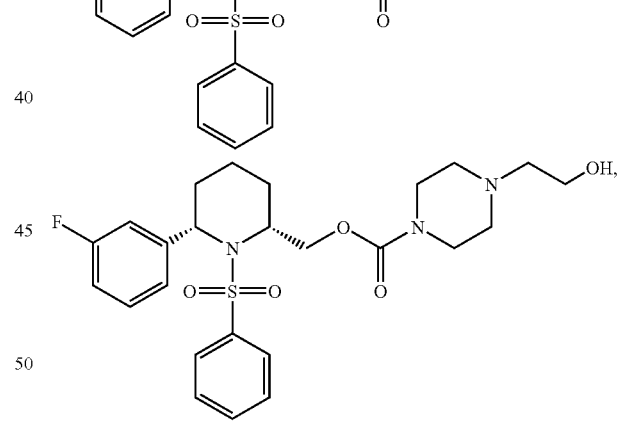
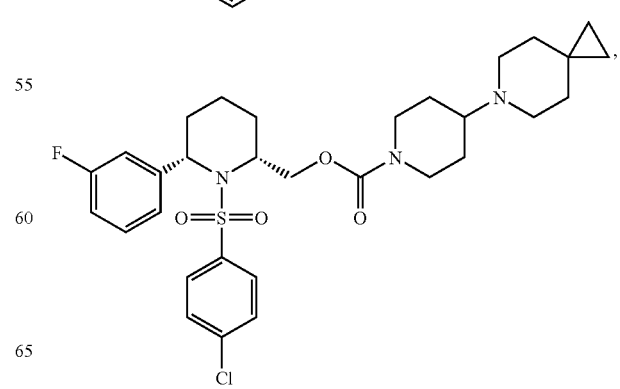

281
-continued
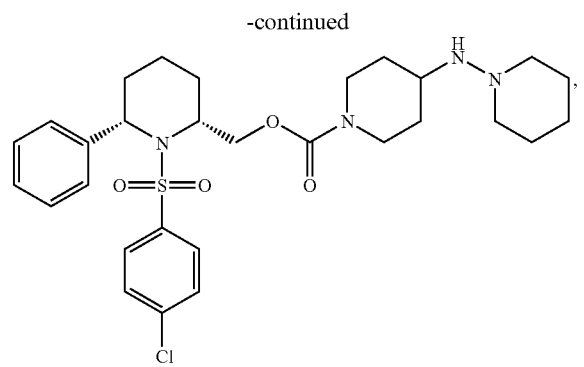
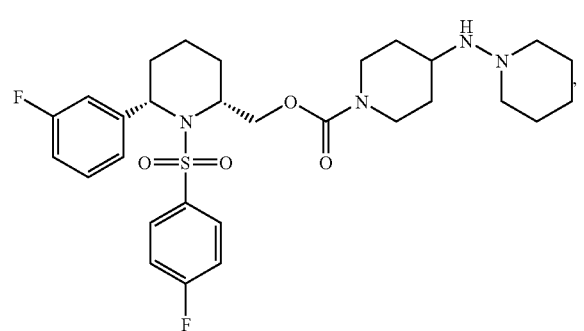
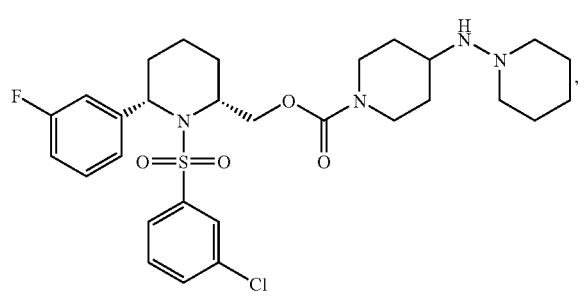
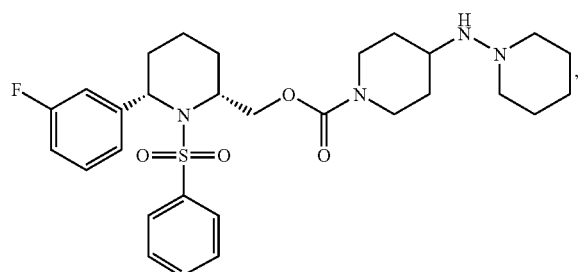
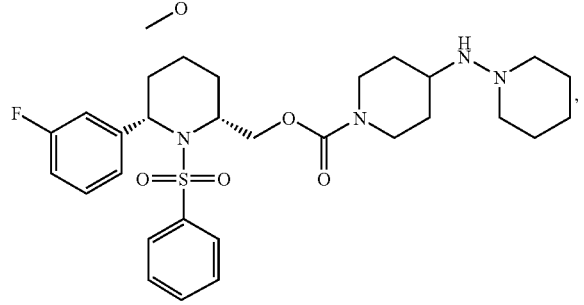
282
-continued
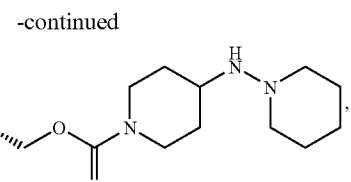

283
-continued
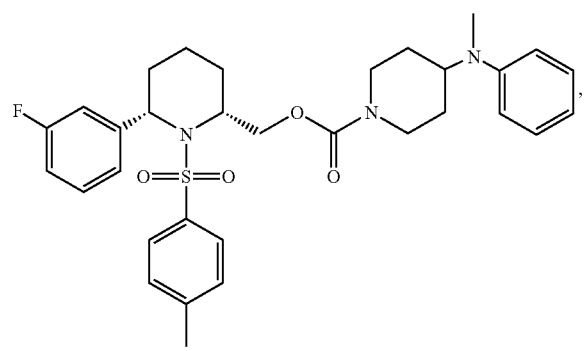
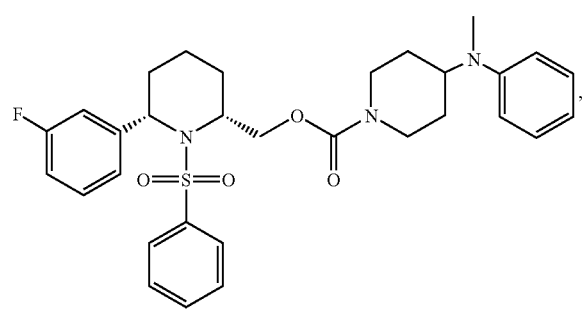
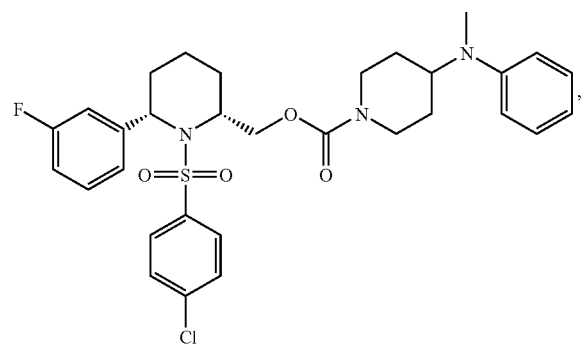
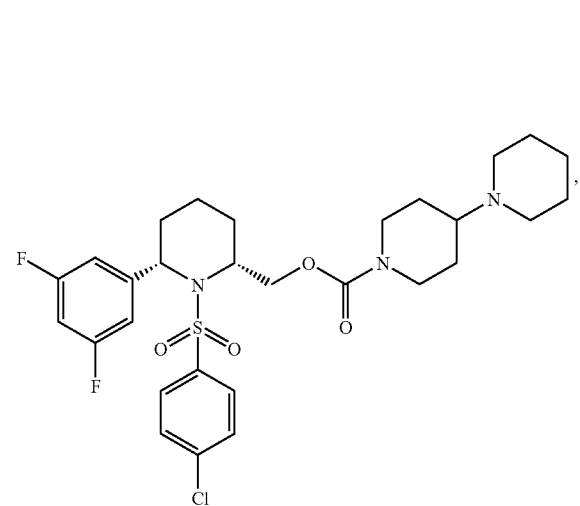
284
-continued
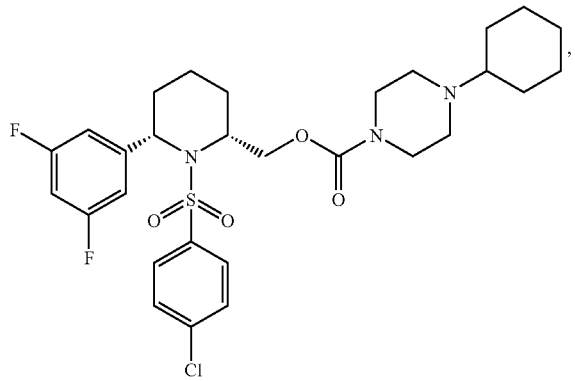
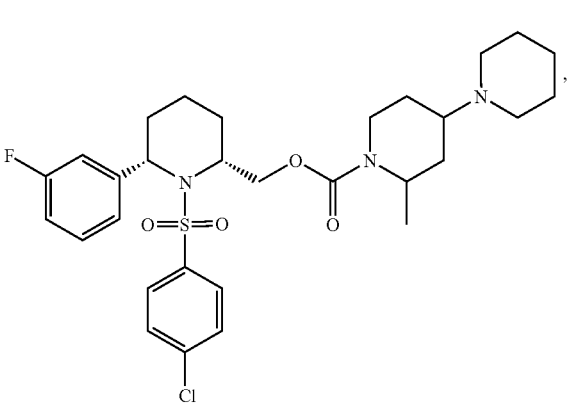
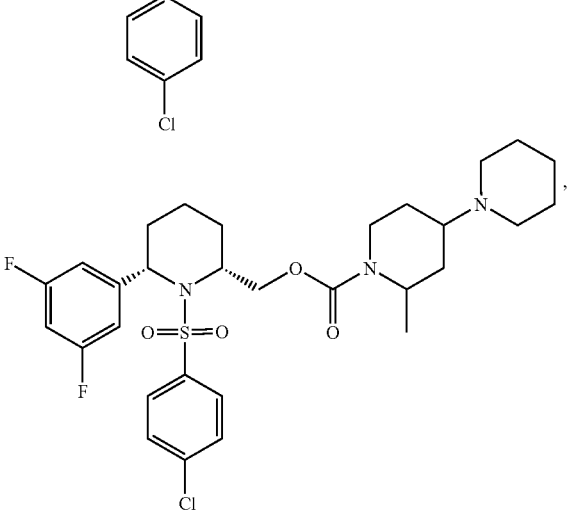

-continued
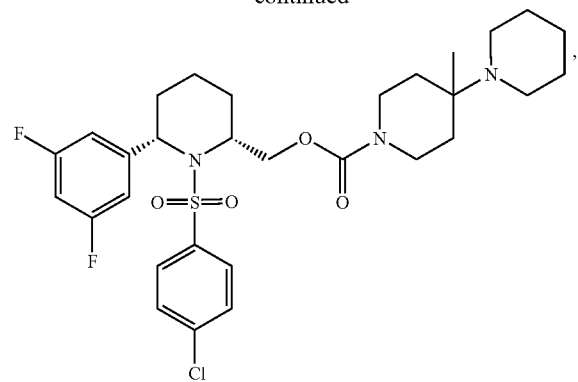
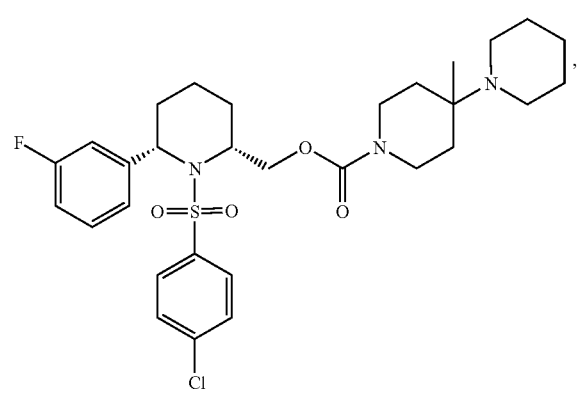
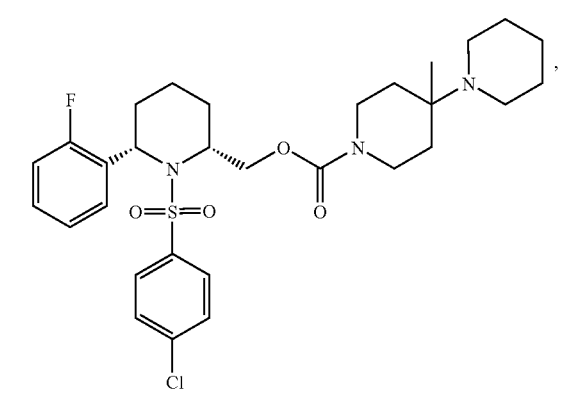
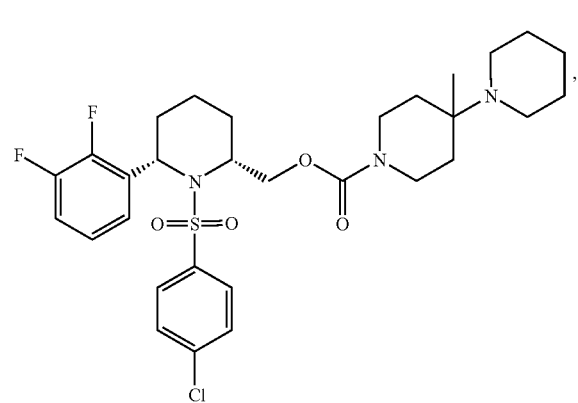
-continued
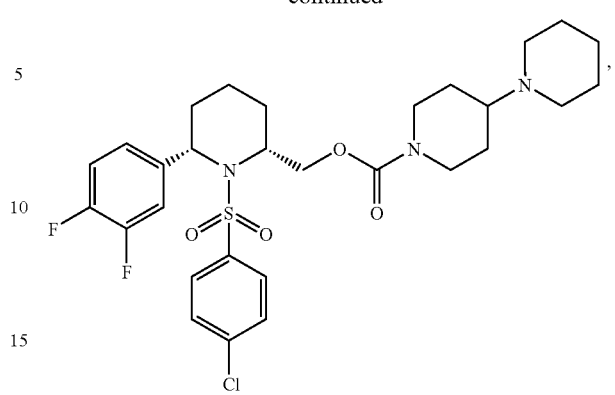

-continued
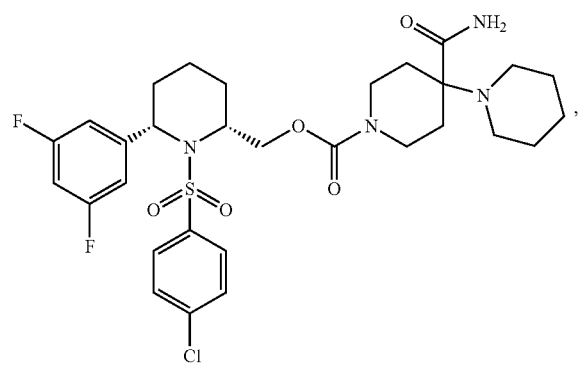
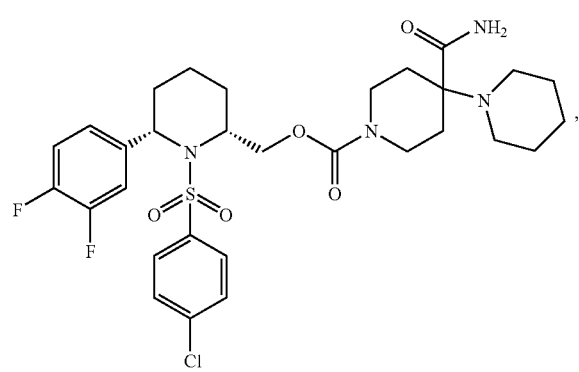
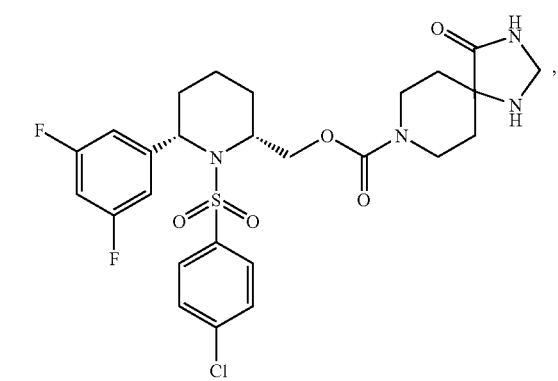
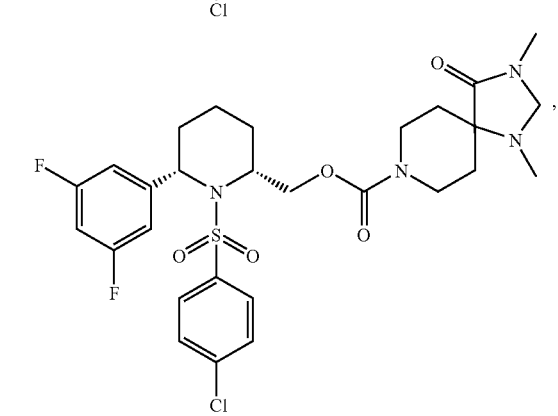
-continued
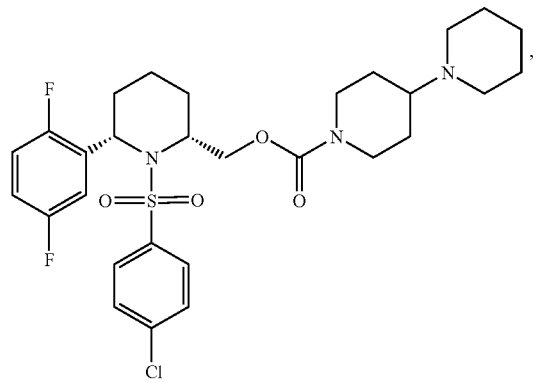
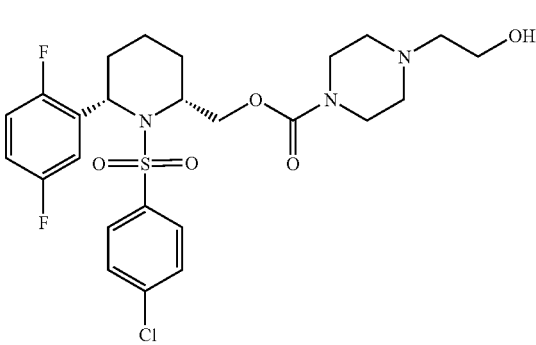
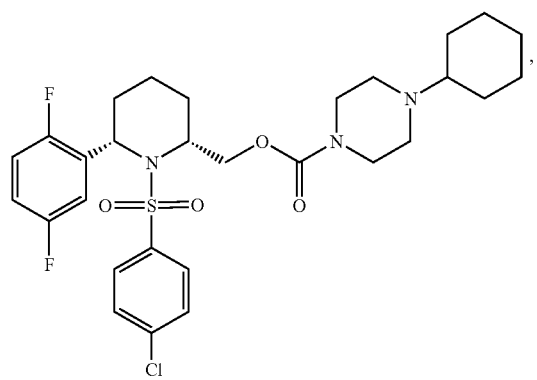
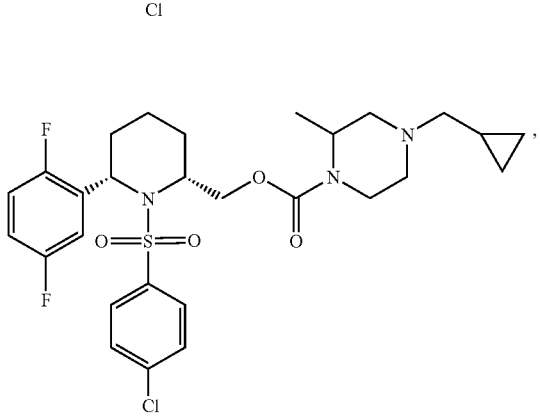

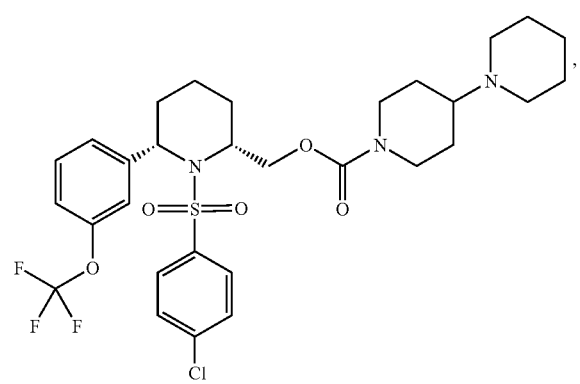
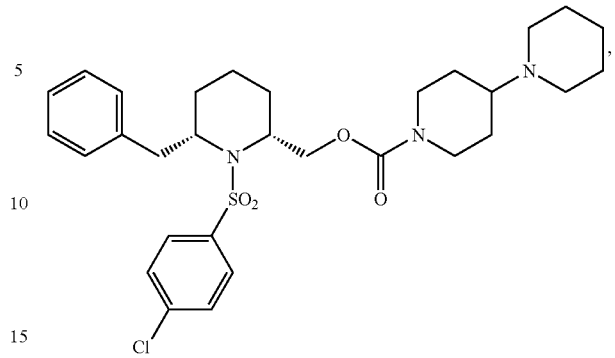
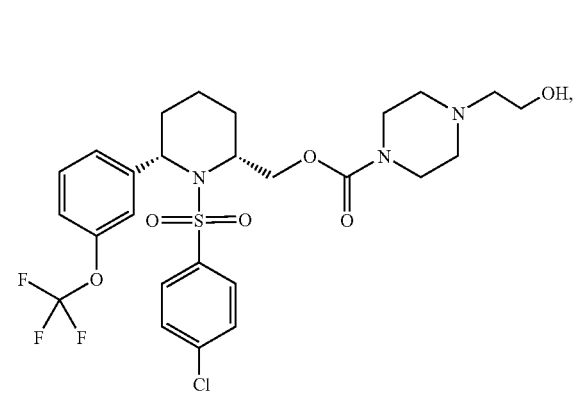
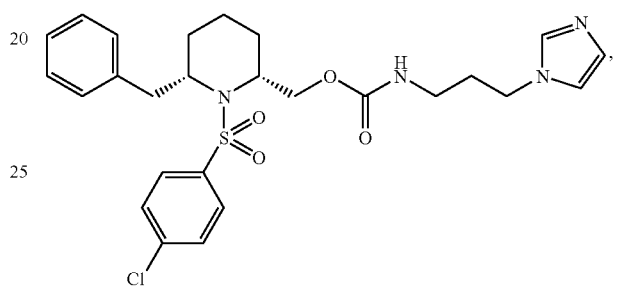
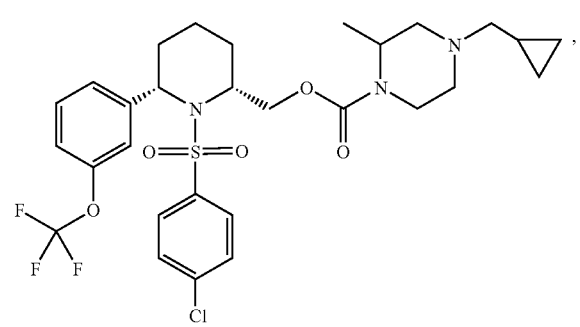
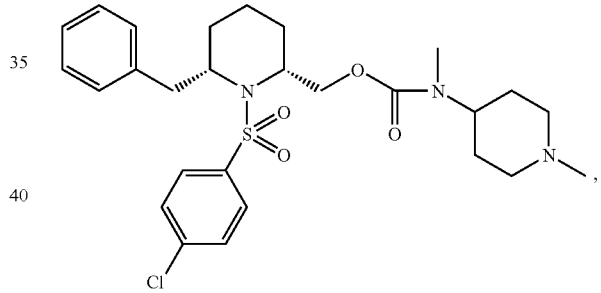
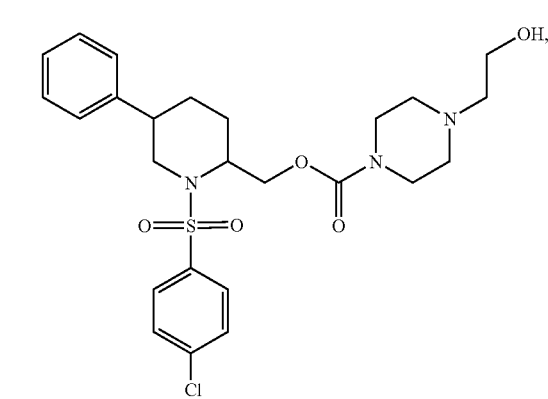
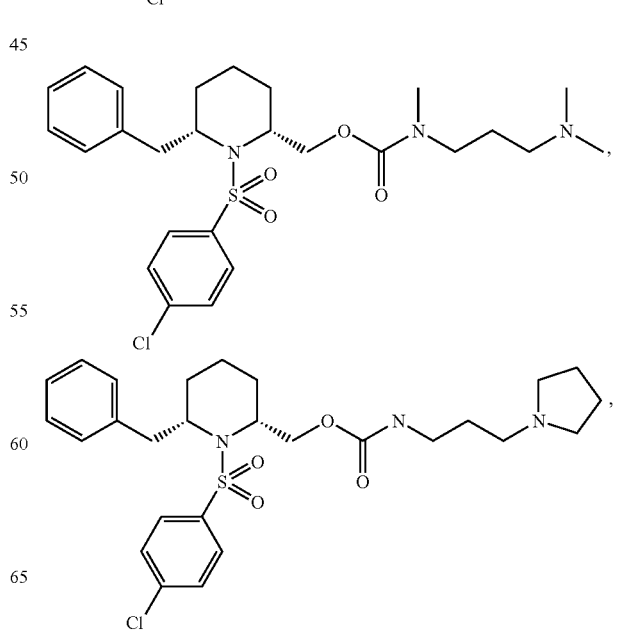

291
-continued
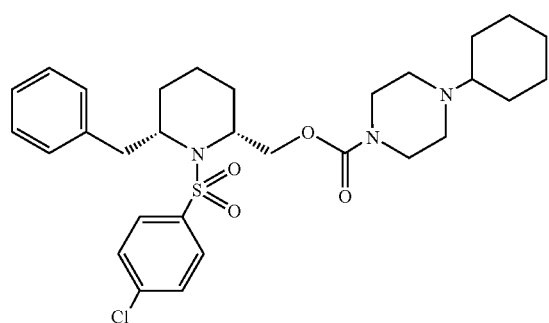
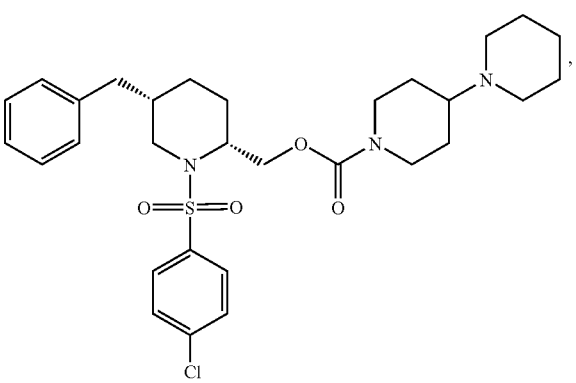
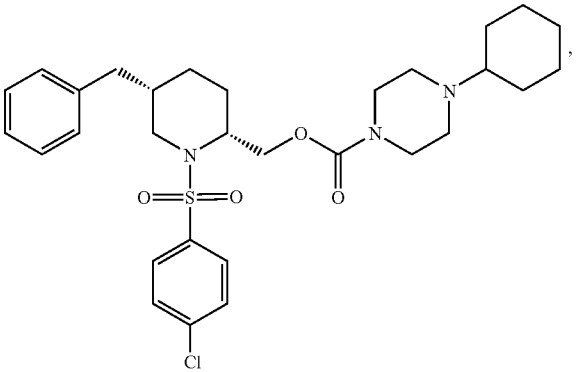
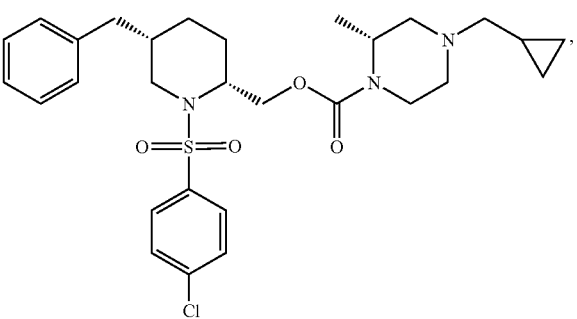
292
-continued
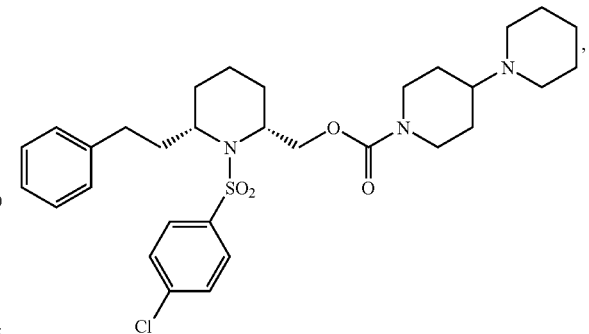
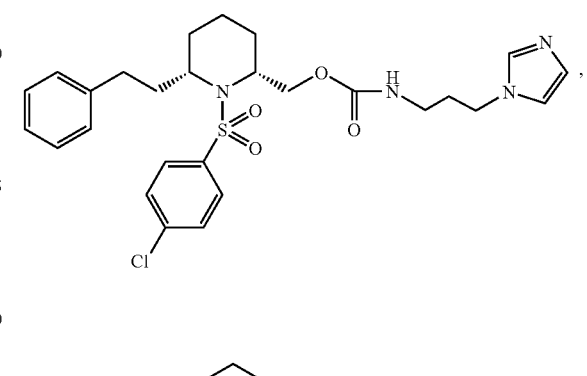
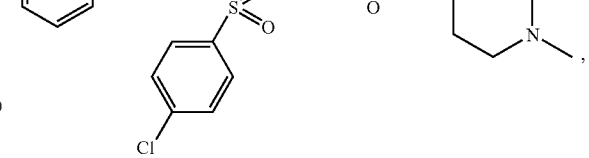
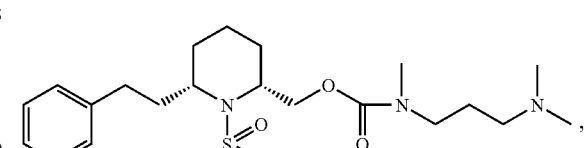
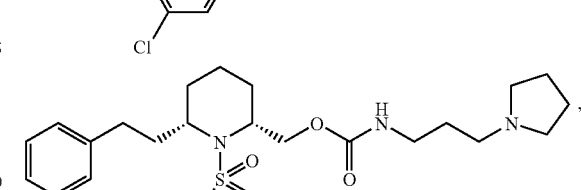
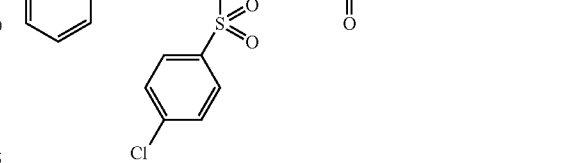

293
-continued
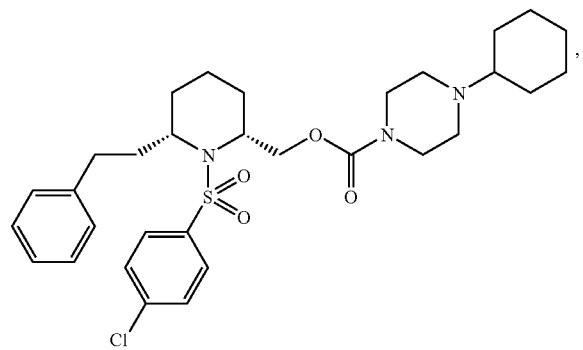
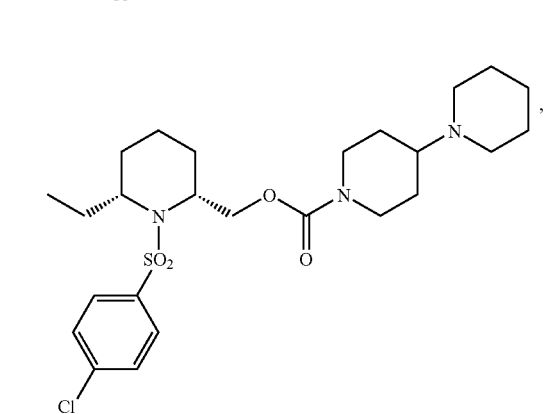
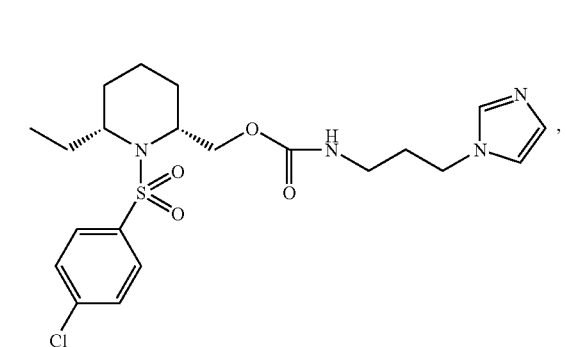
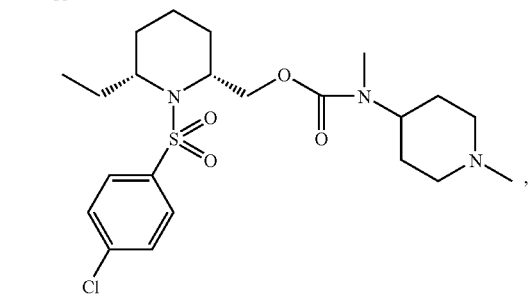
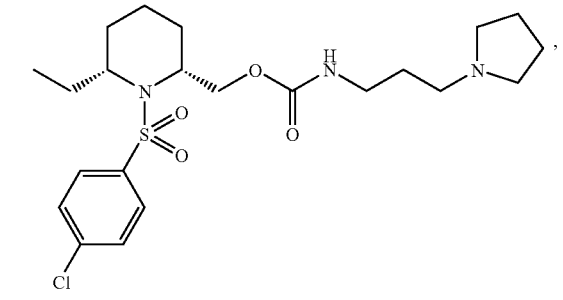
294
-continued
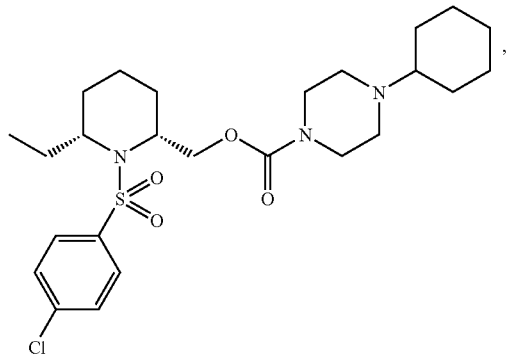
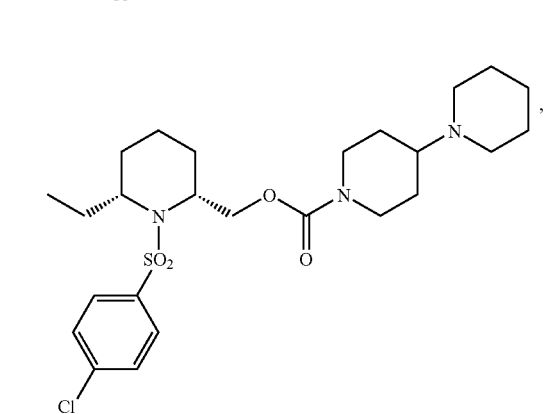
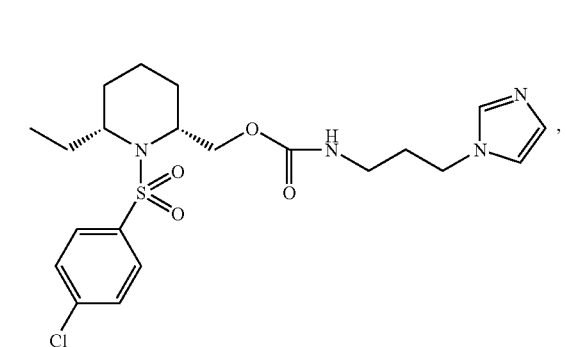
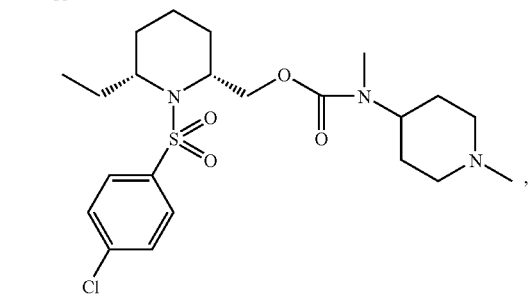
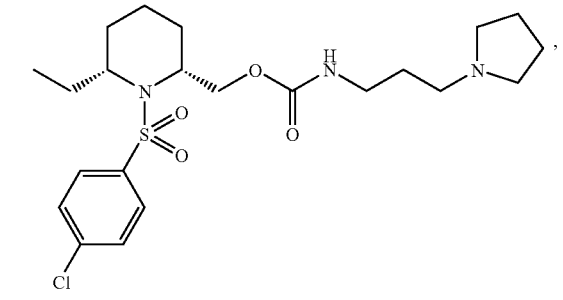

295
-continued
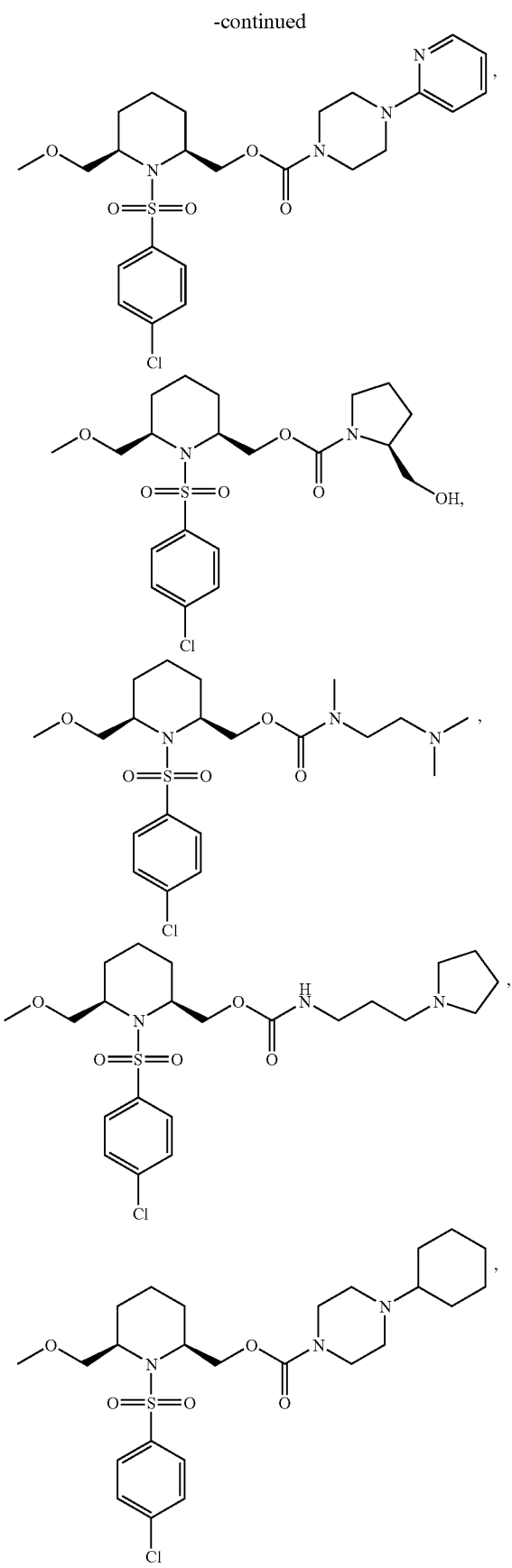
296
-continued
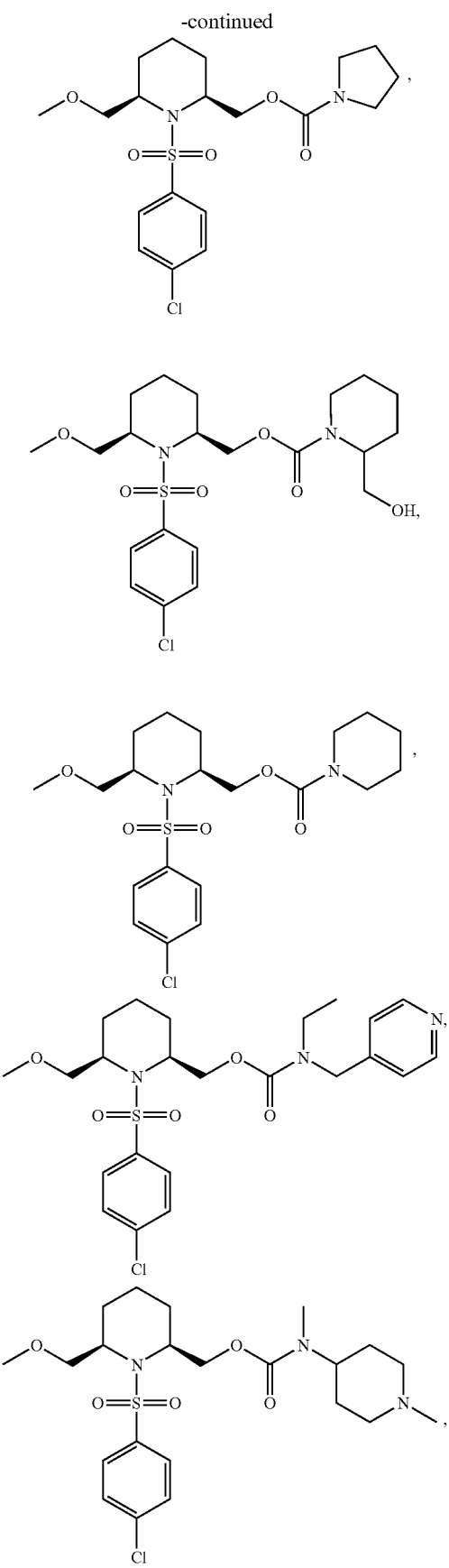

297
-continued
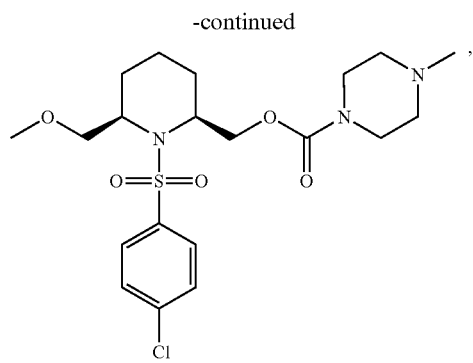
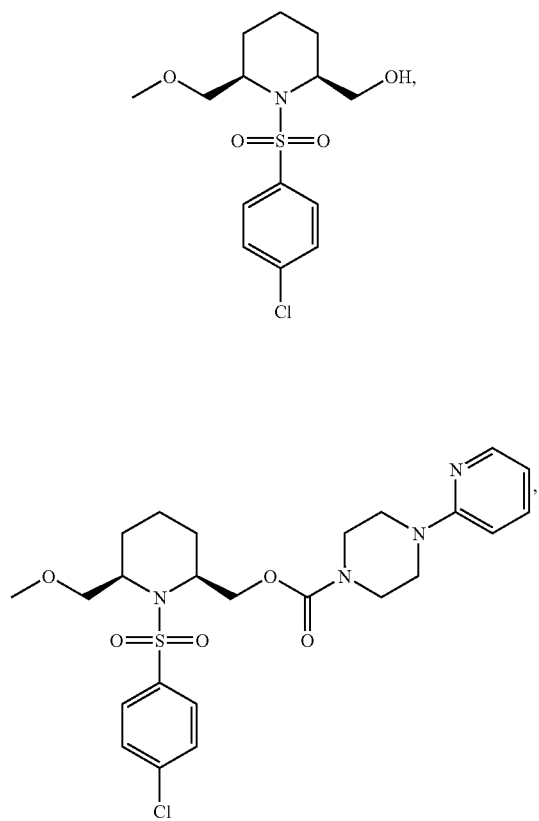
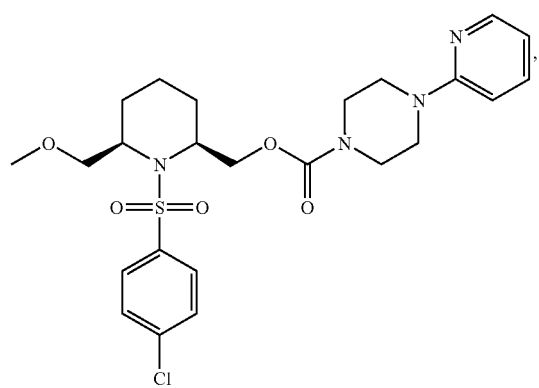
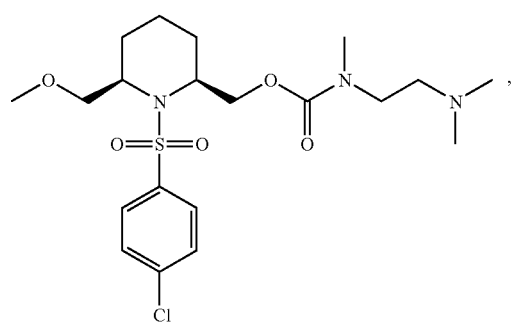
298
-continued
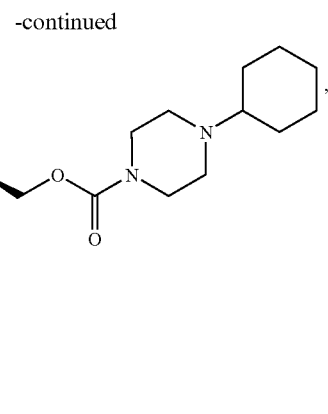
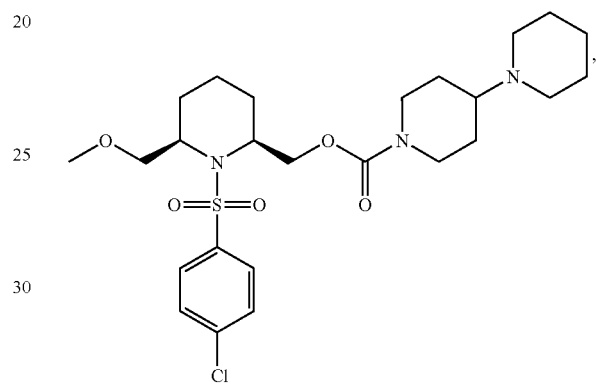
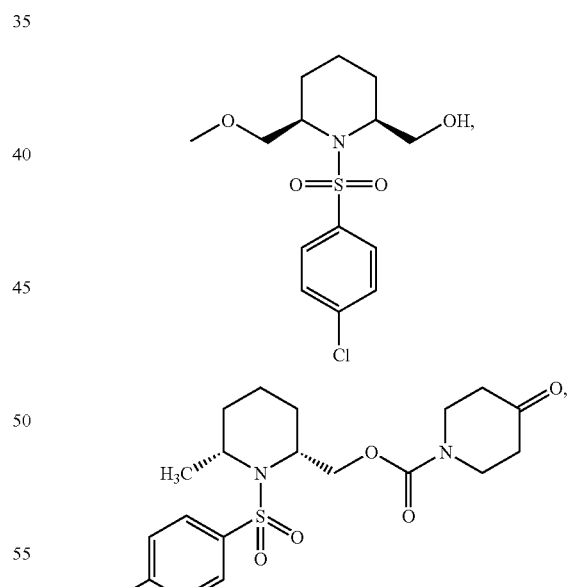
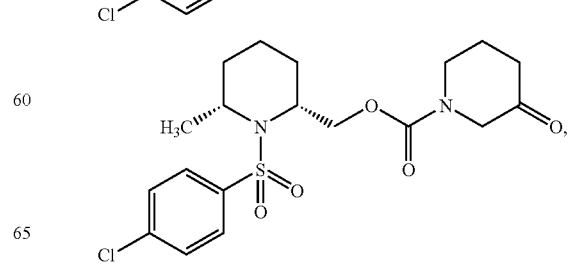

-continued
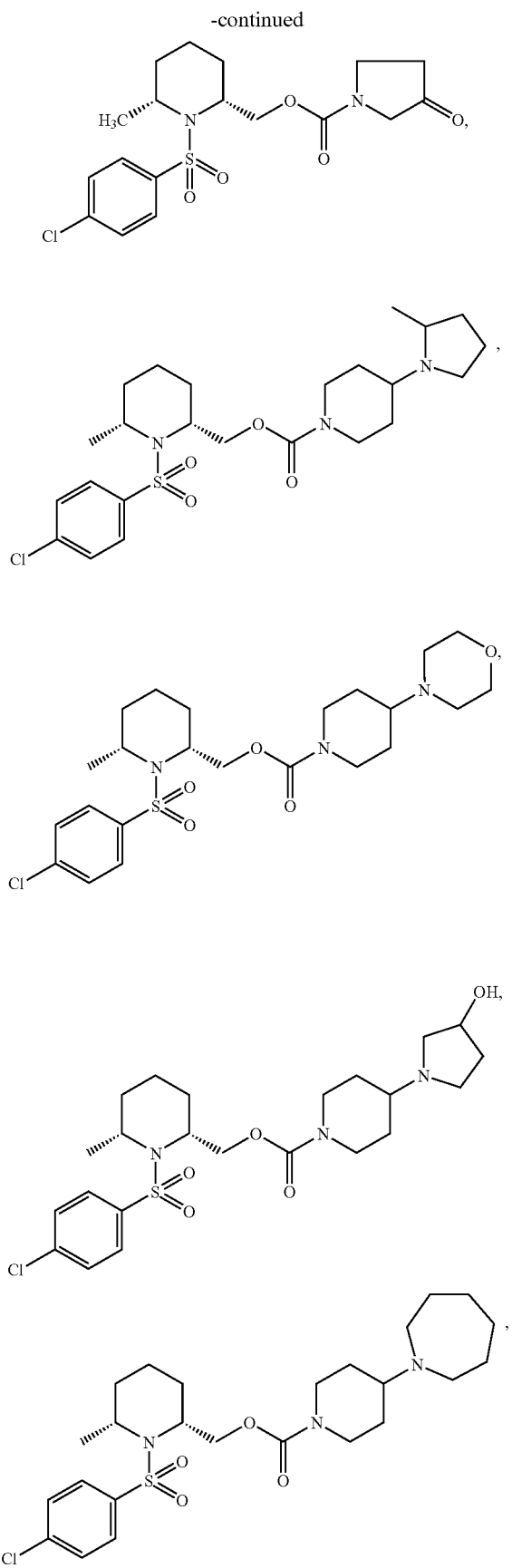
-continued
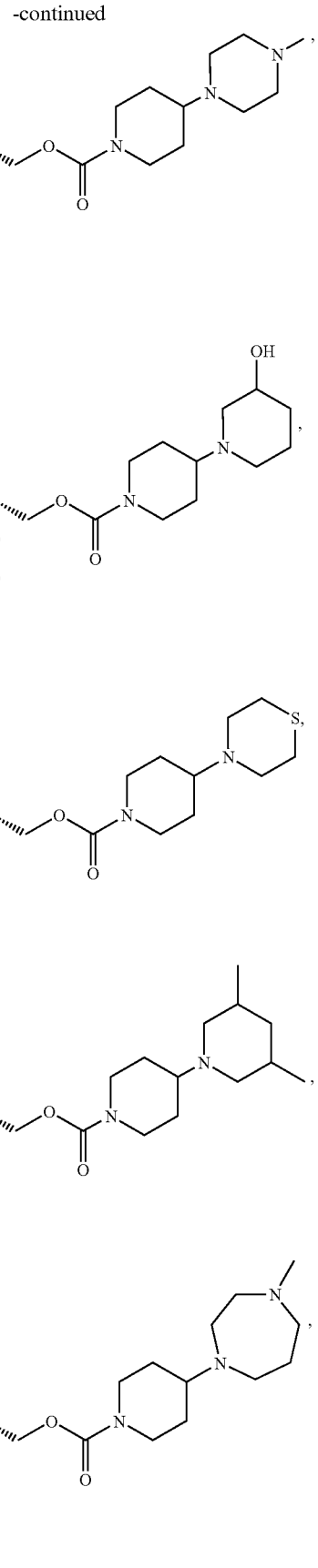

301
-continued
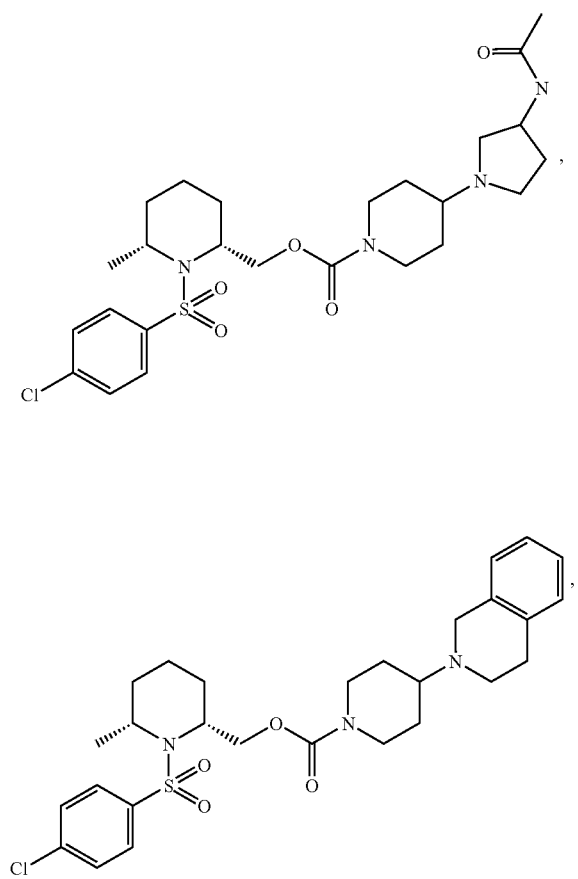
302
-continued
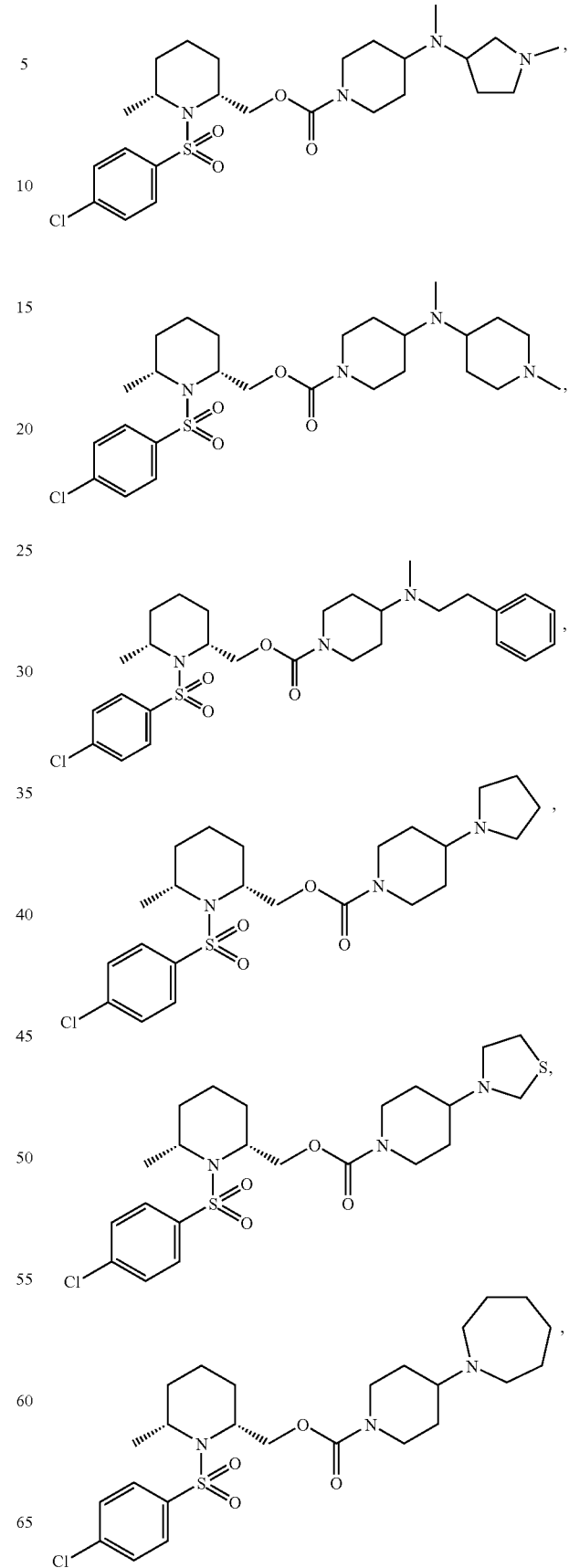

303
-continued
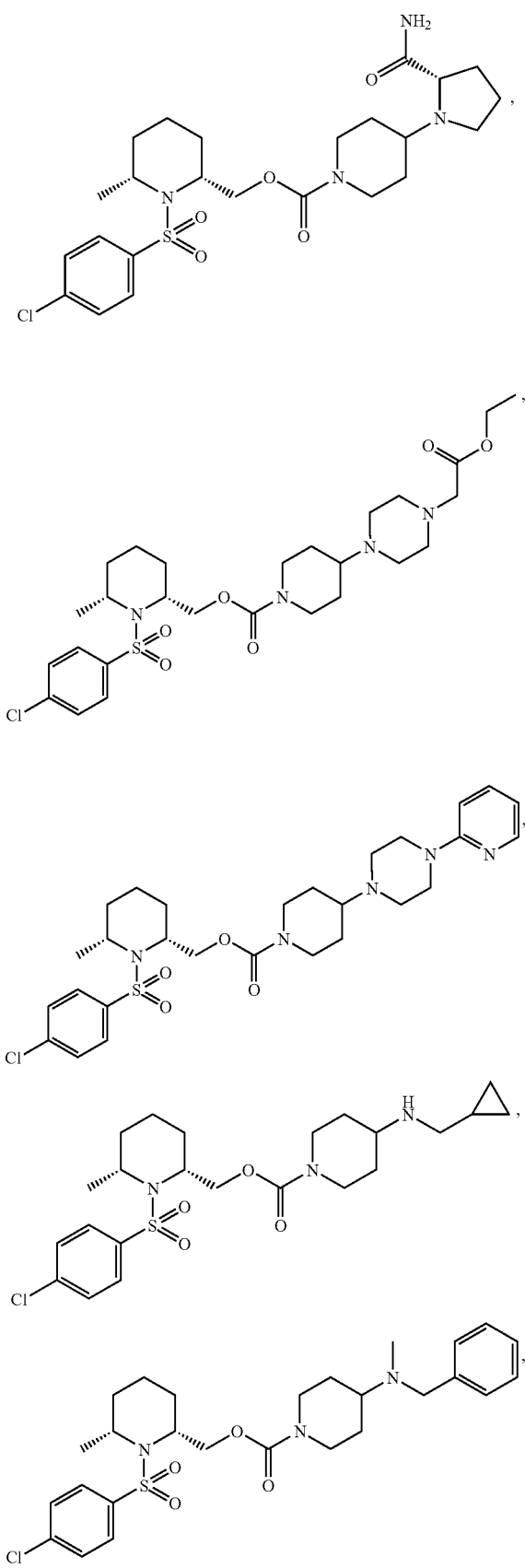
304
-continued
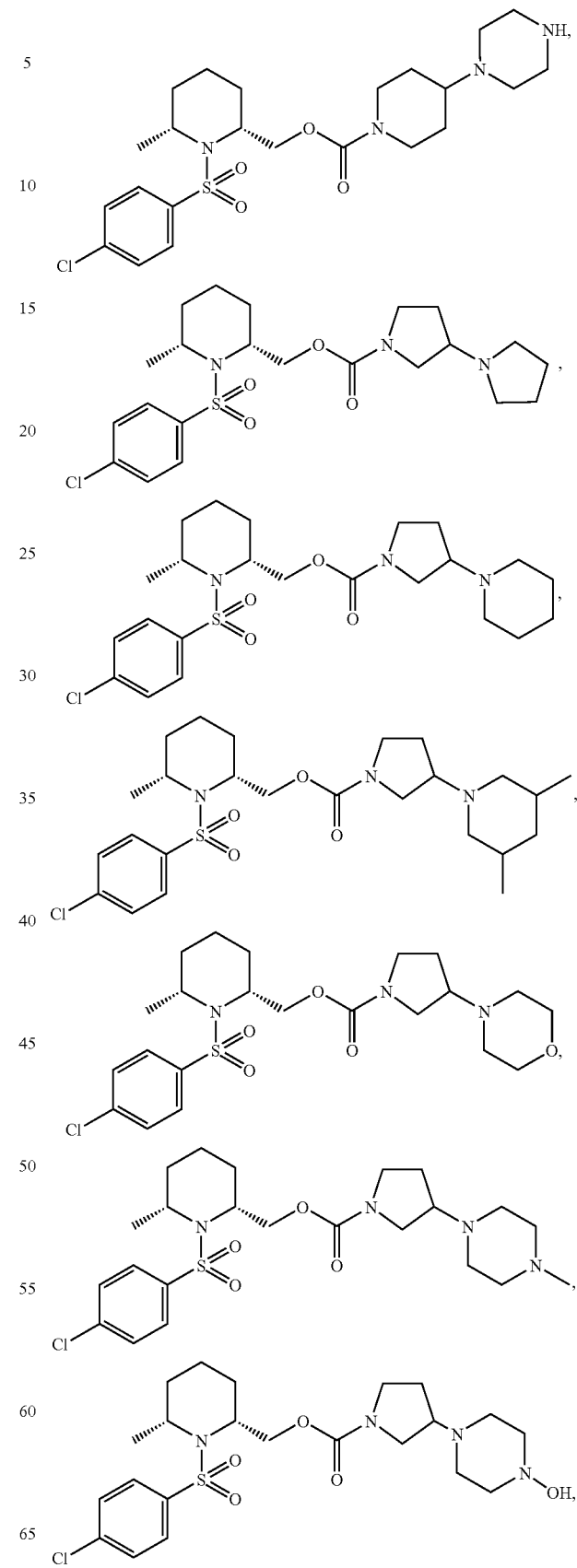

305
-continued
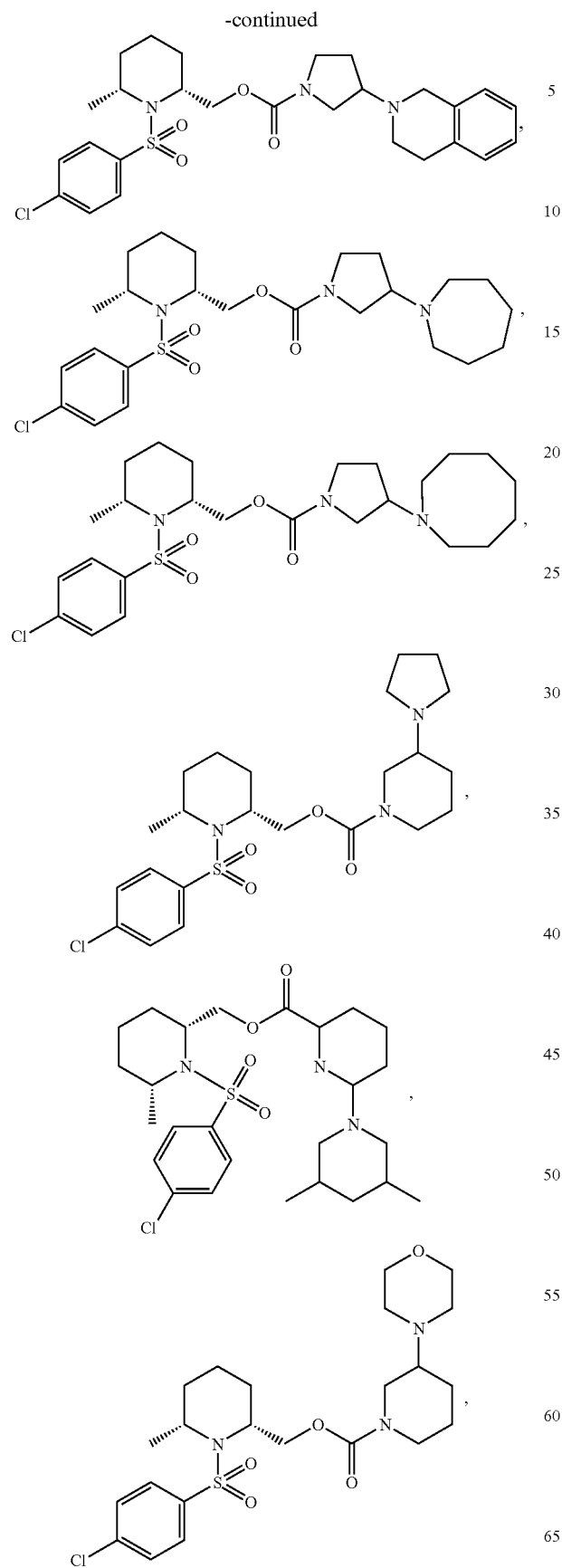
306
-continued
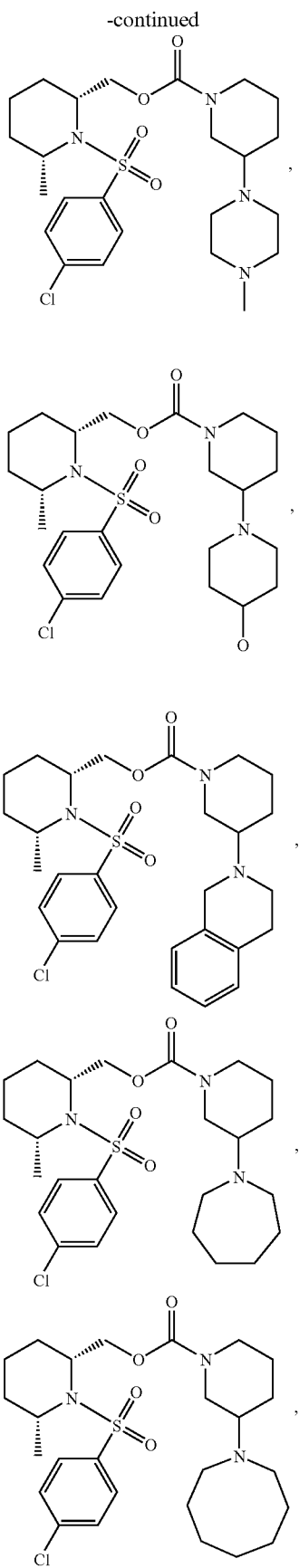

307
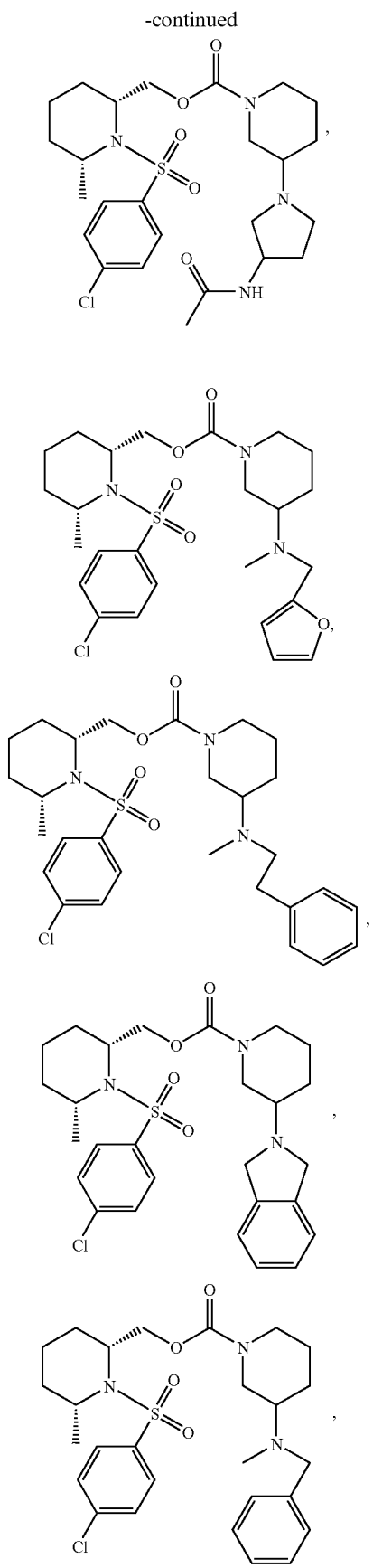
308
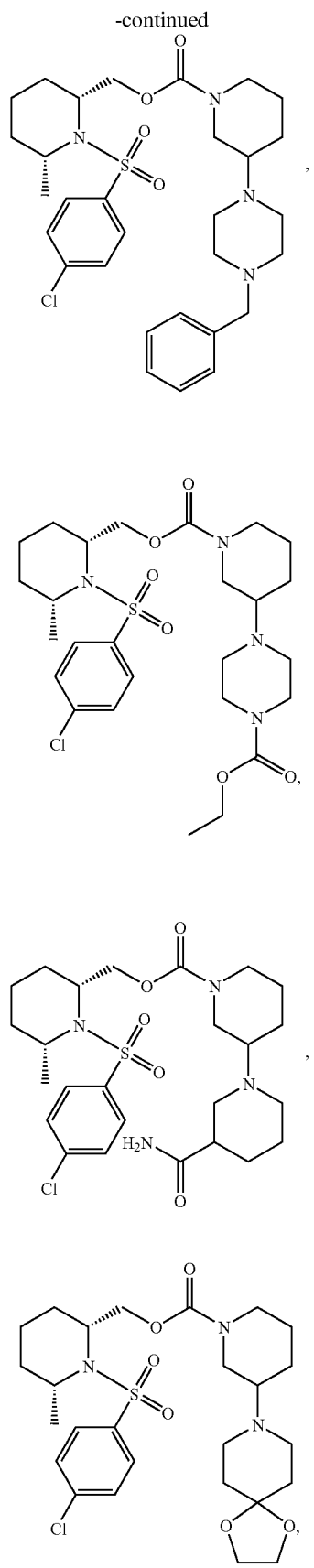

309
-continued
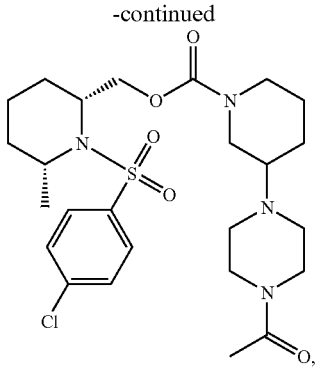
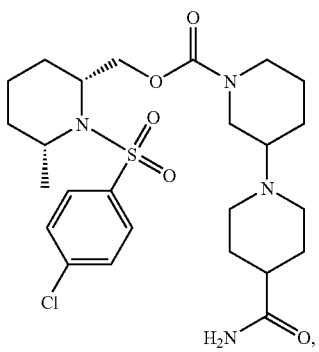
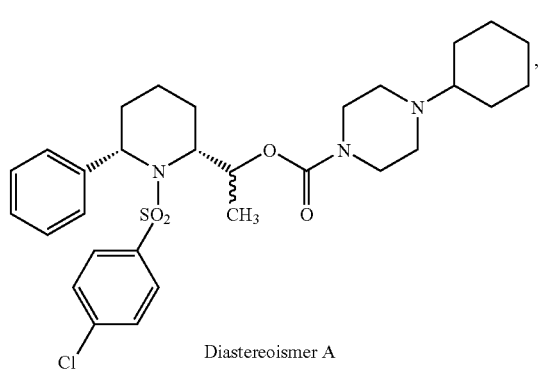
Diastereoismer A
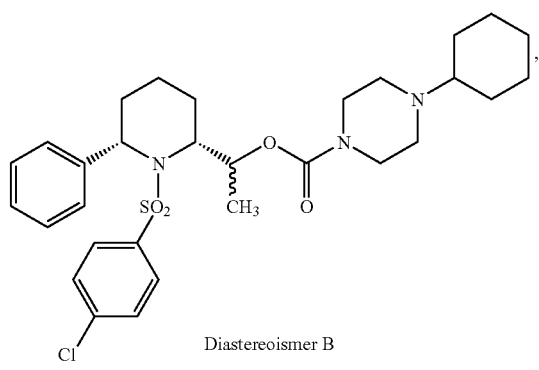
Diastereoismer B
310
-continued
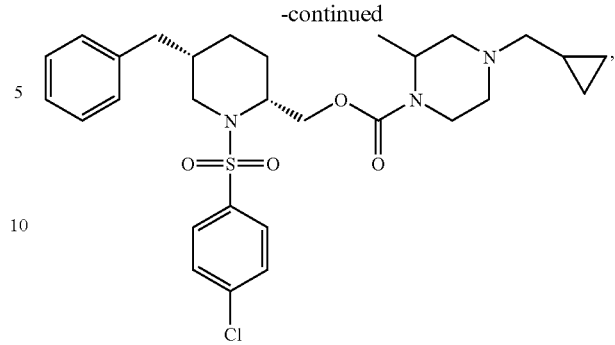
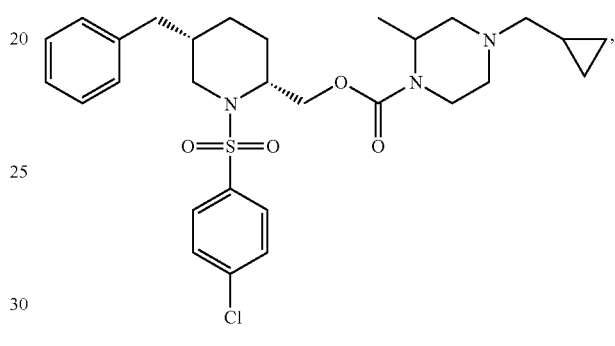
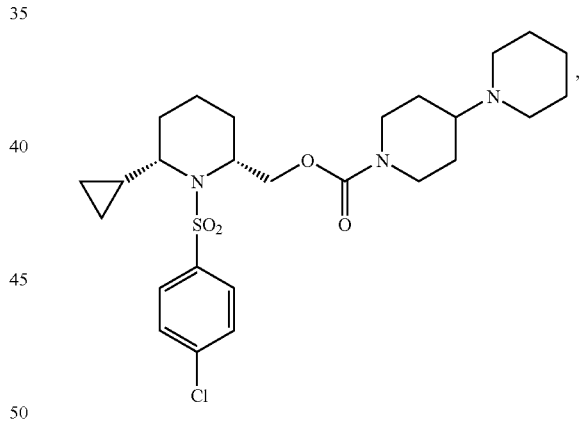
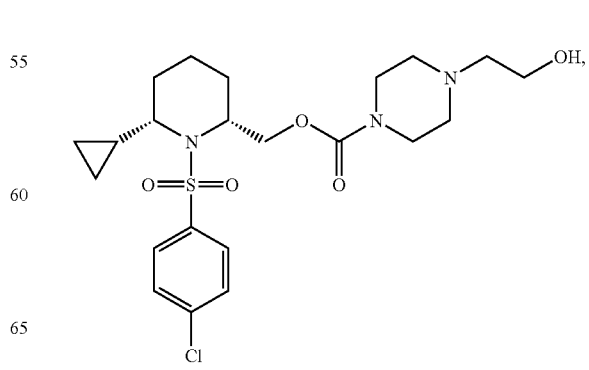

311
-continued
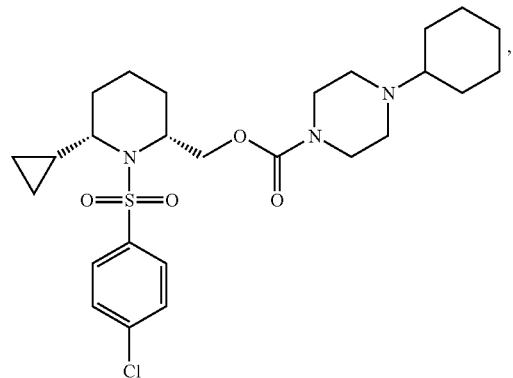
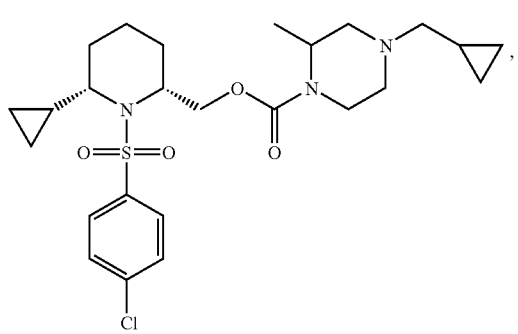
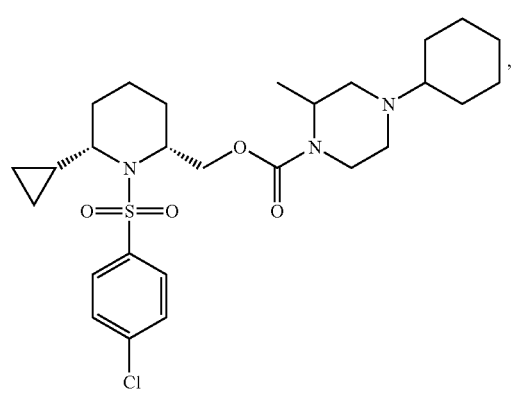
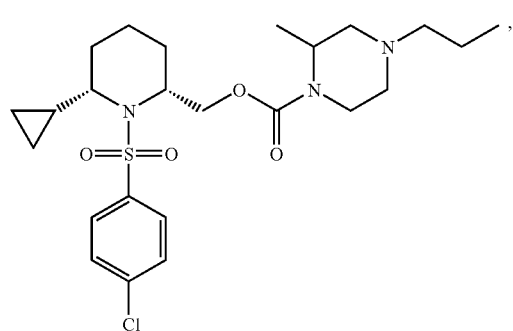
312
-continued
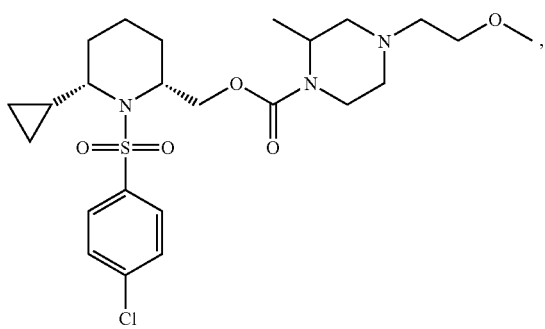
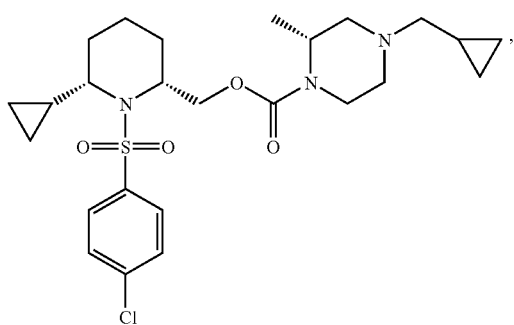
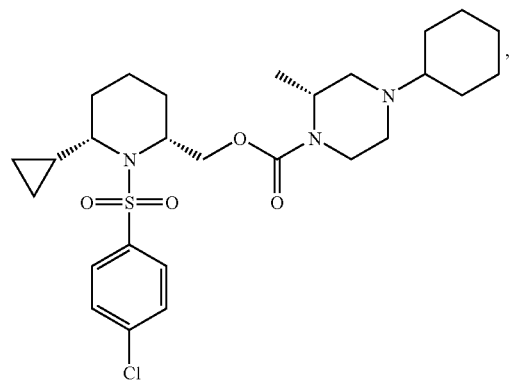
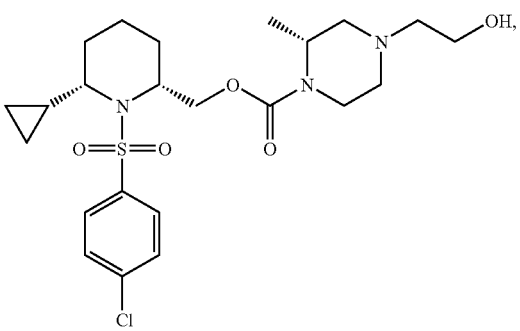

-continued
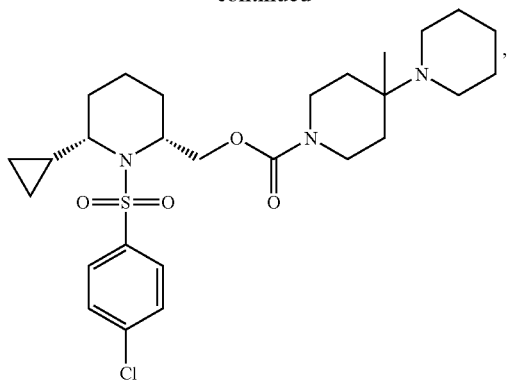
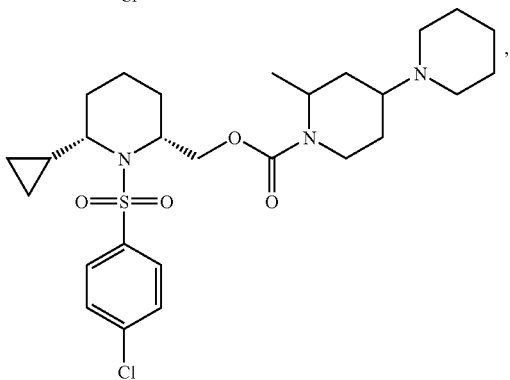
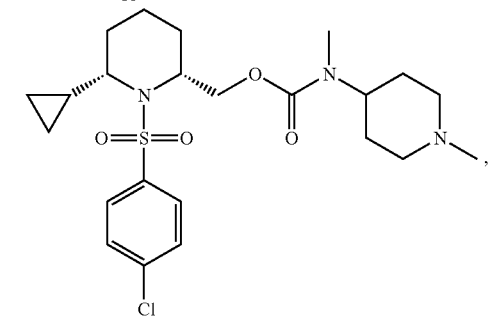
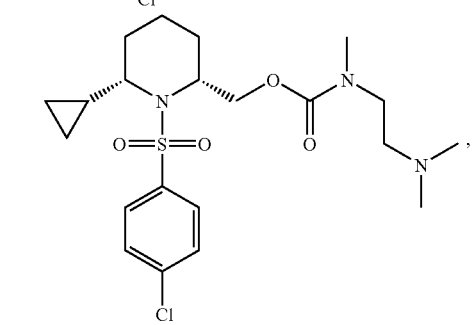
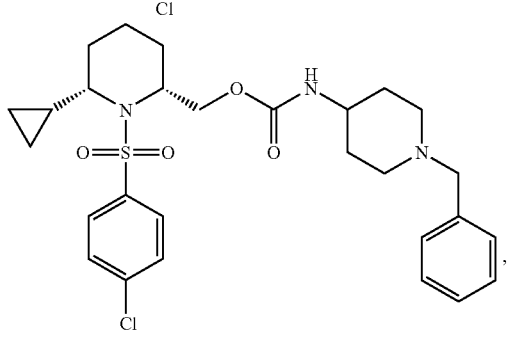
-continued
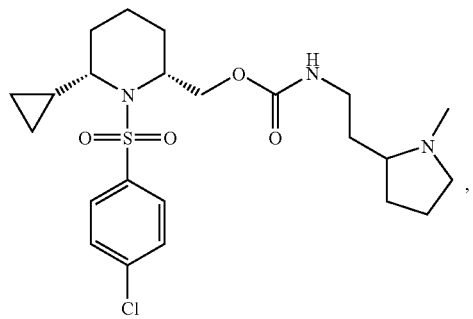
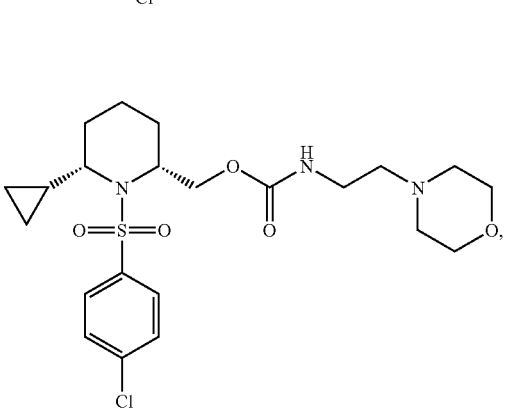
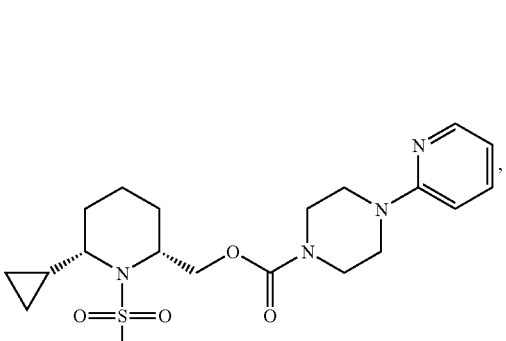
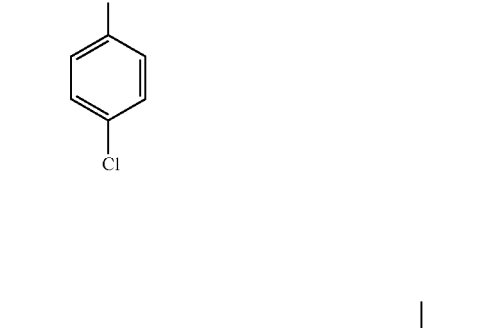
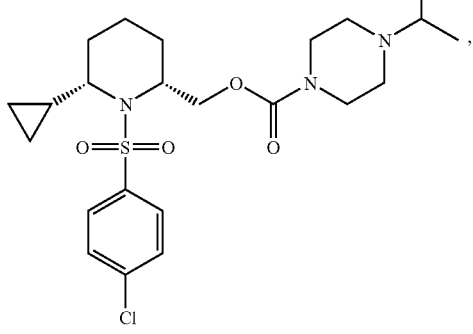

315
-continued
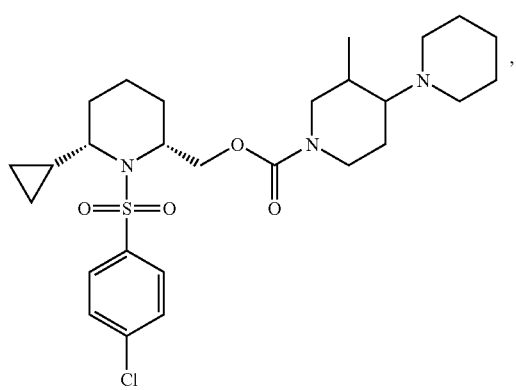
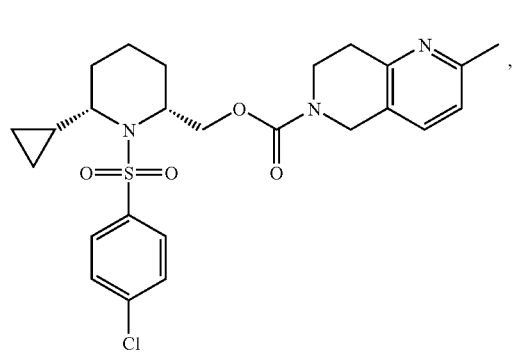
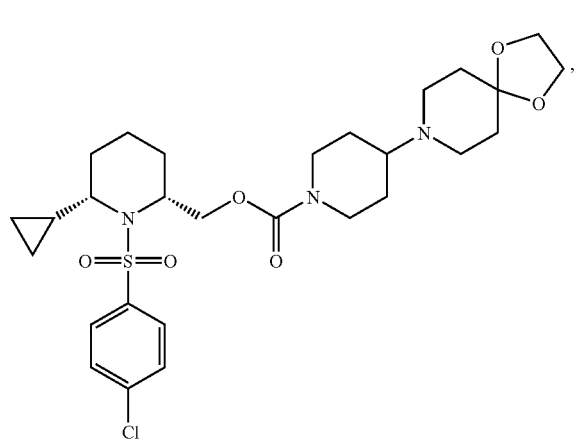
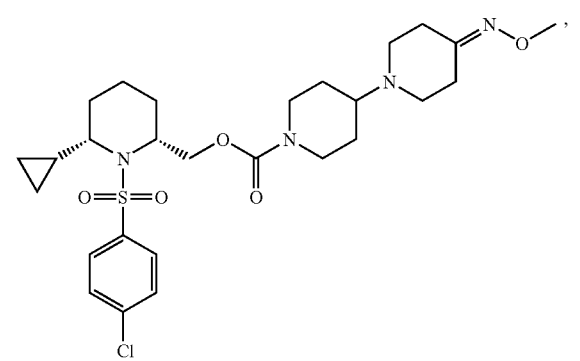
316
-continued
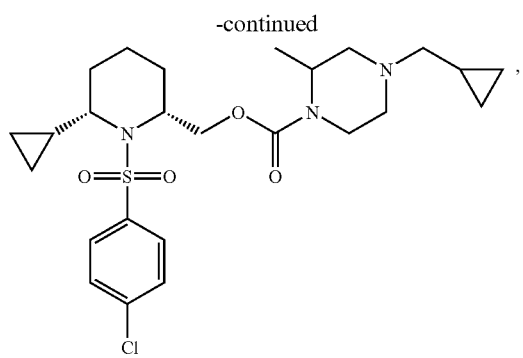
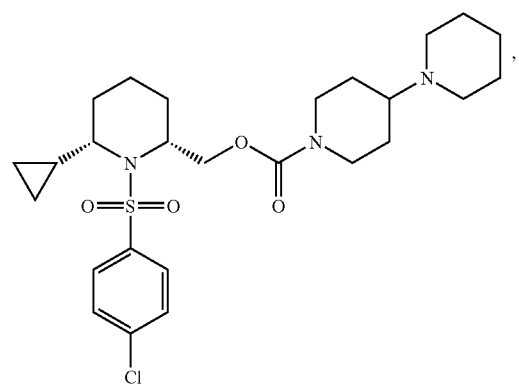
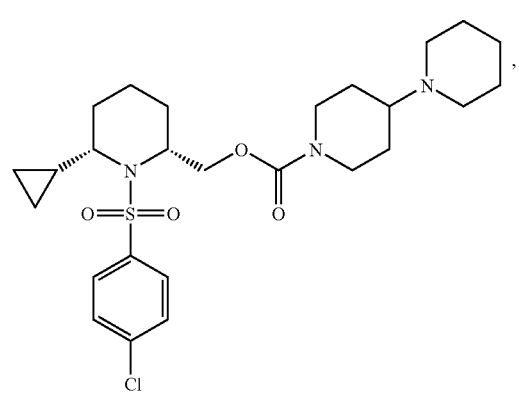
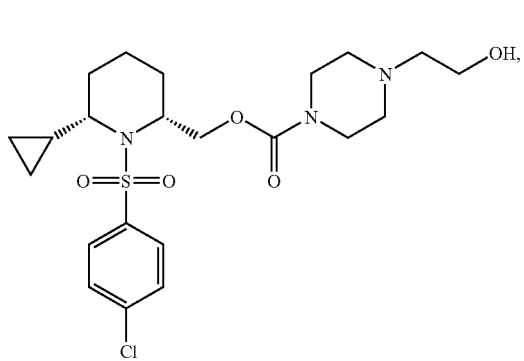

317
-continued
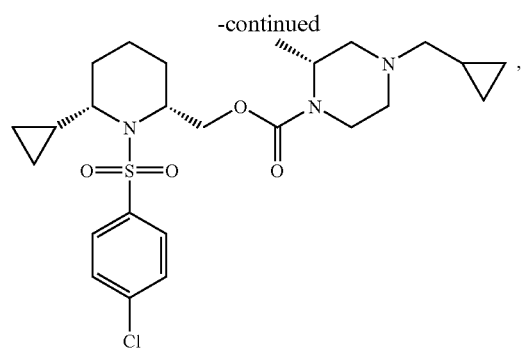
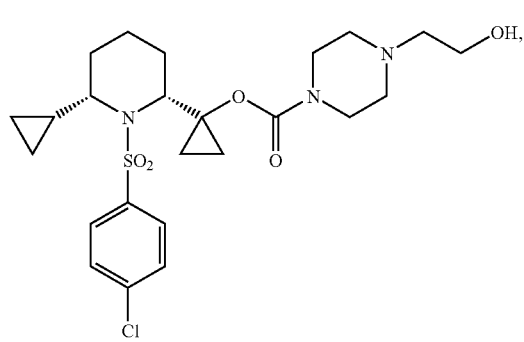
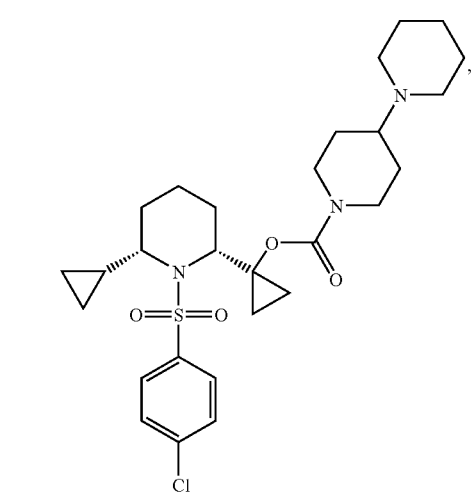
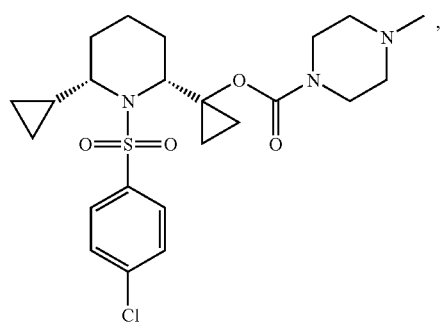
318
-continued
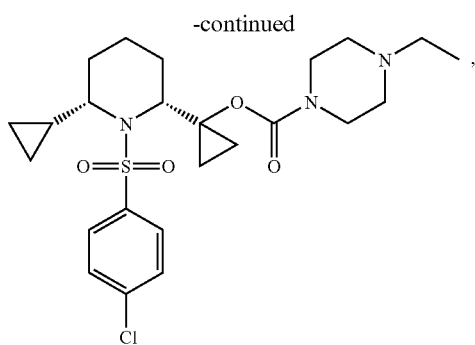
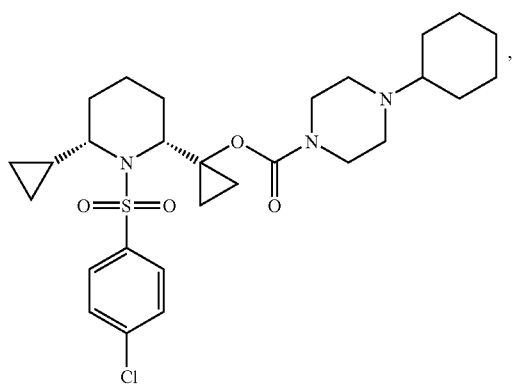
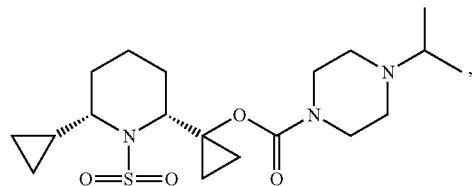
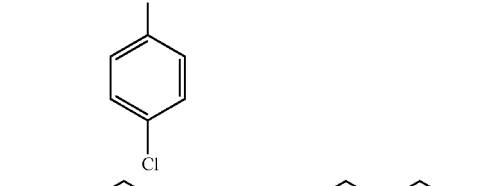
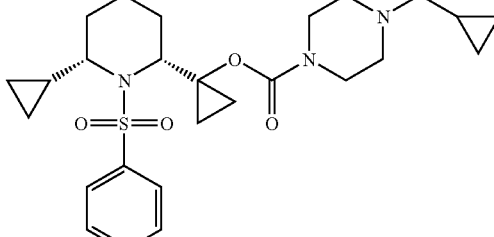
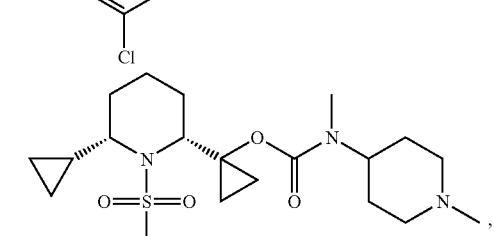
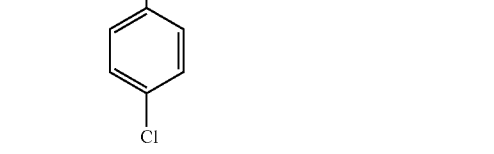

-continued
319
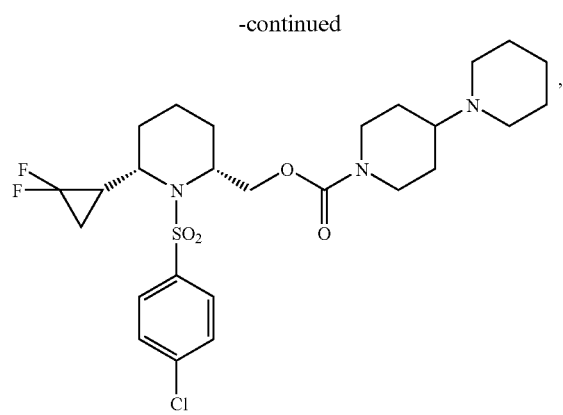
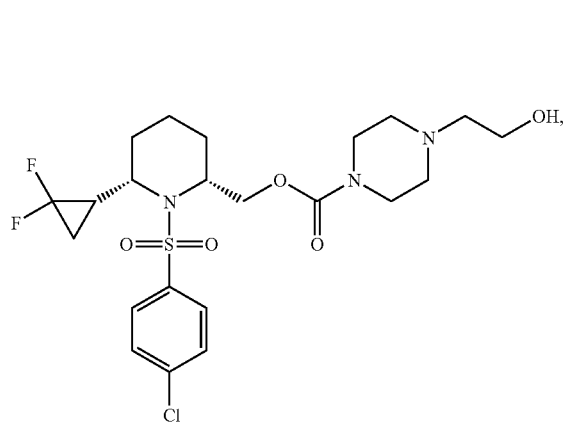
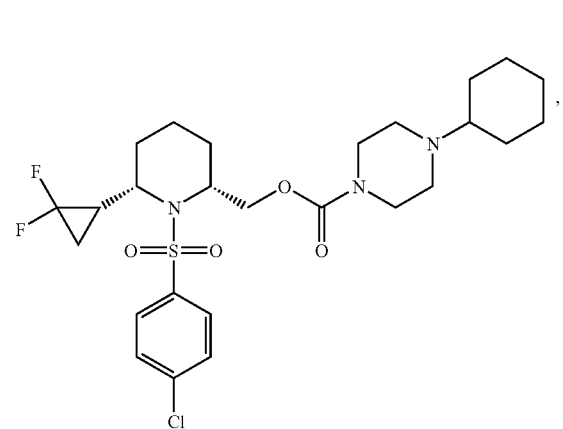
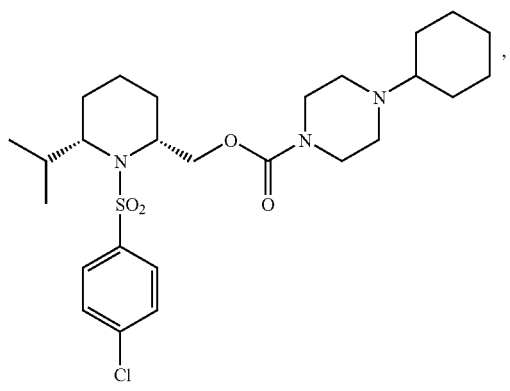
-continued
320
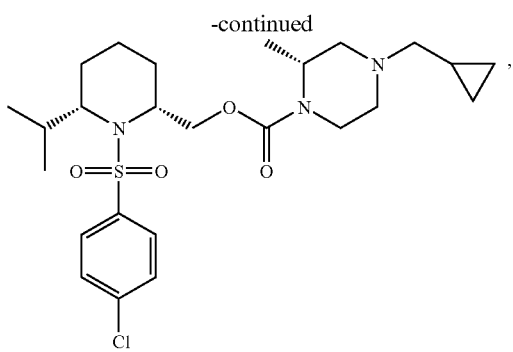
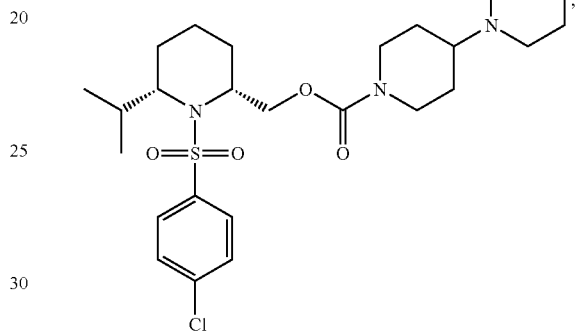
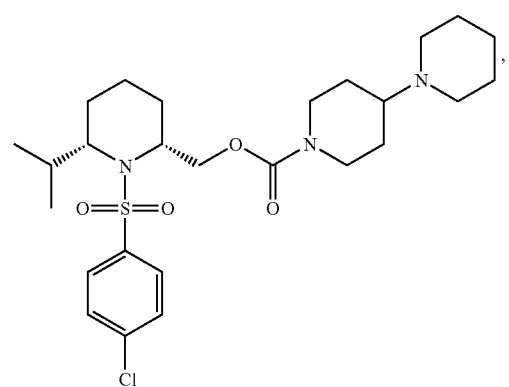
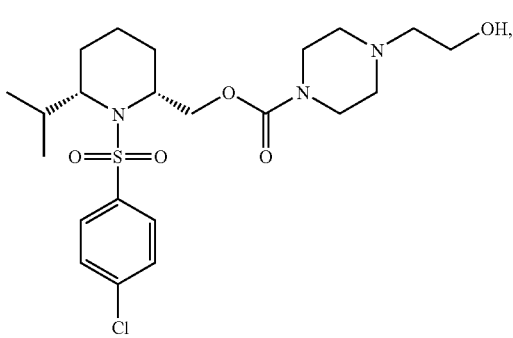
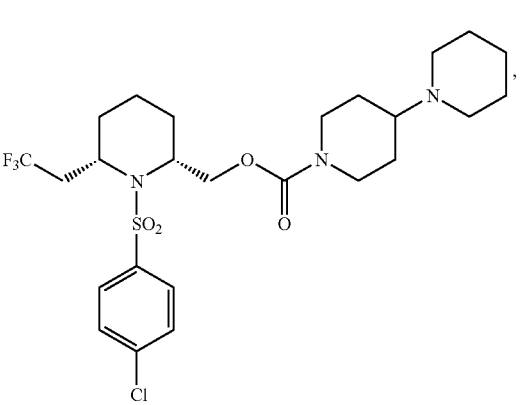

321
-continued
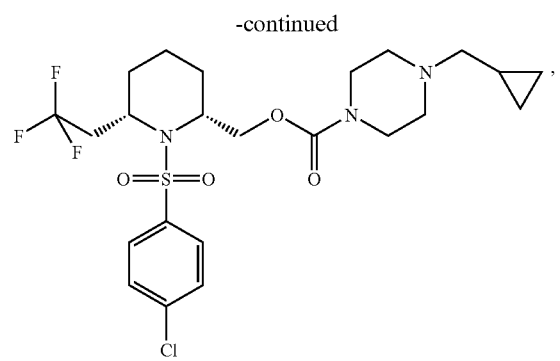
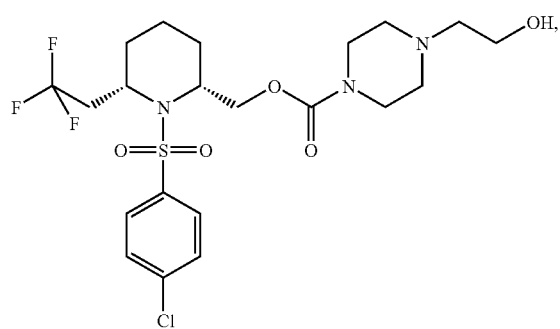
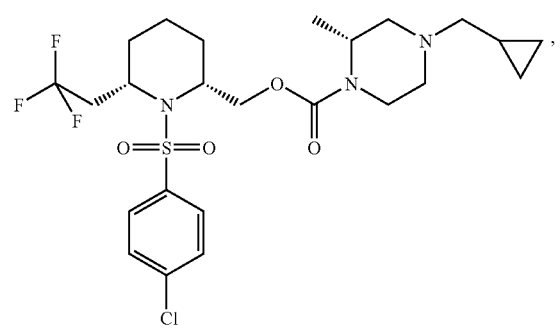
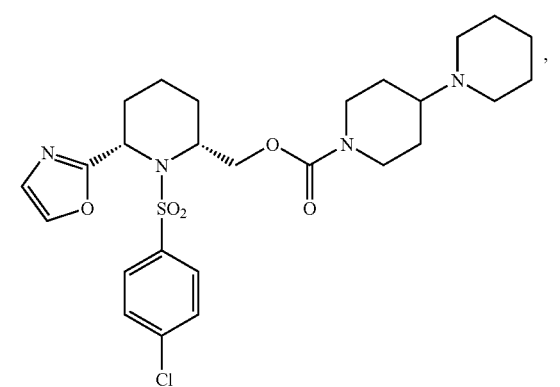
322
-continued
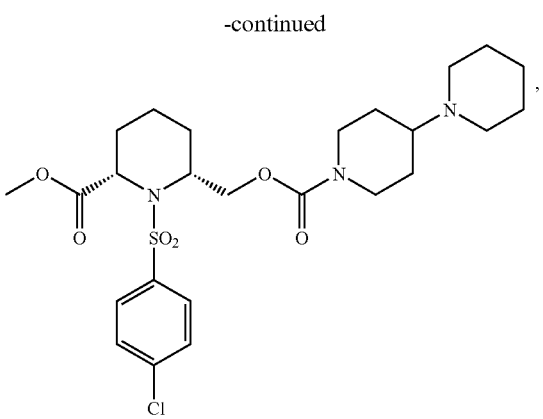
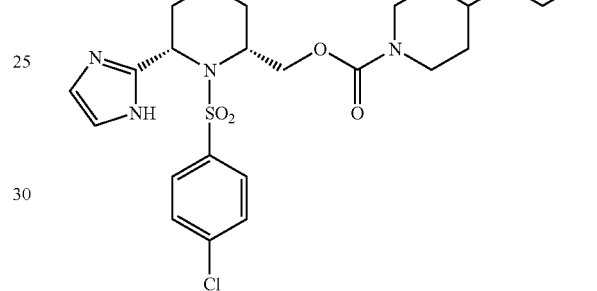
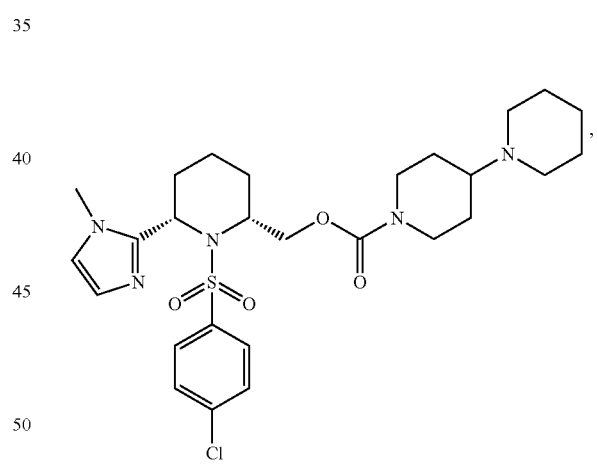
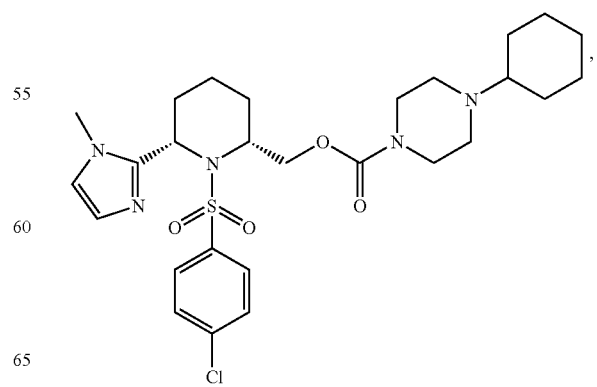

323 324
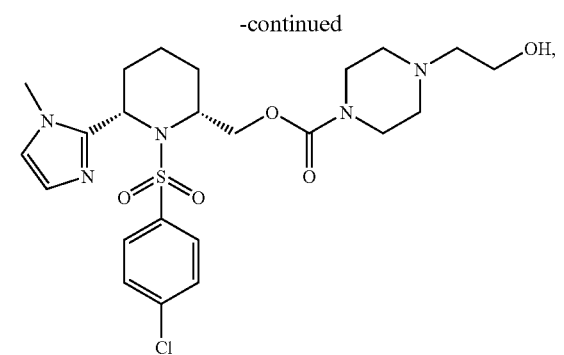
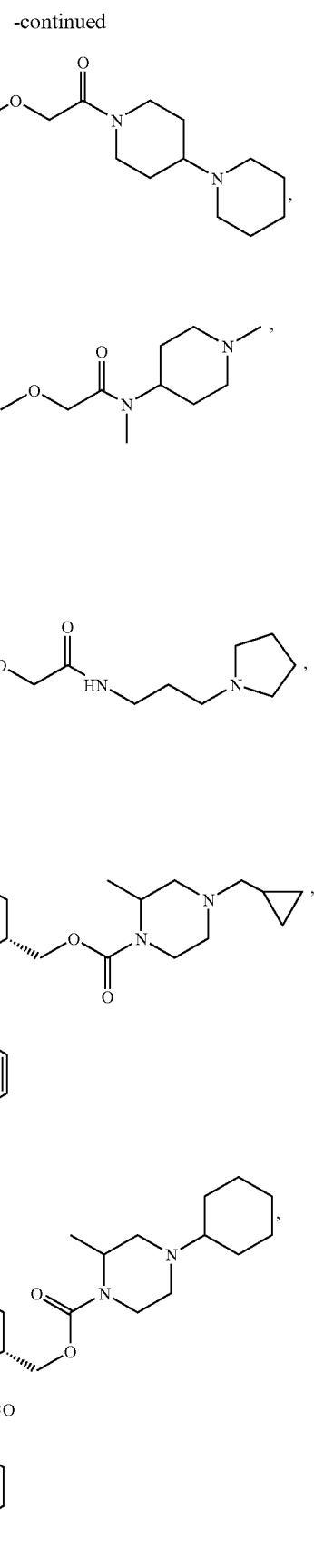

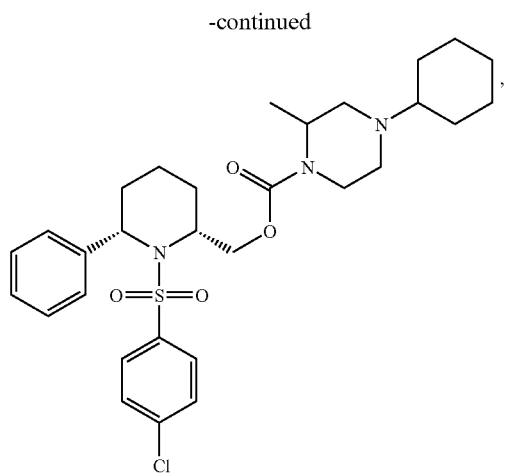
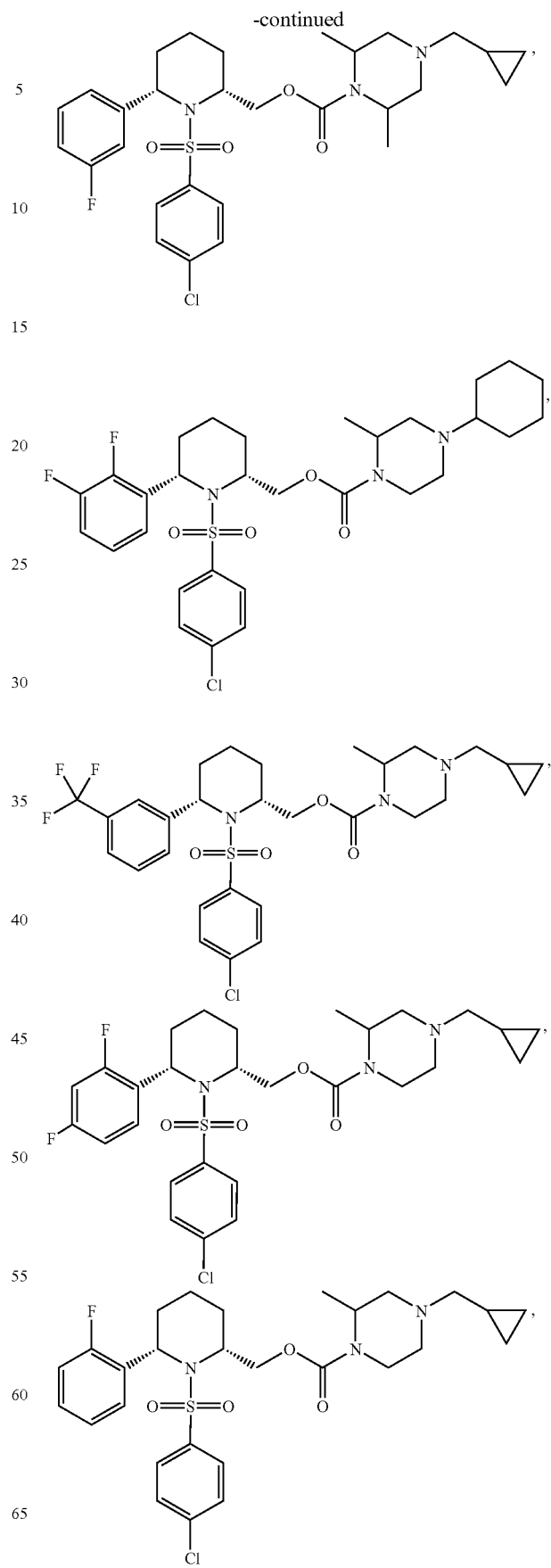

327
-continued
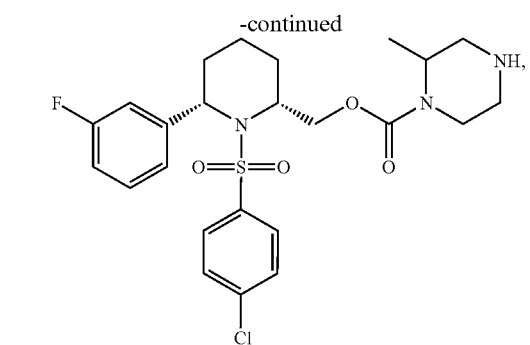
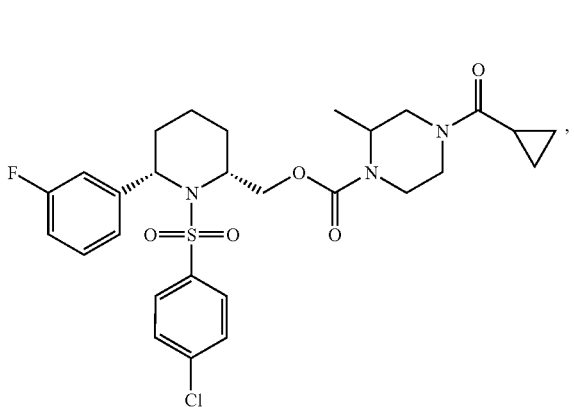
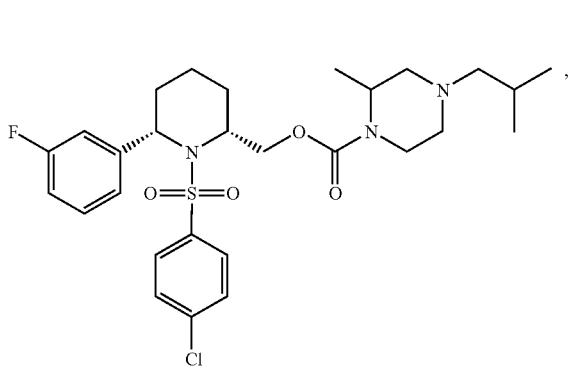
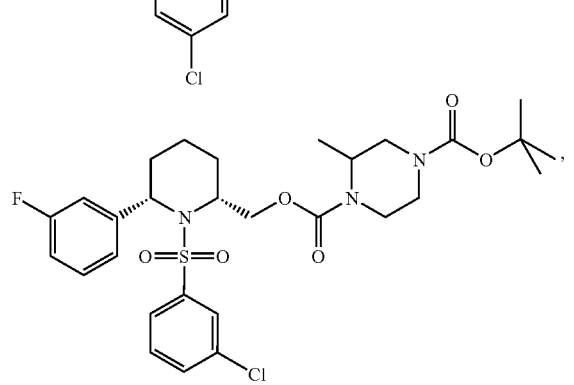
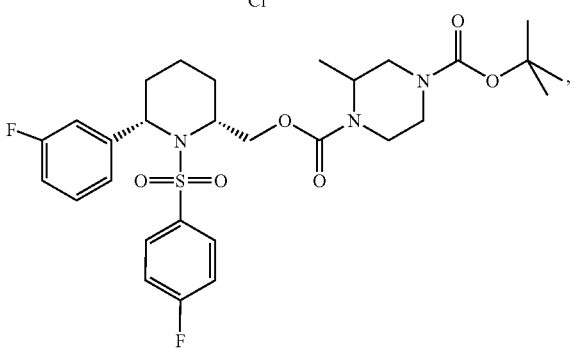
328
-continued
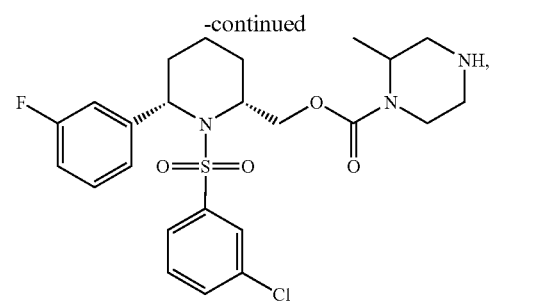
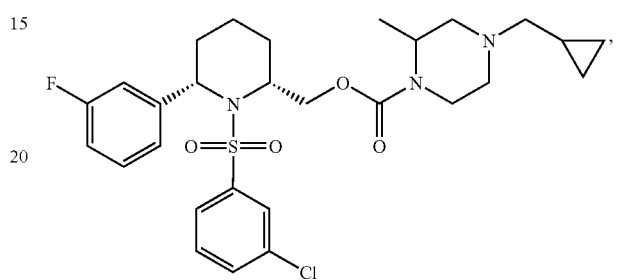
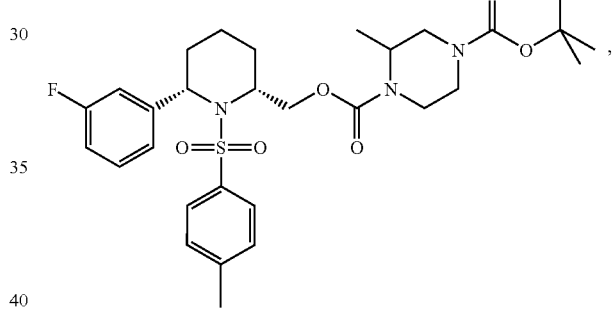
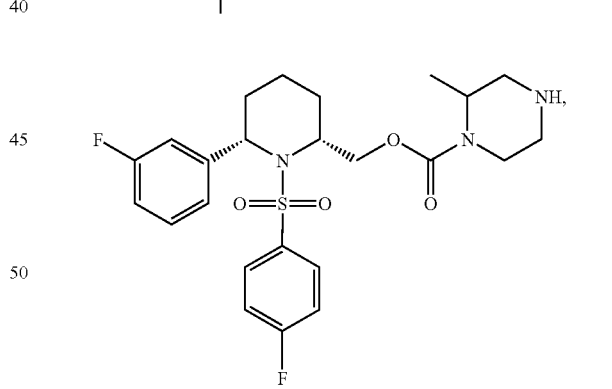
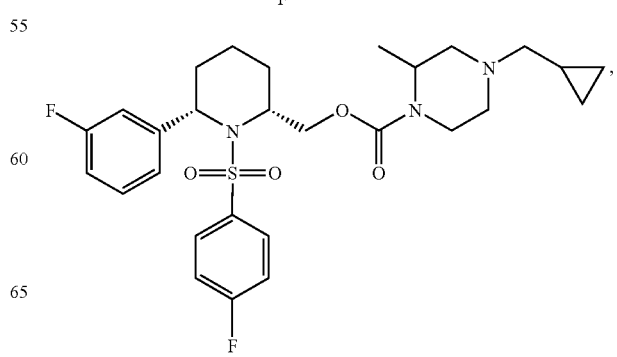

-continued
329
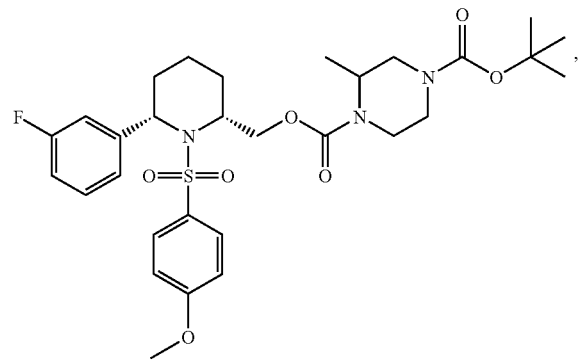
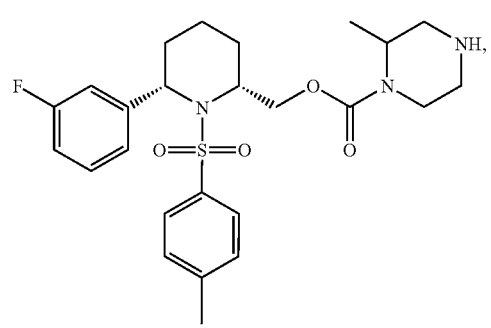
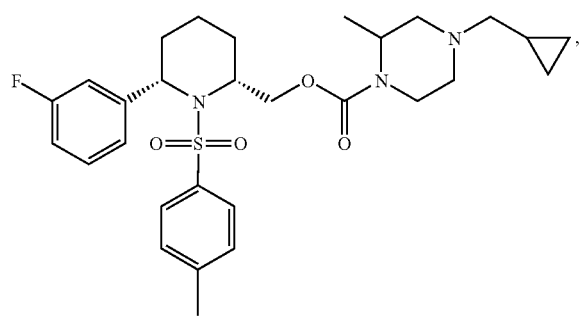
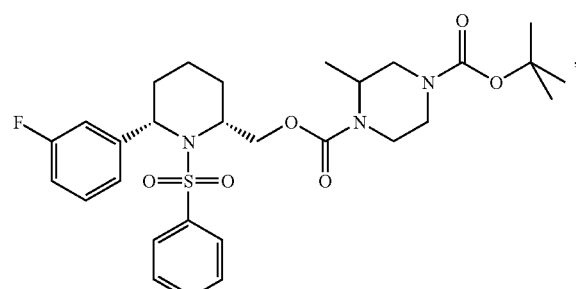
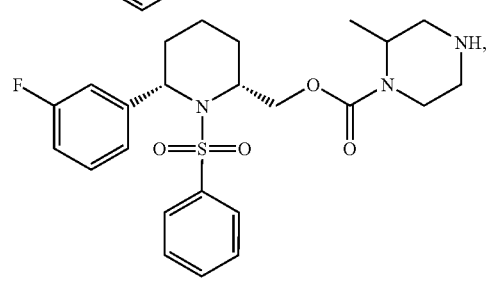
330
-continued
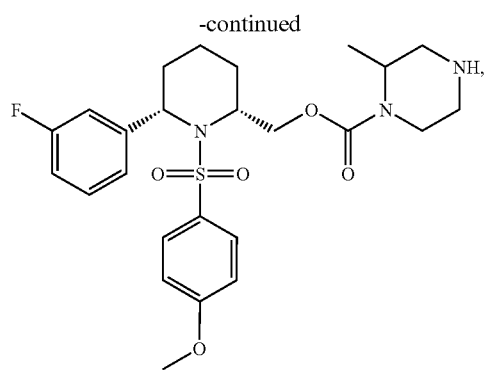
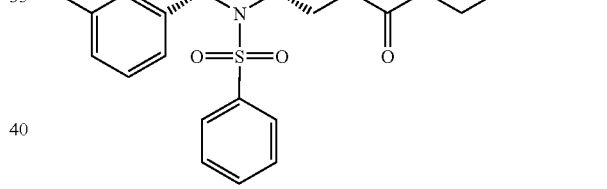
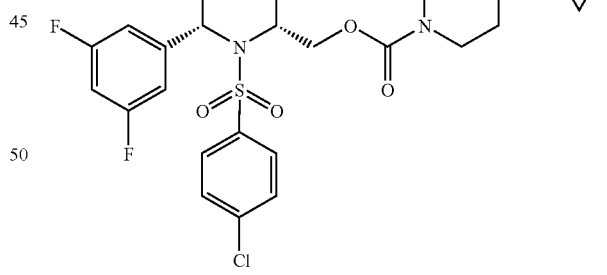
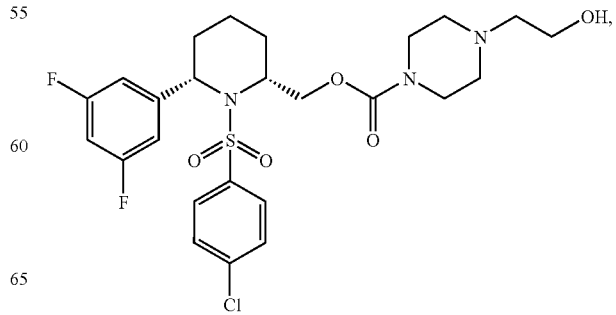

-continued
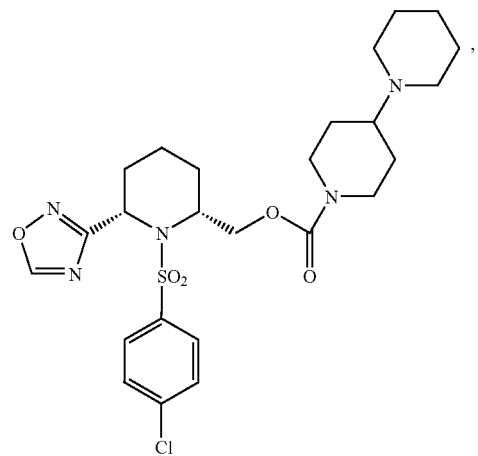
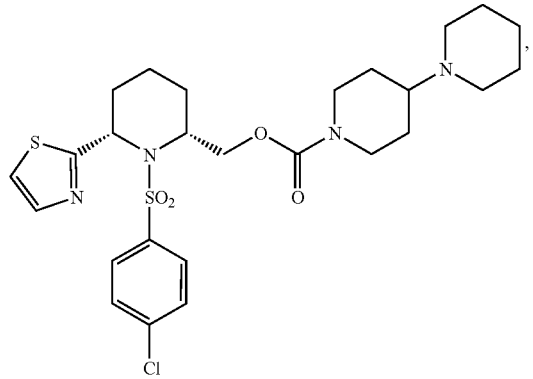
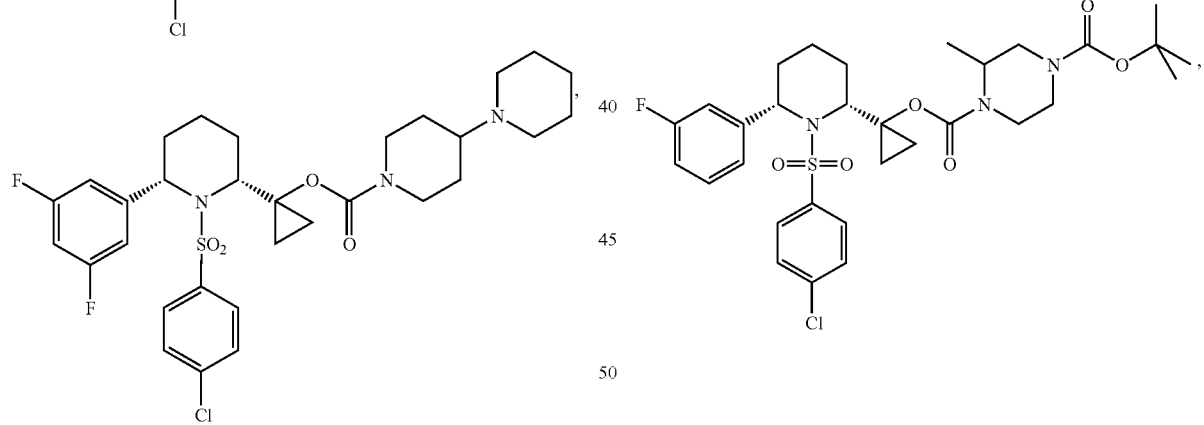
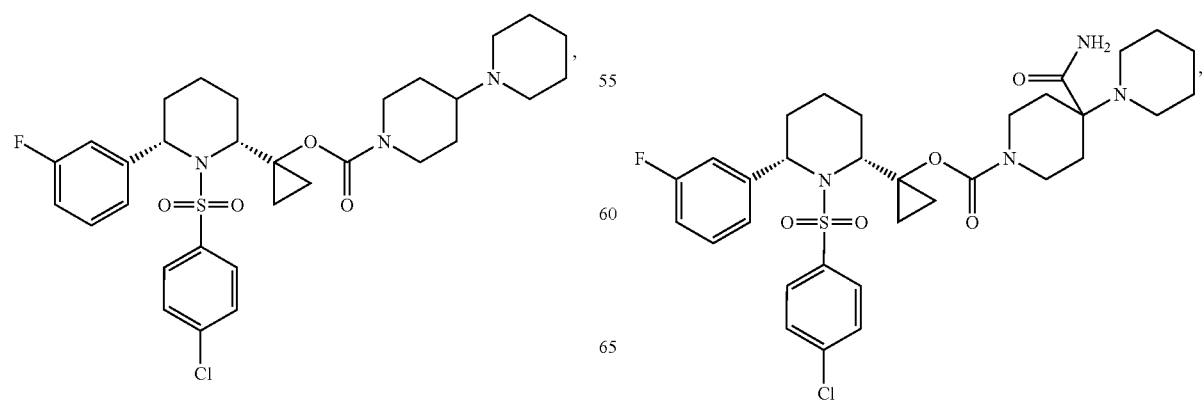
-continued
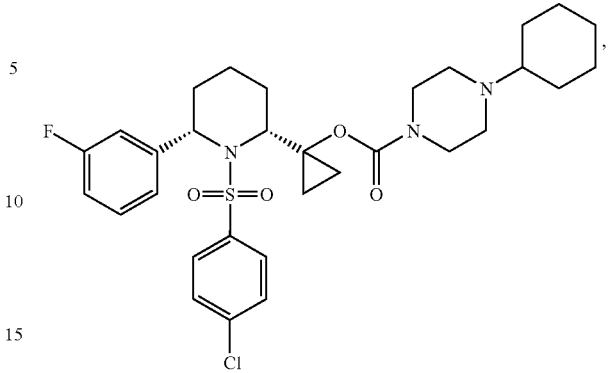
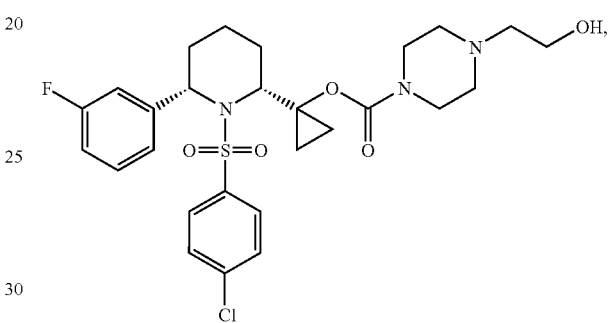
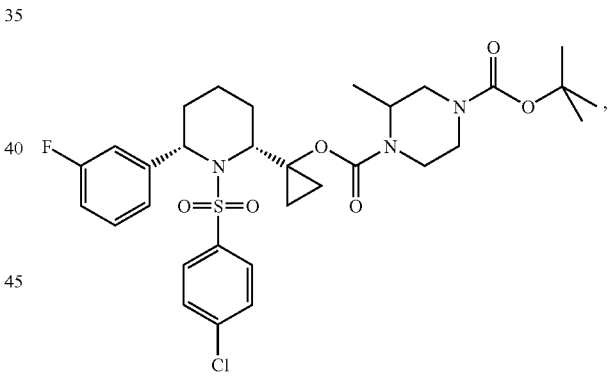
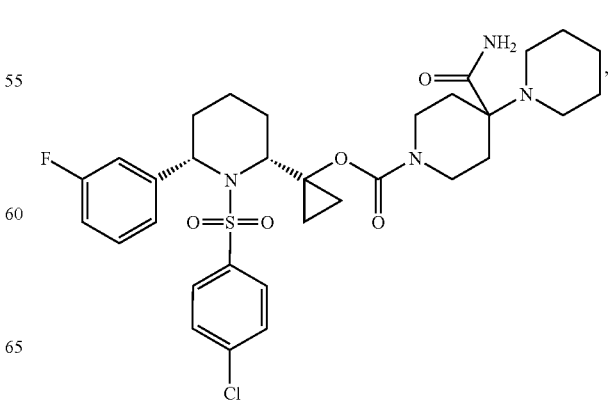

333
-continued
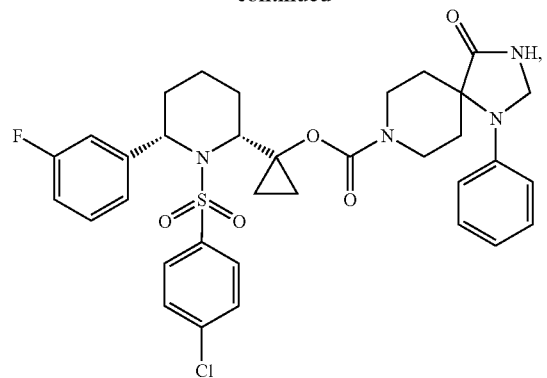
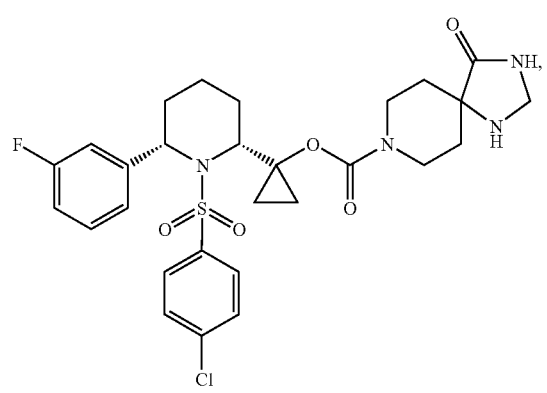
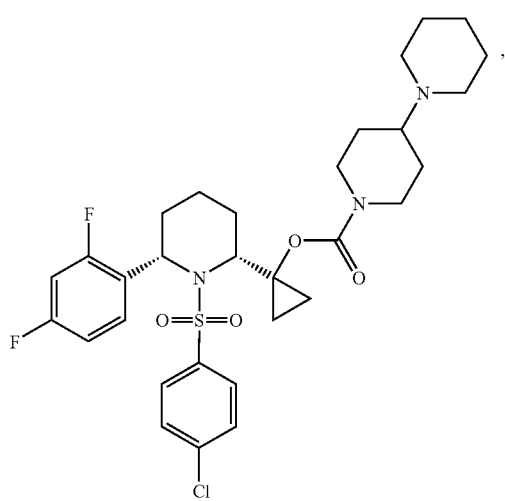
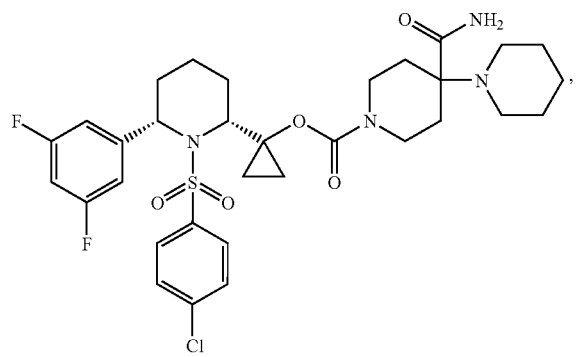
334
-continued
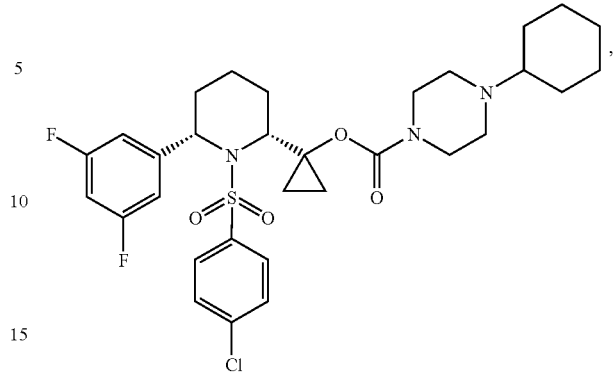
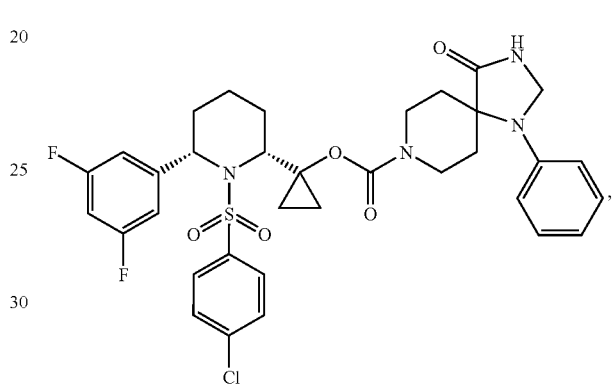
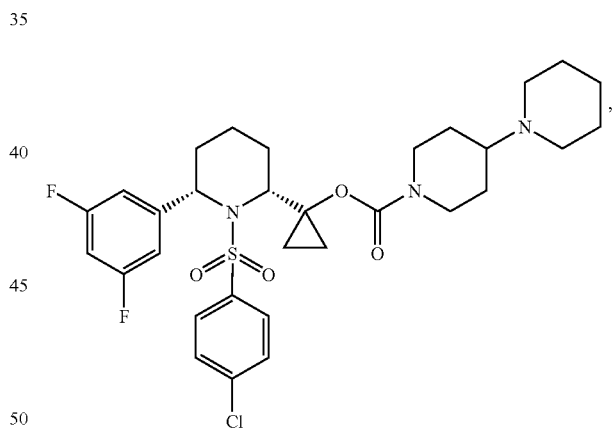
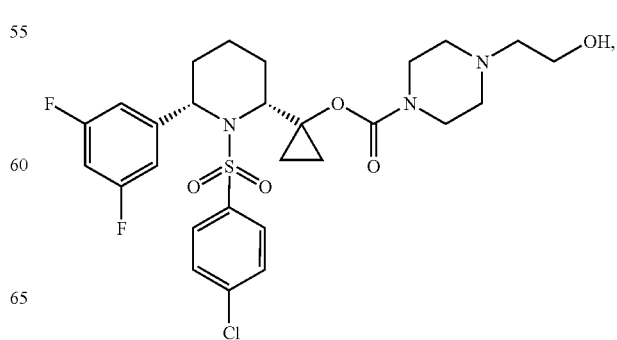

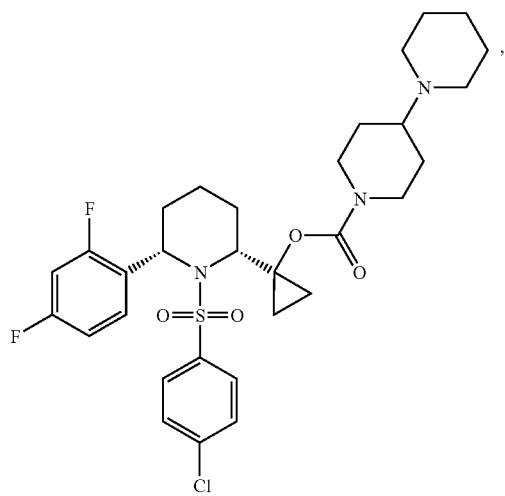
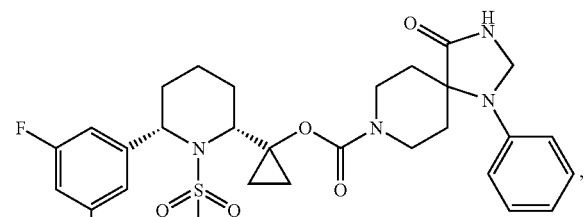
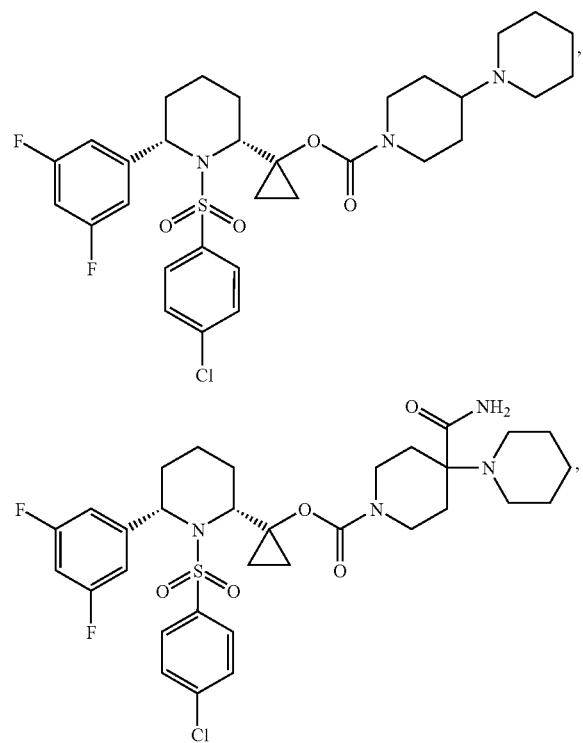
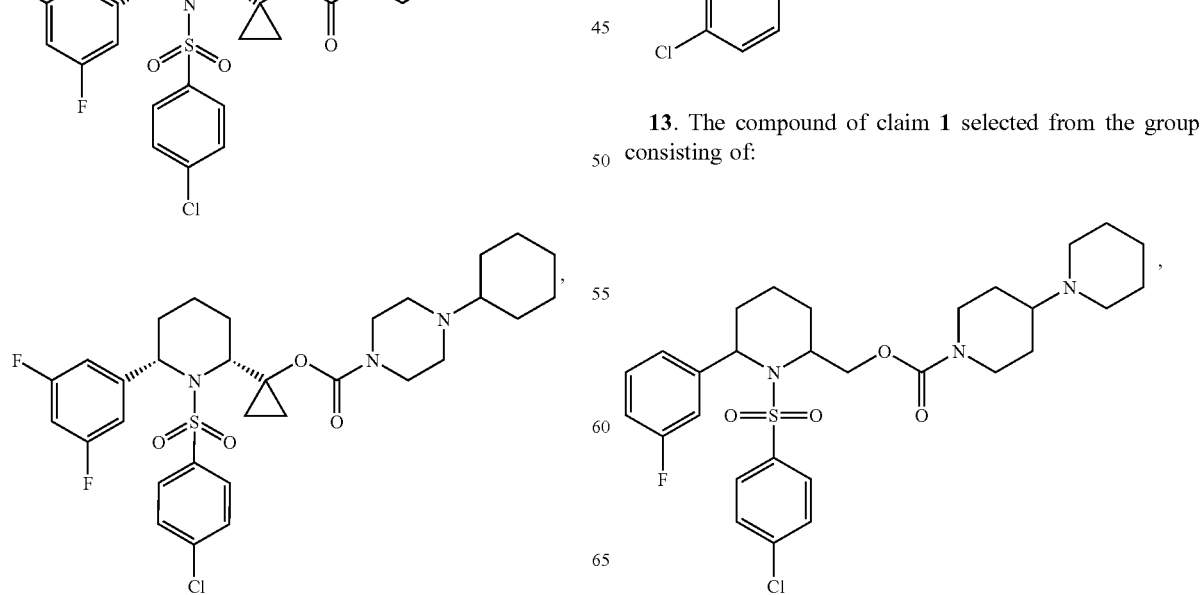
13. The compound of claim 1 selected from the group consisting of:

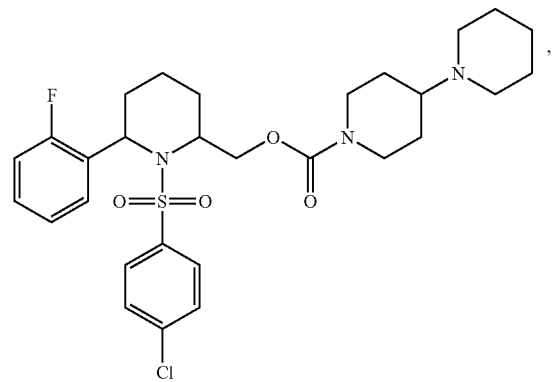
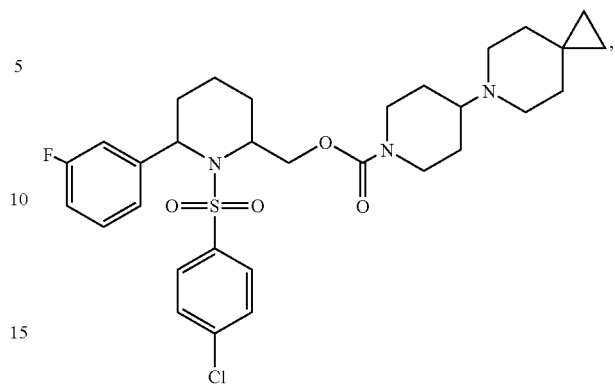
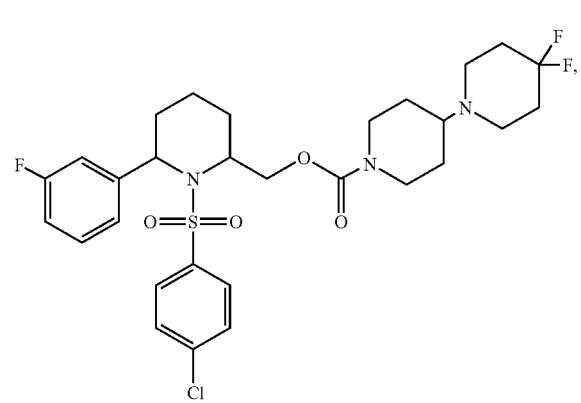
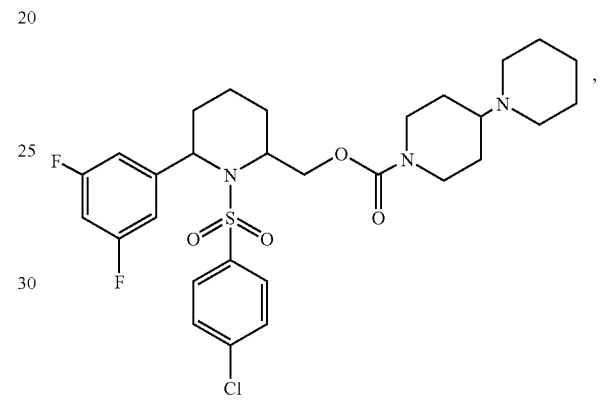
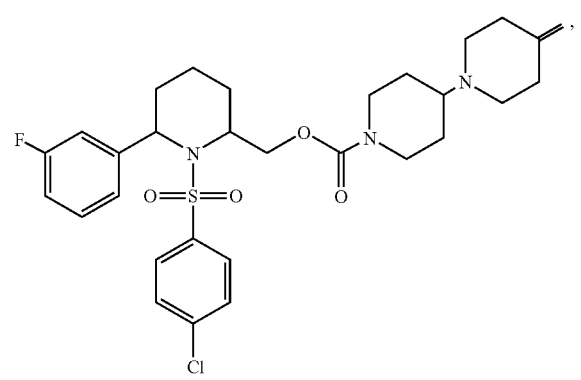
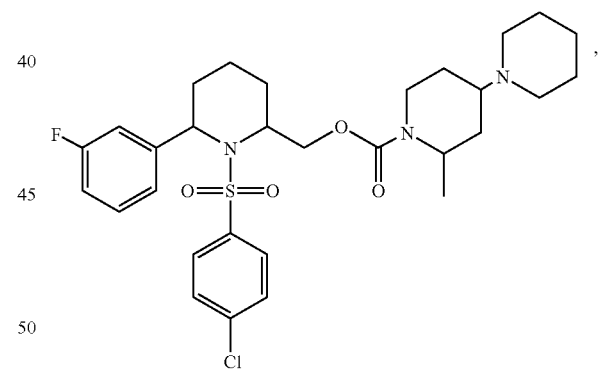
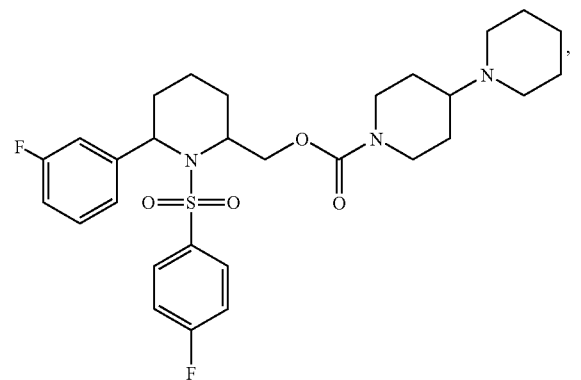
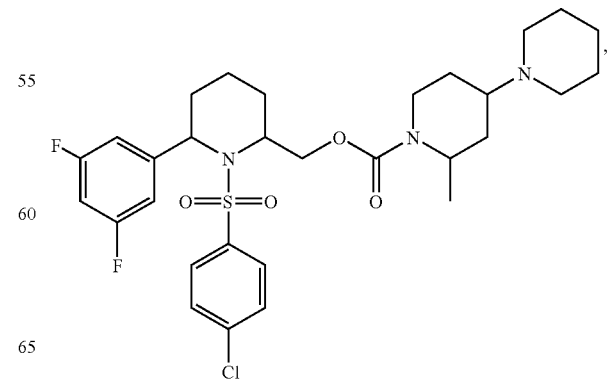

339
-continued
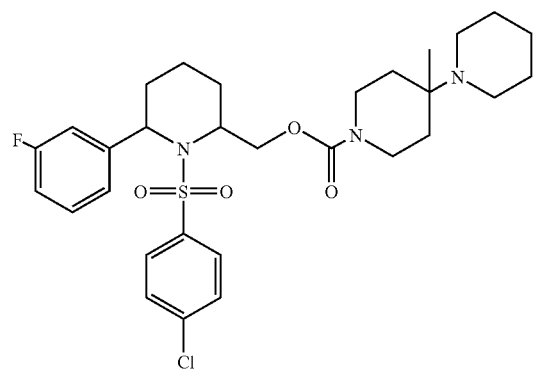
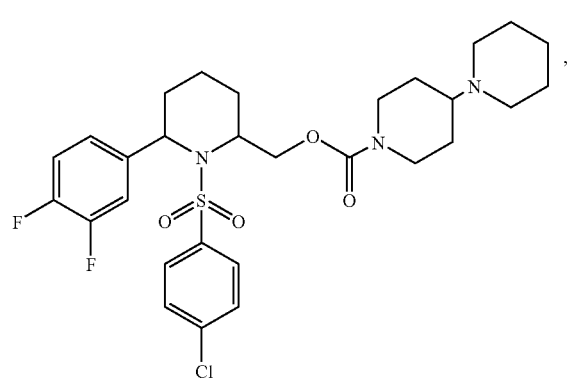
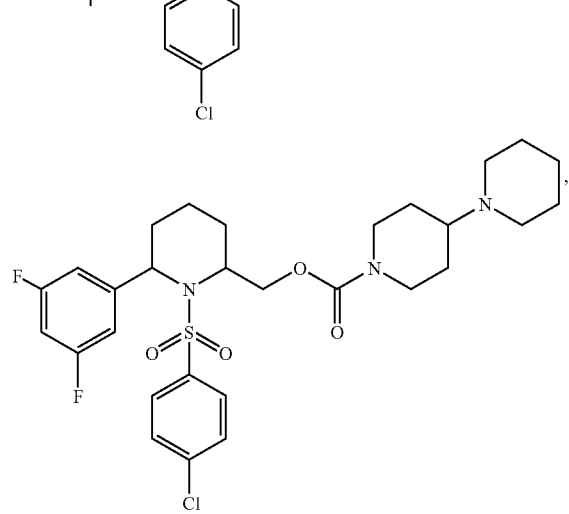
340
-continued
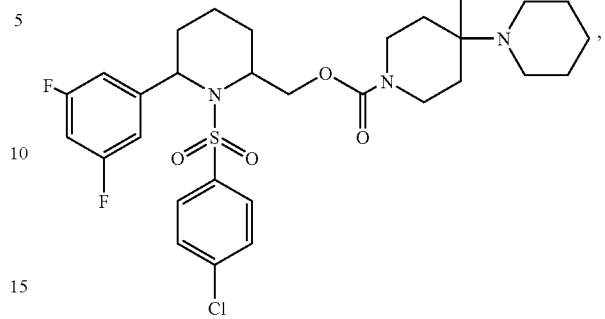
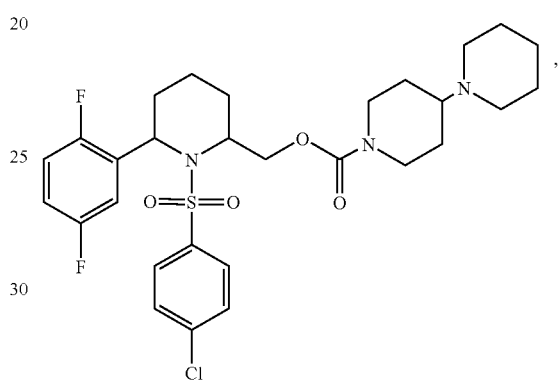
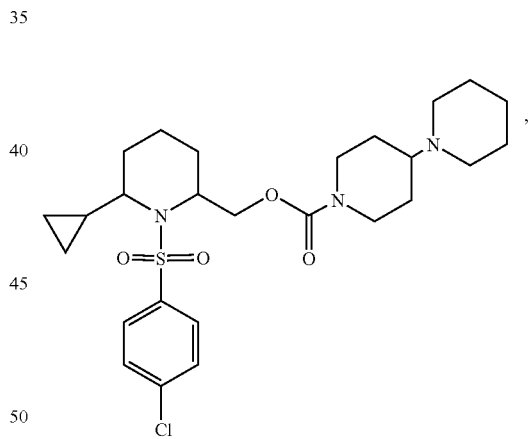
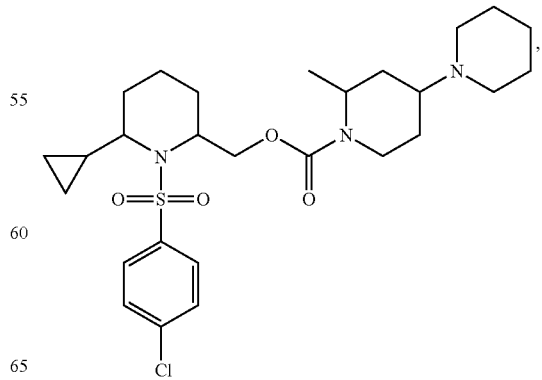

341 342
-continued -continued
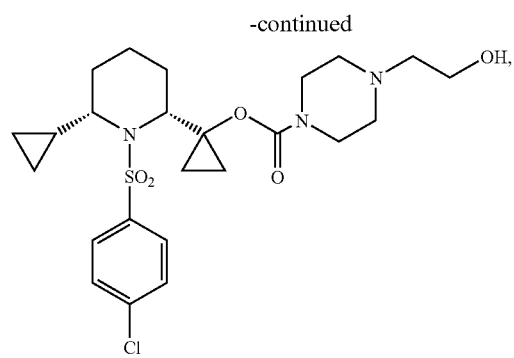
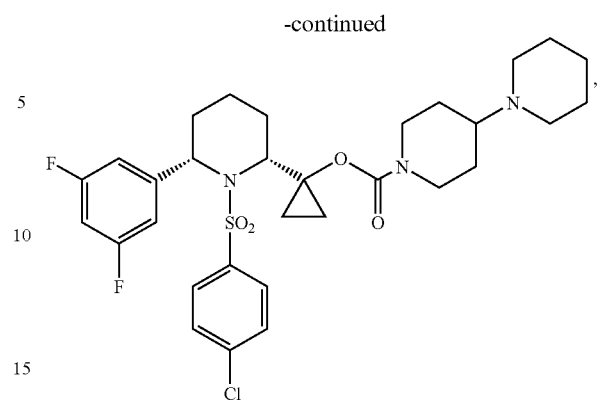
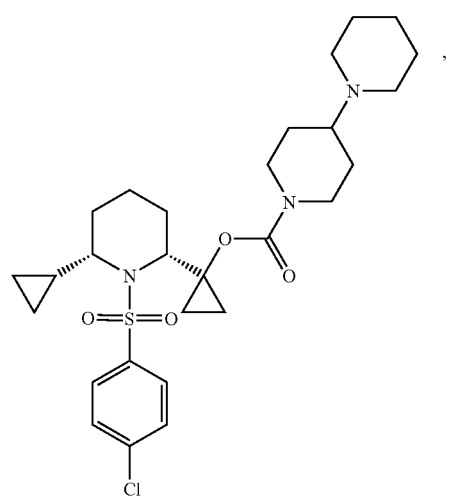
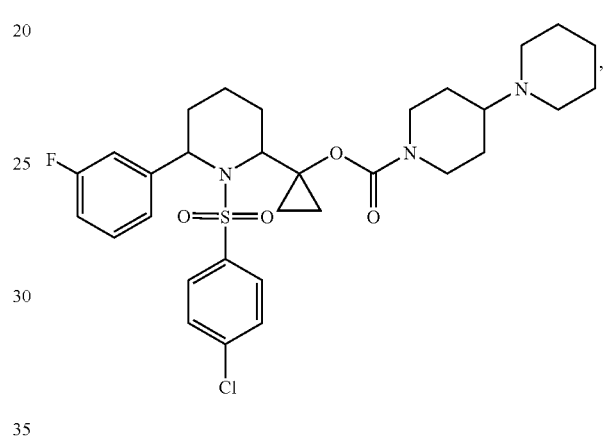
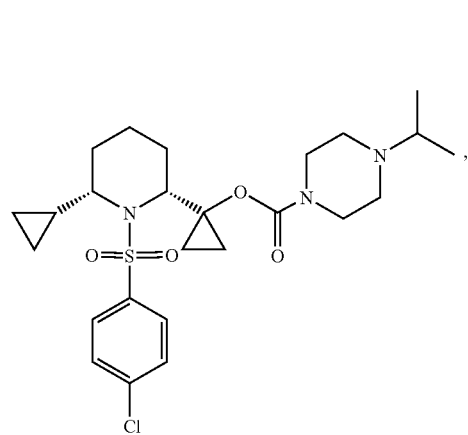
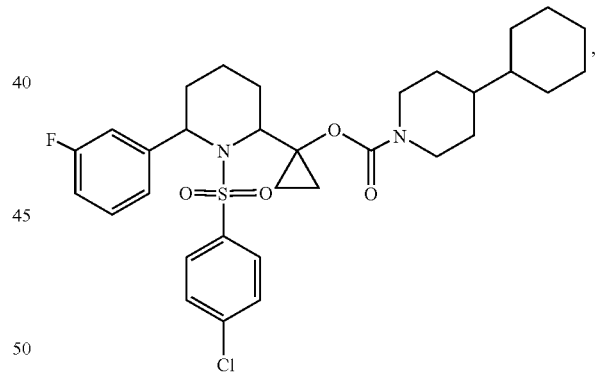
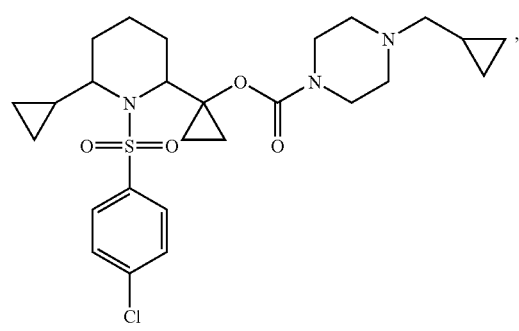
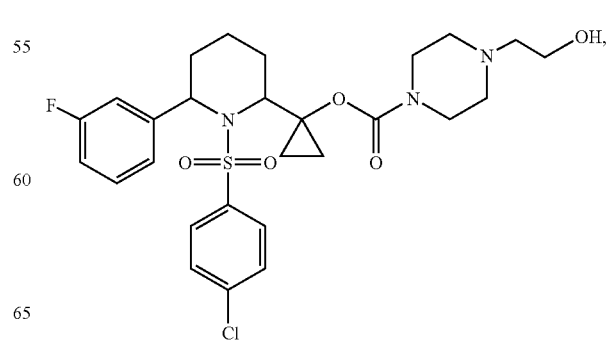

-continued
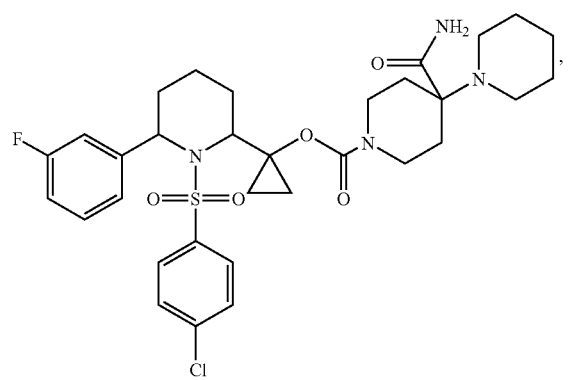
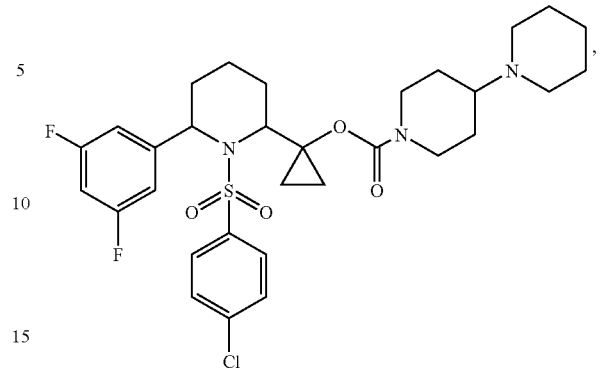
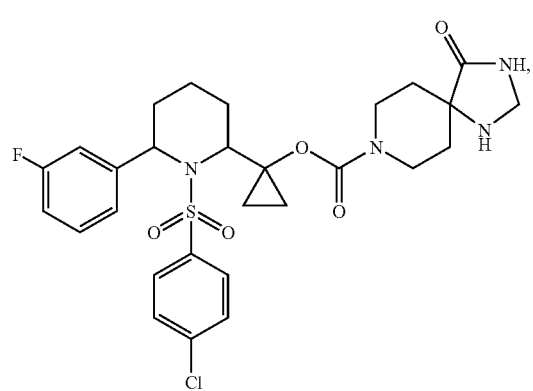
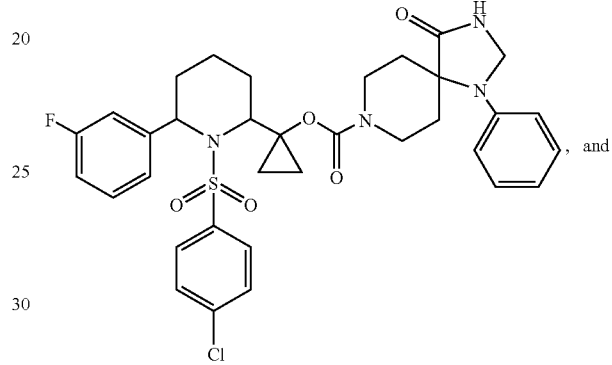, and
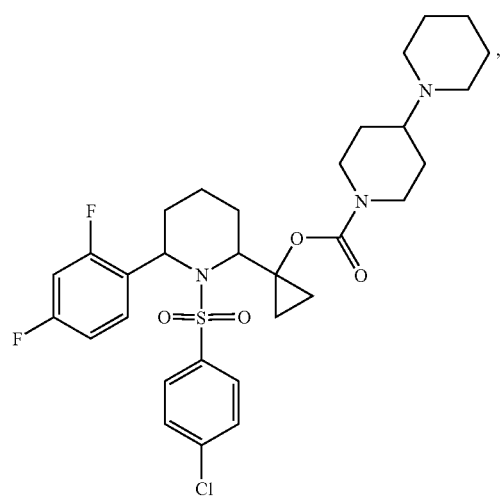
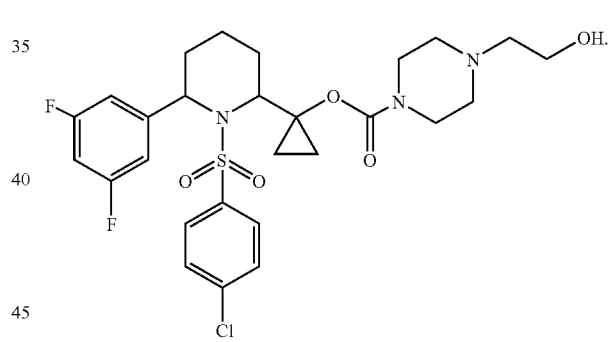
14. The compound of claim 1 selected from the group consisting of:
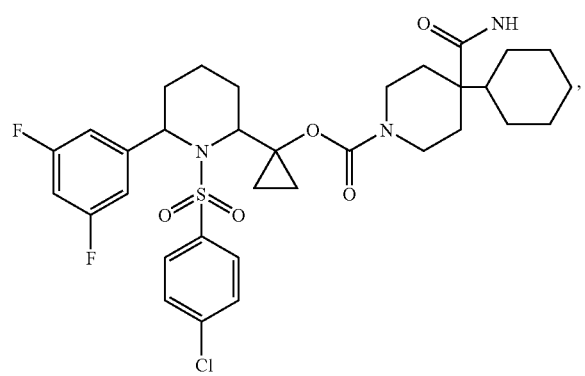
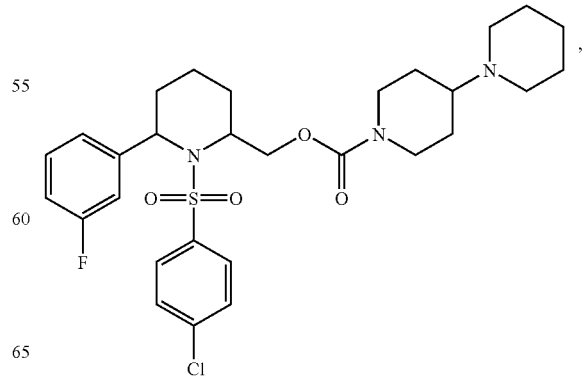

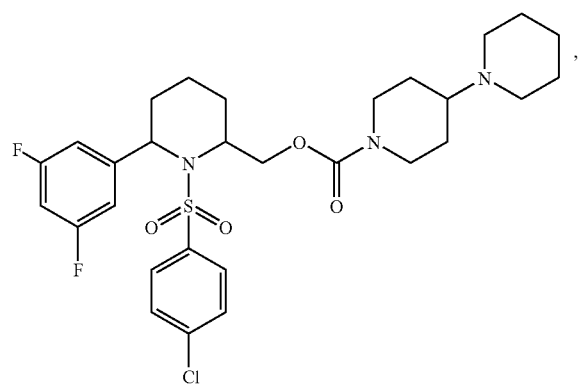
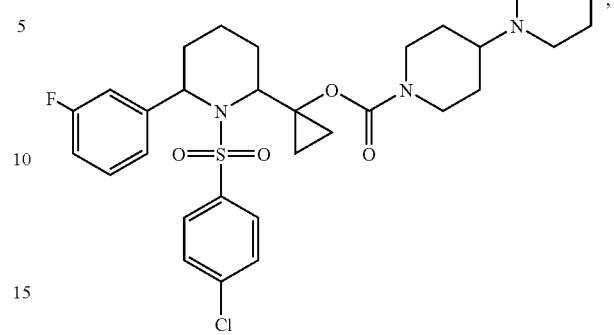
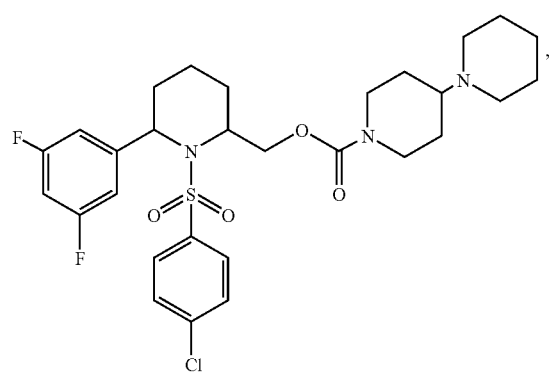
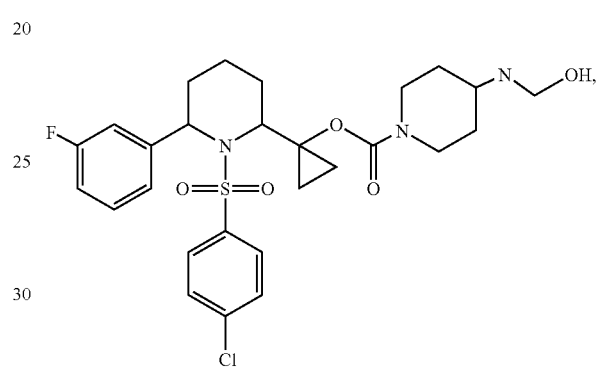
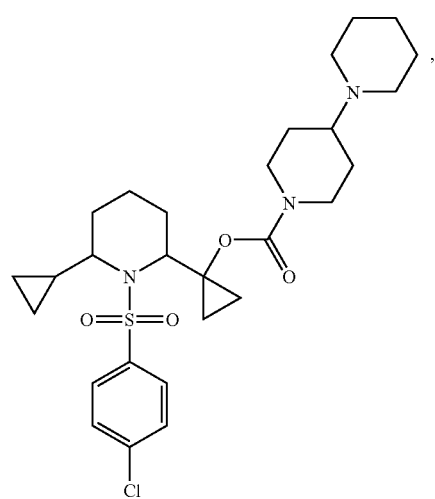
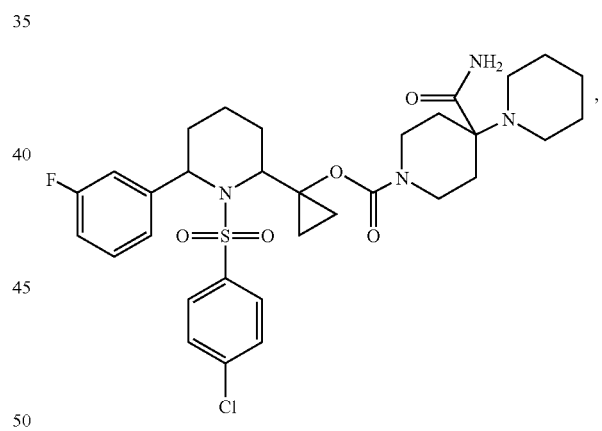
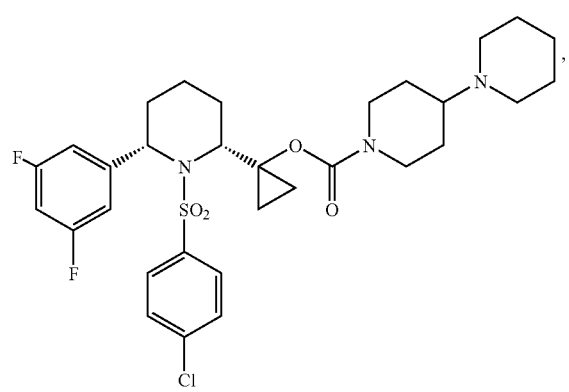
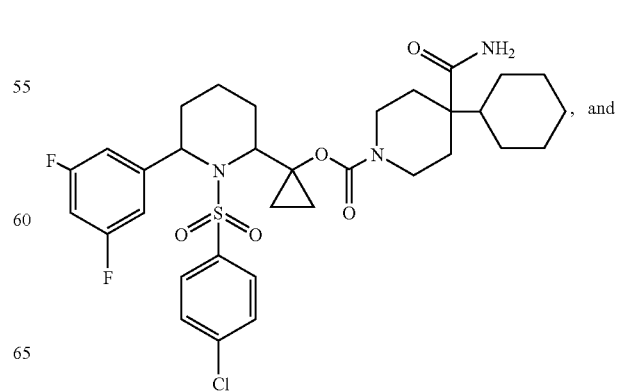

-continued

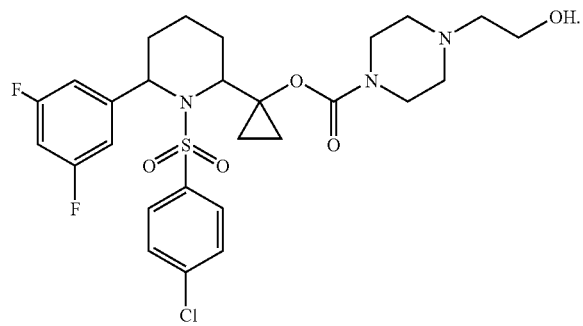

15. A pharmaceutical composition comprising at least one compound of claim 1 and at least one pharmaceutically acceptable carrier.

16. A method of inhibiting gamma-secretase in a patient in need of such treatment comprising administering to said patient a therapeutically effective amount of one or more compounds of claim 1.

17. A method of treating one or more neurodegenerative diseases in a patient in need of such treatment comprising administering to said patient a therapeutically effective amount of one or more compounds of claim 1.

18. A method of inhibiting the deposition of beta amyloid protein in a patient in need of such treatment comprising administering to said patient a therapeutically effective amount of one more compounds of claim 1.

19. A method of treating Alzheimer's disease in a patient in need of such treatment comprising administering to said patient a therapeutically effective amount of one or more compounds of claim 1.

* * * * *